United States Patent
Guillonneau et al.

(10) Patent No.: US 12,168,694 B2
(45) Date of Patent: Dec. 17, 2024

(54) ANTI-HUMAN CD45RC ANTIBODIES AND USES THEREOF

(71) Applicants: INSERM (INSTITUT NATIONAL DE LA SANTÉ ET DE LA RECHERCHE MÉDICALE), Paris (FR); UNIVERSITÉ DE NANTES, Nantes (FR); CENTRE HOSPITALIER UNIVERSITAIRE DE NANTES, Nantes (FR)

(72) Inventors: Carole Guillonneau, La Chevrolière (FR); Ignacio Anegon, Nantes (FR)

(73) Assignees: INSERM (INSTITUT NATIONAL DE LA SANTÉ ET DE LA RECHERCHE MÉDICALE), Paris (FR); NANTES UNIVERSITE, Nantes (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 945 days.

(21) Appl. No.: 17/277,511

(22) PCT Filed: Sep. 20, 2019

(86) PCT No.: PCT/EP2019/075374
§ 371 (c)(1),
(2) Date: Mar. 18, 2021

(87) PCT Pub. No.: WO2020/058495
PCT Pub. Date: Mar. 26, 2020

(65) Prior Publication Data
US 2022/0033500 A1 Feb. 3, 2022

(30) Foreign Application Priority Data
Sep. 21, 2018 (EP) .................... 18306230

(51) Int. Cl.
*A61P 37/06* (2006.01)
*C07K 16/28* (2006.01)
*A61K 39/00* (2006.01)

(52) U.S. Cl.
CPC ............ *C07K 16/289* (2013.01); *A61P 37/06* (2018.01); *A61K 2039/505* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

2017/0226209 A1* 8/2017 Guillonneau ............. A61P 7/04

FOREIGN PATENT DOCUMENTS

| WO | WO-2016016442 A1 * | 2/2016 | .......... A61K 31/436 |
| WO | 2019115791 A1 | 6/2019 | |

OTHER PUBLICATIONS

Bezie et al., "Ex Vivo Expanded Human Non-Cytotoxic CD8+ CD45RClow/-Tregs Efficiently Delay Skin Graft Rejection and GVHD in Humanized Mice". Front Immunol. Jan. 3, 2018l. vol. 8, Article 2014. 16 pages.
Birkeland et al., "Changes in CD45 isoform expression accompany antigen-induced murine T-cell activation". Proc Natl Acad Sci U S A. Sep. 1989. 86(17):6734-8.
Desai et al., "The catalytic activity of the CD45 membrane-proximal phosphatase domain is required for TCR signaling and regulation". EMBO J. Sep. 1, 1994. 13(17):4002-10.
Garnett et al., "Treatment and management of graft-versus-host disease: improving response and survival". Ther Adv Hematol. Dec. 2013. 4(6):366-78.
Guillonneau et al., "CD40Ig treatment results in allograft acceptance mediated by CD8CD45RC T cells, IFN-gamma, and indoleamine 2,3-dioxygenase". J Clin Invest. Apr. 2007. 117(4):1096-106. 12 pages.
Hermiston et al., "CD45: A Critical Regulator of Signaling Thresholds in Immune Cells". Annu Rev Immunol. 2003. 21:107-37.
Holmes, "CD45: all is not yet crystal clear". Immunology. Feb. 2006. 117(2):145-55.
Koch et al., "Multiparameter flow cytometric analysis of CD4 and CD8 T cell subsets in young and old people". Immun Ageing. Jul. 25, 2008. 5:6. 12 pages.
Lowell, "Src-family kinases: rheostats of immune cell signaling". Mol Immunol. Jul. 2004. 41(6-7):631-43.
Lynch, "Consequences of regulated pre-mRNA splicing in the immune system". Nat Rev Immunol. Dec. 2004. 4(12):931-40.
Ordonez et al., "A Higher Risk of Acute Rejection of Human Kidney Allografts Can be Predicted from the Level of CD45RC Expressed by the Recipients' CD8 T cells". PLoS One. Jul. 24, 2013. 8(7):e69791. 12 pages.
Quisse et al., "Immunophenotype of a Rat Model of Duchenne's Disease and Demonstration of Improved Muscle Strength After Anti-CD45RC Antibody Treatment". Front Immunol. Sep. 9, 2019. vol. 10, Article 2131. 15 pages.

(Continued)

*Primary Examiner* — Daniel E Kolker
*Assistant Examiner* — Katherine Ann Holtzman
(74) *Attorney, Agent, or Firm* — Maier & Maier, PLLC

(57) ABSTRACT

Isolated anti-human CD45RC antibodies or binding fragments thereof, nucleic acids and expression vector encoding the same, compositions including the same, and uses thereof as medicaments, including for the prevention and/or treatment of $CD45RC^{high}$-related diseases (including autoimmune diseases, undesired immune responses, monogenic diseases, and lymphoma or cancer), in particular for use in preventing and/or treating graft-versus-host disease (GVHD).

20 Claims, 21 Drawing Sheets
Specification includes a Sequence Listing.

(56) References Cited

OTHER PUBLICATIONS

Palacios et al., "Function of the Src-family kinases, Lck and Fyn, in T-cell development and activation". Oncogene. Oct. 18, 2004. 23(48):7990-8000.

Picarda et al., "Transient antibody targeting of CD45RC induces transplant tolerance and potent antigen-specific regulatory T cells". JCI Insight. Feb. 9, 2017. 2(3):e90088. 21 pages.

Powrie et al., "OX-22high CD4+ T Cells Induce Wasting Disease with Multiple Organ Pathology: Prevention by the OX-22low Subset". J Exp Med. Dec. 1, 1990. 172(6):1701-8.

Rosenberg et al., "Immune-mediated pathology in Duchenne muscular dystrophy". Sci Transl Med. Aug. 5, 2015. 7(299):299rv4. 12 pages.

Rudikoff et al., "Single amino acid substitution altering antigen-binding specificity". Proc Natl Acad Sci U S A. Mar. 1982. 79(6):1979-83.

Spickett et al., "MRC OX-22, a monoclonal antibody that labels a new subset of T lymphocytes and reacts with the high molecular weight form of the leukocyte-common antigen". J Exp Med. Sep. 1, 1983. 158(3):795-810.

Trowbridge et al., "CD45: An Emerging Role as a Protein Tyrosine Phosphatase Required for Lymphocyte Activation and Development". Annu Rev Immunol. 1994. 12:85-116.

Villalta et al., "Regulatory T cells suppress muscle inflammation and injury in muscular dystrophy". Sci Transl Med. Oct. 15, 2014. 6(258):258ra142. 11 pages.

Xystrakis et al., "Alloreactive CD4 T lymphocytes responsible for acute and chronic graft-versus-host disease are contained within the CD45RChigh but not the CD45RClow subset". Eur J Immunol. Feb. 2004. 34(2):408-17.

Xystrakis et al., "Identification of a novel natural regulatory CD8 T-cell subset and analysis of its mechanism of regulation". Blood. Nov. 15, 2004. 104(10):3294-301.

\* cited by examiner

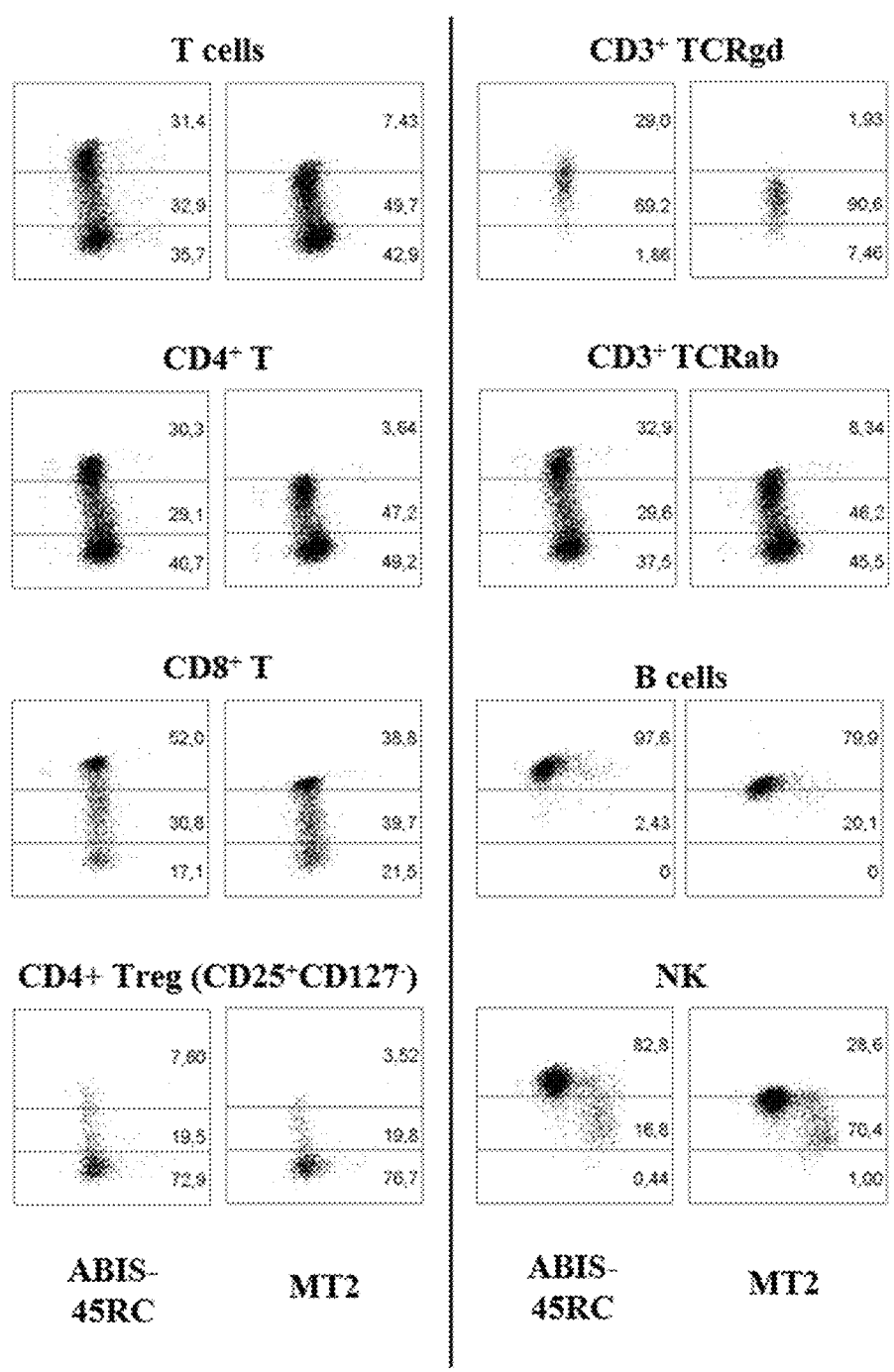
FIG. 1 A(1)

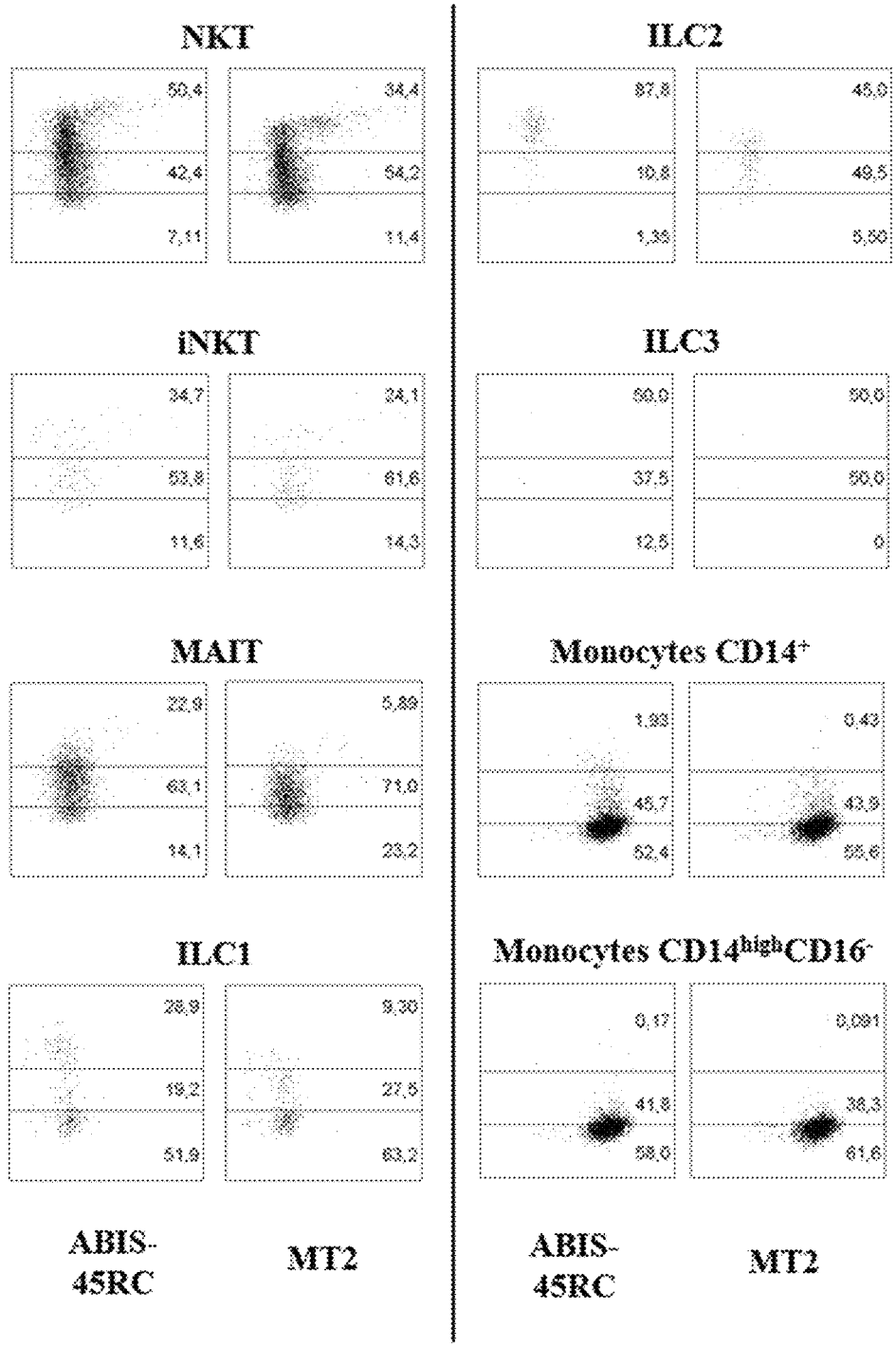
FIG. 1 A(2)

FIG. 1 A(3)

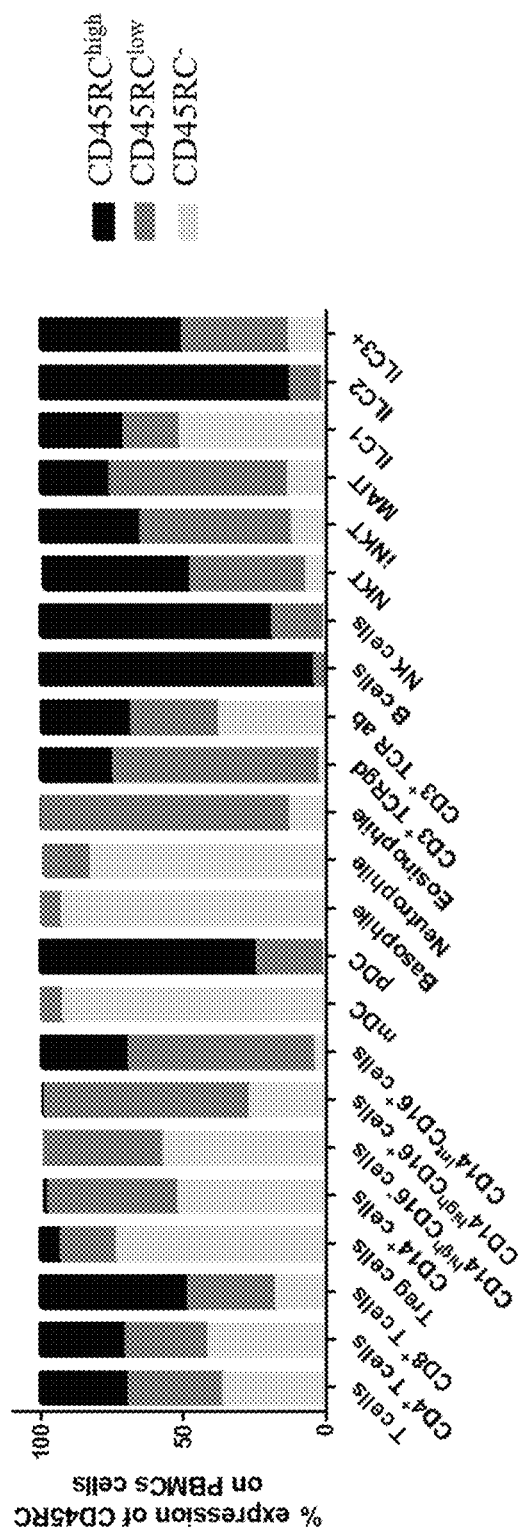
FIG. 1 B(1)

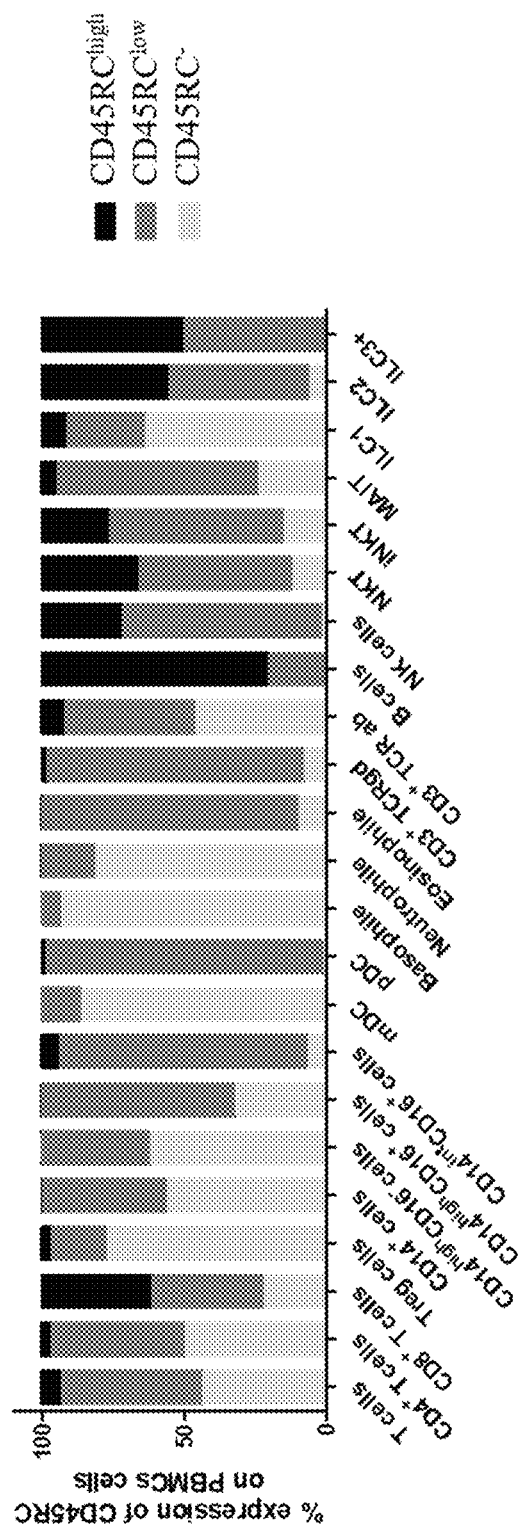
FIG. 1B(2)

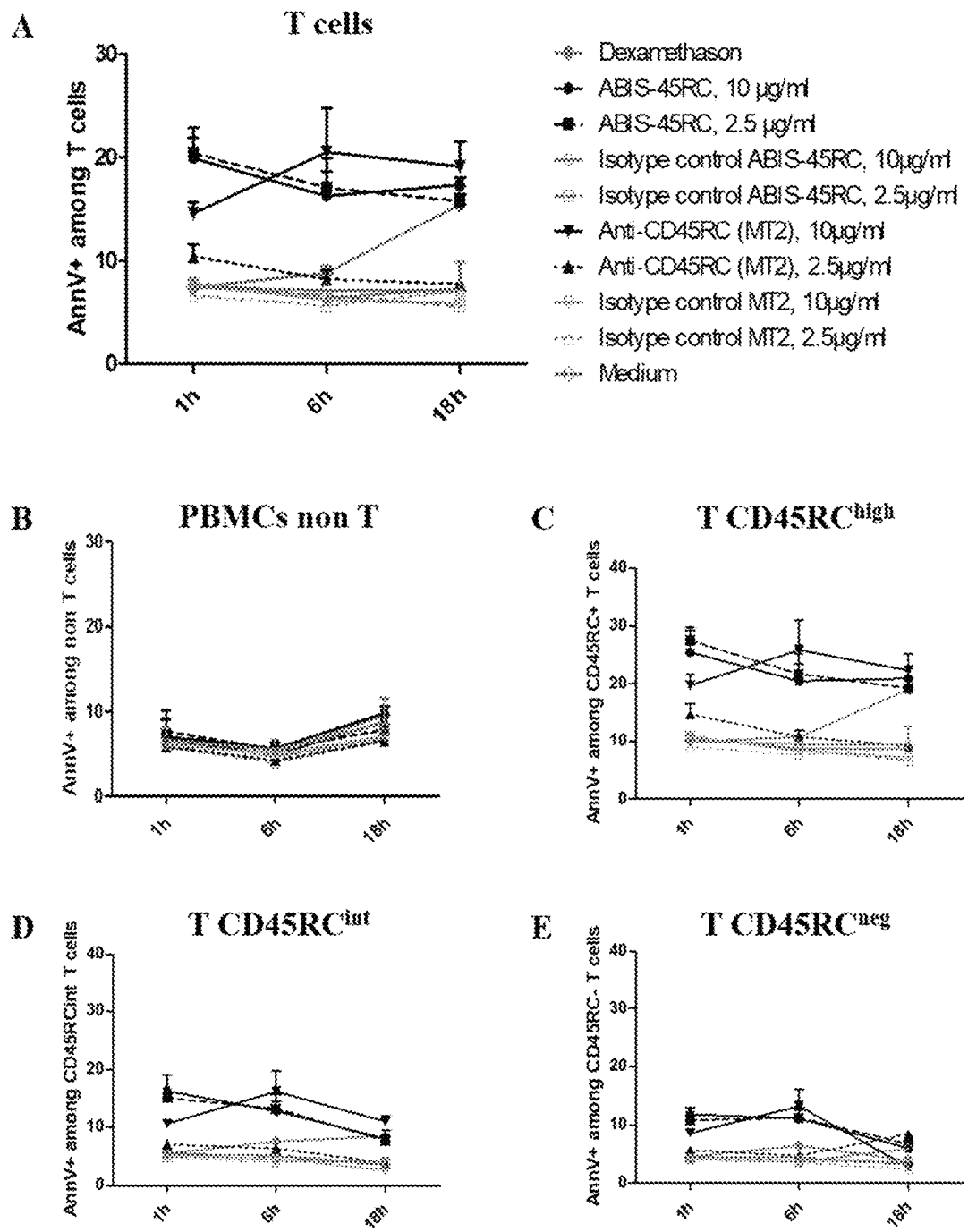
FIG. 3 A-E

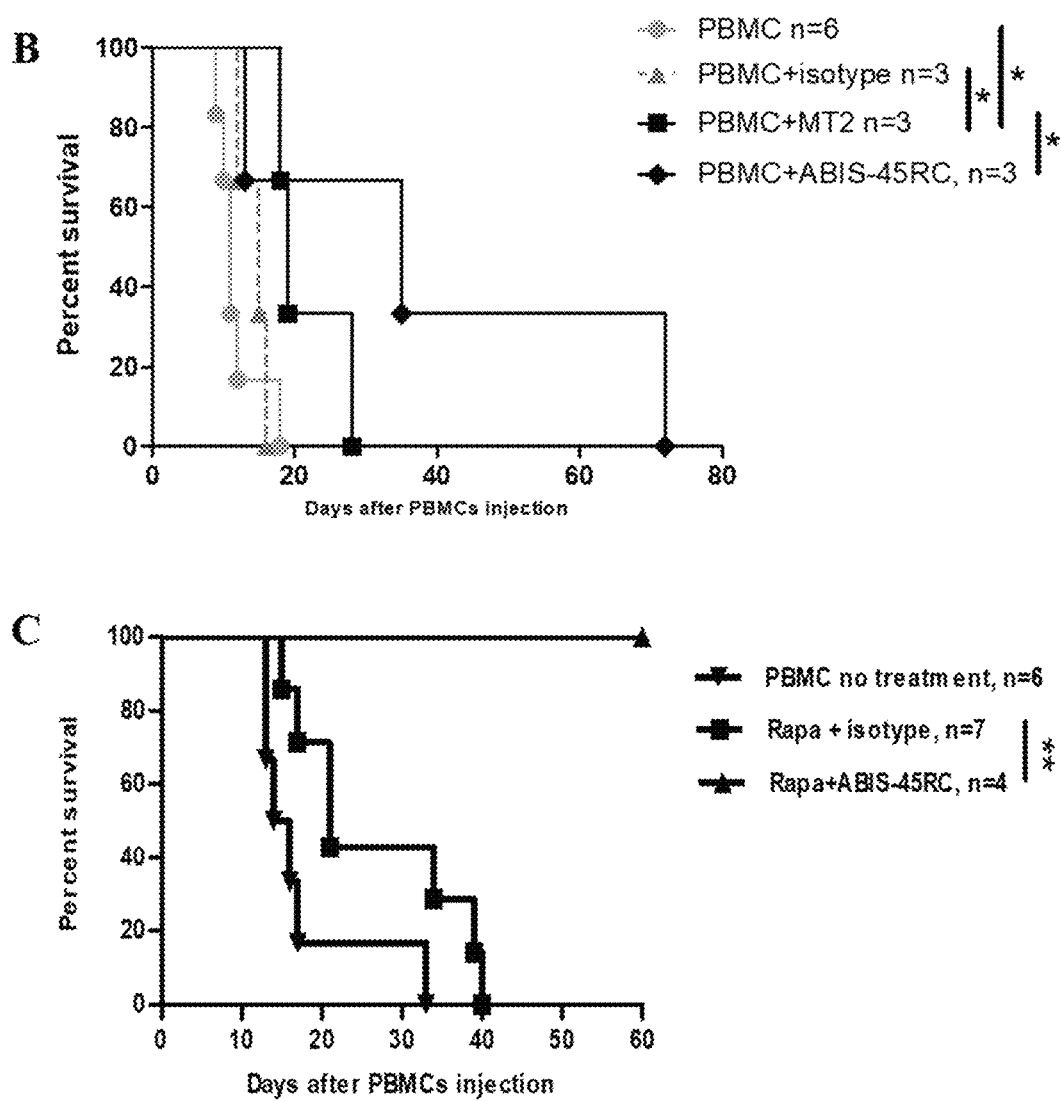
FIG. 4 B-C

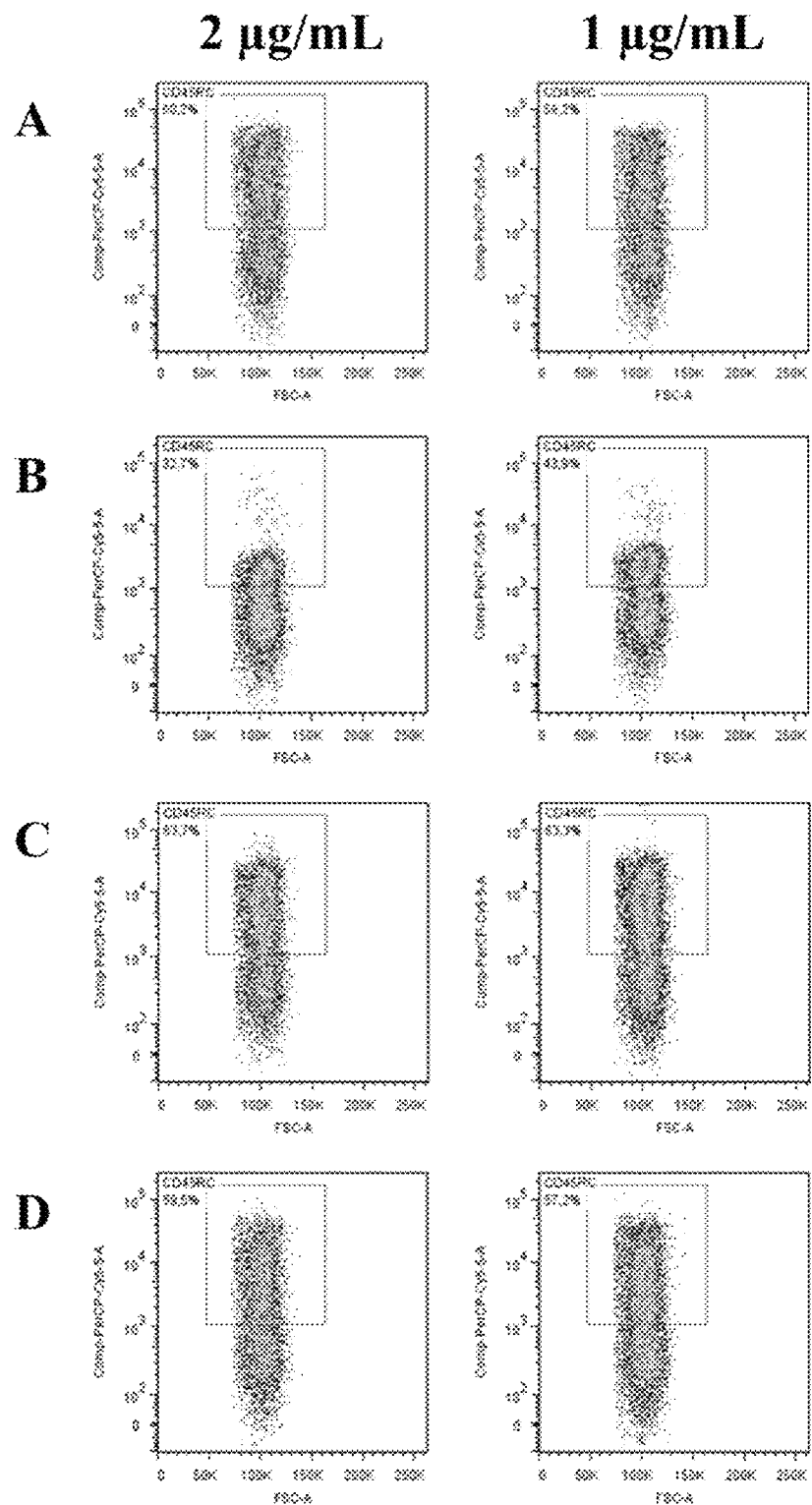
FIG. 5 A-D

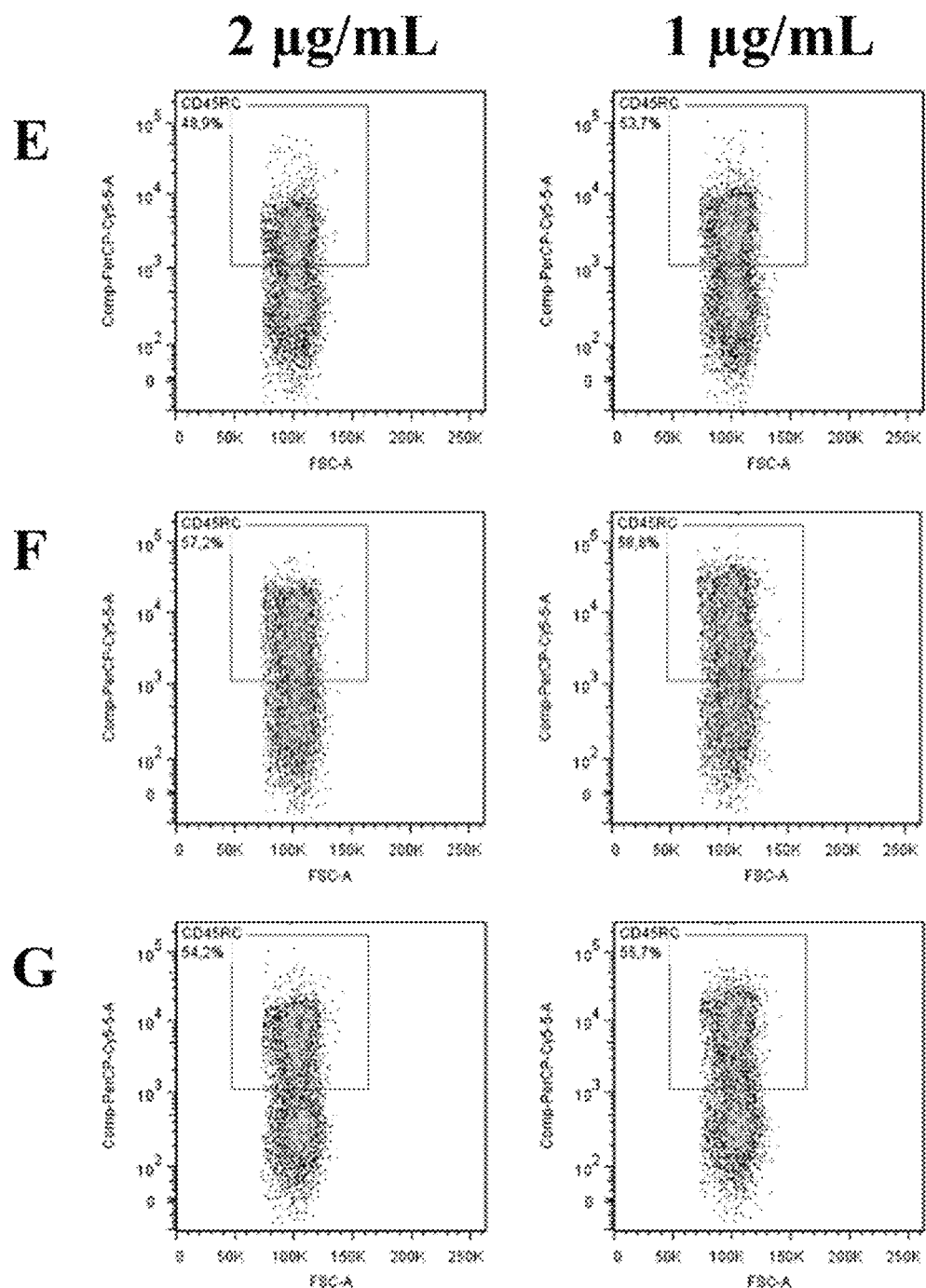
FIG. 5 E-G

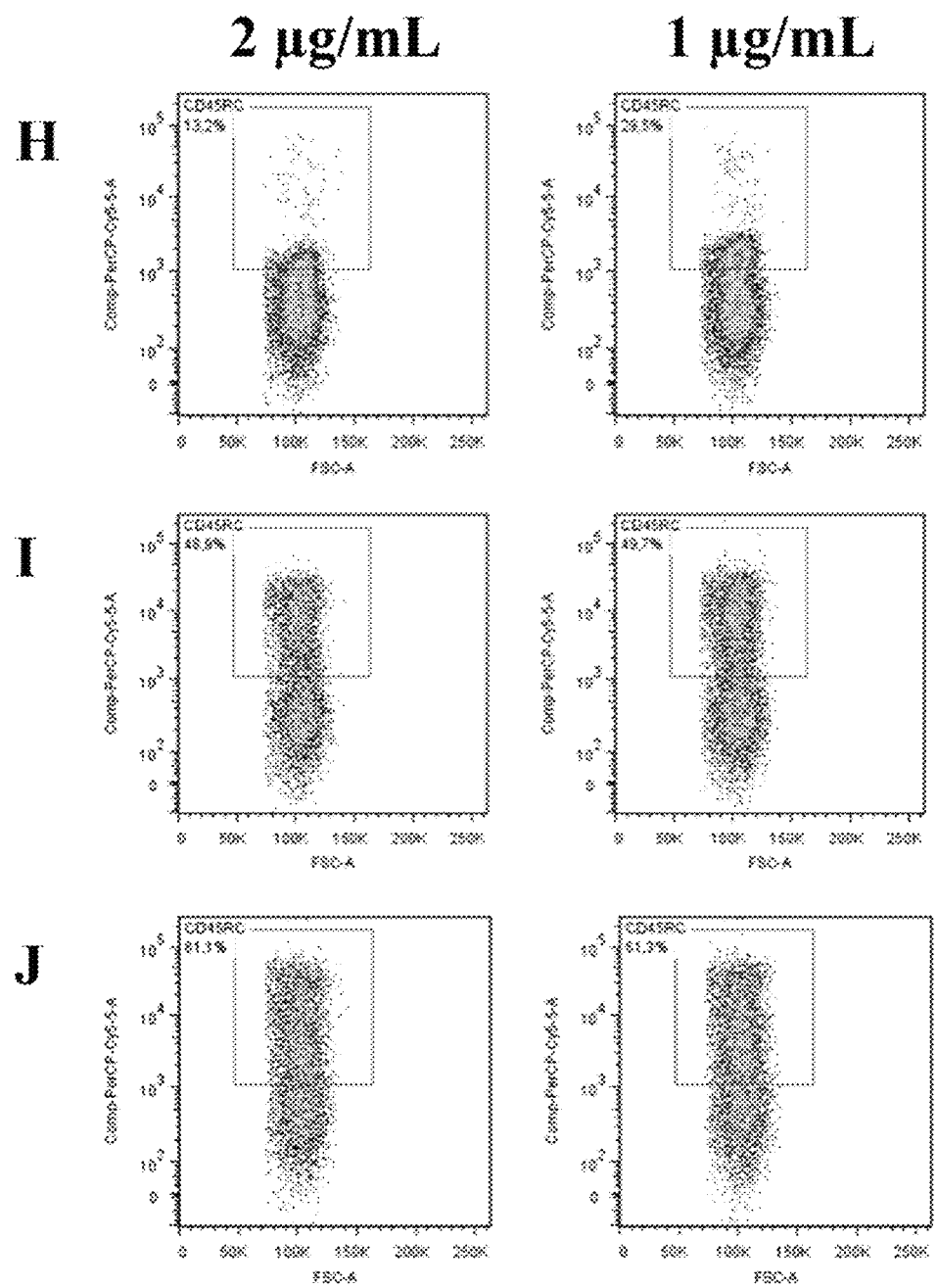
FIG. 5 H-J

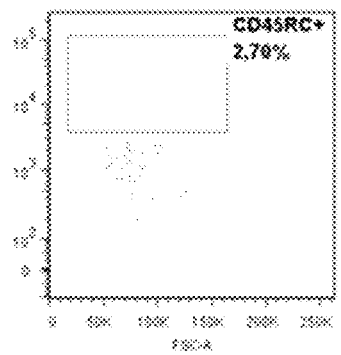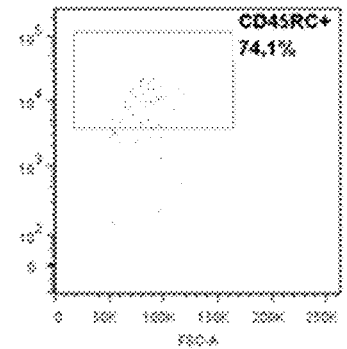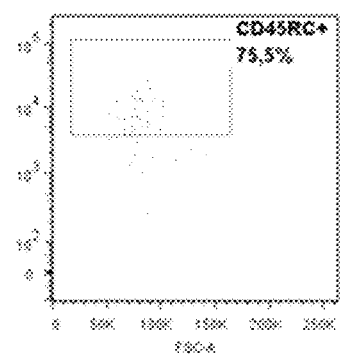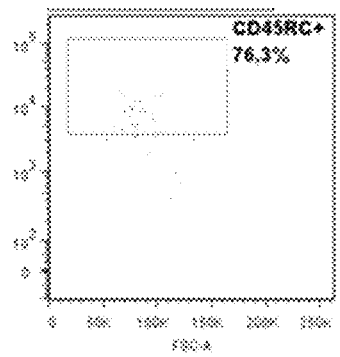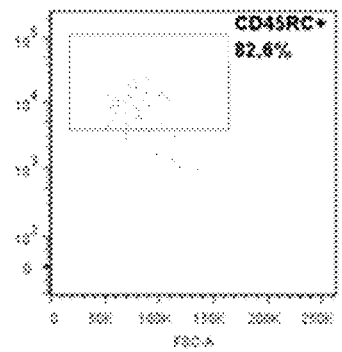
FIG. 9B

ANTI-HUMAN CD45RC ANTIBODIES AND USES THEREOF

FIELD

The present invention relates to isolated anti-human CD45RC antibodies or binding fragments thereof, to nucleic acids and expression vector encoding the same, to compositions comprising the same, and to uses thereof as medicaments, including for the prevention and/or treatment of CD45RC$^{high}$-related diseases (including autoimmune diseases, undesired immune responses, monogenic diseases, and lymphoma or cancer), in particular for use in preventing and/or treating graft-versus-host disease (GVHD).

BACKGROUND

CD45 (also known as leukocyte common antigen (LCA), EC3.1.3.48, T200, Ly5, and PTPRC) constitutes the first and prototypic receptor-like protein tyrosine phosphatase (RPTP). Its expression is restricted to all nucleated hematopoietic cells, where it is one of the most abundant cell surface glycoproteins, constituting almost 10 percent of the cell surface, and estimated to be present at approximately 25 µM in the plasma membrane (Trowbridge & Thomas, 1994. *Annu Rev Immunol.* 12:85-116; Hermiston et al., 2003. *Annu Rev Immunol.* 21:107-37; Holmes, 2006. *Immunology.* 117 (2):145-55).

CD45 comprises an extracellular domain, a single transmembrane domain and a large cytoplasmic domain. The transmembrane and cytoplasmic domains are highly conserved amongst species. In particular, the cytoplasmic domain of CD45 comprises two tandemly duplicated phosphatase domains, of which only the membrane-proximal domain has enzymatic activity (Desai et al., 1994. *EMBO J.* 13(17):4002-10). The function of the more C-terminal second phosphatase domain in CD45 remains uncertain although it is suggested that it may contribute to CD45 activity indirectly by stabilizing the first domain. Through this cytoplasmic domain, CD45 functions as a central regulator of phosphotyrosine levels in hematopoietic cells, by modulating the activity of Src family of tyrosine-protein kinases (such as Lck in T cells; or Lyn, Fyn and Lck in B cells) (Palacios & Weiss, 2004. *Oncogene.* 23(48):7990-8000; Lowell, 2004. *Mol Immunol.* 41(6-7):631-43).

By contrast with the transmembrane and cytoplasmic domains, the extracellular domain of CD45 shows a higher polymorphism among different leukocyte lineages. Indeed, this extracellular domain is heavily glycosylated and contains three alternatively spliced exons (4, 5, and 6—which encode the A, B and C determinants, respectively) that are both O-linked glycosylated and sialylated (Hermiston et al., 2003. *Annu Rev Immunol.* 21:107-37; Holmes, 2006. *Immunology.* 117(2):145-55). CD45 isoforms differing in size, shape, and charge can therefore be generated by a dynamically-controlled alternative splicing in both leukocyte differentiation and cellular activation, leading to changes in the extracellular domain of the molecule (Hall et al., 1988. *J Immunol.* 141(8):2781-7; Lynch, 2004. *Nat Rev Immunol.* 4(12):931-40).

The largest CD45 isoform containing all three alternatively spliced exons, CD45RABC, is approximately 235 kDa, while the smallest isoform lacking all three exons, CD45RO, is approximately 180 kDa. In between, isoforms comprising only two (CD45RAB, CD45RAC, CD45RBC) or only one (CD45RA, CD45RB, CD45RC) of the three exons are possible.

While the function of the different CD45 isoforms is not clear, differential expression of these isoforms has been associated with the level of activation of T cells and allows dissociation of naive vs memory T cells (Birkeland et al., 1989. *Proc Natl Acad Sci USA.* 86(17):6734-8). For example, CD45RA is present on peripheral naive mature CD4$^+$ T cells, while CD45RO is expressed on activated and memory CD4$^+$ T cells. CD45RABC is expressed on B cells and their precursors, on a sub-group of dendritic cells and other antigen-presenting cells. Effector memory RA T cells (TEMA), a subtype of terminally differentiated memory T cells, also re-express the naive T cell marker CD45RA (Koch et al., 2008. *Immun Ageing.* 5:6). Importantly, this pattern of isoforms expression is highly conserved across species emphasizing its functional role and importance (Hermiston et al., 2003. *Annu Rev Immunol.* 21:107-37).

The expression pattern of the CD45RC isoform on CD4$^+$ and CD8$^+$ T cells allows to differentiate between functionally distinct alloreactive T cell subsets that behave differently in terms of proliferation and cytokine secretion. In rodents for example, it has been shown that both CD4$^+$ and CD8$^+$ T cells CD45RC$^{high}$ are potent $T_h1$ effector cells capable of promoting transplant rejection and organ inflammation (Spickett et al., 1983. *J Exp Med.* 158(3):795-810; Xystrakis et al., 2004. *Eur J Immunol.* 34(2):408-17), while T cells expressing undetectable or low levels of CD45RC$^{low/-}$ are $T_h2$ and regulatory T cells and inhibit allograft rejection, graft-versus-host disease (GVHD) and cell-mediated autoimmune diseases (Xystrakis et al., 2004. *Blood.* 104(10):3294-30; Guillonneau et al., 2007. *J Clin Invest.* 117(4):1096-106; Powrie & Mason, 1990. *J Exp Med.* 172(6):1701-8). In humans, a high proportion of CD45RC$^+$ CD8$^+$ T cells before transplantation has been correlated with decreased graft survival in kidney transplanted patients (Ordonez et al., 2013. *PLoS One.* 8(7): e69791).

The elimination of the CD45RC$^{high}$ T cells population represents therefore a promising approach for inducing immune tolerance in human, thus for preventing, reducing and/or treating transplant rejection (in particular GVHD) and autoimmune diseases.

GVHD is a significant cause of morbidity and mortality in stem cell transplant patients. It is a T cell-mediated immunoreactive process in which donor cells react against recipient cells. Presently, immunosuppression with immunomodulating drugs such as corticosteroids are the mainstay of GVHD prevention. Whilst progresses have been made with improvements in survival outcomes over time, corticosteroids do not prevent GVHD in a high proportion of patients (less than 50% of patients with acute GVHD and 40-50% of patients with chronic GVHD depending on initial disease severity—Garnett et al., 2013. *Ther Adv Hematol.* 4(6):366-378), are associated with significant toxicities, and many of the currently available salvage therapies are associated with increased immunosuppression and infectious complications. Thus, there remains an unmet need for the development of new treatment strategies for GVHD to improve long-term post-transplant outcomes.

The Inventors have previously described that the depletion of CD45RC$^{high}$ T cells may represent a potential new therapy in preventing or reducing transplant rejection by decreasing aggressive effector T cells and B cells, while increasing tolerogenic regulatory T cells. Indeed, transient anti-CD45RC mAb treatment triggers rapid CD45RC$^{high}$ T cell apoptosis, while preserving memory immunity. Moreover, the Inventors showed that short term anti-CD45RC antibody treatment results in permanent allograft survival with no signs of chronic rejection (International patent WO2016016442; Picarda et al., 2017. *JCI Insight.* 2(3): e90088).

Here, the Inventors have developed a new monoclonal antibody directed against human CD45RC. This antibody competes with the anti-human CD45RC antibodies currently available on the market (such as the MT2 clone), exhibiting a comparable pattern of reactivity, however with a significantly better cytotoxic activity to T cells and at a lowest concentration. Indeed, the anti-hCD45RC antibody according to the present invention shows a better affinity than other antibodies currently available, and thereby have better therapeutic effects.

Interestingly, the antibody according to the invention may also be useful in the prevention or treatment of certain monogenic diseases in which immune responses are involved in the pathology. Monogenic diseases are caused by single-gene defects. Over 4000 human diseases are caused by these defects linked to one particular gene. Up to now, most treatment options revolve around treating the symptoms of the disorders, in an attempt to improve patient quality of life. Gene therapy is the main hope for durable treatments of this type of diseases. However, major obstacles have been encountered during the development of techniques for the delivery of genes to the appropriate cells affected by the disorder as well as the fact that immune responses against the transgene product or the vector limit the therapeutic efficacy.

Among monogenic diseases, some are linked to genes involved in the immune system (such as T and/or B cells primary immunodeficiencies and polyendocrinopathy candidiasis-ectodermal dystrophy [APECED]), or to genes not associated with immune functions but whose deficiency is associated with inflammation and/or immune reactions [such as Duchenne muscular dystrophy (DMD)]

APECED, also known as auto-immune polyglandular syndrome type I (APS 1) is a rare multi-organ autosomal recessive auto-immune disease caused by mutations in the AIRE gene, a transcription regulator that allows the expression of tissue-restricted antigens (TRA) in medullary epithelial thymic cells (mTECs) and auto-reactive T cells deletion. In human, more than 100 mutations have been described in the AIRE gene to cause APECED with a prevalence of 1-9:1000000 (Orphanet, http://www.orpha.net). The clinical phenotype of APECED is usually defined by the presence of 2 of the 3 major symptoms: hypoparathyroidism, adrenal insufficiency (Addison's disease) and chronical muco-cutaneous candidiasis (CMC). This disease is also associated with multiple autoimmune and ectodermal features such as type 1 diabetes, enamel hypoplasia, vitiligo, premature ovarian failure, keratitis, pernicious anemia, alopecia, exocrine pancreatitis, interstitial lung disease, nephritis and other disorders.

DMD is a monogenic disease wherein mutations of the DMD gene coding for the protein dystrophin lead to severe X-linked muscular dystrophy, which affects all voluntary muscles as well as the heart and breathing muscles in later stages. Immune responses are involved in the pathophysiology of disease in both DMD patients and mdx mice (for a review, see Rosenberg et al., 2015. *Sci Transl Med.* 7(299): 299rv4). The standard treatments of DMD are corticoids, such as prednisolone. In mdx mice, treatments decreasing effector immune responses or inflammation have also been employed, such as intravenous immunoglobulins, tranilast, heme oxygenase-1 inducers, IL-1 receptor antagonist and IL-2, to amplify regulatory T cells (Tregs) (Villalta et al., 2014. *Sci Transl Med.* 6(258):258ra142; Rosenberg et al., 2015. *Sci Transl Med.* 7(299):299rv4). However, despite recent promising new treatments, the average life expectancy of DMD patients is still severely reduced.

Surprisingly, the Inventors have demonstrated that treatment of Dmd$^{-/-}$ rats (Dmd$^{mdx}$) with an anti-CD45RC antibody specifically depleting CD45RC$^{high}$ cells ameliorated muscle strength (Ouisse et al., 2019. *Front Immunol.* In press). They have also demonstrated that administration to Aire$^{-/-}$ rats of an anti-CD45RC monoclonal antibody results in a strong depletion of CD45RC$^{high}$ T cells, and to the removal of symptoms characteristics of APECED (manuscript in preparation; International patent application WO2019115791).

The antibody according to the present invention represents therefore a promising approach for preventing and/or treating monogenic diseases such as DMD and APECED.

SUMMARY

The present invention relates to an isolated anti-human CD45RC antibody or binding fragment thereof, wherein said antibody or binding fragment thereof comprises:
(a) a HCVR which comprises the following three CDRs:
  (i) VH-CDR1 of sequence SEQ ID NO: 1;
  (ii) VH-CDR2 with a sequence selected from the group comprising sequences SEQ ID NOs: 4, 5, 6, 8, 100, 116, 117, 118 and 119; and
  (iii) VH-CDR3 of sequence SEQ ID NO: 3; and
(b) a LCVR which comprises the following three CDRs:
  (i) VL-CDR1 with a sequence selected from the group comprising sequences SEQ ID NO: 15 (SASSSVS-X$_{12}$-YMH) and 18 (RASSSVS-X$_{12}$-YMH), wherein X12 is absent or is selected from Asn (N), Ser (S) and Gly (G);
  (ii) VL-CDR2 of sequence SEQ ID NO: 16; and
  (iii) VL-CDR3 of sequence SEQ ID NO: 17.

In one embodiment, said antibody or binding fragment thereof comprises:
(a) a HCVR which comprises the following three CDRs:
  (i) VH-CDR1 of sequence SEQ ID NO: 1;
  (ii) VH-CDR2 with a sequence selected from the group comprising sequences SEQ ID NOs: 4 and 5; and
  (iii) VH-CDR3 of sequence SEQ ID NO: 3; and
(b) a LCVR which comprises the following three CDRs:
  (i) VL-CDR1 of sequence SEQ ID NO: 15, wherein X$_{12}$ is absent;
  (ii) VL-CDR2 of sequence SEQ ID NO: 16; and
  (iii) VL-CDR3 of sequence SEQ ID NO: 17.

In one embodiment, said antibody or binding fragment thereof comprises:
(a) a HCVR which comprises the following three CDRs:
  (i) VH-CDR1 of sequence SEQ ID NO: 1;
  (ii) VH-CDR2 of sequence 4; and
  (iii) VH-CDR3 of sequence SEQ ID NO: 3; and
(b) a LCVR which comprises the following three CDRs:
  (i) VL-CDR1 of sequence SEQ ID NO: 15, wherein X$_{12}$ is absent;
  (ii) VL-CDR2 of sequence SEQ ID NO: 16; and
  (iii) VL-CDR3 of sequence SEQ ID NO: 17.

In one embodiment, said antibody or binding fragment thereof comprises:
(a) a HCVR which comprises the following three CDRs:
  (i) VH-CDR1 of sequence SEQ ID NO: 1;
  (ii) VH-CDR2 with a sequence selected from the group comprising sequences SEQ ID NOs: 4, 6, and 100; and
  (iii) VH-CDR3 of sequence SEQ ID NO: 3; and (b) a LCVR which comprises the following three CDRs:
   (i) VL-CDR1 with a sequence selected from the group comprising sequences SEQ ID NOs: 15 and 18, wherein $X_{12}$ is absent;
   (ii) VL-CDR2 of sequence SEQ ID NO: 16; and
   (iii) VL-CDR3 of sequence SEQ ID NO: 17.

In one embodiment, said antibody or binding fragment thereof comprises:
1) a HCVR of sequence SEQ ID NO: 61 and a LCVR of sequence SEQ ID NO: 81;
2) a HCVR of sequence SEQ ID NO: 62 and a LCVR of sequence SEQ ID NO: 82;
3) a HCVR of sequence SEQ ID NO: 62 and a LCVR of sequence SEQ ID NO: 83;
4) a HCVR of sequence SEQ ID NO: 62 and a LCVR of sequence SEQ ID NO: 84;
5) a HCVR of sequence SEQ ID NO: 63 and a LCVR of sequence SEQ ID NO: 82;
6) a HCVR of sequence SEQ ID NO: 63 and a LCVR of sequence SEQ ID NO: 83;
7) a HCVR of sequences SEQ ID NO: 63 and a LCVR of sequence SEQ ID NO: 84;
8) a HCVR of sequence SEQ ID NO: 64 and a LCVR of sequence SEQ ID NO: 82;
9) a HCVR of sequence SEQ ID NO: 64 and a LCVR of sequence SEQ ID NO: 83;
10) a HCVR of sequence SEQ ID NO: 64 and a LCVR of sequence SEQ ID NO: 84;
11) a HCVR of sequence SEQ ID NO: 101 and a LCVR of sequence SEQ ID NO: 85;
12) a HCVR of sequence SEQ ID NO: 101 and a LCVR of sequence SEQ ID NO: 103;
13) a HCVR of sequence SEQ ID NO: 65 and a LCVR of sequence SEQ ID NO: 85;
14) a HCVR of sequence SEQ ID NO: 65 and a LCVR of sequence SEQ ID NO: 103;
15) a HCVR of sequence SEQ ID NO: 62 and a LCVR of sequence SEQ ID NO: 85;
16) a HCVR of sequence SEQ ID NO: 101 and a LCVR of sequence SEQ ID NO: 82;
17) a HCVR of sequence SEQ ID NO: 121 and a LCVR of sequence SEQ ID NO: 85;
18) a HCVR of sequence SEQ ID NO: 122 and a LCVR of sequence SEQ ID NO: 85;
19) a HCVR of sequence SEQ ID NO: 123 and a LCVR of sequence SEQ ID NO: 85;
20) a HCVR of sequence SEQ ID NO: 124 and a LCVR of sequence SEQ ID NO: 85;
21) a HCVR of sequence SEQ ID NO: 63 and a LCVR of sequence SEQ ID NO: 85;
22) a HCVR of sequence SEQ ID NO: 67 and a LCVR of sequence SEQ ID NO: 85;
23) a HCVR of sequence SEQ ID NO: 67 and a LCVR of sequence SEQ ID NO: 103; or
24) a HCVR and a LCVR comprising a sequence of the non-CDR regions sharing at least 70% of identity with the sequence of the non-CDR regions of the HCVR and LCVR according to 1) to 23).

In one embodiment, said antibody or binding fragment thereof comprises:
(a) a HCVR which comprises the following three CDRs:
   (i) VH-CDR1 of sequence SEQ ID NO: 1;
   (ii) VH-CDR2 with a sequence selected from the group comprising sequences SEQ ID NOs: 4, 5, 6, 8, 100, 116, 117, 118 and 119; and
   (iii) VH-CDR3 of sequence SEQ ID NO: 3; and
(b) a LCVR which comprises the following three CDRs:
   (i) VL-CDR1 with a sequence selected from the group comprising sequences SEQ ID NOs: 15 and 18, wherein $X_{12}$ in SEQ ID NOs: 15 and 18 is selected from Asn (N), Ser (S) and Gly (G);
   (ii) VL-CDR2 of sequence SEQ ID NO: 16; and
   (iii) VL-CDR3 of sequence SEQ ID NO: 17;
preferably wherein the amino acid residue at Kabat position L71 of the LCVR is Phe (F).

The present invention further relates to a nucleic acid encoding the isolated antibody or binding fragment thereof according to the invention.

The present invention further relates to an expression vector comprising the nucleic acid according to claim 7.

The present invention further relates to a cell comprising the nucleic acid according to the invention or the expression vector according to the invention.

The present invention further relates to a pharmaceutical composition comprising the isolated antibody or binding fragment thereof according to the invention, the nucleic acid according to the invention, the expression vector according to the invention or the cell according to the invention, and at least one pharmaceutically acceptable excipient.

The present invention further relates to the isolated antibody or binding fragment thereof according to the invention, the nucleic acid according to the invention, the expression vector according to the invention, the cell according to the invention or the pharmaceutical composition according to the invention, for use as a medicament.

The present invention further relates to the isolated antibody or binding fragment thereof according to the invention, the nucleic acid according to the invention, the expression vector according to the invention, the cell according to the invention or the pharmaceutical composition according to the invention, for use in:
inducing immune tolerance in a subject in need thereof; and/or
preventing and/or reducing transplant rejections.

The present invention further relates to the isolated antibody or binding fragment thereof according to the invention, the nucleic acid according to the invention, the expression vector according to the invention, the cell according to the invention or the pharmaceutical composition according to the invention, for use in preventing, reducing and/or treating $CD45RC^{high}$-related conditions, preferably wherein the $CD45RC^{high}$-related condition is selected from the group comprising autoimmune diseases, undesired immune responses, monogenic diseases, and lymphoma or cancer.

The present invention further relates to the isolated antibody or binding fragment thereof according to the invention, the nucleic acid according to the invention, the expression vector according to the invention, the cell according to the invention or the pharmaceutical composition according to the invention, for use in preventing and/or treating graft-versus-host disease (GVHD).

The present invention further relates to an in vitro method for detecting or quantifying hCD45RC in a sample, cell, tissue or organ, comprising contacting said sample, cell, tissue or organ with the isolated antibody or binding fragment thereof according to the present invention, optionally wherein the isolated antibody or binding fragment thereof is labelled.

"Antibody" or "Immunoglobulin"

As used herein, the term "immunoglobulin" refers to a protein having a combination of two heavy and two light chains whether or not it possesses any relevant specific immunoreactivity. "Antibodies" refers to such assemblies which have significant known specific immunoreactive activity to an antigen of interest (e.g., human CD45RC). The term "anti-hCD45RC antibodies" is used herein to refer to antibodies which exhibit immunological specificity for human CD45RC protein. As explained elsewhere herein, "specificity" for human CD45RC does not exclude cross-reaction with species homologues of hCD45RC.

Antibodies and immunoglobulins comprise light and heavy chains, with or without an interchain covalent linkage between them. Basic immunoglobulin structures in vertebrate systems are relatively well understood. The generic term "immunoglobulin" comprises five distinct classes of antibody that can be distinguished biochemically. Although the following discussion will generally be directed to the IgG class of immunoglobulin molecules, all five classes of antibodies are within the scope of the present invention. With regard to IgG, immunoglobulins comprise two identical light polypeptide chains of molecular weight of about 23 kDa, and two identical heavy chains of molecular weight of about 53-70 kDa. The four chains are joined by disulfide bonds in a "Y" configuration wherein the light chains bracket the heavy chains starting at the mouth of the "Y" and continuing through the variable region. The light chains of an antibody are classified as either kappa (κ) or lambda (λ). Each heavy chain class may be bonded with either a κ or λ light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma (γ), mu (μ), alpha (α), delta (δ) or epsilon (ε) with some subclasses among them (e.g., γ1-γ4). It is the nature of this chain that determines the "class" of the antibody as IgG, IgM, IgA IgD or IgE, respectively. The immunoglobulin subclasses or "isotypes" (e.g., IgG1, IgG2, IgG3, IgG4, IgA1, etc.) are well characterized and are known to confer functional specialization. Modified versions of each of these classes and isotypes are readily discernable to the skilled artisan in view of the instant disclosure and, accordingly, are within the scope of the present invention. As indicated above, the variable region of an antibody allows the antibody to selectively recognize and specifically bind epitopes on antigens. That is, the light chain variable domain ($V_L$ domain) and heavy chain variable domain ($V_H$ domain) of an antibody combine to form the variable region that defines a three-dimensional antigen binding site. This quaternary antibody structure forms the antigen binding site presents at the end of each arm of the "Y". More specifically, the antigen binding site is defined by three complementarity determining regions (CDRs) on each of the $V_H$ and $V_L$ chains.

"Characterized as Having [ . . . ] Amino Acids being Substituted by a Different Amino Acid"

As used herein, the phrase "characterized as having [ . . . ] amino acids being substituted by a different amino acid" in reference to a given sequence, refers to the occurrence, in said sequence, of "conservative amino acid modifications".

"Conservative Amino Add Modifications"

"Conservative amino acid modifications" refers to modifications that do not significantly affect or alter the binding characteristics of the antibody or binding fragment thereof containing the amino acid sequence. Such conservative modifications include amino acid substitutions, additions and deletions. Modifications can be introduced into an antibody or binding fragment thereof by standard techniques known in the art, such as site-directed mutagenesis and PCR-mediated mutagenesis.

Conservative amino acid substitutions are typically those in which an amino acid residue is replaced with an amino acid residue having a side chain with similar physicochemical properties. Specified variable region and CDR sequences may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acid insertions, deletions and/or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), β-branched side chains (e.g., threonine, valine, isoleucine) and aromatic side chains (e.g., tyrosine, phenylalanine, tryptophan, histidine). Thus, one or more amino acid residues within the CDRs and/or variable regions of the antibody or binding fragment thereof according to the present invention can be replaced with other amino acid residues from the same side chain family and the altered antibody can be tested for retained function (i.e., the properties set forth herein, such as, e.g., the binding to hCD45RC) using the assays described herein. In another embodiments, a string of amino acids within the CDRs and/or variable regions of the antibody or binding fragment thereof according to the present invention can be replaced with a structurally similar string that differs in order and/or composition of side chain family members.

"CD45"

As used herein, the term "CD45" (also known as CD45R or PTPRC) refers to a transmembrane glycoprotein existing in different isoforms. These distinct isoforms of CD45 differ in their extracellular domain structures which arise from alternative splicing of 3 variable exons (exons 4, 5 and 6) coding for the A, B and C determinants, respectively, of the CD45 extracellular region. Antibodies reactive with restricted epitope are clustered as "CD45R". Hence, anti-CD45RA, anti-CD45RB and anti-CD45RC antibodies recognize CD45 isoforms which include the expression of the A, B and C determinants, respectively. The various isoforms of CD45 have different extracellular domains, but have an identical extracellular sequence proximal to the membrane, as well as for the transmembrane domain and a large cytoplasmic tail segments containing two tandemly homologous highly conserved phosphatase domains of approximately 300 residues. CD45 and its isoforms non-covalently associate with lymphocyte phosphatase-associated phosphoprotein (LPAP) on T and B lymphocytes. CD45 has been reported to be associated with several other cell surface antigens, including CD1, CD2, CD3, and CD4. CD45 is involved in signaling lymphocytes activation. When preceded by the letter "h" (e.g., hCD45), it is implied that the CD45 is of human origin.

"CD45RC"

As used herein, the term "CD45RC" refers to a 200-220 kDa single chain type I membrane glycoprotein well-known from the skilled artisan. CD45RC is an alternative splicing isoform of CD45 comprising exon 6 encoding the C determinant (hence the terminology CD45RC, i.e., CD45 Restricted to the C determinant), but lacking exons 4 and 5, respectively encoding the A and B determinants. An amino acid sequence of human CD45RC is given in SEQ ID NO: 104, corresponding to UniProt Accession P08575-10 (version 10, modified Mar. 28, 2018—Checksum: F92C874C9A114890). This CD45RC isoform is expressed on B cells, and a subset of $CD8^+$ T cells and $CD4^+$ T cells, but not on $CD8^+$ or $CD4^+$ Treg, $CD14^+$ monocytes or PMN (Picarda et al., 2017. *JCI Insight.* 2(3):e90088). While some monoclonal antibodies can recognize an epitope in the portion of CD45 common to all the different isoforms (these are termed anti-CD45 antibodies), other monoclonal antibodies have restricted specificity to a given isoform, depending on which determinant they recognize (A, B or C). When preceded by the letter "h" (e.g., hCD45RC), it is implied that the CD45RC is of human origin.

"$CD45RC^{high}$ Cell Antigen" or "$CD45RC^{high}$ Cell Surface Marker"

As used herein, the terms "$CD45RC^{high}$ cell antigen" or "$CD45RC^{high}$ cell surface marker" refer to an antigen (or epitope) of sequence SEQ ID NO: 23, which is expressed or displayed at the surface of a $CD45RC^{high}$ cells (including T cells, B cells and natural killer (NK) cells) which can be targeted with an anti-CD45RC agent which binds thereto (such as an antibody or an aptamer). Exemplary $CD45RC^{high}$ T cell surface markers include but are not limited to the CD45RC as previously described or other antigens that characterize said population of T cells. The $CD45RC^{high}$ T cells surface marker of particular interest is preferentially expressed on $CD45RC^{high}$ T cells compared to other non-$CD45RC^{high}$ T cells of a mammal.

Then, after raising antibodies directed against the CD45RC cell surface marker as above described, the skilled man in the art can easily select those that act on $CD45RC^{high}$ cells, and that can be used to deplete $CD45RC^{high}$ cells via antibody-dependent cell mediated cytotoxicity (ADCC), complement dependent cytotoxicity (CDC), or induction of $CD45RC^{high}$ but not $CD45RC^{low/-}$ cell death (e.g., via apoptosis) after direct binding of the antibody (Picarda et al., 2017. *JCI Insight.* 2(3):e90088).

"CDR" or "Complementarity Determining Region"

As used herein, the term "CDR" or "complementarity determining region" means the non-contiguous antigen combining sites found within the variable region of both heavy and light chain polypeptides. CDRs were identified according to the rules of Table 1, as deduced from Kabat et al., 1991. *Sequences of proteins of immunological interest* (5$^{th}$ ed.). Bethesda, MD: U.S. Dep. of Health and Human Services; and Chothia and Lesk, 1987. *J Mol Biol.* 196(4): 901-17:

TABLE 1

| Heavy chain variable region (HCVR or $V_H$) | | | |
|---|---|---|---|
| | $V_H$-CDR1 | $V_H$-CDR2 | $V_H$-CDR3 |
| Start | Approx. at residue 26 (always 4 after a Cys) according to Chothia/AbM's definition Kabat's definition starts 5 residues later | Always 15 residues after the end of $V_H$-CDR1 according to Kabat/AbM's definition | Always 33 residues after end of $V_H$-CDR2 Always 2 residues after a Cys |
| Residue before | Always Cys-Xaa-Xaa-Xaa, with Xaa being any amino acid according to Chothia/AbM's definition | Typically, Leu-Glu-Trp-Ile-Gly, but a number of variations | Always Cys-Xaa-Xaa, with Xaa being any amino acid Typically, Cys-Ala-Arg |
| Residue after | Always Trp Typically, Trp-Val, but also, Trp-Ile or Trp-Ala | Lys/Arg-Leu/Ile/Val/Phe/Thr/Ala-Thr/Ser/Ile/Ala | Always Trp-Gly-Xaa-Gly, with Xaa being any amino acid |
| Length | 10 to 12 residues according to AbM's definition Chothia's definition excludes the last 4 residues 5 to 7 residues according to Kabat's definition | 16 to 19 residues according to Kabat's definition AbM's definition ends 7 residues earlier | 3 to 25 residues |

| Light chain variable region (LCVR or $V_L$) | | | |
|---|---|---|---|
| | $V_L$-CDR1 | $V_L$-CDR2 | $V_L$-CDR3 |
| Start | Approx. at residue 24 | Always 16 residues after the end of $V_L$-CDR1 | Always 33 residues after end of $V_L$-CDR2 (except NEW (PDB ID: 7FAB) which has the deletion at the end of CDR-L2*) |
| Residue before | Always Cys | Generally, Ile-Tyr, but also, Val-Tyr, Ile-Lys or Ile-Phe | Always Cys |
| Residue after | Always Trp Typically, Trp-Tyr-Gln, but also, Trp-Leu-Gln, Trp-Phe-Gln or Trp-Tyr-Leu | | Always Phe-Gly-Xaa-Gly, with Xaa being any amino acid |
| Length | 10 to 17 residues | Always 7 residues (except NEW (PDB ID: 7FAB) which has a deletion in this region*) | 7 to 11 residues |

* Saul & Poljak, 1992. *Proteins.* 14(3):363-71

"Epitope"

As used herein, the term "epitope" refers to a specific arrangement of amino acids located on a protein or proteins to which an antibody or binding fragment thereof binds. Epitopes often consist of a chemically active surface grouping of molecules such as amino acids or sugar side chains, and have specific three-dimensional structural characteristics as well as specific charge characteristics. Epitopes can be linear (or sequential) or conformational, i.e., involving two or more sequences of amino acids in various regions of the antigen that may not necessarily be contiguous.

"Framework Region" or "FR" or "Non-CDR Regions"

As used herein, the terms "framework region", "FR" or "non-CDR regions" include the amino acid residues that are part of the variable region, but are not part of the CDRs (e.g., using the Kabat/Chothia definition of CDRs). Therefore, a variable region framework is between about 100-120 amino acids in length but includes only those amino acids outside of the CDRs.

For the specific example of a HCVR and for the CDRs as defined by Kabat/Chothia:

FR1 may correspond to the domain of the variable region encompassing amino acids 1-25 according to Chothia/AbM's definition, or 5 residues later according to Kabat's definition;

FR2 may correspond to the domain of the variable region encompassing amino acids 36-49;

FR3 may correspond to the domain of the variable region encompassing amino acids 67-98; and FR4 may correspond to the domain of the variable region from amino acids 104-110 to the end of the variable region.

The framework regions for the light chain are similarly separated by each of the LCVR's CDRs. In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainders of the heavy and light variable domains show less intermolecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Heavy Chain Region"

As used herein, the term "heavy chain region" includes amino acid sequences derived from the constant domains of an immunoglobulin heavy chain. A protein comprising a heavy chain region comprises at least one of a $C_H1$ domain, a hinge (e.g., upper, middle, and/or lower hinge region) domain, a $C_H2$ domain, a $C_H3$ domain, or a variant or fragment thereof. In an embodiment, the antibody or binding fragment thereof according to the present invention may comprise the Fc region of an immunoglobulin heavy chain (e.g., a hinge portion, a $C_H2$ domain, and a $C_H3$ domain). In another embodiment, the antibody or binding fragment thereof according to the present invention lacks at least a region of a constant domain (e.g., all or part of a $C_H2$ domain). In certain embodiments, at least one, and preferably all, of the constant domains are derived from a human immunoglobulin heavy chain. For example, in one preferred embodiment, the heavy chain region comprises a fully human hinge domain. In other preferred embodiments, the heavy chain region comprising a fully human Fc region (e.g., hinge, $C_H2$ and $C_H3$ domain sequences from a human immunoglobulin). In certain embodiments, the constituent constant domains of the heavy chain region are from different immunoglobulin molecules. For example, a heavy chain region of a protein may comprise a $C_H2$ domain derived from an IgG1 molecule and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. As set forth above, it will be understood by one of ordinary skill in the art that the constant domains of the heavy chain region may be modified such that they vary in amino acid sequence from the naturally occurring (wild-type) immunoglobulin molecule. That is, the antibody or binding fragment thereof according to the present invention may comprise alterations or modifications to one or more of the heavy chain constant domains (CHI, hinge, $C_H2$ or $C_H3$) and/or to the light chain constant domain ($C_L$). Exemplary modifications include additions, deletions or substitutions of one or more amino acids in one or more domains.

"Hinge Region"

As used herein, the term "hinge region" includes the region of a heavy chain molecule that joins the $C_H1$ domain to the $C_H2$ domain. This hinge region comprises approximately residues and is flexible, thus allowing the two N-terminal antigen binding regions to move independently. Hinge regions can be subdivided into three distinct domains: upper, middle, and lower hinge domains (Roux et al., 1998. *J Immunol.* 161(8):4083-90).

"Hypervariable Loop"

The term "hypervariable loop" is not strictly synonymous to complementarity determining region (CDR), since the hypervariable loops (HVs) are defined on the basis of structure, whereas CDRs are defined based on sequence variability (Kabat et al., 1991. *Sequences of proteins of immunological interest* (5$^{th}$ ed.). Bethesda, MD: U.S. Dep. of Health and Human Services) and the limits of the HVs and the CDRs may be different in some $V_H$ and $V_L$ domains. The CDRs of the $V_L$ and $V_H$ domains can typically be defined by the Kabat/Chothia definition as already explained hereinabove.

"Identity" or "Identical"

As used herein, the term "identity" or "identical", when used in a relationship between the sequences of two or more amino acid sequences, or of two or more nucleic acid sequences, refers to the degree of sequence relatedness between amino acid sequences or nucleic acid sequences, as determined by the number of matches between strings of two or more amino acid residues or nucleic acid residues. "Identity" measures the percent of identical matches between the smaller of two or more sequences with gap alignments (if any) addressed by a particular mathematical model or computer program (i.e., "algorithms").

Identity of related amino acid sequences or nucleic acid sequences can be readily calculated by known methods. Such methods include, but are not limited to, those described in Lesk A. M. (1988). *Computational molecular biology: Sources and methods for sequence analysis*. New York, NY: Oxford University Press; Smith D. W. (1993). *Biocomputing: Informatics and genome projects*. San Diego, CA: Academic Press; Griffin A. M. & Griffin H. G. (1994). *Computer analysis of sequence data, Part* 1. Totowa, NJ: Humana Press; von Heijne G. (1987). *Sequence analysis in molecular biology: treasure trove or trivial pursuit*. San Diego, CA: Academic press; Gribskov M. R. & Devereux J. (1991). *Sequence analysis primer.* New York, NY: Stockton Press; Carillo et al., 1988. *SIAM J Appl Math.* 48(5):1073-82.

Preferred methods for determining identity are designed to give the largest match between the sequences tested. Methods of determining identity are described in publicly available computer programs. Preferred computer program methods for determining identity between two sequences include the GCG program package, including GAP (Genetics Computer Group, University of Wisconsin, Madison, WI; Devereux et al., 1984. *Nucleic Acids Res.* 12(1 Pt 1):387-95), BLASTP, BLASTN, and FASTA (Altschul et al., 1990. *J Mol Biol.* 215(3):403-10). The BLASTX program is publicly available from the National Center for Biotechnology Information (NCBI) and other sources (BLAST Manual, Altschul et al. NCB/NLM/NIH Bethesda, Md. 20894). The well-known Smith Waterman algorithm may also be used to determine identity.

"Immunospecific", "Specific For" or "Specifically Bind"

As used herein, an antibody or binding fragment thereof is said to be "immunospecific", "specific for" or to "specifically bind" an antigen if it reacts at a detectable level with said antigen (e.g., hCD45RC), preferably with an affinity constant ($K_A$) of greater than or equal to about $10^6$ $M^{-1}$, preferably greater than or equal to about $10^7$ $M^{-1}$, $10^8$ $M^{-1}$, $5\times10^8$ $M^{-1}$, $10^9$ $M^{-1}$, $5\times10^9$ $M^{-1}$ or more.

Affinity of an antibody or binding fragment thereof for its cognate antigen is also commonly expressed as an equilibrium dissociation constant ($K_D$), an antibody or binding fragment thereof is said to be "immunospecific", "specific for" or to "specifically bind" an antigen if it reacts at a detectable level with said antigen (e.g., hCD45RC), preferably with a $K_D$ of less than or equal to $10^{-6}$ M, preferably less than or equal to $10^{-7}$ M, $5\times10^{-8}$ M, $10^{-8}$ M, $5\times10^{-9}$ M, $10^{-9}$ M or less.

Affinities of antibodies or binding fragment thereof can be readily determined using conventional techniques, for example, those described by Scatchard, 1949. *Ann NY Acad Sci.* 51:660-672. Binding properties of an antibody or binding fragment thereof to antigens, cells or tissues may generally be determined and assessed using immunodetection methods including, for example, ELISA, immunofluorescence-based assays, such as immuno-histochemistry (IHC) and/or fluorescence-activated cell sorting (FACS) or by surface plasmon resonance (SPR, e.g., using BIAcore®).

"Monoclonal Antibody"

As used herein, the term "monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies or binding fragment thereof according to the present invention may be prepared by the hybridoma methodology first described by Kohler et al., 1975. *Nature.* 256(5517):495-7, or may be made using recombinant DNA methods in bacterial, eukaryotic animal or plant cells (U.S. Pat. No. 4,816,567). The "monoclonal antibodies" may also be isolated from phage antibody libraries using the techniques described in Clackson et al., 1991. *Nature.* 352(6336):624-8 and Marks et al., 1991. *J Mol Biol.* 222(3):581-97, for example.

"Prevent" or "Preventing" or "Prevention"

As used herein, the terms "prevent", "preventing" and "prevention" refer to prophylactic and preventative measures, wherein the object is to reduce the chances that a subject will develop the pathologic condition or disorder over a given period of time. Such a reduction may be reflected, e.g., in a delayed onset of at least one symptom of the pathologic condition or disorder in the subject.

"Subject"

As used herein, the term "subject" refers to a mammal, preferably a human. In one embodiment, a subject may be a "patient", i.e., a warm-blooded animal, more preferably a human, who/which is awaiting the receipt of, or is receiving medical care or was/is/will be the object of a medical procedure, or is monitored for the development of a disease. The term "mammal" refers here to any mammal, including humans, domestic and farm animals, and zoo, sports, or pet animals, such as dogs, cats, cattle, horses, sheep, pigs, goats, rabbits, etc. Preferably, the mammal is a primate, more preferably a human.

"Variable Region" or "Variable Domain"

As used herein, the term "variable" refers to the fact that certain regions of the variable domains $V_H$ and $V_L$ differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the $V_L$ domain and the $V_H$ domain which form part of the antigen binding site.

The first, second and third hypervariable loops of the Vλ light chain domain are referred to herein as L1 (λ), L2 (λ) and L3 (λ) and may be defined as comprising residues 24-33 (L1(λ), consisting of 9, 10 or 11 amino acid residues), 49-53 L2 (λ), consisting of 3 residues) and 90-96(L3(λ), consisting of 6 residues) in the $V_L$ domain (Morea et al., 2000. *Methods.* 20(3):267-79).

The first, second and third hypervariable loops of the Vκ light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the $V_L$ domain (Morea et al., 2000. *Methods.* 20(3):267-79).

The first, second and third hypervariable loops of the $V_H$ domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the $V_H$ domain (Morea et al., 2000. *Methods.* 20(3):267-79).

Unless otherwise indicated, the terms L1, L2 and L3 respectively refer to the first, second and third hypervariable loops of a $V_L$ domain, and encompass hypervariable loops obtained from both Vκ and Vλ isotypes. The terms H1, H2 and H3 respectively refer to the first, second and third hypervariable loops of the $V_H$ domain, and encompass hypervariable loops obtained from any of the known heavy chain isotypes, including gamma (γ), mu (μ), alpha (α), delta (δ) or epsilon (ε). The hypervariable loops L1, L2, L3, H1, H2 and H3 may each comprise part of a "complementarity determining region" or "CDR", as defined hereinabove.

"Treating" or "Treatment" or "Alleviation"

As used herein, the terms "treating" or "treatment" or "alleviation" refer to therapeutic treatment, excluding prophylactic or preventative measures; wherein the object is to slow down (lessen) the targeted pathologic condition or disorder. Those in need of treatment include those already with the disorder as well those suspected to have the disorder. A subject is successfully "treated" for the targeted pathological condition or disorder if, after receiving a therapeutic amount of the isolated antibody or binding fragment thereof, nucleic acid, expression vector, composition, pharmaceutical composition or medicament according to the present invention, said subject shows observable and/or measurable reduction in or absence of one or more of the following: reduction in the number of $CD45RC^{high}$ cells; reduction in the percent of total cells that are $CD45RC^{high}$; relief to some extent, of one or more of the symptoms associated with the specific disease or condition; reduced morbidity and mortality; and/or improvement in quality of life issues. The above parameters for assessing successful treatment and improvement in the disease are readily measurable by routine procedures familiar to a physician.

BRIEF DESCRIPTION OF THE DRAWINGS

FIG. 1 A(1), 1A(2) 1A(3), 1B(1) and 1B(2) show the expression level of CD45RC (as detected by ABIS-45RC or by the commercially available MT2 antibody) on different leukocyte types in human blood. Staining with ABIS-45RC or MT2 was realized on different cell types in total blood (EDTA) from healthy volunteers. Red blood cells were then lysed (Versalyse, Beckman Coulter) before cytometer analysis (Navios, Beckman Coulter). Cells were first gated on morphology, doublet cells and lived cells. (A(1) through A(3)) Representative dot plot analysis of CD45RC expression detected by ABIS-45RC or MT2 from one out of three healthy volunteers analyzed on different leukocyte types. ABIS-45RC is shown on left panels and MT2 on right panels. x-axis shows the fluorescence intensity of cell lineage markers labelling for each type of leukocytes as indicated; y-axis represents the fluorescence intensity of anti-CD45RC antibody labelling. The horizontal lines define cells with high, intermediate/low and negative levels of CD45RC expression as indicated in the upper left dot plot and numbers represent the percentage of cells in each category. (B(1) and B(2)) Mean expression+/−SEM of $CD45RC^{high}$, $CD45RC^{low}$ and $CD45RC^-$ on different leukocyte types of three donors labelled with ABIS-45RC (B(1)) or MT2 (B(2)).

FIGS. 5A-D, 5E-G, and 5H-J are a combination of flow cytometry dot plots, showing the reactivity against human T cells of humanized ABIS-45RC antibodies variants and of the murine ABIS-45RC antibody, at two concentrations (2 µg/mL on the left panel, 1 µg/mL on the right panel). (A) humanized ABIS-45RC variant A; (B) humanized ABIS-45RC variant B; (C) humanized ABIS-45RC variant C; (D) humanized ABIS-45RC variant D; (E) humanized ABIS-45RC variant E; (F) humanized ABIS-45RC variant F; (G) humanized ABIS-45RC variant G; (H) humanized ABIS-45RC variant H; (I) humanized ABIS-45RC variant I; (J) murine ABIS-45RC.

FIGS. 9A and 9B show the expression level of CD45RC (as detected by ABIS-45RC or humanized variants A, A1 and A3) on $CD3^+$ cells (A) and $CD3^-$ cells (B) in macaque blood. Cells were first gated on morphology, doublet cells and lived cells. Representative dot plot analysis of CD45RC expression detected by ABIS-45RC or ABIS-45RC humanized variants A, A1 and A3. x-axis shows the FSC; y-axis represents the fluorescence intensity of anti-CD45RC antibody labelling. The squares define cells with positive levels of CD45RC expression as indicated and numbers represent the percentage of cells.

DETAILED DESCRIPTION

Figure 2:
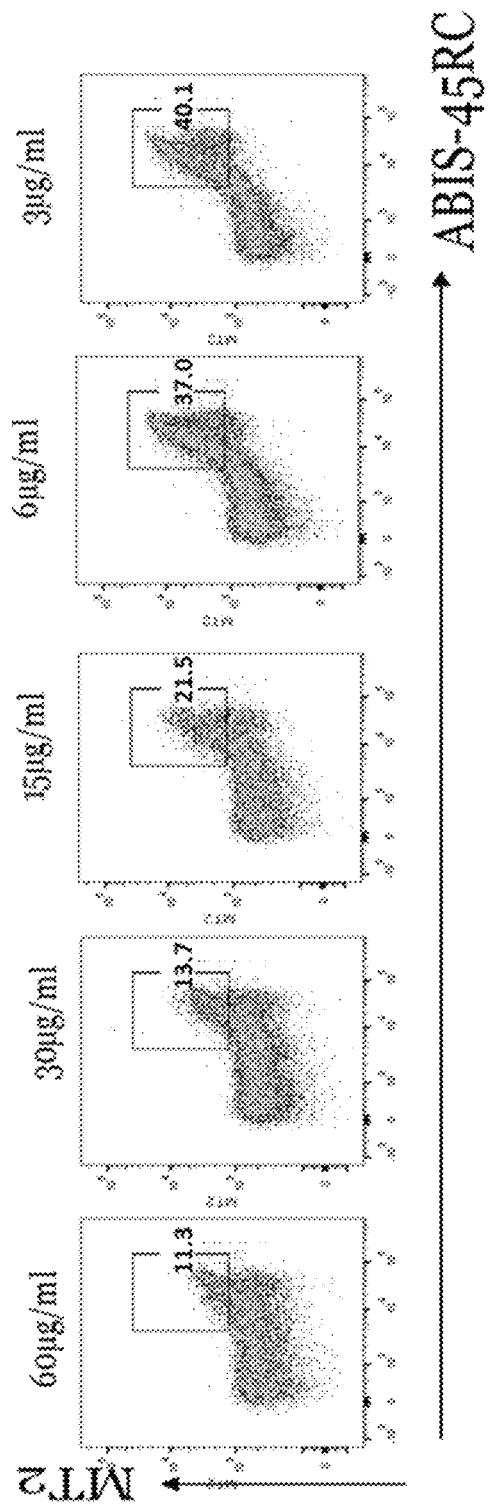
FIG. 2 shows that both ABIS-45RC and the commercial anti-CD45RC MT2 antibody compete for the same epitope. PBMCs were isolated from blood of healthy volunteers and T cells were labeled with an anti-CD3 labeled Mab, with chimeric ABIS-45RC (at the indicated concentrations) and anti-CD45RC (mouse clone MT2)-FITC labeled at 1.33 mg/mL. ABIS-45RC reactivity was revealed using a biotin donkey anti-human IgG+Strepta PercpCy 5.5 secondary antibody. Numbers in the windows of the dot plots of the upper row represent the percentage of cells that were co-labeled by both antibodies.

The present invention relates to an isolated antibody or a binding fragment thereof, binding to human CD45RC (hCD45RC).

An "isolated antibody", as used herein, is intended to refer to an antibody that is substantially free of other antibodies having different antigenic specificities (e.g., an isolated antibody that specifically binds hCD45RC is substantially free of antibodies that specifically bind antigens other than hCD45RC). An isolated antibody that specifically binds hCD45RC may, however, have cross-reactivity to other antigens, such as CD45RC molecules from other species. Moreover, an isolated antibody may be substantially free of other cellular material and/or chemicals, in particular those that would interfere with diagnostic or therapeutic uses of the antibody, including without limitation, enzymes, hormones, and other proteinaceous or non-proteinaceous components.

In one embodiment, the isolated antibody or a binding fragment thereof is purified.

In one embodiment, the isolated antibody or a binding fragment thereof is purified to:
(1) greater than 80%, 85%, 90%, 91%, 92%, 93%, 94%, 95% or more by weight of antibody or binding fragment thereof as determined by the Lowry method, and most preferably more than 96%, 97%, 98% or 99% by weight;
(2) a degree sufficient to obtain at least 15 residues of N-terminal or internal amino acid sequence by use of a spinning cup sequenator, or
(3) homogeneity as shown by SDS-PAGE under reducing or non-reducing conditions and using Coomassie blue or, preferably, silver staining.

In one embodiment, the antibody or binding fragment thereof according to the present invention binds to the extracellular domain of hCD45RC. In one embodiment, the antibody or binding fragment thereof according to the present invention binds to at least one epitope present on the extracellular domain of hCD45RC.

In one embodiment, the antibody or binding fragment thereof according to the present invention binds to the C determinant encoded by exon 6 of hCD45. In one embodiment, the antibody or binding fragment thereof according to the present invention binds to at least one epitope on the C determinant encoded by exon 6 of hCD45.

In one embodiment, the amino acid sequence of the C determinant encoded by exon 6 of hCD45 comprises or consists of SEQ ID NO: 23. In one embodiment, the nucleic acid sequence of exon 6 encoding the C determinant of hCD45 comprises or consists of SEQ ID NO: 24.

SEQ ID NO: 23
DVPGERSTASTFPTDPVSPLTTTLSLAHHSSAALPARTSNTTITANTS

SEQ ID NO: 24
GATGTCCCAGGAGAGAGGAGTACAGCCAGCACCTTTCCTACAGACCCAGT

TTCCCCATTGACAACCACCCTCAGCCTTGCACACCACAGCTCTGCTGCCT

TACCTGCACGCACCTCCAACACCACCATCACAGCGAACACCTCA

In one embodiment, the antibody or binding fragment thereof according to the present invention binds to at least one epitope comprising or consisting of SEQ ID NO: 23 or a fragment thereof.

In one embodiment, the antibody or binding fragment thereof according to the present invention binds to at least one epitope comprising or consisting of a sequence sharing at least about 70%, preferably at least 75%, 80%, 85%, 90%, 91%, 92%, 93%, 94%, 95%, 96%, 97%, 98%, 99% or more identity with SEQ ID NO: 23 or a fragment thereof.

In one embodiment, the antibody or binding fragment thereof according to the present invention binds to at least one epitope encoded by a nucleic acid sequence comprising or consisting of SEQ ID NO: 24 or a fragment thereof.

In one embodiment, the antibody or binding fragment thereof according to the present invention binds to at least one epitope encoded by a nucleic acid sequence comprising or consisting of a sequence sharing at least about 70%, preferably at least 75%, 80%, 85%, 90%, 91%, 92%, 93%, 94%, 95%, 96%, 97%, 98%, 99% or more identity with SEQ ID NO: 24 or a fragment thereof.

In one embodiment, the antibody or binding fragment thereof according to the present invention binds to at least one epitope comprising or consisting of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 or 47 amino acids of SEQ ID NO: 23 or a fragment thereof; or of a sequence sharing at least about 70%, preferably at least 75%, 80%, 85%, 90%, 91%, 92%, 93%, 94%, 95%, 96%, 97%, 98%, 99% or more identity with SEQ ID NO: 23 or a fragment thereof.

In one embodiment, the antibody or binding fragment thereof according to the present invention binds to at least one epitope comprising or consisting of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 or 47 contiguous amino acids of SEQ ID NO: 23 or a fragment thereof; or of a sequence sharing at least about 70%, preferably at least 75%, 80%, 85%, 90%, 91%, 92%, 93%, 94%, 95%, 96%, 97%, 98%, 99% or more identity with SEQ ID NO: 23 or a fragment thereof.

In one embodiment, a fragment of the at least one epitope comprising or consisting of SEQ ID NO: 23 comprises or consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 or 47 amino acid residues.

In one embodiment, a fragment of the at least one epitope comprising or consisting of SEQ ID NO: 23 comprises or consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 or 47 amino acid residues spread over a span of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 73, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100 or more contiguous amino acid residues of a sequence comprising or consisting of SEQ ID NO: 23.

In one embodiment, a sequence comprising SEQ ID NO: 23 is the sequence of hCD45 set forth in SEQ ID NO: 99, corresponding to UniProt Accession P08575-3 (version 3, modified Mar. 28, 2018—Checksum: 6E942E2BF6B 17AC5).

SEQ ID NO: 99
(wherein SEQ ID NO: 23 is underlined)
MTMYLWLKLLAFGFAFLDTEVFVTGQSPTPSPTGLTTAKMPSVPLSSDPL

PTHTTAFSPASTFERENDFSETTTSLSPDNTSTQVSPDSLDNASAFNTTG

VSSVQTPHLPTHADSQTPSAGTDTQTFSGSAANAKLNPTPGSNAISDVPG

ERSTASTFPTDPVSPLTTTLSLAHHSSAALPARTSNTTITANTSDAYLNA

SETTTLSPSGSAVISTTTIATTPSKPTCDEKYANITVDYLYNKETKLFTA

KLNVNENVECGNNTCTNNEVHNLTECKNASVSISHNSCTAPDKTLILDVP

PGVEKFQLHDCTQVEKADTTICLKWKNIETFTCDTQNITYRFQCGNMIFD

NKEIKLENLEPEHEYKCDSEILYNNHKFTNASKIIKTDFGSPGEPQIIFC

RSEAAHQGVITWNPPQRSFHNFTLCYIKETEKDCLNLDKNLIKYDLQNLK

PYTKYVLSLHAYIIAKVQRNGSAAMCHFTTKSAPPSQVWNMTVSMTSDNS

MHVKCRPPRDRNGPHERYHLEVEAGNTLVRNESHKNCDFRVKDLQYSTDY

TFKAYFHNGDYPGEPFILHHSTSYNSKALIAFLAFLIIVTSIALLVVLYK

IYDLHKKRSCNLDEQQELVERDDEKQLMNVEPIHADILLETYKRKIADEG

RLFLAEFQSIPRVFSKFPIKEARKPFNQNKNRYVDILPYDYNRVELSEIN

GDAGSNYINASYIDGFKEPRKYIAAQGPRDETVDDFWRMIWEQKATVIVM

VTRCEEGNRNKCAEYWPSMEEGTRAFGDVVVKINQHKRCPDYIIQKLNIV

NKKEKATGREVTHIQFTSWPDHGVPEDPHLLLKLRRRVNAFSNFFSGPIV

VHCSAGVGRTGTYIGIDAMLEGLEAENKVDVYGYVVKLRRQRCLMVQVEA

QYILIHQALVEYNQFGETEVNLSELHPYLHNMKKRDPPSEPSPLEAEFQR

LPSYRSWRTQHIGNQEENKSKNRNSNVIPYDYNRVPLKHELEMSKESEHD

SDESSDDDSDSEEPSKYINASFIMSYWKPEVMIAAQGPLKETIGDFWQMI

FQRKVKVIVMLTELKHGDQEICAQYWGEGKQTYGDIEVDLKDTDKSSTYT

LRVFELRHSKRKDSRTVYQYQYTNWSVEQLPAEPKELISMIQVVKQKLPQ

KNSSEGNKHHKSTPLLIHCRDGSQQTGIFCALLNLLESAETEEVVDIFQV

VKALRKARPGMVSTFEQYQFLYDVIASTYPAQNGQVKKNNHQEDKIEFDN

EVDKVKQDANCVNPLGAPEKLPEAKEQAEGSEPTSGTEGPEHSVNGPASP

ALNQGS

In one embodiment, a sequence comprising SEQ ID NO: 23 is the sequence of hCD45RC set forth in SEQ ID NO: 104, corresponding to UniProt Accession P08575-10 (version 10, modified Mar. 28, 2018—Checksum: F92C874C9A114890).

SEQ ID NO: 104
(wherein SEQ ID NO: 23 is underlined)
MTMYLWLKLLAFGFAFLDTEVFVTGQSPTPSPTDVPGERSTASTFPTDPV

SPLTTTLSLAHHSSAALPARTSNTTITANTSDAYLNASETTTLSPSGSAV

ISTTTIATTPSKPTCDEKYANITVDYLYNKETKLFTAKLNVNENVECGNN

TCTNNEVHNLTECKNASVSISHNSCTAPDKTLILDVPPGVEKFQLHDCTQ

VEKADTTICLKWKNIETFTCDTQNITYRFQCGNMIFDNKEIKLENLEPEH

EYKCDSEILYNNHKFTNASKIIKTDFGSPGEPQIIFCRSEAAHQGVITWN

PPQRSFHNFTLCYIKETEKDCLNLDKNLIKYDLQNLKPYTKYVLSLHAYI

IAKVQRNGSAAMCHFTTKSAPPSQVWNMTVSMTSDNSMHVKCRPPRDRNG

PHERYHLEVEAGNTLVRNESHKNCDFRVKDLQYSTDYTFKAYFHNGDYPG

EPFILHHSTSYNSKALIAFLAFLIIVTSIALLVVLYKIYDLHKKRSCNLD

EQQELVERDDEKQLMNVEPIHADILLETYKRKIADEGRLFLAEFQSIPRV

FSKFPIKEARKPFNQNKNRYVDILPYDYNRVELSEINGDAGSNYINASYI

DGFKEPRKYIAAQGPRDETVDDFWRMIWEQKATVIVMVTRCEEGNRNKCA

EYWPSMEEGTRAFGDVVVKINQHKRCPDYIIQKLNIVNKKEKATGREVTH

IQFTSWPDHGVPEDPHLLLKLRRRVNAFSNFFSGPIVVHCSAGVGRTGTY

IGIDAMLEGLEAENKVDVYGYVVKLRRQRCLMVQVEAQYILIHQALVEYN

QFGETEVNLSELHPYLHNMKKRDPPSEPSPLEAEFQRLPSYRSWRTQHIG

NQEENKSKNRNSNVIPYDYNRVPLKHELEMSKESEHDSDESSDDDSDSEE

PSKYINASFIMSYWKPEVMIAAQGPLKETIGDFWQMIFQRKVKVIVMLTE

LKHGDQEICAQYWGEGKQTYGDIEVDLKDTDKSSTYTLRVFELRHSKRKD

SRTVYQYQYTNWSVEQLPAEPKELISMIQVVKQKLPQKNSSEGNKHHKST

PLLIHCRDGSQQTGIFCALLNLLESAETEEVVDIFQVVKALRKARPGMVS

TFEQYQFLYDVIASTYPAQNGQVKKNNHQEDKIEFDNEVDKVKQDANCVN

PLGAPEKLPEAKEQAEGSEPTSGTEGPEHSVNGPASPALNQGS

In one embodiment, the antibody or binding fragment thereof according to the present invention does not bind to the A determinant encoded by exon 4 of hCD45. In one embodiment, the antibody or binding fragment thereof according to the present invention does not bind to at least one epitope on the A determinant encoded by exon 4 of hCD45.

In one embodiment, the amino acid sequence of the A determinant encoded by exon 4 of hCD45 comprises or consists of SEQ ID NO: 105.

SEQ ID NO: 105
GLTTAKMPSVPLSSDPLPTHTTAFSPASTFERENDFSETTTSLSPDNTST

QVSPDSLDNASAFNTT

In one embodiment, the antibody or binding fragment thereof according to the present invention does not bind to the B determinant encoded by exon 5 of hCD45. In one embodiment, the antibody or binding fragment thereof according to the present invention does not bind to at least one epitope on the B determinant encoded by exon 5 of hCD45.

In one embodiment, the amino acid sequence of the B determinant encoded by exon 5 of hCD45 comprises or consists of SEQ ID NO: 106.

SEQ ID NO: 106
GVSSVQTPHLPTHADSQTPSAGTDTQTFSGSAANAKLNPTPGSNAIS

In one embodiment, the antibody or binding fragment thereof according to the present invention does not bind to hCD45RA. In one embodiment, the antibody or binding fragment thereof according to the present invention does not bind to at least one epitope of hCD45RA.

In one embodiment, the amino acid sequence of hCD45RA comprises or consists of SEQ ID NO: 107, corresponding to UniProt Accession P08575-8 (version 8, modified Mar. 28, 2018—Checksum: F42C1FEC9EDE4BC0).

SEQ ID NO: 107
MTMYLWLKLLAFGFAFLDTEVFVTGQSPTPSPTGLTTAKMPSVPLSSDPL

PTHTTAFSPASTFERENDFSETTTSLSPDNTSTQVSPDSLDNASAFNTTD

AYLNASETTTLSPSGSAVISTTTIATTPSKPTCDEKYANITVDYLYNKET

KLFTAKLNVNENVECGNNTCTNNEVHNLTECKNASVSISHNSCTAPDKTL

ILDVPPGVEKFQLHDCTQVEKADTTICLKWKNIETFTCDTQNITYRFQCG

NMIFDNKEIKLENLEPEHEYKCDSEILYNNHKFTNASKIIKTDFGSPGEP

QIIFCRSEAAHQGVITWNPPQRSFHNFTLCYIKETEKDCLNLDKNLIKYD

LQNLKPYTKYVLSLHAYIIAKVQRNGSAAMCHFTTKSAPPSQVWNMTVSM

TSDNSMHVKCRPPRDRNGPHERYHLEVEAGNTLVRNESHKNCDFRVKDLQ

YSTDYTFKAYFHNGDYPGEPFILHHSTSYNSKALIAFLAFLIIVTSIALL

VVLYKIYDLHKKRSCNLDEQQELVERDDEKQLMNVEPIHADILLETYKRK

IADEGRLFLAEFQSIPRVFSKFPIKEARKPFNQNKNRYVDILPYDYNRVE

LSEINGDAGSNYINASYIDGFKEPRKYIAAQGPRDETVDDFWRMIWEQKA

TVIVMVTRCEEGNRNKCAEYWPSMEEGTRAFGDVVVKINQHKRCPDYIIQ

KLNIVNKKEKATGREVTHIQFTSWPDHGVPEDPHLLLKLRRRVNAFSNFF

SGPIVVHCSAGVGRTGTYIGIDAMLEGLEAENKVDVYGYVVKLRRQRCLM

VQVEAQYILIHQALVEYNQFGETEVNLSELHPYLHNMKKRDPPSEPSPLE

AEFQRLPSYRSWRTQHIGNQEENKSKNRNSNVIPYDYNRVPLKHELEMSK

ESEHDSDESSDDDSDSEEPSKYINASFIMSYWKPEVMIAAQGPLKETIGD

FWQMIFQRKVKVIVMLTELKHGDQEICAQYWGEGKQTYGDIEVDLKDTDK

SSTYTLRVFELRHSKRKDSRTVYQYQYTNWSVEQLPAEPKELISMIQVVK

QKLPQKNSSEGNKHHKSTPLLIHCRDGSQQTGIFCALLNLLESAETEEVV

DIFQVVKALRKARPGMVSTFEQYQFLYDVIASTYPAQNGQVKKNNHQEDK

IEFDNEVDKVKQDANCVNPLGAPEKLPEAKEQAEGSEPTSGTEGPEHSVN

GPASPALNQGS

In one embodiment, the antibody or binding fragment thereof according to the present invention does not bind to hCD45RB. In one embodiment, the antibody or binding fragment thereof according to the present invention does not bind to at least one epitope of hCD45RB.

In one embodiment, the amino acid sequence of hCD45RB comprises or consists of SEQ ID NO: 108, corresponding to UniProt Accession P08575-9 (version 9, modified Mar. 28, 2018—Checksum: 745870037910C575).

SEQ ID NO: 108
MTMYLWLKLLAFGFAFLDTEVFVTGQSPTPSPTGVSSVQTPHLPTHADSQ

TPSAGTDTQTFSGSAANAKLNPTPGSNAISDAYLNASETTTLSPSGSAVI

STTTIATTPSKPTCDEKYANITVDYLYNKETKLFTAKLNVNENVECGNNT

CTNNEVHNLTECKNASVSISHNSCTAPDKTLILDVPPGVEKFQLHDCTQV

EKADTTICLKWKNIETFTCDTQNITYRFQCGNMIFDNKEIKLENLEPEHE

YKCDSEILYNNHKFTNASKIIKTDFGSPGEPQIIFCRSEAAHQGVITWNP

PQRSFHNFTLCYIKETEKDCLNLDKNLIKYDLQNLKPYTKYVLSLHAYII

AKVQRNGSAAMCHFTTKSAPPSQVWNMTVSMTSDNSMHVKCRPPRDRNGP

HERYHLEVEAGNTLVRNESHKNCDFRVKDLQYSTDYTFKAYFHNGDYPGE

PFILHHSTSYNSKALIAFLAFLIIVTSIALLVVLYKIYDLHKKRSCNLDE

QQELVERDDEKQLMNVEPIHADILLETYKRKIADEGRLFLAEFQSIPRVF

SKFPIKEARKPFNQNKNRYVDILPYDYNRVELSEINGDAGSNYINASYID

GFKEPRKYIAAQGPRDETVDDFWRMIWEQKATVIVMVTRCEEGNRNKCAE

YWPSMEEGTRAFGDVVVKINQHKRCPDYIIQKLNIVNKKEKATGREVTHI

QFTSWPDHGVPEDPHLLLKLRRRVNAFSNFFSGPIVVHCSAGVGRTGTYI

GIDAMLEGLEAENKVDVYGYVVKLRRQRCLMVQVEAQYILIHQALVEYNQ

FGETEVNLSELHPYLHNMKKRDPPSEPSPLEAEFQRLPSYRSWRTQHIGN

QEENKSKNRNSNVIPYDYNRVPLKHELEMSKESEHDSDESSDDDSDSEEP

SKYINASFIMSYWKPEVMIAAQGPLKETIGDFWQMIFQRKVKVIVMLTEL

KHGDQEICAQYWGEGKQTYGDIEVDLKDTDKSSTYTLRVFELRHSKRKDS

RTVYQYQYTNWSVEQLPAEPKELISMIQVVKQKLPQKNSSEGNKHHKSTP

LLIHCRDGSQQTGIFCALLNLLESAETEEVVDIFQVVKALRKARPGMVST

FEQYQFLYDVIASTYPAQNGQVKKNNHQEDKIEFDNEVDKVKQDANCVNP

LGAPEKLPEAKEQAEGSEPTSGTEGPEHSVNGPASPALNQGS

In one embodiment, the antibody or binding fragment thereof according to the present invention does not bind to hCD45RAB. In one embodiment, the antibody or binding fragment thereof according to the present invention does not bind to at least one epitope of hCD45RAB.

In one embodiment, the amino acid sequence of hCD45RAB comprises or consists of SEQ ID NO: 109, corresponding to UniProt Accession P08575-5 (version 5, modified Mar. 28, 2018—Checksum: EA40BE995CD98F7C).

SEQ ID NO: 109
MTMYLWLKLLAFGFAFLDTEVFVTGQSPTPSPTGLTTAKMPSVPLSSDPL

PTHTTAFSPASTFERENDFSETTTSLSPDNTSTQVSPDSLDNASAFNTTG

VSSVQTPHLPTHADSQTPSAGTDTQTFSGSAANAKLNPTPGSNAISDAYL

NASETTTLSPSGSAVISTTTIATTPSKPTCDEKYANITVDYLYNKETKLF

TAKLNVNENVECGNNTCTNNEVHNLTECKNASVSISHNSCTAPDKTLILD

VPPGVEKFQLHDCTQVEKADTTICLKWKNIETFTCDTQNITYRFQCGNMI

FDNKEIKLENLEPEHEYKCDSEILYNNHKFTNASKIIKTDFGSPGEPQII

-continued

FCRSEAAHQGVITWNPPQRSFHNFTLCYIKETEKDCLNLDKNLIKYDLQN

LKPYTKYVLSLHAYIIAKVQRNGSAAMCHFTTKSAPPSQVWNMTVSMTSD

NSMHVKCRPPRDRNGPHERYHLEVEAGNTLVRNESHKNCDFRVKDLQYST

DYTFKAYFHNGDYPGEPFILHHSTSYNSKALIAFLAFLIIVTSIALLVVL

YKIYDLHKKRSCNLDEQQELVERDDEKQLMNVEPIHADILLETYKRKIAD

EGRLFLAEFQSIPRVFSKFPIKEARKPFNQNKNRYVDILPYDYNRVELSE

INGDAGSNYINASYIDGFKEPRKYIAAQGPRDETVDDFWRMIWEQKATVI

VMVTRCEEGNRNKCAEYWPSMEEGTRAFGDVVVKINQHKRCPDYIIQKLN

IVNKKEKATGREVTHIQFTSWPDHGVPEDPHLLLKLRRRVNAFSNFFSGP

IVVHCSAGVGRTGTYIGIDAMLEGLEAENKVDVYGYVVKLRRQRCLMVQV

EAQYILIHQALVEYNQFGETEVNLSELHPYLHNMKKRDPPSEPSPLEAEF

QRLPSYRSWRTQHIGNQEENKSKNRNSNVIPYDYNRVPLKHELEMSKESE

HDSDESSDDDSDSEEPSKYINASFIMSYWKPEVMIAAQGPLKETIGDFWQ

MIFQRKVKVIVMLTELKHGDQEICAQYWGEGKQTYGDIEVDLKDTDKSST

YTLRVFELRHSKRKDSRTVYQYQYTNWSVEQLPAEPKELISMIQVVKQKL

PQKNSSEGNKHHKSTPLLIHCRDGSQQTGIFCALLNLLESAETEEVVDIF

QVVKALRKARPGMVSTFEQYQFLYDVIASTYPAQNGQVKKNNHQEDKIEF

DNEVDKVKQDANCVNPLGAPEKLPEAKEQAEGSEPTSGTEGPEHSVNGPA

SPALNQGS

In one embodiment, the antibody or binding fragment thereof according to the present invention does not bind to hCD45RO. In one embodiment, the antibody or binding fragment thereof according to the present invention does not bind to at least one epitope of hCD45RO.

In one embodiment, the amino acid sequence of hCD45RO comprises or consists of SEQ ID NO: 110, corresponding to UniProt Accession P08575-4 (version 4, modified Mar. 28, 2018—Checksum: D3CB364EF4243384).

SEQ ID NO: 110
MTMYLWLKLLAFGFAFLDTEVFVTGQSPTPSPTDAYLNASETTTLSPSGS

AVISTTTIATTPSKPTCDEKYANITVDYLYNKETKLFTAKLNVNENVECG

NNTCTNNEVHNLTECKNASVSISHNSCTAPDKTLILDVPPGVEKFQLHDC

TQVEKADTTICLKWKNIETFTCDTQNITYRFQCGNMIFDNKEIKLENLEP

EHEYKCDSEILYNNHKFTNASKIIKTDFGSPGEPQIIFCRSEAAHQGVIT

WNPPQRSFHNFTLCYIKETEKDCLNLDKNLIKYDLQNLKPYTKYVLSLHA

YIIAKVQRNGSAAMCHFTTKSAPPSQVWNMTVSMTSDNSMHVKCRPPRDR

NGPHERYHLEVEAGNTLVRNESHKNCDFRVKDLQYSTDYTFKAYFHNGDY

PGEPFILHHSTSYNSKALIAFLAFLIIVTSIALLVVLYKIYDLHKKRSCN

LDEQQELVERDDEKQLMNVEPIHADILLETYKRKIADEGRLFLAEFQSIP

RVFSKFPIKEARKPFNQNKNRYVDILPYDYNRVELSEINGDAGSNYINAS

YIDGFKEPRKYIAAQGPRDETVDDFWRMIWEQKATVIVMVTRCEEGNRNK

CAEYWPSMEEGTRAFGDVVVKINQHKRCPDYIIQKLNIVNKKEKATGREV

THIQFTSWPDHGVPEDPHLLLKLRRRVNAFSNFFSGPIVVHCSAGVGRTG

TYIGIDAMLEGLEAENKVDVYGYVVKLRRQRCLMVQVEAQYILIHQALVE

YNQFGETEVNLSELHPYLHNMKKRDPPSEPSPLEAEFQRLPSYRSWRTQH

IGNQEENKSKNRNSNVIPYDYNRVPLKHELEMSKESEHDSDESSDDDSDS

EEPSKYINASFIMSYWKPEVMIAAQGPLKETIGDFWQMIFQRKVKVIVML

TELKHGDQEICAQYWGEGKQTYGDIEVDLKDTDKSSTYTLRVFELRHSKR

KDSRTVYQYQYTNWSVEQLPAEPKELISMIQVVKQKLPQKNSSEGNKHHK

STPLLIHCRDGSQQTGIFCALLNLLESAETEEVVDIFQVVKALRKARPGM

VSTFEQYQFLYDVIASTYPAQNGQVKKNNHQEDKIEFDNEVDKVKQDANC

VNPLGAPEKLPEAKEQAEGSEPTSGTEGPEHSVNGPASPALNQGS

In one embodiment, the at least one epitope is a conformational epitope. In another embodiment, the at least one epitope is a sequential epitope.

In one embodiment, the antibody or binding fragment thereof according to the present invention binds to hCD45RC with an equilibrium dissociation constant ($K_d$) of about $5 \times 10^{-7}$ M or less, preferably of about $2.5 \times 10^{-7}$ M or less, about $1 \times 10^{-7}$ M or less, about $7.5 \times 10^{-8}$ M or less, about $5 \times 10^{-8}$ M or less, about $1 \times 10^{-8}$ M or less.

In one embodiment, the antibody or binding fragment thereof according to the present invention binds to hCD45RC with an association rate ($K_{on}$) of about $1 \times 10^4$ M$^{-1}$ sec$^{-1}$ or more, preferably of about $5 \times 10^4$ M$^{-1}$ sec$^{-1}$ or more, about $1 \times 10^5$ M$^{-1}$ sec$^{-1}$ or more, about $2.5 \times 10^5$ M$^{-1}$ sec$^{-1}$ or more, about $5 \times 10^5$ M$^{-1}$ sec$^{-1}$ or more.

In one embodiment, the antibody or binding fragment thereof according to the present invention binds to hCD45RC with a dissociation rate ($K_{off}$) of about $5 \times 10^{-2}$ sec$^{-1}$ or less, preferably of about $4 \times 10^{-2}$ sec$^{-1}$ or less, about $3 \times 10^{-2}$ sec$^{-1}$ or less, about $2 \times 10^{-2}$ sec$^{-1}$ or less, about $1.5 \times 10^{-2}$ sec$^{-1}$ or less.

In one embodiment, the antibody or binding fragment thereof according to the present invention binds to hCD45RC with at least one of, preferably at least two of, more preferably the three of:
  an equilibrium dissociation constant ($K_d$) of about $5 \times 10^{-7}$ M or less, preferably of about $2.5 \times 10^{-7}$ M or less, about $1 \times 10^{-7}$ M or less, about $7.5 \times 10^{-8}$ M or less, about $5 \times 10^{-8}$ M or less, about $1 \times 10^{-8}$ M or less;
  an association rate ($K_{on}$) of about $1 \times 10^4$ M$^{-1}$ sec$^{-1}$ or more, preferably of about $5 \times 10^4$ M$^{-1}$ sec$^{-1}$ or more, about $1 \times 10^5$ M$^{-1}$ sec$^{-1}$ or more, about $2.5 \times 10^5$ M$^{-1}$ sec$^{-1}$ or more, about $5 \times 10^5$ M$^{-1}$ sec$^{-1}$ or more; and
  a dissociation rate ($K_{off}$) of about $5 \times 10^{-2}$ sec$^{-1}$ or less, preferably of about $4 \times 10^{-2}$ sec$^{-1}$ or less, about $3 \times 10^{-2}$ sec$^{-1}$ or less, about $2 \times 10^{-2}$ sec$^{-1}$ or less, about $1.5 \times 10^{-2}$ sec$^{-1}$ or less.

Methods for determining the affinity (including, for example, determining the $K_d$, $k_{off}$ and $k_{on}$) of an antibody or binding fragment thereof for its ligand are well-known in the art, and include, without limitation, surface plasmon resonance (SPR), fluorescence-activated cell sorting (FACS), enzyme-linked immunosorbent assay (ELISA), AlphaLISA and KinExA.

A preferred method is BIAcore®, which relies on SPR using immobilized CD45RC to determine the affinity of an antibody or binding fragment thereof. A way of implementing this method will be further illustrated in the Examples section.

In one embodiment, the antibody or binding fragment thereof according to the present invention is a polyclonal antibody or binding fragment thereof.

In a preferred embodiment, the antibody or binding fragment thereof according to the present invention is a monoclonal antibody or binding fragment thereof.

In one embodiment, the antibody or binding fragment thereof according to the present invention is a molecule selected from the group comprising or consisting of a whole antibody, a single-chain antibody, a dimeric single chain antibody, a single-domain antibody, a Fv, a Fab, a Fab', a Fab'-SH, a F(ab')2, a Fd, a defucosylated antibody, a bi-specific antibody, a diabody, a triabody and a tetrabody.

The term "binding fragment", as used herein, refers to a part or region of the antibody according to the present invention, which comprises fewer amino acid residues than the whole antibody. A "binding fragment" binds antigen and/or competes with the whole antibody from which it was derived for antigen binding (e.g., specific binding to human CD45RC). Antibody binding fragments encompasses, without any limitation, single chain antibodies, Fv, Fab, Fab', Fab'-SH, F(ab')2, Fd, defucosylated antibodies, diabodies, triabodies and tetrabodies.

"Single chain antibody", as used herein, refers to any antibody or fragment thereof that is a protein having a primary structure comprising or consisting of one uninterrupted sequence of contiguous amino acid residues, including without limitation (1) single-chain Fv molecules (scFv); (2) single chain proteins containing only one light chain variable domain, or a fragment thereof that contains the three CDRs of the light chain variable domain, without an associated heavy chain moiety; and (3) single chain proteins containing only one heavy chain variable region, or a fragment thereof containing the three CDRs of the heavy chain variable region, without an associated light chain moiety.

"Single-chain Fv", also abbreviated as "sFv" or "scFv", refers to antibody fragments that comprise the $V_H$ and $V_L$ antibody domains connected into a single amino acid chain.

Preferably, the scFv amino acid sequence further comprises a peptide linker between the $V_H$ and $V_L$ domains that enables the scFv to form the desired structure for antigen binding (Pluckthun, 1994. Antibodies from *Escherichia coli*. In Rosenberg & Moore (Eds.), *The pharmacology of monoclonal antibodies*. Handbook of Experimental Pharmacology, 113:269-315. Springer: Berlin, Heidelberg).

"Fv", as used herein, refers to the minimum antibody fragment that contains a complete antigen-recognition and -binding site. This fragment consists of a dimer of one HCVR and one LCVR in tight, non-covalent association. From the folding of these two domains emanate six hypervariable loops (three loops each from the heavy and light chain) that contribute to antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Diabodies", as used herein, refers to small antibody fragments prepared by constructing scFv fragments with short linkers (about 5-10 residues) between the HCVR and LCVR such that inter-chain but not intra-chain pairing of the variable domains is achieved, resulting in a bivalent fragment, i.e., fragment having two antigen-binding sites. Bi-specific diabodies are heterodimers of two "crossover" scFv fragments in which the HCVR and LCVR of the two antibodies are present on different polypeptide chains. Diabodies are described more fully in Patent EP0404097, Patent application WO1993011161; and Holliger et al., 1993. *Proc Natl Acad Sci USA*. 90(14):6444-8.

Antibody binding fragments can be obtained using standard methods. For instance, Fab or F(ab')2 fragments may be produced by protease digestion of the isolated antibodies, according to conventional techniques.

It will also be appreciated that antibodies or binding fragments thereof according to the present invention can be modified using known methods. For example, to slow clearance in vivo and obtain a more desirable pharmacokinetic profile, the antibody or binding fragment thereof may be modified with polyethylene glycol (PEG). Methods for coupling and site-specifically conjugating PEG to an antibody or binding fragment thereof are described in, e.g., Leong et al., 2001. *Cytokine*. 16(3):106-19; Delgado et al., 1996. *Br J Cancer*. 73(2):175-82.

In one embodiment, the antibody or binding fragment thereof according to the present invention is a molecule selected from the group comprising or consisting of a unibody, a domain antibody, and a nanobody.

"Unibodies" are well-known in the art and refer to antibody fragments lacking the hinge region of IgG4 antibodies. The deletion of the hinge region results in a molecule that is essentially half the size of traditional IgG4 antibodies and has a univalent binding region rather than the bivalent biding region of IgG4 antibodies.

"Domain antibodies" are well-known in the art and refer to the smallest functional binding units of antibodies, corresponding to the variable regions of either the heavy or light chains of antibodies.

"Single-domain antibodies" are well-known in the art and refer to antibody-derived proteins that contain the unique structural and functional properties of naturally-occurring heavy chain antibodies (Muyldermans, 2013. *Annu Rev Biochem*. 82:775-97). These heavy chain antibodies may contain a single variable domain ($V_HH$)—one such example is Nanobodies®—, or a single variable domain ($V_HH$) and two constant domains ($C_H2$ and $C_H3$)—such as camelid antibodies-, or a single variable domain ($V_HH$) and five constant domains ($C_H1$, $C_H2$, $C_H3$, $C_H4$ and $C_H5$)—such as shark antibodies.

In one embodiment, the antibody or binding fragment thereof according to the present invention is a mimetic selected from the group comprising or consisting of an affibody, an affilin, an affitin, an adnectin, an atrimer, an evasin, a DARPin, an anticalin, an avimer, a fynomer, a versabody and a duocalin.

"Affibodies" are well-known in the art and refer to affinity proteins based on a 58 amino acid residue protein domain, derived from one of the IgG binding domain of staphylococcal protein A (Frejd & Kim, 2017. *Exp Mol Med*. 49(3):e306; U.S. Pat. No. 5,831,012).

"DARPins" (Designed Ankyrin Repeat Proteins) are well-known in the art and refer to an antibody mimetic DRP (designed repeat protein) technology developed to exploit the binding abilities of non-antibody proteins (Binz et al., 2003. *J Mol Biol*. 332(2):489-503; Pluchthun, 2015. *Annu Rev Pharmacol Toxicol*. 55:489-511).

"Anticalins" are well-known in the art and refer to another antibody mimetic technology, wherein the binding specificity is derived from lipocalins (Skerra, 2008. *FEBS J*. 275 (11):2677-83). Anticalins may also be formatted as dual targeting protein, called "duocalins" (Schlehuber & Skerra, 2001. *Biol Chem*. 382(9):1335-42).

"Avimers" are well-known in the art and refer to another antibody mimetic technology (Silverman et al., 2005. *Nat Biotechnol.* 23(12):1556-61).

"Versabodies" are well-known in the art and refer to another antibody mimetic technology (Patent Application US20070191272). They are small proteins of 3-5 kDa with >15% cysteines, which form a high disulfide density scaffold, replacing the hydrophobic core the typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T cell epitopes, because the residues that contribute most to MHC presentation are hydrophobic. All four of these properties are well-known to affect immunogenicity, and together they are expected to cause a large decrease in immunogenicity.

In one embodiment, the antibody or binding fragment thereof according to the present invention also encompasses multispecific antibodies or binding fragments thereof, i.e., being immunospecific for more than one, such as at least two, different antigens, one of which being hCD45RC according to the present invention.

In one embodiment, the antibody or binding fragment thereof according to the present invention also encompasses polymers of antibodies or binding fragments thereof, i.e., more than one, such as at least two, antibodies or binding fragments thereof, whether identical or different, being covalently linked together, directly or indirectly.

In one embodiment, the antibody or binding fragment thereof according to the present invention is an immunoconjugate comprising said antibody or binding fragment thereof, further conjugated to a therapeutic agent.

In one embodiment, the antibody or binding fragment thereof according to the present invention is a conjugate comprising said antibody or binding fragment thereof further conjugated to an imaging agent. Said conjugate could be used, e.g., for imaging applications.

In the following, and unless explicitly mentioned otherwise, CDR numbering and definitions are according to the Kabat/Chothia definition.

In one embodiment, the antibody or binding fragment thereof according to the present invention comprises a heavy chain variable region (abbreviated herein as HCVR or $V_H$) which comprises at least one, preferably at least two, more preferably the following three complementary-determining regions (CDRs):

$V_H$-CDR1: NYYIG; (SEQ ID NO: 1)

$V_H$-CDR2: $X_1$-IF-$X_2$-GG-$X_3$-Y-$X_4$-N-$X_5$-$X_6$-$X_7$-$X_8$-$X_9$-$X_{10}$-G; (SEQ ID NO: 2)
and $V_H$-CDR3: RNFDY, (SEQ ID NO: 3)

with:
$X_1$ being selected from Asp (D), Ile (I) and Arg (R);
$X_2$ being selected from Pro (P) and Ser (S);
$X_3$ being selected from Asp (D), Ser (S) and Gly (G);
$X_4$ being selected from Ala (A) and Thr (T);
$X_5$ being selected from Ser (S) and Tyr (Y);
$X_6$ being selected from Asn (N), Ala (A) and Ser (S);
$X_7$ being selected from Glu (E), Asp (D), Pro (P) and Gln (Q);
$X_8$ being selected from Lys (K) and Ser (S);
$X_9$ being selected from Phe (F) and Val (V); and
$X_{10}$ being selected from Lys (K) and Gln (Q).

In one embodiment, the antibody or binding fragment thereof according to the present invention comprises a HCVR which comprises the following three CDRs:

$V_H$-CDR1: NYYIG; (SEQ ID NO: 1)

$V_H$-CDR2: $X_1$-IF-$X_2$-GG-$X_3$-Y-$X_4$-N-$X_5$-$X_6$-$X_7$-$X_8$-$X_9$-$X_{10}$-G; (SEQ ID NO: 2)
and $V_H$-CDR3: RNFDY, (SEQ ID NO: 3)
with: DIFPGGDYANSNEKFKG $X_1$ being selected from Asp (D), Ile (I) and Arg (R);
$X_2$ being selected from Pro (P) and Ser (S);
$X_3$ being selected from Asp (D), Ser (S) and Gly (G);
$X_4$ being selected from Ala (A) and Thr (T);
$X_5$ being selected from Ser (S) and Tyr (Y);
$X_6$ being selected from Asn (N), Ala (A) and Ser (S);
$X_7$ being selected from Glu (E), Asp (D), Pro (P) and Gln (Q);
$X_8$ being selected from Lys (K) and Ser (S);
$X_9$ being selected from Phe (F) and Val (V); and
$X_{10}$ being selected from Lys (K) and Gln (Q).

In one embodiment, the antibody or binding fragment thereof according to the present invention comprises a HCVR which comprises at least one, preferably at least two, more preferably the following three CDRs:

$V_H$-CDR1: NYYIG; (SEQ ID NO: 1)

$V_H$-CDR2: DIFPGGDYANSNEKFKG; (SEQ ID NO: 4)
and $V_H$-CDR3: RNFDY. (SEQ ID NO: 3)

In one embodiment, the antibody or binding fragment thereof according to the present invention comprises a HCVR which comprises the following three CDRs:

$V_H$-CDR1: NYYIG; (SEQ ID NO: 1)

$V_H$-CDR2: DIFPGGDYANSNEKFKG; (SEQ ID NO: 4)
and $V_H$-CDR3: RNFDY. (SEQ ID NO: 3)

In one embodiment, the antibody or binding fragment thereof according to the present invention comprises a HCVR which comprises at least one, preferably at least two, more preferably the following three CDRs:

$V_H$-CDR1: NYYIG; (SEQ ID NO: 1)

$V_H$-CDR2: DIFPGGDYANSNEKVKG; (SEQ ID NO: 5)
and

```
                                         (SEQ ID NO: 3)
V_H-CDR3: RNFDY.
```

In one embodiment, the antibody or binding fragment thereof according to the present invention comprises a HCVR which comprises the following three CDRs:

```
                                         (SEQ ID NO: 1)
V_H-CDR1: NYYIG;

(SEQ ID NO: 5)
V_H-CDR2: DIFPGGDYANSNEKVKG;
and (SEQ ID NO: 3)
V_H-CDR3: RNFDY.
```

In one embodiment, the antibody or binding fragment thereof according to the present invention comprises a HCVR which comprises at least one, preferably at least two, more preferably the following three CDRs:

```
                                         (SEQ ID NO: 1)
V_H-CDR1: NYYIG;

(SEQ ID NO: 6)
V_H-CDR2: DIFPGGGYTNYAEKFQG;
and (SEQ ID NO: 3)
V_H-CDR3: RNFDY.
```

In one embodiment, the antibody or binding fragment thereof according to the present invention comprises a HCVR which comprises the following three CDRs:

```
                                         (SEQ ID NO: 1)
V_H-CDR1: NYYIG;

(SEQ ID NO: 6)
V_H-CDR2: DIFPGGGYTNYAEKFQG;
and (SEQ ID NO: 3)
V_H-CDR3: RNFDY.
```

In one embodiment, the antibody or binding fragment thereof according to the present invention comprises a HCVR which comprises at least one, preferably at least two, more preferably the following three CDRs:

```
                                         (SEQ ID NO: 1)
V_H-CDR1: NYYIG;

(SEQ ID NO: 7)
V_H-CDR2: DIFPGGSYTNYSESFQG;
and (SEQ ID NO: 3)
V_H-CDR3: RNFDY.
```

In one embodiment, the antibody or binding fragment thereof according to the present invention comprises a HCVR which comprises the following three CDRs:

```
                                         (SEQ ID NO: 1)
V_H-CDR1: NYYIG;

(SEQ ID NO: 7)
V_H-CDR2: DIFPGGSYTNYSESFQG;
and (SEQ ID NO: 3)
V_H-CDR3: RNFDY.
```

In one embodiment, the antibody or binding fragment thereof according to the present invention comprises a HCVR which comprises at least one, preferably at least two, more preferably the following three CDRs:

```
                                         (SEQ ID NO: 1)
V_H-CDR1: NYYIG;

(SEQ ID NO: 8)
V_H-CDR2: DIFPGGSYTNYADSVKG;
and (SEQ ID NO: 3)
V_H-CDR3: RNFDY.
```

In one embodiment, the antibody or binding fragment thereof according to the present invention comprises a HCVR which comprises the following three CDRs:

```
                                         (SEQ ID NO: 1)
V_H-CDR1: NYYIG;

(SEQ ID NO: 8)
V_H-CDR2: DIFPGGSYTNYADSVKG;
and (SEQ ID NO: 3)
V_H-CDR3: RNFDY.
```

In one embodiment, the antibody or binding fragment thereof according to the present invention comprises a HCVR which comprises at least one, preferably at least two, more preferably the following three CDRs:

```
                                         (SEQ ID NO: 1)
V_H-CDR1: NYYIG;

(SEQ ID NO: 9)
V_H-CDR2: RIFPGGGYTNYAQKFQG;
and (SEQ ID NO: 3)
V_H-CDR3: RNFDY.
```

In one embodiment, the antibody or binding fragment thereof according to the present invention comprises a HCVR which comprises the following three CDRs:

```
                                         (SEQ ID NO: 1)
V_H-CDR1: NYYIG;

(SEQ ID NO: 9)
V_H-CDR2: RIFPGGGYTNYAQKFQG;
and (SEQ ID NO: 3)
V_H-CDR3: RNFDY.
```

In one embodiment, the antibody or binding fragment thereof according to the present invention comprises a HCVR which comprises at least one, preferably at least two, more preferably the following three CDRs:

```
                                         (SEQ ID NO: 1)
V_H-CDR1: NYYIG;
```

```
                              (SEQ ID NO: 10)
VH-CDR2: IIFPGGSYTNYSPSFQG;
and (SEQ ID NO: 3)
VH-CDR3: RNFDY.
```

In one embodiment, the antibody or binding fragment thereof according to the present invention comprises a HCVR which comprises the following three CDRs:

```
                               (SEQ ID NO: 1)
VH-CDR1: NYYIG;

(SEQ ID NO: 10)
VH-CDR2: IIFPGGSYTNYSPSFQG;
and (SEQ ID NO: 3)
VH-CDR3: RNFDY.
```

In one embodiment, the antibody or binding fragment thereof according to the present invention comprises a HCVR which comprises at least one, preferably at least two, more preferably the following three CDRs:

```
                               (SEQ ID NO: 1)
VH-CDR1: NYYIG;

(SEQ ID NO: 11)
VH-CDR2: DIFSGGSYTNYADSVKG;
and (SEQ ID NO: 3)
VH-CDR3: RNFDY.
```

In one embodiment, the antibody or binding fragment thereof according to the present invention comprises a HCVR which comprises the following three CDRs:

```
                               (SEQ ID NO: 1)
VH-CDR1: NYYIG;

(SEQ ID NO: 11)
VH-CDR2: DIFSGGSYTNYADSVKG;
and (SEQ ID NO: 3)
VH-CDR3: RNFDY.
```

In one embodiment, the antibody or binding fragment thereof according to the present invention comprises a HCVR which comprises at least one, preferably at least two, more preferably the following three CDRs:

```
                               (SEQ ID NO: 1)
VH-CDR1: NYYIG;

(SEQ ID NO: 100)
VH-CDR2: DIFPGGDYTNYAEKFQG;
and (SEQ ID NO: 3)
VH-CDR3: RNFDY.
```

In one embodiment, the antibody or binding fragment thereof according to the present invention comprises a HCVR which comprises the following three CDRs:

```
                               (SEQ ID NO: 1)
VH-CDR1: NYYIG;

(SEQ ID NO: 100)
VH-CDR2: DIFPGGDYTNYAEKFQG;
and (SEQ ID NO: 3)
VH-CDR3: RNFDY.
```

In one embodiment, the antibody or binding fragment thereof according to the present invention comprises a HCVR which comprises at least one, preferably at least two, more preferably the following three CDRs:

```
                               (SEQ ID NO: 1)
VH-CDR1: NYYIG;

(SEQ ID NO: 116)
VH-CDR2: DIFPGGGYANYAEKFQG;
and (SEQ ID NO: 3)
VH-CDR3: RNFDY.
```

In one embodiment, the antibody or binding fragment thereof according to the present invention comprises a HCVR which comprises the following three CDRs:

```
                               (SEQ ID NO: 1)
VH-CDR1: NYYIG;

(SEQ ID NO: 116)
VH-CDR2: DIFPGGGYANYAEKFQG;
and (SEQ ID NO: 3)
VH-CDR3: RNFDY.
```

In one embodiment, the antibody or binding fragment thereof according to the present invention comprises a HCVR which comprises at least one, preferably at least two, more preferably the following three CDRs:

```
                               (SEQ ID NO: 1)
VH-CDR1: NYYIG;

(SEQ ID NO: 117)
VH-CDR2: DIFPGGGYTNYAEKFKG;
and (SEQ ID NO: 3)
VH-CDR3: RNFDY.
```

In one embodiment, the antibody or binding fragment thereof according to the present invention comprises a HCVR which comprises the following three CDRs:

```
                               (SEQ ID NO: 1)
VH-CDR1: NYYIG;

(SEQ ID NO: 117)
VH-CDR2: DIFPGGGYTNYAEKFKG;
and (SEQ ID NO: 3)
VH-CDR3: RNFDY.
```

In one embodiment, the antibody or binding fragment thereof according to the present invention comprises a HCVR which comprises at least one, preferably at least two, more preferably the following three CDRs:

V$_H$-CDR1: NYYIG; (SEQ ID NO: 1)

V$_H$-CDR2: DIFPGGGYTNYNEKFQG; (SEQ ID NO: 118)
and

V$_H$-CDR3: RNFDY. (SEQ ID NO: 3)

In one embodiment, the antibody or binding fragment thereof according to the present invention comprises a HCVR which comprises the following three CDRs:

V$_H$-CDR1: NYYIG; (SEQ ID NO: 1)

V$_H$-CDR2: DIFPGGGYTNYNEKFQG; (SEQ ID NO: 118)
and

V$_H$-CDR3: RNFDY. (SEQ ID NO: 3)

In one embodiment, the antibody or binding fragment thereof according to the present invention comprises a HCVR which comprises at least one, preferably at least two, more preferably the following three CDRs:

V$_H$-CDR1: NYYIG; (SEQ ID NO: 1)

V$_H$-CDR2: DIFPGGGYTNSAEKFQG; (SEQ ID NO: 119)
and

V$_H$-CDR3: RNFDY. (SEQ ID NO: 3)

In one embodiment, the antibody or binding fragment thereof according to the present invention comprises a HCVR which comprises the following three CDRs:

V$_H$-CDR1: NYYIG; (SEQ ID NO: 1)

V$_H$-CDR2: DIFPGGGYTNSAEKFQG; (SEQ ID NO: 119)
and

V$_H$-CDR3: RNFDY. (SEQ ID NO: 3)

In one embodiment, the antibody or binding fragment thereof according to the present invention comprises a light chain variable region (abbreviated herein as LCVR or V$_L$) which comprises at least one, preferably at least two, more preferably the following three complementary-determining regions (CDRs):

V$_L$-CDR1: X$_{11}$-ASSSVS-X$_{12}$-YMH; (SEQ ID NO: 12)

V$_L$-CDR2: X$_{13}$-TSN-X$_{14}$-X$_{15}$-X$_{16}$; (SEQ ID NO: 13)
and

V$_L$-CDR3: X$_{17}$-QRSSYPLTF, (SEQ ID NO: 14)

with:
X$_{11}$ being selected from Ser (S) and Arg (R);
X$_{12}$ being absent or being selected from Asn (N), Ser (S) and Gly (G);
X$_{13}$ being selected from Asn (N) and Ala (A); or X$_{13}$ being any amino acid but Ala (A) or Asn (N);
X$_{14}$ being selected from Leu (L), Ser (S) and Arg (R);
X$_{15}$ being selected from Pro (P), Ala (A) and Gln (Q);
X$_{16}$ being selected from Ser (S) and Thr (T); and
X$_{17}$ being selected from Gln (Q) and His (H).

In one embodiment, the antibody or binding fragment thereof according to the present invention comprises a LCVR which comprises the following three CDRs:

V$_L$-CDR1: X$_{11}$-ASSSVS-X$_{12}$-YMH; (SEQ ID NO: 12)

V$_L$-CDR2: X$_{13}$-TSN-X$_{14}$-X$_{15}$-X$_{16}$; (SEQ ID NO: 13)
and

V$_L$-CDR3: X$_{17}$-QRSSYPLTF, (SEQ ID NO: 14)

with:
X$_{11}$ being selected from Ser (S) and Arg (R);
X$_{12}$ being absent or being selected from Asn (N), Ser (S) and Gly (G);
X$_{13}$ being selected from Asn (N) and Ala (A); or X$_{13}$ being any amino acid but Ala (A) or Asn (N);
X$_{14}$ being selected from Leu (L), Ser (S) and Arg (R);
X$_{15}$ being selected from Pro (P), Ala (A) and Gln (Q);
X$_{16}$ being selected from Ser (S) and Thr (T); and
X$_{17}$ being selected from Gln (Q) and His (H).

In one embodiment, the antibody or binding fragment thereof according to the present invention comprises a LCVR which comprises at least one, preferably at least two, more preferably the following three complementary-determining regions (CDRs):

V$_L$-CDR1: X$_{11}$-ASSSVS-X$_{12}$-YMH; (SEQ ID NO: 12)

V$_L$-CDR2: X$_{13}$-TSN-X$_{14}$-X$_{15}$-X$_{16}$; (SEQ ID NO: 13)
and

V$_L$-CDR3: X$_{17}$-QRSSYPLTF, (SEQ ID NO: 14)

with:
X$_{11}$ being Ser (S);
X$_{12}$ being absent or being selected from Asn (N), Ser (S) and Gly (G);
X$_{13}$ being Asn (N); or X$_{13}$ being any amino acid but Ala (A) or Asn (N);
X$_{14}$ being Leu (L);
X$_{15}$ being Pro (P);
X$_{16}$ being Ser (S); and
X$_{17}$ being Gln (Q).

In one embodiment, the antibody or binding fragment thereof according to the present invention comprises a LCVR which comprises the following three CDRs:

V$_L$-CDR1: X$_{11}$-ASSSVS-X$_{12}$-YMH; (SEQ ID NO: 12)

```
V_L-CDR2: X_13-TSN-X_14-X_15-X_16;    (SEQ ID NO: 13)
and

V_L-CDR3: X_17-QRSSYPLTF,             (SEQ ID NO: 14)
``` with:
- X_11 being Ser (S);
- X_12 being absent or being selected from Asn (N), Ser (S) and Gly (G);
- X_13 being Asn (N); or X_13 being any amino acid but Ala (A) or Asn (N);
- X_14 being Leu (L);
- X_15 being Pro (P);
- X_16 being Ser (S); and
- X_17 being Gln (Q).

In one embodiment, the antibody or binding fragment thereof according to the present invention comprises a LCVR which comprises at least one, preferably at least two, more preferably the following three CDRs:

```
V_L-CDR1: SASSSVS-X_12-YMH;           (SEQ ID NO: 15)

V_L-CDR2: NTSNLPS;                    (SEQ ID NO: 16)
and

V_L-CDR3: QQRSSYPLTF,                 (SEQ ID NO: 17)
``` with:
X_12 being absent or being selected from Asn (N), Ser (S) and Gly (G).

In one embodiment, the antibody or binding fragment thereof according to the present invention comprises a LCVR which comprises the following three CDRs:

```
V_L-CDR1: SASSSVS-X_12-YMH;           (SEQ ID NO: 15)

V_L-CDR2: NTSNLPS;                    (SEQ ID NO: 16)
and

V_L-CDR3: QQRSSYPLTF,                 (SEQ ID NO: 17)
``` with:
X_12 being absent or being selected from Asn (N), Ser (S) and Gly (G).

In one embodiment, the antibody or binding fragment thereof according to the present invention comprises a LCVR which comprises at least one, preferably at least two, more preferably the following three CDRs:

```
V_L-CDR1: SASSSVSYMH;                 (SEQ ID NO: 15)

V_L-CDR2: NTSNLPS;                    (SEQ ID NO: 16)
and

V_L-CDR3: QQRSSYPLTF.                 (SEQ ID NO: 17)
```

In one embodiment, the antibody or binding fragment thereof according to the present invention comprises a LCVR which comprises the following three CDRs:

```
V_L-CDR1: SASSSVSYMH;                 (SEQ ID NO: 15)

V_L-CDR2: NTSNLPS;                    (SEQ ID NO: 16)
and

V_L-CDR3: QQRSSYPLTF.                 (SEQ ID NO: 17)
```

In one embodiment, the antibody or binding fragment thereof according to the present invention comprises a LCVR which comprises at least one, preferably at least two, more preferably the following three CDRs:

```
V_L-CDR1: SASSSVS-X_12-YMH;           (SEQ ID NO: 15)

V_L-CDR2: NTSNLPS;                    (SEQ ID NO: 16)
and

V_L-CDR3: QQRSSYPLTF,                 (SEQ ID NO: 17)
``` with:
X_12 being selected from Asn (N), Ser (S) and Gly (G).

In one embodiment, the antibody or binding fragment thereof according to the present invention comprises a LCVR which comprises the following three CDRs:

```
V_L-CDR1: SASSSVS-X_12-YMH;           (SEQ ID NO: 15)

V_L-CDR2: NTSNLPS;                    (SEQ ID NO: 16)
and

V_L-CDR3: QQRSSYPLTF,                 (SEQ ID NO: 17)
``` with:
X_12 being selected from Asn (N), Ser (S) and Gly (G).

In one embodiment, the antibody or binding fragment thereof according to the present invention comprises a LCVR which comprises at least one, preferably at least two, more preferably the following three CDRs:

```
V_L-CDR1: RASSSVS-X_12-YMH;           (SEQ ID NO: 18)

V_L-CDR2: NTSNLPS;                    (SEQ ID NO: 16)
and

V_L-CDR3: QQRSSYPLTF,                 (SEQ ID NO: 17)
``` with:
X_12 being absent or being selected from Asn (N), Ser (S) and Gly (G).

In one embodiment, the antibody or binding fragment thereof according to the present invention comprises a LCVR which comprises the following three CDRs:

```
V_L-CDR1: RASSSVS-X_12-YMH;           (SEQ ID NO: 18)

V_L-CDR2: NTSNLPS;                    (SEQ ID NO: 16)
```

-continued and

V<sub>L</sub>-CDR3: QQRSSYPLTF, (SEQ ID NO: 17)

with:

X$_{12}$ being absent or being selected from Asn (N), Ser (S) and Gly (G).

In one embodiment, the antibody or binding fragment thereof according to the present invention comprises a LCVR which comprises at least one, preferably at least two, more preferably the following three CDRs:

V$_L$-CDR1: RASSSVSYMH; (SEQ ID NO: 18)

V$_L$-CDR2: NTSNLPS; (SEQ ID NO: 16)
and

V$_L$-CDR3: QQRSSYPLTF. (SEQ ID NO: 17)

In one embodiment, the antibody or binding fragment thereof according to the present invention comprises a LCVR which comprises the following three CDRs:

V$_L$-CDR1: RASSSVSYMH; (SEQ ID NO: 18)

V$_L$-CDR2: NTSNLPS; (SEQ ID NO: 16)
and

V$_L$-CDR3: QQRSSYPLTF. (SEQ ID NO: 17)

In one embodiment, the antibody or binding fragment thereof according to the present invention comprises a LCVR which comprises at least one, preferably at least two, more preferably the following three CDRs:

V$_L$-CDR1: RASSSVS-X$_{12}$-YMH; (SEQ ID NO: 18)

V$_L$-CDR2: NTSNLPS; (SEQ ID NO: 16)
and

V$_L$-CDR3: QQRSSYPLTF, (SEQ ID NO: 17)

with:

X$_{12}$ being selected from Asn (N), Ser (S) and Gly (G).

In one embodiment, the antibody or binding fragment thereof according to the present invention comprises a LCVR which comprises the following three CDRs:

V$_L$-CDR1: RASSSVS-X$_{12}$-YMH; (SEQ ID NO: 18)

V$_L$-CDR2: NTSNLPS; (SEQ ID NO: 16)
and

V$_L$-CDR3: QQRSSYPLTF, (SEQ ID NO: 17)

with:

X$_{12}$ being selected from Asn (N), Ser (S) and Gly (G).

In one embodiment, the antibody or binding fragment thereof according to the present invention comprises a LCVR which comprises at least one, preferably at least two, more preferably the following three CDRs:

V$_L$-CDR1:
RASSSVS-X$_{12}$-YMH; (SEQ ID NO: 18)

V$_L$-CDR2:
NTSNSPS; (SEQ ID NO: 19)
and

V$_L$-CDR3:
QQRSSYPLTF, (SEQ ID NO: 17)

with:

X$_{12}$ being absent or being selected from Asn (N), Ser (S) and Gly (G).

In one embodiment, the antibody or binding fragment thereof according to the present invention comprises a LCVR which comprises the following three CDRs:

V$_L$-CDR1:
RASSSVS-X$_{12}$-YMH; (SEQ ID NO: 18)

V$_L$-CDR2:
NTSNSPS; (SEQ ID NO: 19)
and

V$_L$-CDR3:
QQRSSYPLTF, (SEQ ID NO: 17)

with:

X$_{12}$ being absent or being selected from Asn (N), Ser (S) and Gly (G).

In one embodiment, the antibody or binding fragment thereof according to the present invention comprises a LCVR which comprises at least one, preferably at least two, more preferably the following three CDRs:

V$_L$-CDR1:
RASSSVSYMH; (SEQ ID NO: 18)

V$_L$-CDR2:
NTSNSPS; (SEQ ID NO: 19)
and

V$_L$-CDR3:
QQRSSYPLTF. (SEQ ID NO: 17)

In one embodiment, the antibody or binding fragment thereof according to the present invention comprises a LCVR which comprises the following three CDRs:

V$_L$-CDR1:
RASSSVSYMH; (SEQ ID NO: 18)

V$_L$-CDR2:
NTSNSPS; (SEQ ID NO: 19)

and

V$_L$-CDR3:
QQRSSYPLTF. (SEQ ID NO: 17)

In one embodiment, the antibody or binding fragment thereof according to the present invention comprises a LCVR which comprises at least one, preferably at least two, more preferably the following three CDRs:

V$_L$-CDR1:
RASSSVS-X$_{12}$-YMH; (SEQ ID NO: 18)

V$_L$-CDR2:
NTSNSPS; (SEQ ID NO: 19)
and

V$_L$-CDR3:
QQRSSYPLTF, (SEQ ID NO: 17)

with:
X$_{12}$ being selected from Asn (N), Ser (S) and Gly (G).

In one embodiment, the antibody or binding fragment thereof according to the present invention comprises a LCVR which comprises the following three CDRs:

V$_L$-CDR1:
RASSSVS-X$_{12}$-YMH; (SEQ ID NO: 18)

V$_L$-CDR2:
NTSNSPS; (SEQ ID NO: 19)
and

V$_L$-CDR3:
QQRSSYPLTF, (SEQ ID NO: 17)

with:
X$_{12}$ being selected from Asn (N), Ser (S) and Gly (G).

In one embodiment, the antibody or binding fragment thereof according to the present invention comprises a LCVR which comprises at least one, preferably at least two, more preferably the following three CDRs:

V$_L$-CDR1:
RASSSVS-X$_{12}$-YMH; (SEQ ID NO: 18)

V$_L$-CDR2:
ATSNLQS; (SEQ ID NO: 20)
and

V$_L$-CDR3:
QQRSSYPLTF, (SEQ ID NO: 17)

with:
X$_{12}$ being absent or being selected from Asn (N), Ser (S) and Gly (G).

In one embodiment, the antibody or binding fragment thereof according to the present invention comprises a LCVR which comprises the following three CDRs:

V$_L$-CDR1:
RASSSVS-X$_{12}$-YMH; (SEQ ID NO: 18)

V$_L$-CDR2:
ATSNLQS; (SEQ ID NO: 20)
and

V$_L$-CDR3:
QQRSSYPLTF, (SEQ ID NO: 17)

with:
X$_{12}$ being absent or being selected from Asn (N), Ser (S) and Gly (G).

In one embodiment, the antibody or binding fragment thereof according to the present invention comprises a LCVR which comprises at least one, preferably at least two, more preferably the following three CDRs:

V$_L$-CDR1:
RASSSVSYMH; (SEQ ID NO: 18)

V$_L$-CDR2:
ATSNLQS; (SEQ ID NO: 20)
and

V$_L$-CDR3:
QQRSSYPLTF. (SEQ ID NO: 17)

In one embodiment, the antibody or binding fragment thereof according to the present invention comprises a LCVR which comprises the following three CDRs:

V$_L$-CDR1:
RASSSVSYMH; (SEQ ID NO: 18)

V$_L$-CDR2:
ATSNLQS; (SEQ ID NO: 20)
and

V$_L$-CDR3:
QQRSSYPLTF. (SEQ ID NO: 17)

In one embodiment, the antibody or binding fragment thereof according to the present invention comprises a LCVR which comprises at least one, preferably at least two, more preferably the following three CDRs:

V$_L$-CDR1:
RASSSVS-X$_{12}$-YMH; (SEQ ID NO: 18)

V$_L$-CDR2:
ATSNLQS; (SEQ ID NO: 20)
and

V$_L$-CDR3:
QQRSSYPLTF, (SEQ ID NO: 17)

with:
X$_{12}$ being selected from Asn (N), Ser (S) and Gly (G).

In one embodiment, the antibody or binding fragment thereof according to the present invention comprises a LCVR which comprises the following three CDRs:

V$_L$-CDR1:
RASSSVS-X$_{12}$-YMH; (SEQ ID NO: 18)

V$_L$-CDR2:
ATSNLQS; (SEQ ID NO: 20)
and

V$_L$-CDR3:
QQRSSYPLTF, (SEQ ID NO: 17)

In one embodiment, the antibody or binding fragment thereof according to the present invention comprises a LCVR which comprises at least one, preferably at least two, more preferably the following three CDRs:

V$_L$-CDR1:
RASSSVS-X$_{12}$-YMH; (SEQ ID NO: 18)

V$_L$-CDR2:
NTSNSPS; (SEQ ID NO: 19)
and

V$_L$-CDR3:
HQRSSYPLTF, (SEQ ID NO: 21)

with:
X$_{12}$ being absent or being selected from Asn (N), Ser (S) and Gly (G).

In one embodiment, the antibody or binding fragment thereof according to the present invention comprises a LCVR which comprises the following three CDRs:

V$_L$-CDR1:
RASSSVS-X$_{12}$-YMH; (SEQ ID NO: 18)

V$_L$-CDR2:
NTSNSPS; (SEQ ID NO: 19)
and

V$_L$-CDR3:
HQRSSYPLTF, (SEQ ID NO: 21)

with:
X$_{12}$ being absent or being selected from Asn (N), Ser (S) and Gly (G).

In one embodiment, the antibody or binding fragment thereof according to the present invention comprises a LCVR which comprises at least one, preferably at least two, more preferably the following three CDRs:

V$_L$-CDR1:
RASSSVSYMH; (SEQ ID NO: 18)

V$_L$-CDR2:
NTSNSPS; (SEQ ID NO: 19)
and

V$_L$-CDR3:
HQRSSYPLTF. (SEQ ID NO: 21)

In one embodiment, the antibody or binding fragment thereof according to the present invention comprises a LCVR which comprises the following three CDRs:

V$_L$-CDR1:
RASSSVSYMH; (SEQ ID NO: 18)

V$_L$-CDR2:
NTSNSPS; (SEQ ID NO: 19)
and

V$_L$-CDR3:
HQRSSYPLTF. (SEQ ID NO: 21)

In one embodiment, the antibody or binding fragment thereof according to the present invention comprises a LCVR which comprises at least one, preferably at least two, more preferably the following three CDRs:

V$_L$-CDR1:
RASSSVS-X$_{12}$-YMH; (SEQ ID NO: 18)

V$_L$-CDR2:
NTSNSPS; (SEQ ID NO: 19)
and

V$_L$-CDR3:
HQRSSYPLTF, (SEQ ID NO: 21)

with:
X$_{12}$ being selected from Asn (N), Ser (S) and Gly (G).

In one embodiment, the antibody or binding fragment thereof according to the present invention comprises a LCVR which comprises the following three CDRs:

V$_L$-CDR1:
RASSSVS-X$_{12}$-YMH; (SEQ ID NO: 18)

V$_L$-CDR2:
NTSNSPS; (SEQ ID NO: 19)
and

V$_L$-CDR3:
HQRSSYPLTF, (SEQ ID NO: 21)

with:
X$_{12}$ being selected from Asn (N), Ser (S) and Gly (G).

In one embodiment, the antibody or binding fragment thereof according to the present invention comprises a LCVR which comprises at least one, preferably at least two, more preferably the following three CDRs:

V$_L$-CDR1:
RASSSVS-X$_{12}$-YMH; (SEQ ID NO: 18)

V$_L$-CDR2:
NTSNRAT; (SEQ ID NO: 22)
and

V$_L$-CDR3:
QQRSSYPLTF, (SEQ ID NO: 17)

with:

$X_{12}$ being absent or being selected from Asn (N), Ser (S) and Gly (G).

In one embodiment, the antibody or binding fragment thereof according to the present invention comprises a LCVR which comprises the following three CDRs:

```
V_L-CDR1:
                                         (SEQ ID NO: 18)
RASSSVS-X_12-YMH;

V_L-CDR2:
                                         (SEQ ID NO: 22)
NTSNRAT;
and

V_L-CDR3:
                                         (SEQ ID NO: 17)
QQRSSYPLTF,
``` with:

$X_{12}$ being absent or being selected from Asn (N), Ser (S) and Gly (G).

In one embodiment, the antibody or binding fragment thereof according to the present invention comprises a LCVR which comprises at least one, preferably at least two, more preferably the following three CDRs:

```
V_L-CDR1:
                                         (SEQ ID NO: 18)
RASSSVSYMH;

V_L-CDR2:
                                         (SEQ ID NO: 22)
NTSNRAT;
and

V_L-CDR3:
                                         (SEQ ID NO: 17)
QQRSSYPLTF.
```

In one embodiment, the antibody or binding fragment thereof according to the present invention comprises a LCVR which comprises the following three CDRs:

```
V_L-CDR1:
                                         (SEQ ID NO: 18)
RASSSVSYMH;

V_L-CDR2:
                                         (SEQ ID NO: 22)
NTSNRAT;
and

V_L-CDR3:
                                         (SEQ ID NO: 17)
QQRSSYPLTF.
```

In one embodiment, the antibody or binding fragment thereof according to the present invention comprises a LCVR which comprises at least one, preferably at least two, more preferably the following three CDRs:

```
V_L-CDR1:
                                         (SEQ ID NO: 18)
RASSSVS-X_12-YMH;

V_L-CDR2:
                                         (SEQ ID NO: 22)
NTSNRAT;
and

V_L-CDR3:
                                         (SEQ ID NO: 17)
QQRSSYPLTF,
``` with:

$X_{12}$ being selected from Asn (N), Ser (S) and Gly (G).

In one embodiment, the antibody or binding fragment thereof according to the present invention comprises a LCVR which comprises the following three CDRs:

```
V_L-CDR1:
                                         (SEQ ID NO: 18)
RASSSVS-X_12-YMH;

V_L-CDR2:
                                         (SEQ ID NO: 22)
NTSNRAT;
and

V_L-CDR3:
                                         (SEQ ID NO: 17)
QQRSSYPLTF,
``` with:

$X_{12}$ being selected from Asn (N), Ser (S) and Gly (G).

In one embodiment, the antibody or binding fragment thereof according to the present invention comprises a LCVR which comprises at least one, preferably at least two, more preferably the following three CDRs:

```
V_L-CDR1:
                                         (SEQ ID NO: 18)
RASSSVS-X_12-YMH;

V_L-CDR2:
                                         (SEQ ID NO: 111)
ATSNLPS;
and V_L-CDR3:
                                         (SEQ ID NO: 17)
QQRSSYPLTF,
``` with:

$X_{12}$ being absent or being selected from Asn (N), Ser (S) and Gly (G).

In one embodiment, the antibody or binding fragment thereof according to the present invention comprises a LCVR which comprises the following three CDRs:

```
V_L-CDR1:
                                         (SEQ ID NO: 18)
RASSSVS-X_12-YMH;

V_L-CDR2:
                                         (SEQ ID NO: 111)
ATSNLPS;
and V_L-CDR3:
                                         (SEQ ID NO: 17)
QQRSSYPLTF,
``` with:

$X_{12}$ being absent or being selected from Asn (N), Ser (S) and Gly (G).

In one embodiment, the antibody or binding fragment thereof according to the present invention comprises a LCVR which comprises at least one, preferably at least two, more preferably the following three CDRs:

```
V_L-CDR1:
                                    (SEQ ID NO: 18)
RASSSVSYMH;

V_L-CDR2:
                                    (SEQ ID NO: 111)
ATSNLPS;
and

V_L-CDR3:
                                    (SEQ ID NO: 17)
QQRSSYPLTF.
```

In one embodiment, the antibody or binding fragment thereof according to the present invention comprises a LCVR which comprises the following three CDRs:

```
V_L-CDR1:
                                    (SEQ ID NO: 18)
RASSSVSYMH;

V_L-CDR2:
                                    (SEQ ID NO: 111)
ATSNLPS;
and

V_L-CDR3:
                                    (SEQ ID NO: 17)
QQRSSYPLTF.
```

In one embodiment, the antibody or binding fragment thereof according to the present invention comprises a LCVR which comprises at least one, preferably at least two, more preferably the following three CDRs:

```
V_L-CDR1:
                                    (SEQ ID NO: 18)
RASSSVS-X_12-YMH;

V_L-CDR2:
                                    (SEQ ID NO: 111)
ATSNLPS;
and

V_L-CDR3:
                                    (SEQ ID NO: 17)
QQRSSYPLTF,
``` with:

$X_{12}$ being selected from Asn (N), Ser (S) and Gly (G).

In one embodiment, the antibody or binding fragment thereof according to the present invention comprises a LCVR which comprises the following three CDRs:

```
V_L-CDR1:
                                    (SEQ ID NO: 18)
RASSSVS-X_12-YMH;

V_L-CDR2:
                                    (SEQ ID NO: 111)
ATSNLPS;
and

V_L-CDR3:
                                    (SEQ ID NO: 17)
QQRSSYPLTF,
``` with:

$X_{12}$ being selected from Asn (N), Ser (S) and Gly (G).

In one embodiment, the antibody or binding fragment thereof according to the present invention comprises a LCVR which comprises at least one, preferably at least two, more preferably the following three CDRs:

```
V_L-CDR1:
                                    (SEQ ID NO: 15)
SASSSVS-X_12-YMH;

V_L-CDR2:
                                    (SEQ ID NO: 120)
NTANLPS;
and

V_L-CDR3:
                                    (SEQ ID NO: 17)
QQRSSYPLTF,
``` with:

$X_{12}$ being absent or being selected from Asn (N), Ser (S) and Gly (G).

In one embodiment, the antibody or binding fragment thereof according to the present invention comprises a LCVR which comprises the following three CDRs:

```
V_L-CDR1:
                                    (SEQ ID NO: 15)
SASSSVS-X_12-YMH;

V_L-CDR2:
                                    (SEQ ID NO: 120)
NTANLPS;
and

V_L-CDR3:
                                    (SEQ ID NO: 17)
QQRSSYPLTF,
``` with:

$X_{12}$ being absent or being selected from Asn (N), Ser (S) and Gly (G).

In one embodiment, the antibody or binding fragment thereof according to the present invention comprises a LCVR which comprises at least one, preferably at least two, more preferably the following three CDRs:

```
V_L-CDR1:
                                    (SEQ ID NO: 15)
SASSSVS-X_12-YMH;

V_L-CDR2:
                                    (SEQ ID NO: 120)
NTANLPS;
and

V_L-CDR3:
                                    (SEQ ID NO: 17)
QQRSSYPLTF,
```

In one embodiment, the antibody or binding fragment thereof according to the present invention comprises a LCVR which comprises the following three CDRs:

```
V_L-CDR1:
                                    (SEQ ID NO: 15)
SASSSVS-X_12-YMH;

V_L-CDR2:
                                    (SEQ ID NO: 120)
NTANLPS;
and

V_L-CDR3:
                                    (SEQ ID NO: 17)
QQRSSYPLTF,
```

In one embodiment, the antibody or binding fragment thereof according to the present invention comprises a LCVR which comprises at least one, preferably at least two, more preferably the following three CDRs:

$V_L$-CDR1:
(SEQ ID NO: 15)
SASSSVS-$X_{12}$-YMH;

$V_L$-CDR2:
(SEQ ID NO: 120)
NTANLPS;
and $V_L$-CDR3:
(SEQ ID NO: 17)
QQRSSYPLTF, with:
$X_{12}$ being selected from Asn (N), Ser (S) and Gly (G).

In one embodiment, the antibody or binding fragment thereof according to the present invention comprises a LCVR which comprises the following three CDRs:

$V_L$-CDR1:
(SEQ ID NO: 15)
SASSSVS-$X_{12}$-YMH;

$V_L$-CDR2:
(SEQ ID NO: 120)
NTANLPS;
and $V_L$-CDR3:
(SEQ ID NO: 17)
QQRSSYPLTF, with:
$X_{12}$ being selected from Asn (N), Ser (S) and Gly (G).

In one embodiment, the antibody or binding fragment thereof according to the present invention comprises a LCVR which comprises at least one, preferably at least two, more preferably the following three CDRs:

$V_L$-CDR1:
(SEQ ID NO: 18)
RASSSVS-$X_{12}$-YMH;

$V_L$-CDR2:
(SEQ ID NO: 127)
$X_{13}$-TSNLPS;
and $V_L$-CDR3:
(SEQ ID NO: 17)
QQRSSYPLTF, with:
$X_{12}$ being absent or being selected from Asn (N), Ser (S) and Gly (G), and
$X_{13}$ being any amino acid but Ala (A) or Asn (N).

In one embodiment, the antibody or binding fragment thereof according to the present invention comprises a LCVR which comprises the following three CDRs:

$V_L$-CDR1:
(SEQ ID NO: 18)
RASSSVS-$X_{12}$-YMH;

$V_L$-CDR2:
(SEQ ID NO: 127)
$X_{13}$-TSNLPS;
and $V_L$-CDR3:
(SEQ ID NO: 17)
QQRSSYPLTF, with:
$X_{12}$ being absent or being selected from Asn (N), Ser (S) and Gly (G), and
$X_{13}$ being any amino acid but Ala (A) or Asn (N).

In one embodiment, the antibody or binding fragment thereof according to the present invention comprises a LCVR which comprises at least one, preferably at least two, more preferably the following three CDRs:

$V_L$-CDR1:
(SEQ ID NO: 18)
RASSSVS-$X_{12}$-YMH;

$V_L$-CDR2:
(SEQ ID NO: 127)
$X_{13}$-TSNLPS;
and $V_L$-CDR3:
(SEQ ID NO: 17)
QQRSSYPLTF.

with:
$X_{13}$ being any amino acid but Ala (A) or Asn (N).

In one embodiment, the antibody or binding fragment thereof according to the present invention comprises a LCVR which comprises the following three CDRs:

$V_L$-CDR1:
(SEQ ID NO: 18)
RASSSVS-$X_{12}$-YMH;

$V_L$-CDR2:
(SEQ ID NO: 127)
$X_{13}$-TSNLPS;
and $V_L$-CDR3:
(SEQ ID NO: 17)
QQRSSYPLTF.

with:
$X_{13}$ being any amino acid but Ala (A) or Asn (N).

In one embodiment, the antibody or binding fragment thereof according to the present invention comprises a LCVR which comprises at least one, preferably at least two, more preferably the following three CDRs:

$V_L$-CDR1:
(SEQ ID NO: 18)
RASSSVS-$X_{12}$-YMH;

-continued

V$_L$-CDR2:
(SEQ ID NO: 127)
X$_{13}$-TSNLPS;
and

V$_L$-CDR3:
(SEQ ID NO: 17)
QQRSSYPLTF, with:
X$_{12}$ being absent or being selected from Asn (N), Ser (S) and Gly (G), and
X$_{13}$ being any amino acid but Ala (A) or Asn (N).

In one embodiment, the antibody or binding fragment thereof according to the present invention comprises:
a HCVR which comprises at least one, preferably at least two, more preferably the following three CDRs:

V$_H$-CDR1:
(SEQ ID NO: 1)
NYYIG;

V$_H$-CDR2:
(SEQ ID NO: 2)
X$_1$-IF-X$_2$-GG-X$_3$-Y-X$_4$-N-X$_5$-X$_6$-X$_7$-X$_8$-X$_9$-X$_{10}$-G;
and

V$_H$-CDR3:
(SEQ ID NO: 3)
RNFDY;

and
a LCVR which comprises at least one, preferably at least two, more preferably the following three CDRs:

V$_L$-CDR1:
(SEQ ID NO: 12)
X$_{11}$-ASSSVS-X$_{12}$-YMH;

V$_L$-CDR2:
(SEQ ID NO: 13)
X$_{13}$-TSN-X$_{14}$-X$_{15}$-X$_{16}$;
and

V$_L$-CDR3:
(SEQ ID NO: 14)
X17-QRSSYPLTF, with:
X$_1$ being selected from Asp (D), Ile (I) and Arg (R);
X$_2$ being selected from Pro (P) and Ser (S);
X$_3$ being selected from Asp (D), Ser (S) and Gly (G);
X$_4$ being selected from Ala (A) and Thr (T);
X$_5$ being selected from Ser (S) and Tyr (Y);
X$_6$ being selected from Asn (N), Ala (A) and Ser (S);
X$_7$ being selected from Glu (E), Asp (D), Pro (P) and Gln (Q);
X$_8$ being selected from Lys (K) and Ser (S);
X$_9$ being selected from Phe (F) and Val (V);
X$_{10}$ being selected from Lys (K) and Gln (Q);
X$_{11}$ being selected from Ser (S) and Arg (R);
X$_{12}$ being absent or being selected from Asn (N), Ser (S) and Gly (G);
X$_{13}$ being selected from Asn (N) and Ala (A); or X$_{13}$ being any amino acid but Ala (A) or Asn (N);
X$_{14}$ being selected from Leu (L), Ser (S) and Arg (R);
X$_{15}$ being selected from Pro (P), Ala (A) and Gln (Q);
X$_{16}$ being selected from Ser (S) and Thr (T); and
X$_{17}$ being selected from Gln (Q) and His (H).

In one embodiment, the antibody or binding fragment thereof according to the present invention comprises:

a HCVR which comprises the following three CDRs:

V$_H$-CDR1:
(SEQ ID NO: 1)
NYYIG;

V$_H$-CDR2:
(SEQ ID NO: 2)
X$_1$-IF-X$_2$-GG-X$_3$-Y-X$_4$-N-X$_5$-X$_6$-X$_7$-X$_8$-X$_9$-X$_{10}$-G;
and

V$_H$-CDR3:
(SEQ ID NO: 3)
RNFDY;

and
a LCVR which comprises the following three CDRs:

V$_L$-CDR1:
(SEQ ID NO: 12)
X$_{11}$-ASSSVS-X$_{12}$-YMH;

V$_L$-CDR2:
(SEQ ID NO: 13)
X$_{13}$-TSN-X$_{14}$-X$_{15}$-X$_{16}$;
and

V$_L$-CDR3:
(SEQ ID NO: 14)
X$_{17}$-QRSSYPLTF, with:
X$_1$ being selected from Asp (D), Ile (I) and Arg (R);
X$_2$ being selected from Pro (P) and Ser (S);
X$_3$ being selected from Asp (D), Ser (S) and Gly (G);
X$_4$ being selected from Ala (A) and Thr (T);
X$_5$ being selected from Ser (S) and Tyr (Y);
X$_6$ being selected from Asn (N), Ala (A) and Ser (S);
X$_7$ being selected from Glu (E), Asp (D), Pro (P) and Gln (Q);
X$_8$ being selected from Lys (K) and Ser (S);
X$_9$ being selected from Phe (F) and Val (V);
X$_{10}$ being selected from Lys (K) and Gln (Q);
X$_{11}$ being selected from Ser (S) and Arg (R);
X$_{12}$ being absent or being selected from Asn (N), Ser (S) and Gly (G);
X$_{13}$ being selected from Asn (N) and Ala (A); or X$_{13}$ being any amino acid but Ala (A) or Asn (N);
X$_{14}$ being selected from Leu (L), Ser (S) and Arg (R);
X$_{15}$ being selected from Pro (P), Ala (A) and Gln (Q);
X$_{16}$ being selected from Ser (S) and Thr (T); and
X$_{17}$ being selected from Gln (Q) and His (H).

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being as defined in Table 2.

In one embodiment, the antibody or binding fragment thereof according to the present invention comprises a combination of (i) three HCVR's CDRs and (ii) three LCVR's CDRs, said combination being as defined in Table 2.

TABLE 2

Preferred combinations of HCVR's and LCVR's CDRs. The CDRs are defined by their SEQ ID NOs (with, wherever applicable, $X_{12}$ being absent or being selected from Asn (N), Ser (S) and Gly (G); and $X_{13}$ being any amino acid but Ala (A) or Asn (N)).

| CDRs' combination # | $V_H$-CDR1 | $V_H$-CDR2 | $V_H$-CDR3 | $V_L$-CDR1 | $V_L$-CDR2 | $V_L$-CDR3 |
|---|---|---|---|---|---|---|
| #1 | 1 | 4 | 3 | 15 | 16 | 17 |
| #2 | 1 | 4 | 3 | 18 | 16 | 17 |
| #3 | 1 | 4 | 3 | 18 | 19 | 17 |
| #4 | 1 | 4 | 3 | 18 | 20 | 17 |
| #5 | 1 | 4 | 3 | 18 | 19 | 21 |
| #6 | 1 | 4 | 3 | 18 | 22 | 17 |
| #7 | 1 | 5 | 3 | 15 | 16 | 17 |
| #8 | 1 | 5 | 3 | 18 | 16 | 17 |
| #9 | 1 | 5 | 3 | 18 | 19 | 17 |
| #10 | 1 | 5 | 3 | 18 | 20 | 17 |
| #11 | 1 | 5 | 3 | 18 | 19 | 21 |
| #12 | 1 | 5 | 3 | 18 | 22 | 17 |
| #13 | 1 | 6 | 3 | 15 | 16 | 17 |
| #14 | 1 | 6 | 3 | 18 | 16 | 17 |
| #15 | 1 | 6 | 3 | 18 | 19 | 17 |
| #16 | 1 | 6 | 3 | 18 | 20 | 17 |
| #17 | 1 | 6 | 3 | 18 | 19 | 21 |
| #18 | 1 | 6 | 3 | 18 | 22 | 17 |
| #19 | 1 | 7 | 3 | 15 | 16 | 17 |
| #20 | 1 | 7 | 3 | 18 | 16 | 17 |
| #21 | 1 | 7 | 3 | 18 | 19 | 17 |
| #22 | 1 | 7 | 3 | 18 | 20 | 17 |
| #23 | 1 | 7 | 3 | 18 | 19 | 21 |
| #24 | 1 | 7 | 3 | 18 | 22 | 17 |
| #25 | 1 | 8 | 3 | 15 | 16 | 17 |
| #26 | 1 | 8 | 3 | 18 | 16 | 17 |
| #27 | 1 | 8 | 3 | 18 | 19 | 17 |
| #28 | 1 | 8 | 3 | 18 | 20 | 17 |
| #29 | 1 | 8 | 3 | 18 | 19 | 21 |
| #30 | 1 | 8 | 3 | 18 | 22 | 17 |
| #31 | 1 | 9 | 3 | 15 | 16 | 17 |
| #32 | 1 | 9 | 3 | 18 | 16 | 17 |
| #33 | 1 | 9 | 3 | 18 | 19 | 17 |
| #34 | 1 | 9 | 3 | 18 | 20 | 17 |
| #35 | 1 | 9 | 3 | 18 | 19 | 21 |
| #36 | 1 | 9 | 3 | 18 | 22 | 17 |
| #37 | 1 | 10 | 3 | 15 | 16 | 17 |
| #38 | 1 | 10 | 3 | 18 | 16 | 17 |
| #39 | 1 | 10 | 3 | 18 | 19 | 17 |
| #40 | 1 | 10 | 3 | 18 | 20 | 17 |
| #41 | 1 | 10 | 3 | 18 | 19 | 21 |
| #42 | 1 | 10 | 3 | 18 | 22 | 17 |
| #43 | 1 | 11 | 3 | 15 | 16 | 17 |
| #44 | 1 | 11 | 3 | 18 | 16 | 17 |
| #45 | 1 | 11 | 3 | 18 | 19 | 17 |
| #46 | 1 | 11 | 3 | 18 | 20 | 17 |
| #47 | 1 | 11 | 3 | 18 | 19 | 21 |
| #48 | 1 | 11 | 3 | 18 | 22 | 17 |
| #49 | 1 | 100 | 3 | 15 | 16 | 17 |
| #50 | 1 | 100 | 3 | 18 | 16 | 17 |
| #51 | 1 | 100 | 3 | 18 | 19 | 17 |
| #52 | 1 | 100 | 3 | 18 | 20 | 17 |
| #53 | 1 | 100 | 3 | 18 | 19 | 21 |
| #54 | 1 | 100 | 3 | 18 | 22 | 17 |
| #55 | 1 | 4 | 3 | 18 | 111 | 17 |
| #56 | 1 | 5 | 3 | 18 | 111 | 17 |
| #57 | 1 | 6 | 3 | 18 | 111 | 17 |
| #58 | 1 | 7 | 3 | 18 | 111 | 17 |
| #59 | 1 | 8 | 3 | 18 | 111 | 17 |
| #60 | 1 | 9 | 3 | 18 | 111 | 17 |
| #61 | 1 | 10 | 3 | 18 | 111 | 17 |
| #62 | 1 | 11 | 3 | 18 | 111 | 17 |
| #63 | 1 | 100 | 3 | 18 | 111 | 17 |
| #64 | 1 | 116 | 3 | 15 | 16 | 17 |
| #65 | 1 | 116 | 3 | 18 | 16 | 17 |
| #66 | 1 | 116 | 3 | 18 | 19 | 17 |
| #67 | 1 | 116 | 3 | 18 | 20 | 17 |
| #68 | 1 | 116 | 3 | 18 | 19 | 21 |
| #69 | 1 | 116 | 3 | 18 | 22 | 17 |
| #70 | 1 | 116 | 3 | 18 | 111 | 17 |
| #71 | 1 | 117 | 3 | 15 | 16 | 17 |
| #72 | 1 | 117 | 3 | 18 | 16 | 17 |

TABLE 2-continued

Preferred combinations of HCVR's and LCVR's CDRs. The CDRs are defined by their SEQ ID NOs (with, wherever applicable, $X_{12}$ being absent or being selected from Asn (N), Ser (S) and Gly (G); and $X_{13}$ being any amino acid but Ala (A) or Asn (N)).

| CDRs' combination # | $V_H$-CDR1 | $V_H$-CDR2 | $V_H$-CDR3 | $V_L$-CDR1 | $V_L$-CDR2 | $V_L$-CDR3 |
|---|---|---|---|---|---|---|
| #73 | 1 | 117 | 3 | 18 | 19 | 17 |
| #74 | 1 | 117 | 3 | 18 | 20 | 17 |
| #75 | 1 | 117 | 3 | 18 | 19 | 21 |
| #76 | 1 | 117 | 3 | 18 | 22 | 17 |
| #77 | 1 | 117 | 3 | 18 | 111 | 17 |
| #78 | 1 | 118 | 3 | 15 | 16 | 17 |
| #79 | 1 | 118 | 3 | 18 | 16 | 17 |
| #80 | 1 | 118 | 3 | 18 | 19 | 17 |
| #81 | 1 | 118 | 3 | 18 | 20 | 17 |
| #82 | 1 | 118 | 3 | 18 | 19 | 21 |
| #83 | 1 | 118 | 3 | 18 | 22 | 17 |
| #84 | 1 | 118 | 3 | 18 | 111 | 17 |
| #85 | 1 | 119 | 3 | 15 | 16 | 17 |
| #86 | 1 | 119 | 3 | 18 | 16 | 17 |
| #87 | 1 | 119 | 3 | 18 | 19 | 17 |
| #88 | 1 | 119 | 3 | 18 | 20 | 17 |
| #89 | 1 | 119 | 3 | 18 | 19 | 21 |
| #90 | 1 | 119 | 3 | 18 | 22 | 17 |
| #91 | 1 | 119 | 3 | 18 | 111 | 17 |
| #92 | 1 | 4 | 3 | 15 | 120 | 17 |
| #93 | 1 | 5 | 3 | 15 | 120 | 17 |
| #94 | 1 | 6 | 3 | 15 | 120 | 17 |
| #95 | 1 | 7 | 3 | 15 | 120 | 17 |
| #96 | 1 | 8 | 3 | 15 | 120 | 17 |
| #97 | 1 | 9 | 3 | 15 | 120 | 17 |
| #98 | 1 | 10 | 3 | 15 | 120 | 17 |
| #99 | 1 | 11 | 3 | 15 | 120 | 17 |
| #100 | 1 | 100 | 3 | 15 | 120 | 17 |
| #101 | 1 | 116 | 3 | 15 | 120 | 17 |
| #102 | 1 | 117 | 3 | 15 | 120 | 17 |
| #103 | 1 | 118 | 3 | 15 | 120 | 17 |
| #104 | 1 | 119 | 3 | 15 | 120 | 17 |
| #105 | 1 | 4 | 3 | 15 | 127 | 17 |
| #106 | 1 | 5 | 3 | 15 | 127 | 17 |
| #107 | 1 | 6 | 3 | 15 | 127 | 17 |
| #108 | 1 | 7 | 3 | 15 | 127 | 17 |
| #109 | 1 | 8 | 3 | 15 | 127 | 17 |
| #110 | 1 | 9 | 3 | 15 | 127 | 17 |
| #111 | 1 | 10 | 3 | 15 | 127 | 17 |
| #112 | 1 | 11 | 3 | 15 | 127 | 17 |
| #113 | 1 | 100 | 3 | 15 | 127 | 17 |
| #114 | 1 | 116 | 3 | 15 | 127 | 17 |
| #115 | 1 | 117 | 3 | 15 | 127 | 17 |
| #116 | 1 | 118 | 3 | 15 | 127 | 17 |
| #117 | 1 | 119 | 3 | 15 | 127 | 17 |

In one embodiment, any of $V_H$-CDR1, $V_H$-CDR2, $V_H$-CDR3, $V_L$-CDR1, $V_L$-CDR2 and/or $V_L$-CDR3 as defined hereinabove can be characterized as having 1, 2, 3, 4, 5 or more amino acids being substituted by a different amino acid.

In one embodiment, any of $V_H$-CDR1, $V_H$-CDR2, $V_H$-CDR3, $V_L$-CDR1, $V_L$-CDR2 and/or $V_L$-CDR3 as defined hereinabove can be characterized as having an amino acid sequence that shares at least 70%, 75%, 80%, 85%, 90%, 95%, 96%, 97%, 98%, 99% or more of identity with the particular CDR or sets of CDRs as defined hereinabove.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being selected from combinations #1, #2, #7, #14, #20, #26, #49, #50, #63, #65, #72, #79, #86 and #92 as defined in Table 2.

In one embodiment, the antibody or binding fragment thereof according to the present invention comprises a combination of (i) three HCVR's CDRs and (ii) three LCVR's CDRs, said combination being selected from combinations #1, #2, #7, #14, #20, #26, #49, #50, #63, #65, #72, #79, #86 and #92 as defined in Table 2.

In one embodiment, the antibody or binding fragment thereof according to the present invention comprises:
a HCVR which comprises the following three CDRs:
$V_H$-CDR1 of sequence SEQ ID NO: 1;
$V_H$-CDR2 selected from the group comprising or consisting of sequences SEQ ID NOs: 4, 5, 6, 7, 8, 100, 116, 117, 118 and 119; and
$V_H$-CDR3 of sequence SEQ ID NO: 3; and
a LCVR which comprises the following three CDRs:
$V_L$-CDR1 selected from the group comprising or consisting of sequences SEQ ID NOs: 15 and 18, wherein $X_{12}$ is absent or is selected from Asn (N), Ser (S) and Gly (G), preferably $X_{12}$ is absent;
$V_L$-CDR2 selected from the group comprising or consisting of sequences SEQ ID NOs: 16, 111 and 120; and V$_L$-CDR3 of sequence SEQ ID NO: 17.

In one embodiment, the antibody or binding fragment thereof according to the present invention comprises:
a HCVR which comprises the following three CDRs:
V$_H$-CDR1 of sequence SEQ ID NO: 1;
V$_H$-CDR2 selected from the group comprising or consisting of sequences SEQ ID NOs: 4 and 5; and
V$_H$-CDR3 of sequence SEQ ID NO: 3; and
a LCVR which comprises the following three CDRs:
V$_L$-CDR1 of sequence SEQ ID NO: 15, wherein X$_{12}$ is absent or is selected from Asn (N), Ser (S) and Gly (G), preferably X$_{12}$ is absent;
V$_L$-CDR2 of sequence SEQ ID NO: 16; and
V$_L$-CDR3 of sequence SEQ ID NO: 17.

In one embodiment, the antibody or binding fragment thereof according to the present invention comprises:
a HCVR which comprises the following three CDRs:
V$_H$-CDR1 of sequence SEQ ID NO: 1;
V$_H$-CDR2 selected from the group comprising or consisting of sequences SEQ ID NOs: 4, 5, 6 and 100; and
V$_H$-CDR3 of sequence SEQ ID NO: 3; and
a LCVR which comprises the following three CDRs:
V$_L$-CDR1 selected from the group comprising or consisting of sequences SEQ ID NOs: 15 and 18, wherein X$_{12}$ is absent or is selected from Asn (N), Ser (S) and Gly (G), preferably X$_{12}$ is absent;
V$_L$-CDR2 of sequence SEQ ID NO: 16; and
V$_L$-CDR3 of sequence SEQ ID NO: 17.

In one embodiment, the antibody or binding fragment thereof according to the present invention comprises:
a HCVR which comprises the following three CDRs:
V$_H$-CDR1 of sequence SEQ ID NO: 1;
V$_H$-CDR2 selected from the group comprising or consisting of sequences SEQ ID NOs: 4, 6 and 100; and
V$_H$-CDR3 of sequence SEQ ID NO: 3; and
a LCVR which comprises the following three CDRs:
V$_L$-CDR1 selected from the group comprising or consisting of sequences SEQ ID NOs: 15 and 18, wherein X$_{12}$ is absent or is selected from Asn (N), Ser (S) and Gly (G), preferably X$_{12}$ is absent;
V$_L$-CDR2 of sequence SEQ ID NO: 16; and
V$_L$-CDR3 of sequence SEQ ID NO: 17.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #1 as defined in Table 2.

In one embodiment, the antibody or binding fragment thereof according to the present invention comprises a combination of (i) three HCVR's CDRs and (ii) three LCVR's CDRs, said combination being combination #1 as defined in Table 2.

In one embodiment, the antibody or binding fragment thereof according to the present invention comprises a combination of (i) three HCVR's CDRs set forth as SEQ ID NOs: 1, 4 and 3; and (ii) three LCVR's CDRs set forth as SEQ ID NOs: 15, 16 and 17; wherein X$_{12}$ in SEQ ID NOs: 15 is absent or is selected from Asn (N), Ser (S) and Gly (G), preferably X$_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #2 as defined in Table 2.

In one embodiment, the antibody or binding fragment thereof according to the present invention comprises a combination of (i) three HCVR's CDRs and (ii) three LCVR's CDRs, said combination being combination #2 as defined in Table 2.

In one embodiment, the antibody or binding fragment thereof according to the present invention comprises a combination of (i) three HCVR's CDRs set forth as SEQ ID NOs: 1, 4 and 3; and (ii) three LCVR's CDRs set forth as SEQ ID NOs: 18, 16 and 17; wherein X$_{12}$ in SEQ ID NOs: 18 is absent or is selected from Asn (N), Ser (S) and Gly (G), preferably X$_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #7 as defined in Table 2.

In one embodiment, the antibody or binding fragment thereof according to the present invention comprises a combination of (i) three HCVR's CDRs and (ii) three LCVR's CDRs, said combination being combination #7 as defined in Table 2.

In one embodiment, the antibody or binding fragment thereof according to the present invention comprises a combination of (i) three HCVR's CDRs set forth as SEQ ID NOs: 1, 5 and 3; and (ii) three LCVR's CDRs set forth as SEQ ID NOs: 15, 16 and 17; wherein X$_{12}$ in SEQ ID NOs: 15 is absent or is selected from Asn (N), Ser (S) and Gly (G), preferably X$_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #14 as defined in Table 2.

In one embodiment, the antibody or binding fragment thereof according to the present invention comprises a combination of (i) three HCVR's CDRs and (ii) three LCVR's CDRs, said combination being combination #14 as defined in Table 2.

In one embodiment, the antibody or binding fragment thereof according to the present invention comprises a combination of (i) three HCVR's CDRs set forth as SEQ ID NOs: 1, 6 and 3; and (ii) three LCVR's CDRs set forth as SEQ ID NOs: 18, 16 and 17; wherein X$_{12}$ in SEQ ID NOs: 18 is absent or is selected from Asn (N), Ser (S) and Gly (G), preferably X$_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #20 as defined in Table 2.

In one embodiment, the antibody or binding fragment thereof according to the present invention comprises a combination of (i) three HCVR's CDRs and (ii) three LCVR's CDRs, said combination being combination #20 as defined in Table 2.

In one embodiment, the antibody or binding fragment thereof according to the present invention comprises a combination of (i) three HCVR's CDRs set forth as SEQ ID NOs: 1, 7 and 3; and (ii) three LCVR's CDRs set forth as SEQ ID NOs: 18, 16 and 17; wherein $X_{12}$ in SEQ ID NOs: 18 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #26 as defined in Table 2.

In one embodiment, the antibody or binding fragment thereof according to the present invention comprises a combination of (i) three HCVR's CDRs and (ii) three LCVR's CDRs, said combination being combination #26 as defined in Table 2.

In one embodiment, the antibody or binding fragment thereof according to the present invention comprises a combination of (i) three HCVR's CDRs set forth as SEQ ID NOs: 1, 8 and 3; and (ii) three LCVR's CDRs set forth as SEQ ID NOs: 18, 16 and 17; wherein $X_{12}$ in SEQ ID NOs: 18 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #49 as defined in Table 2.

In one embodiment, the antibody or binding fragment thereof according to the present invention comprises a combination of (i) three HCVR's CDRs and (ii) three LCVR's CDRs, said combination being combination #49 as defined in Table 2.

In one embodiment, the antibody or binding fragment thereof according to the present invention comprises a combination of (i) three HCVR's CDRs set forth as SEQ ID NOs: 1, 100 and 3; and (ii) three LCVR's CDRs set forth as SEQ ID NOs: 15, 16 and 17; wherein $X_{12}$ in SEQ ID NOs: 15 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #50 as defined in Table 2.

In one embodiment, the antibody or binding fragment thereof according to the present invention comprises a combination of (i) three HCVR's CDRs and (ii) three LCVR's CDRs, said combination being combination #50 as defined in Table 2.

In one embodiment, the antibody or binding fragment thereof according to the present invention comprises a combination of (i) three HCVR's CDRs set forth as SEQ ID NOs: 1, 100 and 3; and (ii) three LCVR's CDRs set forth as SEQ ID NOs: 18, 16 and 17; wherein $X_{12}$ in SEQ ID NOs: 18 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #63 as defined in Table 2.

In one embodiment, the antibody or binding fragment thereof according to the present invention comprises a combination of (i) three HCVR's CDRs and (ii) three LCVR's CDRs, said combination being combination #63 as defined in Table 2.

In one embodiment, the antibody or binding fragment thereof according to the present invention comprises a combination of (i) three HCVR's CDRs set forth as SEQ ID NOs: 1, 100 and 3; and (ii) three LCVR's CDRs set forth as SEQ ID NOs: 18, 111 and 17; wherein $X_{12}$ in SEQ ID NOs: 18 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #65 as defined in Table 2.

In one embodiment, the antibody or binding fragment thereof according to the present invention comprises a combination of (i) three HCVR's CDRs and (ii) three LCVR's CDRs, said combination being combination #65 as defined in Table 2.

In one embodiment, the antibody or binding fragment thereof according to the present invention comprises a combination of (i) three HCVR's CDRs set forth as SEQ ID NOs: 1, 116 and 3; and (ii) three LCVR's CDRs set forth as SEQ ID NOs: 18, 16 and 17; wherein $X_{12}$ in SEQ ID NOs: 18 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #72 as defined in Table 2.

In one embodiment, the antibody or binding fragment thereof according to the present invention comprises a combination of (i) three HCVR's CDRs and (ii) three LCVR's CDRs, said combination being combination #72 as defined in Table 2.

In one embodiment, the antibody or binding fragment thereof according to the present invention comprises a combination of (i) three HCVR's CDRs set forth as SEQ ID NOs: 1, 117 and 3; and (ii) three LCVR's CDRs set forth as SEQ ID NOs: 18, 16 and 17; wherein $X_{12}$ in SEQ ID NOs: 18 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #79 as defined in Table 2.

In one embodiment, the antibody or binding fragment thereof according to the present invention comprises a combination of (i) three HCVR's CDRs and (ii) three LCVR's CDRs, said combination being combination #79 as defined in Table 2.

In one embodiment, the antibody or binding fragment thereof according to the present invention comprises a combination of (i) three HCVR's CDRs set forth as SEQ ID NOs: 1, 118 and 3; and (ii) three LCVR's CDRs set forth as SEQ ID NOs: 18, 16 and 17; wherein $X_{12}$ in SEQ ID NOs: 18 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #86 as defined in Table 2.

In one embodiment, the antibody or binding fragment thereof according to the present invention comprises a combination of (i) three HCVR's CDRs and (ii) three LCVR's CDRs, said combination being combination #86 as defined in Table 2.

In one embodiment, the antibody or binding fragment thereof according to the present invention comprises a combination of (i) three HCVR's CDRs set forth as SEQ ID NOs: 1, 119 and 3; and (ii) three LCVR's CDRs set forth as SEQ ID NOs: 18, 16 and 17; wherein $X_{12}$ in SEQ ID NOs: 18 is absent or is selected from Asn (N), Ser (S) and Gly (G), preferably $X_{12}$ is absent.

In one embodiment, the antibody or binding fragment thereof according to the present invention comprises a combination of (i) at least one, preferably at least two, more preferably three HCVR's CDRs and (ii) at least one, preferably at least two, more preferably three LCVR's CDRs, said combination being combination #92 as defined in Table 2.

In one embodiment, the antibody or binding fragment thereof according to the present invention comprises a combination of (i) three HCVR's CDRs and (ii) three LCVR's CDRs, said combination being combination #92 as defined in Table 2.

In one embodiment, the antibody or binding fragment thereof according to the present invention comprises a combination of (i) three HCVR's CDRs set forth as SEQ ID NOs: 1, 4 and 3; and (ii) three LCVR's CDRs set forth as SEQ ID NOs: 15, 120 and 17; wherein $X_{12}$ in SEQ ID NOs: 15 is absent or is selected from Asn (N), Ser (S) and Gly (G), preferably $X_{12}$ is absent.

In one embodiment, the antibody or binding fragment thereof according to the present invention comprises a HCVR which comprises at least one, preferably at least two, more preferably at least three, even more preferably the four following framework regions (FRs):

$V_H$-FR1:
(SEQ ID NO: 25)
QVQLQQSGAELVRPGTSVKMSCKAAGYTFT;

$V_H$-FR2:
(SEQ ID NO: 26)
WVKQRPGHGLEWIG;

$V_H$-FR3:
(SEQ ID NO: 27)
KATLTADTSSSTAYMQLSSLTSEDSAIYYCVR;

$V_H$-FR4:
(SEQ ID NO: 28)
WGQGTTLTVSS.

In one embodiment, the antibody or binding fragment thereof according to the present invention comprises a HCVR which comprises the four following FRs:

$V_H$-FR1:
(SEQ ID NO: 25)
QVQLQQSGAELVRPGTSVKMSCKAAGYTFT;

$V_H$-FR2:
(SEQ ID NO: 26)
WVKQRPGHGLEWIG;

$V_H$-FR3:
(SEQ ID NO: 27)
KATLTADTSSSTAYMQLSSLTSEDSAIYYCVR;

$V_H$-FR4:
(SEQ ID NO: 28)
WGQGTTLTVSS.

In one embodiment, the antibody or binding fragment thereof according to the present invention comprises a HCVR which comprises at least one, preferably at least two, more preferably at least three, even more preferably the four following FRs:

$V_H$-FR1:
(SEQ ID NO: 29)
QVQLVQSGAEVKKPGASVKVSCKASGYTFT;

$V_H$-FR2:
(SEQ ID NO: 30)
WVRQAPGQGLEWIG;

$V_H$-FR3:
(SEQ ID NO: 31)
RVTLTADTSISTAYMELSRLRSDDTVVYYCVR;

$V_H$-FR4:
(SEQ ID NO: 32)
WGQGTLVTVSS.

In one embodiment, the antibody or binding fragment thereof according to the present invention comprises a HCVR which comprises the four following FRs:

$V_H$-FR1:
(SEQ ID NO: 29)
QVQLVQSGAEVKKPGASVKVSCKASGYTFT;

$V_H$-FR2:
(SEQ ID NO: 30)
WVRQAPGQGLEWIG;

$V_H$-FR3:
(SEQ ID NO: 31)
RVTLTADTSISTAYMELSRLRSDDTVVYYCVR;

$V_H$-FR4:
(SEQ ID NO: 32)
WGQGTLVTVSS.

In one embodiment, the antibody or binding fragment thereof according to the present invention comprises a HCVR which comprises at least one, preferably at least two, more preferably at least three, even more preferably the four following FRs:

$V_H$-FR1:
(SEQ ID NO: 33)
EVQLVQSGAEVKKPGESLKISCKASGYTFT;

$V_H$-FR2:
(SEQ ID NO: 34)
WVRQMPGKGLEWIG;

V<sub>H</sub>-FR3:
(SEQ ID NO: 35)
QVTLSADKSISTAYLQLSSLKASDTAMYYCVR;

V<sub>H</sub>-FR4:
(SEQ ID NO: 32)
WGQGTLVTVSS.

In one embodiment, the antibody or binding fragment thereof according to the present invention comprises a HCVR which comprises the four following FRs:

V<sub>H</sub>-FR1:
(SEQ ID NO: 33)
EVQLVQSGAEVKKPGESLKISCKASGYTFT;

V<sub>H</sub>-FR2:
(SEQ ID NO: 34)
WVRQMPGKGLEWIG;

V<sub>H</sub>-FR3:
(SEQ ID NO: 35)
QVTLSADKSISTAYLQLSSLKASDTAMYYCVR;

V<sub>H</sub>-FR4:
(SEQ ID NO: 32)
WGQGTLVTVSS.

In one embodiment, the antibody or binding fragment thereof according to the present invention comprises a HCVR which comprises at least one, preferably at least two, more preferably at least three, even more preferably the four following FRs:

V<sub>H</sub>-FR1:
(SEQ ID NO: 36)
QVQLVESGGGLVKPGGSLRLSCAASGYTFT;

V<sub>H</sub>-FR2:
(SEQ ID NO: 37)
WIRQAPGKGLEWIG;

V<sub>H</sub>-FR3:
(SEQ ID NO: 38)
RFTLSADTAKNSAYLQMNSLRAEDTAVYYCVR;

V<sub>H</sub>-FR4:
(SEQ ID NO: 32)
WGQGTLVTVSS.

In one embodiment, the antibody or binding fragment thereof according to the present invention comprises a HCVR which comprises the four following FRs:

V<sub>H</sub>-FR1:
(SEQ ID NO: 36)
QVQLVESGGGLVKPGGSLRLSCAASGYTFT;

V<sub>H</sub>-FR2:
(SEQ ID NO: 37)
WIRQAPGKGLEWIG;

V<sub>H</sub>-FR3:
(SEQ ID NO: 38)
RFTLSADTAKNSAYLQMNSLRAEDTAVYYCVR;

V<sub>H</sub>-FR4:
(SEQ ID NO: 32)
WGQGTLVTVSS.

In one embodiment, the antibody or binding fragment thereof according to the present invention comprises a HCVR which comprises at least one, preferably at least two, more preferably at least three, even more preferably the four following FRs:

V<sub>H</sub>-FR1:
(SEQ ID NO: 39)
EVQLVQSGAEVKKPGESLKISCKGSGYTFT;

V<sub>H</sub>-FR2:
(SEQ ID NO: 34)
WVRQMPGKGLEWIG;

V<sub>H</sub>-FR3:
(SEQ ID NO: 35)
QVTLSADKSISTAYLQLSSLKASDTAMYYCVR;

V<sub>H</sub>-FR4:
(SEQ ID NO: 32)
WGQGTLVTVSS.

In one embodiment, the antibody or binding fragment thereof according to the present invention comprises a HCVR which comprises the four following FRs:

V<sub>H</sub>-FR1:
(SEQ ID NO: 39)
EVQLVQSGAEVKKPGESLKISCKGSGYTFT;

V<sub>H</sub>-FR2:
(SEQ ID NO: 34)
WVRQMPGKGLEWIG;

V<sub>H</sub>-FR3:
(SEQ ID NO: 35)
QVTLSADKSISTAYLQLSSLKASDTAMYYCVR;

V<sub>H</sub>-FR4:
(SEQ ID NO: 32)
WGQGTLVTVSS.

In one embodiment, the antibody or binding fragment thereof according to the present invention comprises a HCVR which comprises at least one, preferably at least two, more preferably at least three, even more preferably the four following FRs:

V<sub>H</sub>-FR1:
(SEQ ID NO: 40)
QVQLVESGGGLVKPGGSLRLSCAASGFTFS;

V<sub>H</sub>-FR2:
(SEQ ID NO: 37)
WIRQAPGKGLEWIG;

V<sub>H</sub>-FR3:
(SEQ ID NO: 41)
RFTLSADTAKNSLYLQMNSLRAEDTAVYYCVR;

V<sub>H</sub>-FR4:
(SEQ ID NO: 32)
WGQGTLVTVSS.

In one embodiment, the antibody or binding fragment thereof according to the present invention comprises a HCVR which comprises the four following FRs:

V<sub>H</sub>-FR1:
(SEQ ID NO: 40)
QVQLVESGGGLVKPGGSLRLSCAASGFTFS;

V<sub>H</sub>-FR2:
(SEQ ID NO: 37)
WIRQAPGKGLEWIG;

$V_H$-FR3:
(SEQ ID NO: 41)
RFTLSADTAKNSLYLQMNSLRAEDTAVYYCVR;

$V_H$-FR4:
(SEQ ID NO: 32)
WGQGTLVTVSS.

In one embodiment, the antibody or binding fragment thereof according to the present invention comprises a HCVR which comprises at least one, preferably at least two, more preferably at least three, even more preferably the four following FRs:

$V_H$-FR1:
(SEQ ID NO: 42)
EVQLVQSGAEVKKPGESLKISCKGSGYSFT;

$V_H$-FR2:
(SEQ ID NO: 34)
WVRQMPGKGLEWIG;

$V_H$-FR3:
(SEQ ID NO: 35)
QVTLSADKSISTAYLQLSSLKASDTAMYYCVR;

$V_H$-FR4:
(SEQ ID NO: 32)
WGQGTLVTVSS.

In one embodiment, the antibody or binding fragment thereof according to the present invention comprises a HCVR which comprises the four following FRs:

$V_H$-FR1:
(SEQ ID NO: 42)
EVQLVQSGAEVKKPGESLKISCKGSGYSFT;

$V_H$-FR2:
(SEQ ID NO: 34)
WVRQMPGKGLEWIG;

$V_H$-FR3:
(SEQ ID NO: 35)
QVTLSADKSISTAYLQLSSLKASDTAMYYCVR;

$V_H$-FR4:
(SEQ ID NO: 32)
WGQGTLVTVSS.

In one embodiment, the antibody or binding fragment thereof according to the present invention comprises a HCVR which comprises at least one, preferably at least two, more preferably at least three, even more preferably the four following FRs:

$V_H$-FR1:
(SEQ ID NO: 40)
QVQLVESGGGLVKPGGSLRLSCAASGFTFS;

$V_H$-FR2:
(SEQ ID NO: 43)
WIRQAPGKGLEWVG;

$V_H$-FR3:
(SEQ ID NO: 41)
RFTLSADTAKNSLYLQMNSLRAEDTAVYYCVR;

$V_H$-FR4:
(SEQ ID NO: 32)
WGQGTLVTVSS.

In one embodiment, the antibody or binding fragment thereof according to the present invention comprises a HCVR which comprises the four following FRs:

$V_H$-FR1:
(SEQ ID NO: 40)
QVQLVESGGGLVKPGGSLRLSCAASGFTFS;

$V_H$-FR2:
(SEQ ID NO: 43)
WIRQAPGKGLEWVG;

$V_H$-FR3:
(SEQ ID NO: 41)
RFTLSADTAKNSLYLQMNSLRAEDTAVYYCVR;

$V_H$-FR4:
(SEQ ID NO: 32)
WGQGTLVTVSS.

In one embodiment, the antibody or binding fragment thereof according to the present invention comprises a LCVR which comprises at least one, preferably at least two, more preferably at least three, even more preferably the four following FRs:

$V_L$-FR1:
(SEQ ID NO: 44)
QIVLTQSPTIMSASPGEKVTITC;

$V_L$-FR2:
(SEQ ID NO: 45)
WFQQKTGTSPRLWIY;

$V_L$-FR3:
(SEQ ID NO: 46)
GVPARFSGSGSGTS-$X_{18}$-SLTISRMEAEDAATYYC;

$V_L$-FR4:
(SEQ ID NO: 47)
GAGTKLELK, with:
$X_{18}$ being selected from Tyr (Y) and Phe (F), preferably $X_{18}$ being Tyr (Y).

In one embodiment, the antibody or binding fragment thereof according to the present invention comprises a LCVR which comprises the four following FRs:

$V_L$-FR1:
(SEQ ID NO: 44)
QIVLTQSPTIMSASPGEKVTITC;

$V_L$-FR2:
(SEQ ID NO: 45)
WFQQKTGTSPRLWIY;

$V_L$-FR3:
(SEQ ID NO: 46)
GVPARFSGSGSGTS-$X_{18}$-SLTISRMEAEDAATYYC;

$V_L$-FR4:
(SEQ ID NO: 47)
GAGTKLELK with:
$X_{15}$ being selected from Tyr (Y) and Phe (F), preferably $X_{15}$ being Tyr (Y).

In one embodiment, the antibody or binding fragment thereof according to the present invention comprises a LCVR which comprises at least one, preferably at least two, more preferably at least three, even more preferably the four following FRs:

$V_L$-FR1:

(SEQ ID NO: 48)
DIQLTQSPSFLSASVGDRVTITC;

$V_L$-FR2:

(SEQ ID NO: 49)
WFQQKPGKAPKLWIY;

$V_L$-FR3:

(SEQ ID NO: 50)
GVPSRFSGSGSGTE-$X_{18}$-TLTISSLQPEDFATYYC;

$V_L$-FR4:

(SEQ ID NO: 51)
GGGTKVEIK, with:

$X_{15}$ being selected from Tyr (Y) and Phe (F), preferably $X_{15}$ being Tyr (Y).

In one embodiment, the antibody or binding fragment thereof according to the present invention comprises a LCVR which comprises the four following FRs:

$V_L$-FR1:

(SEQ ID NO: 48)
DIQLTQSPSFLSASVGDRVTITC;

$V_L$-FR2:

(SEQ ID NO: 49)
WFQQKPGKAPKLWIY;

$V_L$-FR3:

(SEQ ID NO: 50)
GVPSRFSGSGSGTE-$X_{18}$-TLTISSLQPEDFATYYC;

$V_L$-FR4:

(SEQ ID NO: 51)
GGGTKVEIK, with:

$X_{15}$ being selected from Tyr (Y) and Phe (F), preferably $X_{15}$ being Tyr (Y).

In one embodiment, the antibody or binding fragment thereof according to the present invention comprises a LCVR which comprises at least one, preferably at least two, more preferably at least three, even more preferably the four following FRs:

$V_L$-FR1:

(SEQ ID NO: 52)
EIVLTQSPDFQSVTPKEKVTITC;

$V_L$-FR2:

(SEQ ID NO: 53)
WFQQKPDQSPKLWIY;

$V_L$-FR3:

(SEQ ID NO: 54)
GVPSRFSGSGSGTD-$X_{18}$-TLTINSLEAEDAATYYC;

$V_L$-FR4:

(SEQ ID NO: 51)
GGGTKVEIK, with:

$X_{15}$ being selected from Tyr (Y) and Phe (F), preferably $X_{15}$ being Tyr (Y).

In one embodiment, the antibody or binding fragment thereof according to the present invention comprises a LCVR which comprises the four following FRs:

$V_L$-FR1:

(SEQ ID NO: 52)
EIVLTQSPDFQSVTPKEKVTITC;

$V_L$-FR2:

(SEQ ID NO: 53)
WFQQKPDQSPKLWIY;

$V_L$-FR3:

(SEQ ID NO: 54)
GVPSRFSGSGSGTD-$X_{18}$-TLTINSLEAEDAATYYC;

$V_L$-FR4:

(SEQ ID NO: 51)
GGGTKVEIK, with:

$X_{15}$ being selected from Tyr (Y) and Phe (F), preferably $X_{15}$ being Tyr (Y).

In one embodiment, the antibody or binding fragment thereof according to the present invention comprises a LCVR which comprises at least one, preferably at least two, more preferably at least three, even more preferably the four following FRs:

$V_L$-FR1:

(SEQ ID NO: 55)
EIVLTQSPATLSLSPGERATLSC;

$V_L$-FR2:

(SEQ ID NO: 56)
WFQQKPGQAPRLWIY;

$V_L$-FR3:

(SEQ ID NO: 57)
GIPARFSGSGSGTD-$X_{18}$-TLTISSLEPEDFAVYYC;

$V_L$-FR4:

(SEQ ID NO: 51)
GGGTKVEIK, with:

$X_{15}$ being selected from Tyr (Y) and Phe (F), preferably $X_{15}$ being Tyr (Y).

In one embodiment, the antibody or binding fragment thereof according to the present invention comprises a LCVR which comprises the four following FRs:

$V_L$-FR1:

(SEQ ID NO: 55)
EIVLTQSPATLSLSPGERATLSC;

$V_L$-FR2:

(SEQ ID NO: 56)
WFQQKPGQAPRLWIY;

$V_L$-FR3:

(SEQ ID NO: 57)
GIPARFSGSGSGTD-$X_{18}$-TLTISSLEPEDFAVYYC;

$V_L$-FR4:

(SEQ ID NO: 51)
GGGTKVEIK, with:

$X_{15}$ being selected from Tyr (Y) and Phe (F), preferably $X_{15}$ being Tyr (Y).

In one embodiment, the antibody or binding fragment thereof according to the present invention comprises a LCVR which comprises at least one, preferably at least two, more preferably at least three, even more preferably the four following FRs:

```
V_L-FR1:
                                    (SEQ ID NO: 48)
DIQLTQSPSFLSASVGDRVTITC;

V_L-FR2:
                                    (SEQ ID NO: 58)
WYQQKPGKAPKLWIY;

V_L-FR3:
                                    (SEQ ID NO: 50)
GVPSRFSGSGSGTE-X_18-TLTISSLQPEDFATYYC;

V_L-FR4:
                                    (SEQ ID NO: 51)
GGGTKVEIK,
``` with:

$X_{15}$ being selected from Tyr (Y) and Phe (F), preferably $X_{15}$ being Tyr (Y).

In one embodiment, the antibody or binding fragment thereof according to the present invention comprises a LCVR which comprises the four following FRs:

```
V_L-FR1:
                                    (SEQ ID NO: 48)
DIQLTQSPSFLSASVGDRVTITC;

V_L-FR2:
                                    (SEQ ID NO: 58)
WYQQKPGKAPKLWIY;

V_L-FR3:
                                    (SEQ ID NO: 50)
GVPSRFSGSGSGTE-X_18-TLTISSLQPEDFATYYC;

V_L-FR4:
                                    (SEQ ID NO: 51)
GGGTKVEIK,
``` with:

$X_{15}$ being selected from Tyr (Y) and Phe (F), preferably $X_{15}$ being Tyr (Y).

In one embodiment, the antibody or binding fragment thereof according to the present invention comprises a LCVR which comprises at least one, preferably at least two, more preferably at least three, even more preferably the four following FRs:

```
V_L-FR1:
                                    (SEQ ID NO: 48)
DIQLTQSPSFLSASVGDRVTITC;

V_L-FR2:
                                    (SEQ ID NO: 58)
WYQQKPGKAPKLWIY;

V_L-FR3:
                                    (SEQ ID NO: 50)
GVPSRFSGSGSGTE-X_18-TLTISSLQPEDFATYYC;

V_L-FR4:
                                    (SEQ ID NO: 51)
GGGTKVEIK,
``` with:

$X_{15}$ being selected from Tyr (Y) and Phe (F), preferably $X_{15}$ being Phe (F).

In one embodiment, the antibody or binding fragment thereof according to the present invention comprises a LCVR which comprises the four following FRs:

```
V_L-FR1:
                                    (SEQ ID NO: 48)
DIQLTQSPSFLSASVGDRVTITC;

V_L-FR2:
                                    (SEQ ID NO: 58)
WYQQKPGKAPKLWIY;

V_L-FR3:
                                    (SEQ ID NO: 50)
GVPSRFSGSGSGTE-X_18-TLTISSLQPEDFATYYC;

V_L-FR4:
                                    (SEQ ID NO: 51)
GGGTKVEIK,
``` with:

$X_{18}$ being selected from Tyr (Y) and Phe (F), preferably $X_{18}$ being Phe (F).

In one embodiment, the antibody or binding fragment thereof according to the present invention comprises a LCVR which comprises at least one, preferably at least two, more preferably at least three, even more preferably the four following FRs:

```
V_L-FR1:
                                    (SEQ ID NO: 52)
EIVLTQSPDFQSVTPKEKVTITC;

V_L-FR2:
                                    (SEQ ID NO: 59)
WYQQKPDQSPKLWIY;

V_L-FR3:
                                    (SEQ ID NO: 54)
GVPSRFSGSGSGTD-X_18-TLTINSLEAEDAATYYC;

V_L-FR4:
                                    (SEQ ID NO: 51)
GGGTKVEIK,
``` with:

$X_{15}$ being selected from Tyr (Y) and Phe (F), preferably $X_{15}$ being Phe (F).

In one embodiment, the antibody or binding fragment thereof according to the present invention comprises a LCVR which comprises the four following FRs:

```
V_L-FR1:
                                    (SEQ ID NO: 52)
EIVLTQSPDFQSVTPKEKVTITC;

V_L-FR2:
                                    (SEQ ID NO: 59)
WYQQKPDQSPKLWIY;

V_L-FR3:
                                    (SEQ ID NO: 54)
GVPSRFSGSGSGTD-X_18-TLTINSLEAEDAATYYC;

V_L-FR4:
                                    (SEQ ID NO: 51)
GGGTKVEIK,
``` with:

$X_{15}$ being selected from Tyr (Y) and Phe (F), preferably $X_{15}$ being Phe (F).

In one embodiment, the antibody or binding fragment thereof according to the present invention comprises a LCVR which comprises at least one, preferably at least two, more preferably at least three, even more preferably the four following FRs:

V$_L$-FR1:
(SEQ ID NO: 55)
EIVLTQSPATLSLSPGERATLSC;

V$_L$-FR2:
(SEQ ID NO: 60)
WYQQKPGQAPRLWIY;

V$_L$-FR3:
(SEQ ID NO: 57)
GIPARFSGSGSGTD-X$_{18}$-TLTISSLEPEDFAVYYC;

V$_L$-FR4:
(SEQ ID NO: 51)
GGGTKVEIK, with:

X$_{15}$ being selected from Tyr (Y) and Phe (F), preferably X$_{15}$ being Phe (F).

In one embodiment, the antibody or binding fragment thereof according to the present invention comprises a LCVR which comprises the four following FRs:

V$_L$-FR1:
(SEQ ID NO: 55)
EIVLTQSPATLSLSPGERATLSC;

V$_L$-FR2:
(SEQ ID NO: 60)
WYQQKPGQAPRLWIY;

V$_L$-FR3:
(SEQ ID NO: 57)
GIPARFSGSGSGTD-X$_{18}$-TLTISSLEPEDFAVYYC;

V$_L$-FR4:
(SEQ ID NO: 51)
GGGTKVEIK, with:

X$_{15}$ being selected from Tyr (Y) and Phe (F), preferably X$_{15}$ being Phe (F).

In one embodiment, the antibody or binding fragment thereof according to the present invention comprises a LCVR which comprises at least one, preferably at least two, more preferably at least three, even more preferably the four following FRs:

V$_L$-FR1:
(SEQ ID NO: 48)
DIQLTQSPSFLSASVGDRVTITC;

V$_L$-FR2:
(SEQ ID NO: 49)
WFQQKPGKAPKLWIY;

V$_L$-FR3:
(SEQ ID NO: 50)
GVPSRFSGSGSGTE-X$_{18}$-TLTISSLQPEDFATYYC;

V$_L$-FR4:
(SEQ ID NO: 51)
GGGTKVEIK, with:

X$_{15}$ being selected from Tyr (Y) and Phe (F), preferably X$_{15}$ being Phe (F).

In one embodiment, the antibody or binding fragment thereof according to the present invention comprises a LCVR which comprises the four following FRs:

V$_L$-FR1:
(SEQ ID NO: 48)
DIQLTQSPSFLSASVGDRVTITC;

V$_L$-FR2:
(SEQ ID NO: 49)
WFQQKPGKAPKLWIY;

V$_L$-FR3:
(SEQ ID NO: 50)
GVPSRFSGSGSGTE-X$_{18}$-TLTISSLQPEDFATYYC;

V$_L$-FR4:
(SEQ ID NO: 51)
GGGTKVEIK, with:

X$_{15}$ being selected from Tyr (Y) and Phe (F), preferably X$_{15}$ being Phe (F).

In one embodiment, the antibody or binding fragment thereof according to the present invention comprises a combination of (i) at least one, preferably at least two, more preferably at least three, even more preferably four HCVR's FRs and (ii) at least one, preferably at least two, more preferably at least three, even more preferably four LCVR's FRs, said combination being as defined in Table 3.

In one embodiment, the antibody or binding fragment thereof according to the present invention comprises a combination of (i) four HCVR's FRs and (ii) four LCVR's FRs, said combination being as defined in Table 3.

TABLE 3

Preferred combinations of HCVR's and LCVR's FRs. The FRs are defined by their SEQ ID NOs (with, wherever applicable, X$_{18}$ being selected from Tyr (Y) and Phe (F)).

| FRs' combination # | V$_H$-FR1 | V$_H$-FR2 | V$_H$-FR3 | V$_H$-FR4 |
|---|---|---|---|---|
| #1 | 25 | 26 | 27 | 28 |
| #2 | 25 | 26 | 27 | 28 |
| #3 | 25 | 26 | 27 | 28 |
| #4 | 25 | 26 | 27 | 28 |
| #5 | 25 | 26 | 27 | 28 |
| #6 | 25 | 26 | 27 | 28 |
| #7 | 25 | 26 | 27 | 28 |
| #8 | 29 | 30 | 31 | 32 |
| #9 | 29 | 30 | 31 | 32 |
| #10 | 29 | 30 | 31 | 32 |
| #11 | 29 | 30 | 31 | 32 |
| #12 | 29 | 30 | 31 | 32 |
| #13 | 29 | 30 | 31 | 32 |
| #14 | 29 | 30 | 31 | 32 |
| #15 | 33 | 34 | 35 | 32 |
| #16 | 33 | 34 | 35 | 32 |
| #17 | 33 | 34 | 35 | 32 |
| #18 | 33 | 34 | 35 | 32 |
| #19 | 33 | 34 | 35 | 32 |
| #20 | 33 | 34 | 35 | 32 |
| #21 | 33 | 34 | 35 | 32 |
| #22 | 36 | 37 | 38 | 32 |
| #23 | 36 | 37 | 38 | 32 |
| #24 | 36 | 37 | 38 | 32 |
| #25 | 36 | 37 | 38 | 32 |
| #26 | 36 | 37 | 38 | 32 |
| #27 | 36 | 37 | 38 | 32 |
| #28 | 36 | 37 | 38 | 32 |
| #29 | 39 | 34 | 35 | 32 |
| #30 | 39 | 34 | 35 | 32 |
| #31 | 39 | 34 | 35 | 32 |
| #32 | 39 | 34 | 35 | 32 |
| #33 | 39 | 34 | 35 | 32 |
| #34 | 39 | 34 | 35 | 32 |
| #35 | 39 | 34 | 35 | 32 |
| #36 | 40 | 37 | 41 | 32 |

TABLE 3-continued

Preferred combinations of HCVR's and LCVR's FRs. The FRs are defined by their SEQ ID NOs (with, wherever applicable, $X_{18}$ being selected from Tyr (Y) and Phe (F)).

| FRs' combination # | $V_H$-FR1 | $V_H$-FR2 | $V_H$-FR3 | $V_H$-FR4 |
|---|---|---|---|---|
| #37 | 40 | 37 | 41 | 32 |
| #38 | 40 | 37 | 41 | 32 |
| #39 | 40 | 37 | 41 | 32 |
| #40 | 40 | 37 | 41 | 32 |
| #41 | 40 | 37 | 41 | 32 |
| #42 | 40 | 37 | 41 | 32 |
| #43 | 42 | 34 | 35 | 32 |
| #44 | 42 | 34 | 35 | 32 |
| #45 | 42 | 34 | 35 | 32 |
| #46 | 42 | 34 | 35 | 32 |
| #47 | 42 | 34 | 35 | 32 |
| #48 | 42 | 34 | 35 | 32 |
| #49 | 42 | 34 | 35 | 32 |
| #50 | 40 | 43 | 41 | 32 |
| #51 | 40 | 43 | 41 | 32 |
| #52 | 40 | 43 | 41 | 32 |
| #53 | 40 | 43 | 41 | 32 |
| #54 | 40 | 43 | 41 | 32 |
| #55 | 40 | 43 | 41 | 32 |
| #56 | 40 | 43 | 41 | 32 |
| #1 | 44 | 45 | 46 | 47 |
| #2 | 48 | 49 | 50 | 51 |
| #3 | 52 | 53 | 54 | 51 |
| #4 | 55 | 56 | 57 | 51 |
| #5 | 48 | 58 | 50 | 51 |
| #6 | 52 | 59 | 54 | 51 |
| #7 | 55 | 60 | 57 | 51 |
| #8 | 44 | 45 | 46 | 47 |
| #9 | 48 | 49 | 50 | 51 |
| #10 | 52 | 53 | 54 | 51 |
| #11 | 55 | 56 | 57 | 51 |
| #12 | 48 | 58 | 50 | 51 |
| #13 | 52 | 59 | 54 | 51 |
| #14 | 55 | 60 | 57 | 51 |
| #15 | 44 | 45 | 46 | 47 |
| #16 | 48 | 49 | 50 | 51 |
| #17 | 52 | 53 | 54 | 51 |
| #18 | 55 | 56 | 57 | 51 |
| #19 | 48 | 58 | 50 | 51 |
| #20 | 52 | 59 | 54 | 51 |
| #21 | 55 | 60 | 57 | 51 |
| #22 | 44 | 45 | 46 | 47 |
| #23 | 48 | 49 | 50 | 51 |
| #24 | 52 | 53 | 54 | 51 |
| #25 | 55 | 56 | 57 | 51 |
| #26 | 48 | 58 | 50 | 51 |
| #27 | 52 | 59 | 54 | 51 |
| #28 | 55 | 60 | 57 | 51 |
| #29 | 44 | 45 | 46 | 47 |
| #30 | 48 | 49 | 50 | 51 |
| #31 | 52 | 53 | 54 | 51 |
| #32 | 55 | 56 | 57 | 51 |
| #33 | 48 | 58 | 50 | 51 |
| #34 | 52 | 59 | 54 | 51 |
| #35 | 55 | 60 | 57 | 51 |
| #36 | 44 | 45 | 46 | 47 |
| #37 | 48 | 49 | 50 | 51 |
| #38 | 52 | 53 | 54 | 51 |
| #39 | 55 | 56 | 57 | 51 |
| #40 | 48 | 58 | 50 | 51 |
| #41 | 52 | 59 | 54 | 51 |
| #42 | 55 | 60 | 57 | 51 |
| #43 | 44 | 45 | 46 | 47 |
| #44 | 48 | 49 | 50 | 51 |
| #45 | 52 | 53 | 54 | 51 |
| #46 | 55 | 56 | 57 | 51 |
| #47 | 48 | 58 | 50 | 51 |
| #48 | 52 | 59 | 54 | 51 |
| #49 | 55 | 60 | 57 | 51 |
| #50 | 44 | 45 | 46 | 47 |
| #51 | 48 | 49 | 50 | 51 |
| #52 | 52 | 53 | 54 | 51 |
| #53 | 55 | 56 | 57 | 51 |
| #54 | 48 | 58 | 50 | 51 |
| #55 | 52 | 59 | 54 | 51 |
| #56 | 55 | 60 | 57 | 51 |

In one embodiment, any of $V_H$-FR1, $V_H$-FR2, $V_H$-FR3, $V_H$-FR4, $V_L$-FR1, $V_L$-FR2, $V_L$-FR3 and/or $V_L$-FR4 as defined hereinabove can be characterized as having 1, 2, 3, 4, 5, 6, 7, 8, 9, 10 or more amino acids being substituted by a different amino acid.

In one embodiment, any of $V_H$-FR1, $V_H$-FR2, $V_H$-FR3, $V_H$-FR4, $V_L$-FR1, $V_L$-FR2, $V_L$-FR3 and/or $V_L$-FR4 as defined hereinabove can be characterized as having an amino acid sequence that shares at least 70%, 75%, 80%, 85%, 90%, 95%, 96%, 97%, 98%, 99% or more of identity with the particular FR or sets of FRs as defined hereinabove.

In one embodiment, the antibody or binding fragment thereof according to the present invention comprises a HCVR comprising or consisting of:
  a $V_H$-FR1 as described hereinabove,
  a $V_H$-CDR1 as described hereinabove,
  a $V_H$-FR2 as described hereinabove,
  a $V_H$-CDR2 as described hereinabove,
  a $V_H$-FR3 as described hereinabove,
  a $V_H$-CDR3 as described hereinabove, and
  a $V_H$-FR4 as described hereinabove.

In one embodiment, the antibody or binding fragment thereof according to the present invention comprises a HCVR comprising or consisting of:
  a $V_H$-FR1 selected from SEQ ID NOs 25, 29, 33, 36, 39, 40 and 42;
  a $V_H$-CDR1 selected from SEQ ID NO 1;
  a $V_H$-FR2 selected from SEQ ID NOs 26, 30, 34, 37 and 43;
  a $V_H$-CDR2 selected from SEQ ID NO 2;
  a $V_H$-FR3 selected from SEQ ID NOs 27, 31, 35, 38 and 41;
  a $V_H$-CDR3 selected from SEQ ID NO 3; and
  a $V_H$-FR4 selected from SEQ ID NOs 28 and 32.

In one embodiment, the antibody or binding fragment thereof according to the present invention comprises a HCVR comprising or consisting of:
  a $V_H$-FR1 selected from SEQ ID NOs 25, 29, 33, 36, 39, 40 and 42;
  a $V_H$-CDR1 selected from SEQ ID NO 1;
  a $V_H$-FR2 selected from SEQ ID NOs 26, 30, 34, 37 and 43;
  a $V_H$-CDR2 selected from SEQ ID NOs 4, 5, 6, 7, 8, 9, 10, 11, 100, 116, 117, 118 and 119;
  a $V_H$-FR3 selected from SEQ ID NOs 27, 31, 35, 38 and 41;
  a $V_H$-CDR3 selected from SEQ ID NO 3; and
  a $V_H$-FR4 selected from SEQ ID NOs 28 and 32.

In a preferred embodiment, the antibody or binding fragment thereof according to the present invention comprises a HCVR comprising or consisting of a combination of a $V_H$-FR1, a $V_H$-CDR1, a $V_H$-FR2, a $V_H$-CDR2, a $V_H$-FR3, a $V_H$-CDR3 and a $V_H$-FR4, said combination being as defined in Table 4.

TABLE 4

Preferred HCVR. The CDRs and FRs are defined by their SEQ ID NOs. The penultimate column refers to the SEQ ID NOs of the whole HCVR.

| HCVR # | $V_H$ FR1 | $V_H$ CDR1 | $V_H$ FR2 | $V_H$ CDR2 | $V_H$ FR3 | $V_H$ CDR3 | $V_H$ FR4 | HCVR sequence | Name |
|---|---|---|---|---|---|---|---|---|---|
| #1  | 25 | 1 | 26 | 4   | 27 | 3 | 28 | 61  | Mouse VH |
| #2  | 29 | 1 | 30 | 4   | 31 | 3 | 32 | 62  | 12VHA |
| #3  | 33 | 1 | 34 | 4   | 35 | 3 | 32 | 63  | 551VHA |
| #4  | 36 | 1 | 37 | 5   | 38 | 3 | 32 | 64  | 311VHA |
| #5  | 29 | 1 | 30 | 6   | 31 | 3 | 32 | 65  | 12VHB |
| #6  | 39 | 1 | 34 | 7   | 35 | 3 | 32 | 66  | 551VHB |
| #7  | 40 | 1 | 37 | 8   | 41 | 3 | 32 | 67  | 311VHB |
| #8  | 29 | 1 | 30 | 9   | 31 | 3 | 32 | 68  | 12VHC |
| #9  | 42 | 1 | 34 | 10  | 35 | 3 | 32 | 69  | 551VHC |
| #10 | 40 | 1 | 43 | 11  | 41 | 3 | 32 | 70  | 331VHC |
| #11 | 29 | 1 | 30 | 100 | 31 | 3 | 32 | 101 | 12VHD |
| #12 | 29 | 1 | 30 | 116 | 31 | 3 | 32 | 121 | 12VHE |
| #13 | 29 | 1 | 30 | 117 | 31 | 3 | 32 | 122 | 12VHF |
| #14 | 29 | 1 | 30 | 118 | 31 | 3 | 32 | 123 | 12VHG |
| #15 | 29 | 1 | 30 | 119 | 31 | 3 | 32 | 124 | 12VHH |

In a preferred embodiment, the antibody or binding fragment thereof according to the present invention comprises a HCVR comprising or consisting of the sequence SEQ ID NO: 61; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 61.

SEQ ID NO: 61
QVQLQQSGAELVRPGTSVKMSCKAAGYTFTNYYIGWVKQRPGHGLEWIGD

IFPGGDYANSNEKFKGKATLTADTSSSTAYMQLSSLTSEDSAIYYCVRRN

FDYWGQGTTLTVSS

In a preferred embodiment, the antibody or binding fragment thereof according to the present invention comprises a HCVR comprising or consisting of the sequence SEQ ID NO: 62; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 62.

SEQ ID NO: 62
QVQLVQSGAEVKKPGASVKVSCKASGYTFTNYYIGWVRQAPGQGLEWIGD

IFPGGDYANSNEKFKGRVTLTADTSISTAYMELSRLRSDDTVVYYCVRRN

FDYWGQGTLVTVSS

In a preferred embodiment, the antibody or binding fragment thereof according to the present invention comprises a HCVR comprising or consisting of the sequence SEQ ID NO: 63; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 63.

SEQ ID NO: 63
EVQLVQSGAEVKKPGESLKISCKASGYTFTNYYIGWVRQMPGKGLEWIGD

IFPGGDYANSNEKFKGQVTLSADKSISTAYLQLSSLKASDTAMYYCVRRN

FDYWGQGTLVTVSS

In a preferred embodiment, the antibody or binding fragment thereof according to the present invention comprises a HCVR comprising or consisting of the sequence SEQ ID NO: 64; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 64.

SEQ ID NO: 64
QVQLVESGGGLVKPGGSLRLSCAASGYTFTNYYIGWIRQAPGKGLEWIGD

IFPGGDYANSNEKVKGRFTLSADTAKNSAYLQMNSLRAEDTAVYYCVRRN

FDYWGQGTLVTVSS

In a preferred embodiment, the antibody or binding fragment thereof according to the present invention comprises a HCVR comprising or consisting of the sequence SEQ ID NO: 65; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 65.

SEQ ID NO: 65
QVQLVQSGAEVKKPGASVKVSCKASGYTFTNYYIGWVRQAPGQGLEWIGD

IFPGGGYTNYAEKFQGRVTLTADTSISTAYMELSRLRSDDTVVYYCVRRN

FDYWGQGTLVTVSS

In a preferred embodiment, the antibody or binding fragment thereof according to the present invention comprises a HCVR comprising or consisting of the sequence SEQ ID NO: 66; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 66.

SEQ ID NO: 66
EVQLVQSGAEVKKPGESLKISCKGSGYTFTNYYIGWVRQMPGKGLEWIGD

IFPGGSYTNYSESFQGQVTLSADKSISTAYLQLSSLKASDTAMYYCVRRN

FDYWGQGTLVTVSS

In a preferred embodiment, the antibody or binding fragment thereof according to the present invention comprises a HCVR comprising or consisting of the sequence SEQ ID NO: 67; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 67.

SEQ ID NO: 67
QVQLVESGGGLVKPGGSLRLSCAASGFTFSNYYIGWIRQAPGKGLEWVGD

IFPGGSYTNYADSVKGRFTLSADTAKNSLYLQMNSLRAEDTAVYYCVRRN

FDYWGQGTLVTVSS

In a preferred embodiment, the antibody or binding fragment thereof according to the present invention comprises a HCVR comprising or consisting of the sequence SEQ ID NO: 68; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 68.

SEQ ID NO: 68
QVQLVQSGAEVKKPGASVKVSCKASGYTFTNYYIGWVRQAPGQGLEWIGR

IFPGGGYTNYAQKFQGRVTLTADTSISTAYMELSRLRSDDTVVYYCVRRN

FDYWGQGTLVTVSS

In a preferred embodiment, the antibody or binding fragment thereof according to the present invention comprises a HCVR comprising or consisting of the sequence SEQ ID NO: 69; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 69.

SEQ ID NO: 69
EVQLVQSGAEVKKPGESLKISCKGSGYSFTNYYIGWVRQMPGKGLEWIGI

IFPGGSYTNYSPSFQGQVTLSADKSISTAYLQLSSLKASDTAMYYCVRRN

FDYWGQGTLVTVSS

In a preferred embodiment, the antibody or binding fragment thereof according to the present invention comprises a HCVR comprising or consisting of the sequence SEQ ID NO: 70; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 70.

SEQ ID NO: 70
QVQLVESGGGLVKPGGSLRLSCAASGFTFSNYYIGWIRQAPGKGLEWVGD

IFSGGSYTNYADSVKGRFTLSADTAKNSLYLQMNSLRAEDTAVYYCVRRN

FDYWGQGTLVTVSS

In a preferred embodiment, the antibody or binding fragment thereof according to the present invention comprises a HCVR comprising or consisting of the sequence SEQ ID NO: 101; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 101.

SEQ ID NO: 101
QVQLVQSGAEVKKPGASVKVSCKASGYTFTNYYIGWVRQAPGQGLEWIGD

IFPGGDYTNYAEKFQGRVTLTADTSISTAYMELSRLRSDDTVVYYCVRRN

FDYWGQGTLVTVSS

In a preferred embodiment, the antibody or binding fragment thereof according to the present invention comprises a HCVR comprising or consisting of the sequence SEQ ID NO: 121; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 121.

SEQ ID NO: 121
QVQLVQSGAEVKKPGASVKVSCKASGYTFTNYYIGWVRQAPGQGLEWIGD

IFPGGGYANYAEKFQGRVTLTADTSISTAYMELSRLRSDDTVVYYCVRRN

FDYWGQGTLVTVSS

In a preferred embodiment, the antibody or binding fragment thereof according to the present invention comprises a HCVR comprising or consisting of the sequence SEQ ID NO: 122; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 122.

SEQ ID NO: 122
QVQLVQSGAEVKKPGASVKVSCKASGYTFTNYYIGWVRQAPGQGLEWIGD

IFPGGGYTNYAEKFKGRVTLTADTSISTAYMELSRLRSDDTVVYYCVRRN

FDYWGQGTLVTVSS

In a preferred embodiment, the antibody or binding fragment thereof according to the present invention comprises a HCVR comprising or consisting of the sequence SEQ ID NO: 123; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of the SEQ ID NO: 123.

SEQ ID NO: 123
QVQLVQSGAEVKKPGASVKVSCKASGYTFTNYYIGWVRQAPGQGLEWIGD

IFPGGGYTNYNEKFQGRVTLTADTSISTAYMELSRLRSDDTVVYYCVRRN

FDYWGQGTLVTVSS

In a preferred embodiment, the antibody or binding fragment thereof according to the present invention comprises a HCVR comprising or consisting of the sequence SEQ ID NO: 124; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 124.

SEQ ID NO: 124
QVQLVQSGAEVKKPGASVKVSCKASGYTFTNYYIGWVRQAPGQGLEWIGD

IFPGGGYTNSAEKFQGRVTLTADTSISTAYMELSRLRSDDTVVYYCVRRN

FDYWGQGTLVTVSS

In one embodiment, the antibody or binding fragment thereof according to the present invention comprises a LCVR comprising or consisting of:
- a $V_L$-FR1 as described hereinabove,
- a $V_L$-CDR1 as described hereinabove,
- a $V_L$-FR2 as described hereinabove,
- a $V_L$-CDR2 as described hereinabove,
- a $V_L$-FR3 as described hereinabove,
- a $V_L$-CDR3 as described hereinabove, and
- a $V_L$-FR4 as described hereinabove.

In one embodiment, the antibody or binding fragment thereof according to the present invention comprises a HCVR comprising or consisting of:
- a $V_L$-FR1 selected from SEQ ID NOs 44, 48, 52 and 55;
- a $V_L$-CDR1 selected from SEQ ID NO 12;
- a $V_L$-FR2 selected from SEQ ID NOs 45, 49, 53, 56, 58, 59 and 60;
- a $V_L$-CDR2 selected from SEQ ID NO 13;
- a $V_L$-FR3 selected from SEQ ID NOs 46, 50, 54 and 57;
- a $V_L$-CDR3 selected from SEQ ID NO 14; and
- a $V_L$-FR4 selected from SEQ ID NOs 47 and 51.

In one embodiment, the antibody or binding fragment thereof according to the present invention comprises a HCVR comprising or consisting of:
- a $V_L$-FR1 selected from SEQ ID NOs 44, 48, 52 and 55;
- a $V_L$-CDR1 selected from SEQ ID NOs 15 and 18;
- a $V_L$-FR2 selected from SEQ ID NOs 45, 49, 53, 56, 58, 59 and 60;
- a $V_L$-CDR2 selected from SEQ ID NOs 16, 19, 20, 22, 111 and 120;
- a $V_L$-FR3 selected from SEQ ID NOs 46, 50, 54 and 57;
- a $V_L$-CDR3 selected from SEQ ID NOs 17 and 21; and
- a $V_L$-FR4 selected from SEQ ID NOs 47 and 51.

In a preferred embodiment, the antibody or binding fragment thereof according to the present invention comprises a LCVR comprising or consisting of a combination of a $V_L$-FR1, a $V_L$-CDR1, a $V_L$-FR2, a $V_L$-CDR2, a $V_L$-FR3, a $V_L$-CDR3 and a $V_L$-FR4, said combination being as defined in Table 5.

TABLE 5

Preferred LCVR. The CDRs and FRs are defined by their SEQ ID NOs. The penultimate column refers to the SEQ ID NOs of the whole LCVR (with a first sequence number with $X_{12}$ being absent or being selected from Asn (N), Ser (S) and Gly (G); and $X_{18}$ being selected from Tyr (Y) and Phe (F); and a second sequence number where preferred $X_{12}$ and $X_{18}$ are defined).

| LCVR # | $V_L$-FR1 | $V_L$-CDR1 | $V_L$-FR2 | $V_L$-CDR2 | $V_L$-FR3 | $V_L$-CDR3 | $V_L$-FR4 | LCVR sequences | Name |
|---|---|---|---|---|---|---|---|---|---|
| #1 | 44 | 15 | 45 | 16 | 46 | 17 | 47 | 71/81 | Mouse VL |
| #2 | 48 | 15 | 49 | 16 | 50 | 17 | 51 | 72/82 | 19VLA |
| #3 | 52 | 15 | 53 | 16 | 54 | 17 | 51 | 73/83 | 621VLA |
| #4 | 55 | 15 | 56 | 16 | 57 | 17 | 51 | 74/84 | 311VLA |
| #5 | 48 | 18 | 58 | 16 | 50 | 17 | 51 | 75/85 | 19VLB |
| #6 | 52 | 18 | 59 | 19 | 54 | 17 | 51 | 76/86 | 621VLB |
| #7 | 55 | 18 | 56 | 16 | 57 | 17 | 51 | 77/87 | 311VLB |
| #8 | 48 | 18 | 58 | 20 | 50 | 17 | 51 | 78/88 | 19VLC |
| #9 | 52 | 18 | 59 | 19 | 54 | 21 | 51 | 79/89 | 621VLC |
| #10 | 55 | 18 | 60 | 22 | 57 | 17 | 51 | 80/90 | 311VLC |
| #11 | 48 | 18 | 49 | 16 | 50 | 17 | 51 | 102/103 | 19VLD |
| #12 | 48 | 18 | 58 | 111 | 50 | 17 | 51 | 112/113 | 19VLB "N50A" |
| #13 | 44 | 15 | 45 | 120 | 46 | 17 | 47 | 125/126 | Mouse "S52A" |
| #14 | 44 | 15 | 45 | 127 | 46 | 17 | 47 | 128/129 | 19VLB "N50X" |

In a one embodiment, the antibody or binding fragment thereof according to the present invention comprises a LCVR comprising or consisting of a combination of a $V_L$-FR1, a $V_L$-CDR1, a $V_L$-FR2, a $V_L$-CDR2, a $V_L$-FR3, a $V_L$-CDR3 and a $V_L$-FR4 as defined hereinabove, wherein $X_{15}$ is Phe (F) if $X_{12}$ is not absent (i.e., if $X_{12}$ is any of Asn (N), Ser (S) or Gly (G)). In a one embodiment, the antibody or binding fragment thereof according to the present invention comprises a LCVR comprising or consisting of a combination of a $V_L$-FR1, a $V_L$-CDR1, a $V_L$-FR2, a $V_L$-CDR2, a $V_L$-FR3, a $V_L$-CDR3 and a $V_L$-FR4 as defined hereinabove, wherein $X_{15}$ is selected from Tyr (Y) and Phe (F) if $X_{12}$ is absent.

In a preferred embodiment, the antibody or binding fragment thereof according to the present invention comprises a LCVR comprising or consisting of the sequence SEQ ID NO: 71, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 71.

SEQ ID NO: 71
QIYLTQSPTIMSASPGEKVTITCSASSSYS-$X_{12}$-YMHWFQQKTGTSPRL

WIYNTSNLPSGVPARFSGSGSGTSFSLTISRMEAEDAATYYCQQRSSYPL

TFGAGTKLELK

In a preferred embodiment, the antibody or binding fragment thereof according to the present invention comprises a LCVR comprising or consisting of the sequence SEQ ID NO: 72, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 72.

SEQ ID NO: 72
DIQLTQSPSFLSASVGDRVTITCSASSSVS-$X_{12}$-YMHWFQQKPGKAPKL

WIYNTSNLPSGVPSRFSGSGSGTEFTLTISSLQPEDFATYYCQQRSSYPL

TFGGGTKVEIK

In a preferred embodiment, the antibody or binding fragment thereof according to the present invention comprises a LCVR comprising or consisting of the sequence SEQ ID NO: 73, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 73.

SEQ ID NO: 73
EIVLTQSPDFQSVTPKEKVTITCSASSSVS-$X_{12}$-YMHWFQQKPDQSPKL

WIYNTSNLPSGVPSRFSGSGSGTDFTLTINSLEAEDAATYYCQQRSSYPL

TFGGGTKVEIK

In a preferred embodiment, the antibody or binding fragment thereof according to the present invention comprises a LCVR comprising or consisting of the sequence SEQ ID NO: 74, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 74.

SEQ ID NO: 74
EIVLTQSPATLSLSPGERATLSCSASSSYS-$X_{12}$-YMHWFQQKPGQAPRL

WIYNTSNLPSGIPARFSGSGSGTDFTLTISSLEPEDFAVYYCQQRSSYPL

TFGGGTKVEIK

In a preferred embodiment, the antibody or binding fragment thereof according to the present invention comprises a LCVR comprising or consisting of the sequence SEQ ID NO: 75, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 75.

SEQ ID NO: 75
DIQLTQSPSFLSASVGDRVTITCRASSSVS-$X_{12}$-YMHWYQQKPGKAPKL

WIYNTSNLPSGVPSRFSGSGSGTEFTLTISSLQPEDFATYYCQQRSSYPL

TFGGGTKVEIK

In a preferred embodiment, the antibody or binding fragment thereof according to the present invention comprises a LCVR comprising or consisting of the sequence SEQ ID NO: 76, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 76.

SEQ ID NO: 76
EIVLTQSPDFQSVTPKEKVTITCRASSSVS-$X_{12}$-YMHWYQQKPDQSPKL

WIYNTSNSPSGVPSRFSGSGSGTDFTLTINSLEAEDAATYYCQQRSSYPL

TFGGGTKVEIK

In a preferred embodiment, the antibody or binding fragment thereof according to the present invention comprises a LCVR comprising or consisting of the sequence SEQ ID NO: 77, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 77.

SEQ ID NO: 77
EIVLTQSPATLSLSPGERATLSCRASSSVS-$X_{12}$-YMHWFQQKPGQAPRL

WIYNTSNLPSGIPARFSGSGSGTDFTLTISSLEPEDFAVYYCQQRSSYPL

TFGGGTKVEIK

In a preferred embodiment, the antibody or binding fragment thereof according to the present invention comprises a LCVR comprising or consisting of the sequence SEQ ID NO: 78, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 78.

SEQ ID NO: 78
DIQLTQSPSFLSASVGDRVTITCRASSSVS-$X_{12}$-YMHWYQQKPGKAPKL

WIYATSNLQSGVPSRFSGSGSGTEFTLTISSLQPEDFATYYCQQRSSYPL

TFGGGTKVEIK

In a preferred embodiment, the antibody or binding fragment thereof according to the present invention comprises a LCVR comprising or consisting of the sequence SEQ ID NO: 79, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 79.

SEQ ID NO: 79
EIVLTQSPDFQSVTPKEKVTITCRASSSVS-$X_{12}$-YMHWYQQKPDQSPKL
WIYNTSNSPSGVPSRFSGSGSGTDFTLTINSLEAEDAATYYCHQRSSYPL
TFGGGTKVEIK

In a preferred embodiment, the antibody or binding fragment thereof according to the present invention comprises a LCVR comprising or consisting of the sequence SEQ ID NO: 80, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 80.

SEQ ID NO: 80
EIVLTQSPATLSLSPGERATLSCRASSSVS-$X_{12}$-YMHWYQQKPGQAPRL
WIYNTSNRATGIPARFSGSGSGTDFTLTISSLEPEDFAVYYCQQRSSYPL
TFGGGTKVEIK

In a preferred embodiment, the antibody or binding fragment thereof according to the present invention comprises a LCVR comprising or consisting of the sequence SEQ ID NO: 102, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 102.

SEQ ID NO: 102
DIQLTQSPSFLSASVGDRVTITCRASSSVS-$X_{12}$-YMHWFQQKPGKAPK
LWIYNTSNLPSGVPSRFSGSGSGTEFTLTISSLQPEDFATYYCQQRSS
YPLTFGGGTKVEIK

In a preferred embodiment, the antibody or binding fragment thereof according to the present invention comprises a LCVR comprising or consisting of the sequence SEQ ID NO: 112, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 112.

SEQ ID NO: 112
DIQLTQSPSFLSASVGDRVTITCRASSSVS-$X_{12}$-YMHWFQQKPGKAPK
LWIYATSNLPSGVPSRFSGSGSGTEFTLTISSLQPEDFATYYCQQRSS
YPLTFGGGTKVEIK

In a preferred embodiment, the antibody or binding fragment thereof according to the present invention comprises a LCVR comprising or consisting of the sequence SEQ ID NO: 125, with $X_{12}$ being selected from Asn (N), Ser (S) and Gly (G); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 125.

SEQ ID NO: 125
QIYLTQSPTIMSASPGEKVTITCSASSSYS-$X_{12}$-YMHWFQQKTGTSPR
LWIYNTANLPSGVPARFSGSGSGTSFSLTISRMEAEDAATYYCQQRSS
YPLTFGAGTKLELK

In a preferred embodiment, the antibody or binding fragment thereof according to the present invention comprises a LCVR comprising or consisting of the sequence SEQ ID NO: 128, with $X_{12}$ being selected from Asn (N), Ser (S) and Gly (G); and $X_{13}$ being any amino acid but Ala (A) or Asn (N); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 128.

SEQ ID NO: 128
DIQLTQSPSFLSASVGDRVTITCRASSSVS-$X_{12}$-YMHWYQQKPGKAPK
LWIY-$X_{13}$-TSNLPSGVPSRFSGSGSGTEFTLTISSLQPEDFATYYCQQ
RSSYPLTFGGGTKVEIK

In one embodiment, the antibody or binding fragment thereof according to the present invention comprises a LCVR comprising or consisting of sequences SEQ ID NO: 71-80, 102, 112, 125 or 128, wherein $X_{12}$ is absent.

In a preferred embodiment, the antibody or binding fragment thereof according to the present invention comprises a LCVR comprising or consisting of the sequence SEQ ID NO: 81; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 81.

SEQ ID NO: 81
QIVLTQSPTIMSASPGEKVTITCSASSSVSYMHWFQQKTGTSPRLWIYN
TSNLPSGVPARFSGSGSGTSYSLTISRMEAEDAATYYCQQRSSYPLTFG
AGTKLELK

In a preferred embodiment, the antibody or binding fragment thereof according to the present invention comprises a LCVR comprising or consisting of the sequence SEQ ID NO: 82; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 82.

SEQ ID NO: 82
DIQLTQSPSFLSASVGDRVTITCSASSSVSYMHWFQQKPGKAPKLWIYN
TSNLPSGVPSRFSGSGSGTEYTLTISSLQPEDFATYYCQQRSSYPLTFG
GGTKVEIK

In a preferred embodiment, the antibody or binding fragment thereof according to the present invention comprises a LCVR comprising or consisting of the sequence SEQ ID NO: 83; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 83.

SEQ ID NO: 83
EIVLTQSPDFQSVTPKEKVTITCSASSSVSYMHWFQQKPDQSPKLWIYN

TSNLPSGVPSRFSGSGSGTDYTLTINSLEAEDAATYYCQQRSSYPLTFG

GGTKVEIK

In a preferred embodiment, the antibody or binding fragment thereof according to the present invention comprises a LCVR comprising or consisting of the sequence SEQ ID NO: 84; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 84.

SEQ ID NO: 84
EIVLTQSPATLSLSPGERATLSCSASSSVSYMHWFQQKPGQAPRLWIYN

TSNLPSGIPARFSGSGSGTDYTLTISSLEPEDFAVYYCQQRSSYPLTFG

GGTKVEIK

In a preferred embodiment, the antibody or binding fragment thereof according to the present invention comprises a LCVR comprising or consisting of the sequence SEQ ID NO: 85; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 85.

SEQ ID NO: 85
DIQLTQSPSFLSASVGDRVTITCRASSSVSYMHWYQQKPGKAPKLWIYN

TSNLPSGVPSRFSGSGSGTEYTLTISSLQPEDFATYYCQQRSSYPLTFG

GGTKVEIK

In a preferred embodiment, the antibody or binding fragment thereof according to the present invention comprises a LCVR comprising or consisting of the sequence SEQ ID NO: 86; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 86.

SEQ ID NO: 86
EIVLTQSPDFQSVTPKEKVTITCRASSSVSYMHWYQQKPDQSPKLWIYN

TSNSPSGVPSRFSGSGSGTDFTLTINSLEAEDAATYYCQQRSSYPLTFG

GGTKVEIK

In a preferred embodiment, the antibody or binding fragment thereof according to the present invention comprises a LCVR comprising or consisting of the sequence SEQ ID NO: 87; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 87.

SEQ ID NO: 87
EIVLTQSPATLSLSPGERATLSCRASSSVSYMHWFQQKPGQAPRLWIYN

TSNLPSGIPARFSGSGSGTDYTLTISSLEPEDFAVYYCQQRSSYPLTFG

GGTKVEIK

In a preferred embodiment, the antibody or binding fragment thereof according to the present invention comprises a LCVR comprising or consisting of the sequence SEQ ID NO: 88; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 88.

SEQ ID NO: 88
DIQLTQSPSFLSASVGDRVTITCRASSSVSYMHWYQQKPGKAPKLWIYA

TSNLQSGVPSRFSGSGSGTEFTLTISSLQPEDFATYYCQQRSSYPLTFG

GGTKVEIK

In a preferred embodiment, the antibody or binding fragment thereof according to the present invention comprises a LCVR comprising or consisting of the sequence SEQ ID NO: 89; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 89.

SEQ ID NO: 89
EIVLTQSPDFQSVTPKEKVTITCRASSSVSYMHWYQQKPDQSPKLWIYN

TSNSPSGVPSRFSGSGSGTDFTLTINSLEAEDAATYYCHQRSSYPLTFG

GGTKVEIK

In a preferred embodiment, the antibody or binding fragment thereof according to the present invention comprises a LCVR comprising or consisting of the sequence SEQ ID NO: 90; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 90.

SEQ ID NO: 90
EIVLTQSPATLSLSPGERATLSCRASSSVSYMHWYQQKPGQAPRLWIYN

TSNRATGIPARFSGSGSGTDFTLTISSLEPEDFAVYYCQQRSSYPLTFG

GGTKVEIK

In a preferred embodiment, the antibody or binding fragment thereof according to the present invention comprises a LCVR comprising or consisting of the sequence SEQ ID NO: 103; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 103.

SEQ ID NO: 103
DIQLTQSPSFLSASVGDRVTITCRASSSVSSYMHWFQQKPGKAPKLWIY

NTSNLPSGVPSRFSGSGSGTEFTLTISSLQPEDFATYYCQQRSSYPLTF

GGGTKVEIK

In a preferred embodiment, the antibody or binding fragment thereof according to the present invention comprises a LCVR comprising or consisting of the sequence SEQ ID NO: 113; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 113.

SEQ ID NO: 113
DIQLTQSPSFLSASVGDRVTITCRASSSVSYMHWYQQKPGKAPKLWIYAT

SNLPSGVPSRFSGSGSGTEYTLTISSLQPEDFATYYCQQRSSYPLTFGGG

TKVEIK

In a preferred embodiment, the antibody or binding fragment thereof according to the present invention comprises a LCVR comprising or consisting of the sequence SEQ ID NO: 126; or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 126.

SEQ ID NO: 126
QIVLTQSPTIMSASPGEKVTITCSASSSVSYMHWFQQKTGTSPRLWIYNT

ANLPSGVPARFSGSGSGTSYSLTISRMEAEDAATYYCQQRSSYPLTFGAG

TKLELK

In a preferred embodiment, the antibody or binding fragment thereof according to the present invention comprises a LCVR comprising or consisting of the sequence SEQ ID NO: 129, with $X_{13}$ being any amino acid but Ala (A) or Asn (N); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NO: 129.

SEQ ID NO: 129
DIQLTQSPSFLSASVGDRVTITCRASSSVSYMHWYQQKPGKAPKLWIY- $X_{13}$-TSNLPSGVPSRFSGSGSGTEYTLTISSLQPEDFATYYCQQRSSYPL

TFGGGTKVEIK

In one embodiment, the antibody or binding fragment thereof according to the present invention comprises:
  a HCVR as defined hereinabove; and
  a LCVR as defined hereinabove.

In one embodiment, the antibody or binding fragment thereof according to the present invention comprises:
  a HCVR selected from SEQ ID NOs: 61, 62, 63, 64, 65, 66, 67, 68, 69, 70, 101, 121, 122, 123 and 124; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NOs: 61, 62, 63, 64, 65, 66, 67, 68, 69, 70, 101, 121, 122, 123 or 124; and
  a LCVR selected from SEQ ID NOs: 71, 72, 73, 74, 75, 76, 77, 78, 79, 80, 102, 112, 125 and 128, with $X_{12}$ being selected from Asn (N), Ser (S) and Gly (G), and $X_{13}$ being any amino acid but Ala (A) or Asn (N); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NOs: 71, 72, 73, 74, 75, 76, 77, 78, 79, 80, 102, 112, 125 or 128.

In one embodiment, the antibody or binding fragment thereof according to the present invention comprises:
  a HCVR selected from SEQ ID NOs: 61, 62, 63, 64, 65, 66, 67, 68, 69, 70, 101, 121, 122, 123 and 124; or a HCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NOs: 61, 62, 63, 64, 65, 66, 67, 68, 69, 70, 101, 121, 122, 123 or 124; and
  a LCVR selected from SEQ ID NOs: 81, 82, 83, 84, 85, 86, 87, 88, 89, 90, 103, 113, 126 and 129, with $X_{13}$ being any amino acid but Ala (A) or Asn (N); or a LCVR comprising or consisting of a sequence of the non-CDR regions sharing at least 70%, 75%, 80%, 85%, 90%, 95%, 96%, 97%, 98%, 99% or more of identity with the sequence of the non-CDR regions of SEQ ID NOs: 81, 82, 83, 84, 85, 86, 87, 88, 89, 90, 103, 113, 126 or 129.

In one embodiment, the antibody or binding fragment thereof according to the present invention comprises a HCVR of SEQ ID NO: 61 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 62 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 63 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 64 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 65 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 66 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 67 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 68 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 69 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 70 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 101 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 121 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 122 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 123 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 71, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 72, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 73, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 74, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 75, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 76, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 77, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 78, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 79, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 80, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 102, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 112, with $X_{12}$ being selected from Asn (N), Ser (S) and Gly (G).

In one embodiment, the antibody or binding fragment thereof according to the present invention comprises a HCVR of SEQ ID NO: 124 and a LCVR of SEQ ID NO: 125, with $X_{12}$ being selected from Asn (N), Ser (S) and Gly (G).

In one embodiment, the antibody or binding fragment thereof according to the present invention comprises a HCVR of SEQ ID NO: 61 and a LCVR of SEQ ID NO: 81.

In one embodiment, the antibody or binding fragment thereof according to the present invention comprises a HCVR of SEQ ID NO: 61 and a LCVR of SEQ ID NO: 82.

In one embodiment, the antibody or binding fragment thereof according to the present invention comprises a HCVR of SEQ ID NO: 61 and a LCVR of SEQ ID NO: 83.

In one embodiment, the antibody or binding fragment thereof according to the present invention comprises a HCVR of SEQ ID NO: 61 and a LCVR of SEQ ID NO: 84.

In one embodiment, the antibody or binding fragment thereof according to the present invention comprises a HCVR of SEQ ID NO: 61 and a LCVR of SEQ ID NO: 85.

In one embodiment, the antibody or binding fragment thereof according to the present invention comprises a HCVR of SEQ ID NO: 61 and a LCVR of SEQ ID NO: 86.

In one embodiment, the antibody or binding fragment thereof according to the present invention comprises a HCVR of SEQ ID NO: 61 and a LCVR of SEQ ID NO: 87.

In one embodiment, the antibody or binding fragment thereof according to the present invention comprises a HCVR of SEQ ID NO: 61 and a LCVR of SEQ ID NO: 88.

In one embodiment, the antibody or binding fragment thereof according to the present invention comprises a HCVR of SEQ ID NO: 61 and a LCVR of SEQ ID NO: 89.

In one embodiment, the antibody or binding fragment thereof according to the present invention comprises a HCVR of SEQ ID NO: 61 and a LCVR of SEQ ID NO: 90.

In one embodiment, the antibody or binding fragment thereof according to the present invention comprises a HCVR of SEQ ID NO: 61 and a LCVR of SEQ ID NO: 103.

In one embodiment, the antibody or binding fragment thereof according to the present invention comprises a HCVR of SEQ ID NO: 61 and a LCVR of SEQ ID NO: 113.

In one embodiment, the antibody or binding fragment thereof according to the present invention comprises a HCVR of SEQ ID NO: 61 and a LCVR of SEQ ID NO: 126.

In one embodiment, the antibody or binding fragment thereof according to the present invention comprises a HCVR of SEQ ID NO: 62 and a LCVR of SEQ ID NO: 81.

In one embodiment, the antibody or binding fragment thereof according to the present invention comprises a HCVR of SEQ ID NO: 62 and a LCVR of SEQ ID NO: 82.

In one embodiment, the antibody or binding fragment thereof according to the present invention comprises a HCVR of SEQ ID NO: 62 and a LCVR of SEQ ID NO: 83.

In one embodiment, the antibody or binding fragment thereof according to the present invention comprises a HCVR of SEQ ID NO: 62 and a LCVR of SEQ ID NO: 84.

In one embodiment, the antibody or binding fragment thereof according to the present invention comprises a HCVR of SEQ ID NO: 62 and a LCVR of SEQ ID NO: 85.

In one embodiment, the antibody or binding fragment thereof according to the present invention comprises a HCVR of SEQ ID NO: 62 and a LCVR of SEQ ID NO: 86.

In one embodiment, the antibody or binding fragment thereof according to the present invention comprises a HCVR of SEQ ID NO: 62 and a LCVR of SEQ ID NO: 87.

In one embodiment, the antibody or binding fragment thereof according to the present invention comprises a HCVR of SEQ ID NO: 62 and a LCVR of SEQ ID NO: 88.

In one embodiment, the antibody or binding fragment thereof according to the present invention comprises a HCVR of SEQ ID NO: 62 and a LCVR of SEQ ID NO: 89.

In one embodiment, the antibody or binding fragment thereof according to the present invention comprises a HCVR of SEQ ID NO: 62 and a LCVR of SEQ ID NO: 90.

In one embodiment, the antibody or binding fragment thereof according to the present invention comprises a HCVR of SEQ ID NO: 62 and a LCVR of SEQ ID NO: 103.

In one embodiment, the antibody or binding fragment thereof according to the present invention comprises a HCVR of SEQ ID NO: 62 and a LCVR of SEQ ID NO: 113.

In one embodiment, the antibody or binding fragment thereof according to the present invention comprises a HCVR of SEQ ID NO: 62 and a LCVR of SEQ ID NO: 126.

In one embodiment, the antibody or binding fragment thereof according to the present invention comprises a HCVR of SEQ ID NO: 63 and a LCVR of SEQ ID NO: 81.

In one embodiment, the antibody or binding fragment thereof according to the present invention comprises a HCVR of SEQ ID NO: 63 and a LCVR of SEQ ID NO: 82.

In one embodiment, the antibody or binding fragment thereof according to the present invention comprises a HCVR of SEQ ID NO: 63 and a LCVR of SEQ ID NO: 83.

In one embodiment, the antibody or binding fragment thereof according to the present invention comprises a HCVR of SEQ ID NO: 63 and a LCVR of SEQ ID NO: 84.

In one embodiment, the antibody or binding fragment thereof according to the present invention comprises a HCVR of SEQ ID NO: 63 and a LCVR of SEQ ID NO: 85.

In one embodiment, the antibody or binding fragment thereof according to the present invention comprises a HCVR of SEQ ID NO: 63 and a LCVR of SEQ ID NO: 86.

In one embodiment, the antibody or binding fragment thereof according to the present invention comprises a HCVR of SEQ ID NO: 63 and a LCVR of SEQ ID NO: 87.

In one embodiment, the antibody or binding fragment thereof according to the present invention comprises a HCVR of SEQ ID NO: 63 and a LCVR of SEQ ID NO: 88.

In one embodiment, the antibody or binding fragment thereof according to the present invention comprises a HCVR of SEQ ID NO: 63 and a LCVR of SEQ ID NO: 89.

In one embodiment, the antibody or binding fragment thereof according to the present invention comprises a HCVR of SEQ ID NO: 63 and a LCVR of SEQ ID NO: 90.

In one embodiment, the antibody or binding fragment thereof according to the present invention comprises a HCVR of SEQ ID NO: 63 and a LCVR of SEQ ID NO: 103.

In one embodiment, the antibody or binding fragment thereof according to the present invention comprises a HCVR of SEQ ID NO: 63 and a LCVR of SEQ ID NO: 113.

In one embodiment, the antibody or binding fragment thereof according to the present invention comprises a HCVR of SEQ ID NO: 63 and a LCVR of SEQ ID NO: 126.

In one embodiment, the antibody or binding fragment thereof according to the present invention comprises a HCVR of SEQ ID NO: 64 and a LCVR of SEQ ID NO: 81.

In one embodiment, the antibody or binding fragment thereof according to the present invention comprises a HCVR of SEQ ID NO: 64 and a LCVR of SEQ ID NO: 82.

In one embodiment, the antibody or binding fragment thereof according to the present invention comprises a HCVR of SEQ ID NO: 64 and a LCVR of SEQ ID NO: 83.

In one embodiment, the antibody or binding fragment thereof according to the present invention comprises a HCVR of SEQ ID NO: 64 and a LCVR of SEQ ID NO: 84.

In one embodiment, the antibody or binding fragment thereof according to the present invention comprises a HCVR of SEQ ID NO: 64 and a LCVR of SEQ ID NO: 85.

In one embodiment, the antibody or binding fragment thereof according to the present invention comprises a HCVR of SEQ ID NO: 64 and a LCVR of SEQ ID NO: 86.

In one embodiment, the antibody or binding fragment thereof according to the present invention comprises a HCVR of SEQ ID NO: 64 and a LCVR of SEQ ID NO: 87.

In one embodiment, the antibody or binding fragment thereof according to the present invention comprises a HCVR of SEQ ID NO: 64 and a LCVR of SEQ ID NO: 88.

In one embodiment, the antibody or binding fragment thereof according to the present invention comprises a HCVR of SEQ ID NO: 64 and a LCVR of SEQ ID NO: 89.

In one embodiment, the antibody or binding fragment thereof according to the present invention comprises a HCVR of SEQ ID NO: 64 and a LCVR of SEQ ID NO: 90.

In one embodiment, the antibody or binding fragment thereof according to the present invention comprises a HCVR of SEQ ID NO: 64 and a LCVR of SEQ ID NO: 103.

In one embodiment, the antibody or binding fragment thereof according to the present invention comprises a HCVR of SEQ ID NO: 64 and a LCVR of SEQ ID NO: 113.

In one embodiment, the antibody or binding fragment thereof according to the present invention comprises a HCVR of SEQ ID NO: 64 and a LCVR of SEQ ID NO: 126.

In one embodiment, the antibody or binding fragment thereof according to the present invention comprises a HCVR of SEQ ID NO: 65 and a LCVR of SEQ ID NO: 81.

In one embodiment, the antibody or binding fragment thereof according to the present invention comprises a HCVR of SEQ ID NO: 65 and a LCVR of SEQ ID NO: 82.

In one embodiment, the antibody or binding fragment thereof according to the present invention comprises a HCVR of SEQ ID NO: 65 and a LCVR of SEQ ID NO: 83.

In one embodiment, the antibody or binding fragment thereof according to the present invention comprises a HCVR of SEQ ID NO: 65 and a LCVR of SEQ ID NO: 84.

In one embodiment, the antibody or binding fragment thereof according to the present invention comprises a HCVR of SEQ ID NO: 65 and a LCVR of SEQ ID NO: 85.

In one embodiment, the antibody or binding fragment thereof according to the present invention comprises a HCVR of SEQ ID NO: 65 and a LCVR of SEQ ID NO: 86.

In one embodiment, the antibody or binding fragment thereof according to the present invention comprises a HCVR of SEQ ID NO: 65 and a LCVR of SEQ ID NO: 87.

In one embodiment, the antibody or binding fragment thereof according to the present invention comprises a HCVR of SEQ ID NO: 65 and a LCVR of SEQ ID NO: 88.

In one embodiment, the antibody or binding fragment thereof according to the present invention comprises a HCVR of SEQ ID NO: 65 and a LCVR of SEQ ID NO: 89.

In one embodiment, the antibody or binding fragment thereof according to the present invention comprises a HCVR of SEQ ID NO: 65 and a LCVR of SEQ ID NO: 90.

In one embodiment, the antibody or binding fragment thereof according to the present invention comprises a HCVR of SEQ ID NO: 65 and a LCVR of SEQ ID NO: 103.

In one embodiment, the antibody or binding fragment thereof according to the present invention comprises a HCVR of SEQ ID NO: 65 and a LCVR of SEQ ID NO: 113.

In one embodiment, the antibody or binding fragment thereof according to the present invention comprises a HCVR of SEQ ID NO: 65 and a LCVR of SEQ ID NO: 126.

In one embodiment, the antibody or binding fragment thereof according to the present invention comprises a HCVR of SEQ ID NO: 66 and a LCVR of SEQ ID NO: 81.

In one embodiment, the antibody or binding fragment thereof according to the present invention comprises a HCVR of SEQ ID NO: 66 and a LCVR of SEQ ID NO: 82.

In one embodiment, the antibody or binding fragment thereof according to the present invention comprises a HCVR of SEQ ID NO: 66 and a LCVR of SEQ ID NO: 83.

In one embodiment, the antibody or binding fragment thereof according to the present invention comprises a HCVR of SEQ ID NO: 66 and a LCVR of SEQ ID NO: 84.

In one embodiment, the antibody or binding fragment thereof according to the present invention comprises a HCVR of SEQ ID NO: 66 and a LCVR of SEQ ID NO: 85.

In one embodiment, the antibody or binding fragment thereof according to the present invention comprises a HCVR of SEQ ID NO: 66 and a LCVR of SEQ ID NO: 86.

In one embodiment, the antibody or binding fragment thereof according to the present invention comprises a HCVR of SEQ ID NO: 66 and a LCVR of SEQ ID NO: 87.

In one embodiment, the antibody or binding fragment thereof according to the present invention comprises a HCVR of SEQ ID NO: 66 and a LCVR of SEQ ID NO: 88.

In one embodiment, the antibody or binding fragment thereof according to the present invention comprises a HCVR of SEQ ID NO: 66 and a LCVR of SEQ ID NO: 89.

In one embodiment, the antibody or binding fragment thereof according to the present invention comprises a HCVR of SEQ ID NO: 66 and a LCVR of SEQ ID NO: 90.

In one embodiment, the antibody or binding fragment thereof according to the present invention comprises a HCVR of SEQ ID NO: 66 and a LCVR of SEQ ID NO: 103.

In one embodiment, the antibody or binding fragment thereof according to the present invention comprises a HCVR of SEQ ID NO: 66 and a LCVR of SEQ ID NO: 113.

In one embodiment, the antibody or binding fragment thereof according to the present invention comprises a HCVR of SEQ ID NO: 66 and a LCVR of SEQ ID NO: 126.

In one embodiment, the antibody or binding fragment thereof according to the present invention comprises a HCVR of SEQ ID NO: 67 and a LCVR of SEQ ID NO: 81.

In one embodiment, the antibody or binding fragment thereof according to the present invention comprises a HCVR of SEQ ID NO: 67 and a LCVR of SEQ ID NO: 82.

In one embodiment, the antibody or binding fragment thereof according to the present invention comprises a HCVR of SEQ ID NO: 67 and a LCVR of SEQ ID NO: 83.

In one embodiment, the antibody or binding fragment thereof according to the present invention comprises a HCVR of SEQ ID NO: 67 and a LCVR of SEQ ID NO: 84.

In one embodiment, the antibody or binding fragment thereof according to the present invention comprises a HCVR of SEQ ID NO: 67 and a LCVR of SEQ ID NO: 85.

In one embodiment, the antibody or binding fragment thereof according to the present invention comprises a HCVR of SEQ ID NO: 67 and a LCVR of SEQ ID NO: 86.

In one embodiment, the antibody or binding fragment thereof according to the present invention comprises a HCVR of SEQ ID NO: 67 and a LCVR of SEQ ID NO: 87.

In one embodiment, the antibody or binding fragment thereof according to the present invention comprises a HCVR of SEQ ID NO: 67 and a LCVR of SEQ ID NO: 88.

In one embodiment, the antibody or binding fragment thereof according to the present invention comprises a HCVR of SEQ ID NO: 67 and a LCVR of SEQ ID NO: 89.

In one embodiment, the antibody or binding fragment thereof according to the present invention comprises a HCVR of SEQ ID NO: 67 and a LCVR of SEQ ID NO: 90.

In one embodiment, the antibody or binding fragment thereof according to the present invention comprises a HCVR of SEQ ID NO: 67 and a LCVR of SEQ ID NO: 103.

In one embodiment, the antibody or binding fragment thereof according to the present invention comprises a HCVR of SEQ ID NO: 67 and a LCVR of SEQ ID NO: 113.

In one embodiment, the antibody or binding fragment thereof according to the present invention comprises a HCVR of SEQ ID NO: 67 and a LCVR of SEQ ID NO: 126.

In one embodiment, the antibody or binding fragment thereof according to the present invention comprises a HCVR of SEQ ID NO: 68 and a LCVR of SEQ ID NO: 81.

In one embodiment, the antibody or binding fragment thereof according to the present invention comprises a HCVR of SEQ ID NO: 68 and a LCVR of SEQ ID NO: 82.

In one embodiment, the antibody or binding fragment thereof according to the present invention comprises a HCVR of SEQ ID NO: 68 and a LCVR of SEQ ID NO: 83.

In one embodiment, the antibody or binding fragment thereof according to the present invention comprises a HCVR of SEQ ID NO: 68 and a LCVR of SEQ ID NO: 84.

In one embodiment, the antibody or binding fragment thereof according to the present invention comprises a HCVR of SEQ ID NO: 68 and a LCVR of SEQ ID NO: 85.

In one embodiment, the antibody or binding fragment thereof according to the present invention comprises a HCVR of SEQ ID NO: 68 and a LCVR of SEQ ID NO: 86.

In one embodiment, the antibody or binding fragment thereof according to the present invention comprises a HCVR of SEQ ID NO: 68 and a LCVR of SEQ ID NO: 87.

In one embodiment, the antibody or binding fragment thereof according to the present invention comprises a HCVR of SEQ ID NO: 68 and a LCVR of SEQ ID NO: 88.

In one embodiment, the antibody or binding fragment thereof according to the present invention comprises a HCVR of SEQ ID NO: 68 and a LCVR of SEQ ID NO: 89.

In one embodiment, the antibody or binding fragment thereof according to the present invention comprises a HCVR of SEQ ID NO: 68 and a LCVR of SEQ ID NO: 90.

In one embodiment, the antibody or binding fragment thereof according to the present invention comprises a HCVR of SEQ ID NO: 68 and a LCVR of SEQ ID NO: 103.

In one embodiment, the antibody or binding fragment thereof according to the present invention comprises a HCVR of SEQ ID NO: 68 and a LCVR of SEQ ID NO: 113.

In one embodiment, the antibody or binding fragment thereof according to the present invention comprises a HCVR of SEQ ID NO: 68 and a LCVR of SEQ ID NO: 126.

In one embodiment, the antibody or binding fragment thereof according to the present invention comprises a HCVR of SEQ ID NO: 69 and a LCVR of SEQ ID NO: 81.

In one embodiment, the antibody or binding fragment thereof according to the present invention comprises a HCVR of SEQ ID NO: 69 and a LCVR of SEQ ID NO: 82.

In one embodiment, the antibody or binding fragment thereof according to the present invention comprises a HCVR of SEQ ID NO: 69 and a LCVR of SEQ ID NO: 83.

In one embodiment, the antibody or binding fragment thereof according to the present invention comprises a HCVR of SEQ ID NO: 69 and a LCVR of SEQ ID NO: 84.

In one embodiment, the antibody or binding fragment thereof according to the present invention comprises a HCVR of SEQ ID NO: 69 and a LCVR of SEQ ID NO: 85.

In one embodiment, the antibody or binding fragment thereof according to the present invention comprises a HCVR of SEQ ID NO: 69 and a LCVR of SEQ ID NO: 86.

In one embodiment, the antibody or binding fragment thereof according to the present invention comprises a HCVR of SEQ ID NO: 69 and a LCVR of SEQ ID NO: 87.

In one embodiment, the antibody or binding fragment thereof according to the present invention comprises a HCVR of SEQ ID NO: 69 and a LCVR of SEQ ID NO: 88.

In one embodiment, the antibody or binding fragment thereof according to the present invention comprises a HCVR of SEQ ID NO: 69 and a LCVR of SEQ ID NO: 89.

In one embodiment, the antibody or binding fragment thereof according to the present invention comprises a HCVR of SEQ ID NO: 69 and a LCVR of SEQ ID NO: 90.

In one embodiment, the antibody or binding fragment thereof according to the present invention comprises a HCVR of SEQ ID NO: 69 and a LCVR of SEQ ID NO: 103.

In one embodiment, the antibody or binding fragment thereof according to the present invention comprises a HCVR of SEQ ID NO: 69 and a LCVR of SEQ ID NO: 113.

In one embodiment, the antibody or binding fragment thereof according to the present invention comprises a HCVR of SEQ ID NO: 69 and a LCVR of SEQ ID NO: 126.

In one embodiment, the antibody or binding fragment thereof according to the present invention comprises a HCVR of SEQ ID NO: 70 and a LCVR of SEQ ID NO: 81.

In one embodiment, the antibody or binding fragment thereof according to the present invention comprises a HCVR of SEQ ID NO: 70 and a LCVR of SEQ ID NO: 82.

In one embodiment, the antibody or binding fragment thereof according to the present invention comprises a HCVR of SEQ ID NO: 70 and a LCVR of SEQ ID NO: 83.

In one embodiment, the antibody or binding fragment thereof according to the present invention comprises a HCVR of SEQ ID NO: 70 and a LCVR of SEQ ID NO: 84.

In one embodiment, the antibody or binding fragment thereof according to the present invention comprises a HCVR of SEQ ID NO: 70 and a LCVR of SEQ ID NO: 85.

In one embodiment, the antibody or binding fragment thereof according to the present invention comprises a HCVR of SEQ ID NO: 70 and a LCVR of SEQ ID NO: 86.

In one embodiment, the antibody or binding fragment thereof according to the present invention comprises a HCVR of SEQ ID NO: 70 and a LCVR of SEQ ID NO: 87.

In one embodiment, the antibody or binding fragment thereof according to the present invention comprises a HCVR of SEQ ID NO: 70 and a LCVR of SEQ ID NO: 88.

In one embodiment, the antibody or binding fragment thereof according to the present invention comprises a HCVR of SEQ ID NO: 70 and a LCVR of SEQ ID NO: 89.

In one embodiment, the antibody or binding fragment thereof according to the present invention comprises a HCVR of SEQ ID NO: 70 and a LCVR of SEQ ID NO: 90.

In one embodiment, the antibody or binding fragment thereof according to the present invention comprises a HCVR of SEQ ID NO: 70 and a LCVR of SEQ ID NO: 103.

In one embodiment, the antibody or binding fragment thereof according to the present invention comprises a HCVR of SEQ ID NO: 70 and a LCVR of SEQ ID NO: 113.

In one embodiment, the antibody or binding fragment thereof according to the present invention comprises a HCVR of SEQ ID NO: 70 and a LCVR of SEQ ID NO: 126.

In one embodiment, the antibody or binding fragment thereof according to the present invention comprises a HCVR of SEQ ID NO: 101 and a LCVR of SEQ ID NO: 81.

In one embodiment, the antibody or binding fragment thereof according to the present invention comprises a HCVR of SEQ ID NO: 101 and a LCVR of SEQ ID NO: 82.

In one embodiment, the antibody or binding fragment thereof according to the present invention comprises a HCVR of SEQ ID NO: 101 and a LCVR of SEQ ID NO: 83.

In one embodiment, the antibody or binding fragment thereof according to the present invention comprises a HCVR of SEQ ID NO: 101 and a LCVR of SEQ ID NO: 84.

In one embodiment, the antibody or binding fragment thereof according to the present invention comprises a HCVR of SEQ ID NO: 101 and a LCVR of SEQ ID NO: 85.

In one embodiment, the antibody or binding fragment thereof according to the present invention comprises a HCVR of SEQ ID NO: 101 and a LCVR of SEQ ID NO: 86.

In one embodiment, the antibody or binding fragment thereof according to the present invention comprises a HCVR of SEQ ID NO: 101 and a LCVR of SEQ ID NO: 87.

In one embodiment, the antibody or binding fragment thereof according to the present invention comprises a HCVR of SEQ ID NO: 101 and a LCVR of SEQ ID NO: 88.

In one embodiment, the antibody or binding fragment thereof according to the present invention comprises a HCVR of SEQ ID NO: 101 and a LCVR of SEQ ID NO: 89.

In one embodiment, the antibody or binding fragment thereof according to the present invention comprises a HCVR of SEQ ID NO: 101 and a LCVR of SEQ ID NO: 90.

In one embodiment, the antibody or binding fragment thereof according to the present invention comprises a HCVR of SEQ ID NO: 101 and a LCVR of SEQ ID NO: 103.

In one embodiment, the antibody or binding fragment thereof according to the present invention comprises a HCVR of SEQ ID NO: 101 and a LCVR of SEQ ID NO: 113.

In one embodiment, the antibody or binding fragment thereof according to the present invention comprises a HCVR of SEQ ID NO: 101 and a LCVR of SEQ ID NO: 126.

In one embodiment, the antibody or binding fragment thereof according to the present invention comprises a HCVR of SEQ ID NO: 121 and a LCVR of SEQ ID NO: 81.

In one embodiment, the antibody or binding fragment thereof according to the present invention comprises a HCVR of SEQ ID NO: 121 and a LCVR of SEQ ID NO: 82.

In one embodiment, the antibody or binding fragment thereof according to the present invention comprises a HCVR of SEQ ID NO: 121 and a LCVR of SEQ ID NO: 83.

In one embodiment, the antibody or binding fragment thereof according to the present invention comprises a HCVR of SEQ ID NO: 121 and a LCVR of SEQ ID NO: 84.

In one embodiment, the antibody or binding fragment thereof according to the present invention comprises a HCVR of SEQ ID NO: 121 and a LCVR of SEQ ID NO: 85.

In one embodiment, the antibody or binding fragment thereof according to the present invention comprises a HCVR of SEQ ID NO: 121 and a LCVR of SEQ ID NO: 86.

In one embodiment, the antibody or binding fragment thereof according to the present invention comprises a HCVR of SEQ ID NO: 121 and a LCVR of SEQ ID NO: 87.

In one embodiment, the antibody or binding fragment thereof according to the present invention comprises a HCVR of SEQ ID NO: 121 and a LCVR of SEQ ID NO: 88.

In one embodiment, the antibody or binding fragment thereof according to the present invention comprises a HCVR of SEQ ID NO: 121 and a LCVR of SEQ ID NO: 89.

In one embodiment, the antibody or binding fragment thereof according to the present invention comprises a HCVR of SEQ ID NO: 121 and a LCVR of SEQ ID NO: 90.

In one embodiment, the antibody or binding fragment thereof according to the present invention comprises a HCVR of SEQ ID NO: 121 and a LCVR of SEQ ID NO: 103.

In one embodiment, the antibody or binding fragment thereof according to the present invention comprises a HCVR of SEQ ID NO: 121 and a LCVR of SEQ ID NO: 113.

In one embodiment, the antibody or binding fragment thereof according to the present invention comprises a HCVR of SEQ ID NO: 121 and a LCVR of SEQ ID NO: 126.

In one embodiment, the antibody or binding fragment thereof according to the present invention comprises a HCVR of SEQ ID NO: 122 and a LCVR of SEQ ID NO: 81.

In one embodiment, the antibody or binding fragment thereof according to the present invention comprises a HCVR of SEQ ID NO: 122 and a LCVR of SEQ ID NO: 82.

In one embodiment, the antibody or binding fragment thereof according to the present invention comprises a HCVR of SEQ ID NO: 122 and a LCVR of SEQ ID NO: 83.

In one embodiment, the antibody or binding fragment thereof according to the present invention comprises a HCVR of SEQ ID NO: 122 and a LCVR of SEQ ID NO: 84.

In one embodiment, the antibody or binding fragment thereof according to the present invention comprises a HCVR of SEQ ID NO: 122 and a LCVR of SEQ ID NO: 85.

In one embodiment, the antibody or binding fragment thereof according to the present invention comprises a HCVR of SEQ ID NO: 122 and a LCVR of SEQ ID NO: 86.

In one embodiment, the antibody or binding fragment thereof according to the present invention comprises a HCVR of SEQ ID NO: 122 and a LCVR of SEQ ID NO: 87.

In one embodiment, the antibody or binding fragment thereof according to the present invention comprises a HCVR of SEQ ID NO: 122 and a LCVR of SEQ ID NO: 88.

In one embodiment, the antibody or binding fragment thereof according to the present invention comprises a HCVR of SEQ ID NO: 122 and a LCVR of SEQ ID NO: 89.

In one embodiment, the antibody or binding fragment thereof according to the present invention comprises a HCVR of SEQ ID NO: 122 and a LCVR of SEQ ID NO: 90.

In one embodiment, the antibody or binding fragment thereof according to the present invention comprises a HCVR of SEQ ID NO: 122 and a LCVR of SEQ ID NO: 103.

In one embodiment, the antibody or binding fragment thereof according to the present invention comprises a HCVR of SEQ ID NO: 122 and a LCVR of SEQ ID NO: 113.

In one embodiment, the antibody or binding fragment thereof according to the present invention comprises a HCVR of SEQ ID NO: 122 and a LCVR of SEQ ID NO: 126.

In one embodiment, the antibody or binding fragment thereof according to the present invention comprises a HCVR of SEQ ID NO: 123 and a LCVR of SEQ ID NO: 81.

In one embodiment, the antibody or binding fragment thereof according to the present invention comprises a HCVR of SEQ ID NO: 123 and a LCVR of SEQ ID NO: 82.

In one embodiment, the antibody or binding fragment thereof according to the present invention comprises a HCVR of SEQ ID NO: 123 and a LCVR of SEQ ID NO: 83.

In one embodiment, the antibody or binding fragment thereof according to the present invention comprises a HCVR of SEQ ID NO: 123 and a LCVR of SEQ ID NO: 84.

In one embodiment, the antibody or binding fragment thereof according to the present invention comprises a HCVR of SEQ ID NO: 123 and a LCVR of SEQ ID NO: 85.

In one embodiment, the antibody or binding fragment thereof according to the present invention comprises a HCVR of SEQ ID NO: 123 and a LCVR of SEQ ID NO: 86.

In one embodiment, the antibody or binding fragment thereof according to the present invention comprises a HCVR of SEQ ID NO: 123 and a LCVR of SEQ ID NO: 87.

In one embodiment, the antibody or binding fragment thereof according to the present invention comprises a HCVR of SEQ ID NO: 123 and a LCVR of SEQ ID NO: 88.

In one embodiment, the antibody or binding fragment thereof according to the present invention comprises a HCVR of SEQ ID NO: 123 and a LCVR of SEQ ID NO: 89.

In one embodiment, the antibody or binding fragment thereof according to the present invention comprises a HCVR of SEQ ID NO: 123 and a LCVR of SEQ ID NO: 90.

In one embodiment, the antibody or binding fragment thereof according to the present invention comprises a HCVR of SEQ ID NO: 123 and a LCVR of SEQ ID NO: 103.

In one embodiment, the antibody or binding fragment thereof according to the present invention comprises a HCVR of SEQ ID NO: 123 and a LCVR of SEQ ID NO: 113.

In one embodiment, the antibody or binding fragment thereof according to the present invention comprises a HCVR of SEQ ID NO: 123 and a LCVR of SEQ ID NO: 126.

In one embodiment, the antibody or binding fragment thereof according to the present invention comprises a HCVR of SEQ ID NO: 124 and a LCVR of SEQ ID NO: 81.

In one embodiment, the antibody or binding fragment thereof according to the present invention comprises a HCVR of SEQ ID NO: 124 and a LCVR of SEQ ID NO: 82.

In one embodiment, the antibody or binding fragment thereof according to the present invention comprises a HCVR of SEQ ID NO: 124 and a LCVR of SEQ ID NO: 83.

In one embodiment, the antibody or binding fragment thereof according to the present invention comprises a HCVR of SEQ ID NO: 124 and a LCVR of SEQ ID NO: 84.

In one embodiment, the antibody or binding fragment thereof according to the present invention comprises a HCVR of SEQ ID NO: 124 and a LCVR of SEQ ID NO: 85.

In one embodiment, the antibody or binding fragment thereof according to the present invention comprises a HCVR of SEQ ID NO: 124 and a LCVR of SEQ ID NO: 86.

In one embodiment, the antibody or binding fragment thereof according to the present invention comprises a HCVR of SEQ ID NO: 124 and a LCVR of SEQ ID NO: 87.

In one embodiment, the antibody or binding fragment thereof according to the present invention comprises a HCVR of SEQ ID NO: 124 and a LCVR of SEQ ID NO: 88.

In one embodiment, the antibody or binding fragment thereof according to the present invention comprises a HCVR of SEQ ID NO: 124 and a LCVR of SEQ ID NO: 89.

In one embodiment, the antibody or binding fragment thereof according to the present invention comprises a HCVR of SEQ ID NO: 124 and a LCVR of SEQ ID NO: 90.

In one embodiment, the antibody or binding fragment thereof according to the present invention comprises a HCVR of SEQ ID NO: 124 and a LCVR of SEQ ID NO: 103.

In one embodiment, the antibody or binding fragment thereof according to the present invention comprises a HCVR of SEQ ID NO: 124 and a LCVR of SEQ ID NO: 113.

In one embodiment, the antibody or binding fragment thereof according to the present invention comprises a HCVR of SEQ ID NO: 124 and a LCVR of SEQ ID NO: 126.

In one embodiment, any of the HCVR and/or LCVR as defined hereinabove can be characterized as having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acids being substituted by a different amino acid.

In one embodiment, the sequence of the non-CDR regions of any of the HCVR and/or LCVR as defined hereinabove can be characterized as having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or more amino acids being substituted by a different amino acid.

In one embodiment, any of the HCVR and/or LCVR as defined hereinabove can be characterized as having an amino acid sequence that shares at least 70%, 75%, 80%, 85%, 90%, 95%, 96%, 97%, 98%, 99% or more of identity with the particular HCVR and/or LCVR as defined hereinabove.

In one embodiment, the sequence of the non-CDR regions of any of the HCVR and/or LCVR as defined hereinabove can be characterized as having an amino acid sequence that shares at least 70%, 75%, 80%, 85%, 90%, 95%, 96%, 97%, 98%, 99% or more of identity with the sequence of the non-CDR regions of the particular HCVR and/or LCVR as defined hereinabove.

In one embodiment, the body or binding fragment thereof according to the present invention comprises a fully or substantially fully human heavy chain constant region (abbreviated herein as HCCR or $C_H$) and/or light chain constant region (abbreviated herein as LCCR or $C_L$).

In one embodiment, the antibody or binding fragment thereof according to the present invention comprises a HCCR comprising or consisting of the sequence SEQ ID NO: 91.

```
                                           SEQ ID NO: 91
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In one embodiment, the antibody or binding fragment thereof according to the present invention comprises a HCCR comprising or consisting of the sequence SEQ ID NO: 114.

```
                                          SEQ ID NO: 114
ASTKGPSVFPLAPSSKSTSGGTAALGCLVKDYFPEPVTVSWNSGALTSGV

TFPAVLQSSGLYSLSSVVTVPSSSLGTQTYICNVNHKPSNTKVDKRVEPK

SCDKTHTCPPCPAPEAAGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPSSIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK
```

In one embodiment, the antibody or binding fragment thereof according to the present invention comprises a HCCR comprising or consisting of the sequence SEQ ID NO: 115.

```
                                          SEQ ID NO: 115
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCVAAAHHHHHH
```

In one embodiment, the antibody or binding fragment thereof according to the present invention comprises a LCCR comprising or consisting of the sequence SEQ ID NO: 92.

```
                                           SEQ ID NO: 92
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

In one embodiment, the antibody or binding fragment thereof according to the present invention comprises:
  a HCCR comprising or consisting of the sequence SEQ ID NO: 91, 114 or 115; and
  a LCCR comprising or consisting of the sequence SEQ ID NO: 92.

In one embodiment, the antibody or binding fragment thereof according to the present invention comprises:
  a HCCR comprising or consisting of the sequence SEQ ID NO: 91; and
  a LCCR comprising or consisting of the sequence SEQ ID NO: 92.

In one embodiment, the antibody or binding fragment thereof according to the present invention comprises:
- a HCCR comprising or consisting of the sequence SEQ ID NO: 114; and
- a LCCR comprising or consisting of the sequence SEQ ID NO: 92.

In one embodiment, the antibody or binding fragment thereof according to the present invention comprises:
- a HCCR comprising or consisting of the sequence SEQ ID NO: 115; and
- a LCCR comprising or consisting of the sequence SEQ ID NO: 92.

In one embodiment, the HCCR with SEQ ID NO: 91, 114 or 115 can be characterized as having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or more amino acids being substituted by a different amino acid.

In one embodiment, the LCCR with SEQ ID NO: 92 can be characterized as having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or more amino acids being substituted by a different amino acid.

In one embodiment, the HCCR with SEQ ID NO: 91, 114 or 115, and/or the LCCR with SEQ ID NO: 92, can be characterized as having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or more amino acids being substituted by a different amino acid.

In one embodiment, the HCCR with SEQ ID NO: 91, 114 or 115, can be characterized as having an amino acid sequence that shares at least 70%, 75%, 80%, 85%, 90%, 95%, 96%, 97%, 98%, 99% or more of identity with SEQ ID NO: 91, 114 or 115, respectively.

In one embodiment, the LCCR with SEQ ID NO: 92 can be characterized as having an amino acid sequence that shares at least 70%, 75%, 80%, 85%, 90%, 95%, 96%, 97%, 98%, 99% or more of identity with SEQ ID NO: 92.

In one embodiment, the HCCR with SEQ ID NO: 91, 114 or 115, and/or the LCCR with SEQ ID NO: 92 can be characterized as having an amino acid sequence that shares at least 70%, 75%, 80%, 85%, 90%, 95%, 96%, 97%, 98%, 99% or more of identity with SEQ ID NO: 91, 114 or 115, and/or SEQ ID NO: 92, respectively.

In one embodiment, the antibody or binding fragment thereof according to the present invention comprises a HCCR and a LCCR comprising amino acid sequences that are homologous to the amino acid sequences of SEQ ID NO: 91, 114 or 115, and SEQ ID NO: 92, respectively, and wherein said antibody or binding fragment thereof retains the desired functional properties.

In one embodiment, the body or binding fragment thereof according to the present invention comprises a fully or substantially fully murine HCCR and/or LCCR.

In one embodiment, the antibody or binding fragment thereof according to the present invention comprises a HCCR comprising or consisting of the sequence SEQ ID NO: 93.

```
                                             SEQ ID NO: 93
AKTTPPSVYPLAPGSAAQTNSMVTLGCLVKGYFPEPVTVTWNSGSLSSGV

HTFPAVLQSDLYTLSSSVTVPSSTWPSETVTCNVAHPASSTKVDKKIVPR

DCGCKPCICTVPEVSSVFIFPPKPKDVLTITLTPKVTCVVVDISKDDPEV

QFSWFVDDVEVHTAQTQPREEQFNSTFRSVSELPIMHQDWLNGKEFKCRV

NSAAFPAPIEKTISKTKGRPKAPQVYTIPPPKEQMAKDKVSLTCMITDFF

PEDITVEWQWNGQPAENYKNTQPIMDTDGSYFVYSKLNVQKSNWEAGNTF

TCSVLHEGLHNHHTEKSLSHSPG
```

In one embodiment, the antibody or binding fragment thereof according to the present invention comprises a LCCR comprising or consisting of the sequence SEQ ID NO: 94.

```
                                             SEQ ID NO: 94
RADAAPTVSIFPPSSEQLTSGGASVVCFLNNFYPKDINVKWKIDGSERQN

GVLNSWTDQDSKDSTYSMSSTLTLTKDEYERHNSYTCEATHKTSTSPIVK

SFNRNEC
```

In one embodiment, the antibody or binding fragment thereof according to the present invention comprises:
- a HCCR comprising or consisting of the sequence SEQ ID NO: 93; and
- a LCCR comprising or consisting of the sequence SEQ ID NO: 94.

In one embodiment, the HCCR with SEQ ID NO: 93 can be characterized as having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 or more amino acids being substituted by a different amino acid.

In one embodiment, the LCCR with SEQ ID NO: 94 can be characterized as having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or more amino acids being substituted by a different amino acid.

In one embodiment, the HCCR with SEQ ID NO: 93 and/or the LCCR with SEQ ID NO: 94 can be characterized as having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 or more amino acids being substituted by a different amino acid.

In one embodiment, the HCCR with SEQ ID NO: 93 can be characterized as having an amino acid sequence that shares at least 70%, 75%, 80%, 85%, 90%, 95%, 96%, 97%, 98%, 99% or more of identity with SEQ ID NO: 93.

In one embodiment, the LCCR with SEQ ID NO: 94 can be characterized as having an amino acid sequence that shares at least 70%, 75%, 80%, 85%, 90%, 95%, 96%, 97%, 98%, 99% or more of identity with SEQ ID NO: 94.

In one embodiment, the HCCR with SEQ ID NO: 93 and/or the LCCR with SEQ ID NO: 94 can be characterized as having an amino acid sequence that shares at least 70%, 75%, 80%, 85%, 90%, 95%, 96%, 97%, 98%, 99% or more of identity with SEQ ID NO: 93 and/or SEQ ID NO: 94, respectively.

In one embodiment, the antibody or binding fragment thereof according to the present invention comprises a HCCR and a LCCR comprising amino acid sequences that are homologous to the amino acid sequences of SEQ ID NO: 93 and SEQ ID NO: 94, respectively, and wherein said antibody or binding fragment thereof retains the desired functional properties.

In one embodiment, the antibody or binding fragment thereof according to the present invention is a murine, a chimeric or a humanized antibody or fragment thereof.

In one embodiment, the antibody or binding fragment thereof according to the present invention is a murine antibody or fragment thereof.

A "murine antibody or binding fragment thereof", as used herein, includes antibodies and binding fragment thereof in which the variable region (including the CDRs and FRs) and the constant region are derived from a mouse.

In one embodiment, the murine antibody or binding fragment thereof according to the present invention comprises at least one, preferably at least two, more preferably the three HCVR's CDRs set forth in SEQ ID NOs: 1, 2 and 3; and/or at least one, preferably at least two, more preferably the three LCVR's CDRs set forth in SEQ ID NOs: 12, 13 and 14, with, wherever applicable, $X_{12}$ being absent.

In a preferred embodiment, the murine antibody or binding fragment thereof according to the present invention comprises at least one, preferably at least two, more preferably the three HCVR's CDRs set forth in SEQ ID NOs: 1, 4 and 3; and/or at least one, preferably at least two, more preferably the three LCVR's CDRs set forth in SEQ ID NOs: 15, 16 and 17, with, wherever applicable, $X_{12}$ being absent.

In a preferred embodiment, the murine antibody or binding fragment thereof according to the present invention may further comprise at least one, preferably at least two, more preferably at least three, even more preferably the four HCVR's FRs set forth in SEQ ID NOs: 25, 26, 27 and 28; and/or at least one, preferably at least two, more preferably at least three, even more preferably the four LCVR's FRs set forth in SEQ ID NOs: 44, 45, 46 and 47, with, wherever applicable, $X_{15}$ being a Tyr (Y).

In a preferred embodiment, the murine antibody or binding fragment thereof according to the present invention may therefore comprise a HCVR as set forth in SEQ ID NO: 61; and/or a LCVR as set forth in SEQ ID NO: 71 or 81.

In a preferred embodiment, the murine antibody or binding fragment thereof according to the present invention may further comprise a HCCR as set forth in SEQ ID NO: 93; and/or a LCCR as set forth in SEQ ID NO: 94.

In a preferred embodiment, the murine antibody or binding fragment thereof according to the present invention may therefore comprise a heavy chain comprising a variable region as set forth in SEQ ID NO: 61; and/or constant region as set forth in SEQ ID NO: 93.

In a preferred embodiment, the murine antibody or binding fragment thereof according to the present invention may therefore comprise a light chain comprising a variable region as set forth in SEQ ID NO: 71 or 81; and/or constant region as set forth in SEQ ID NO: 94.

In one embodiment, the antibody or binding fragment thereof according to the present invention is a chimeric antibody or binding fragment thereof.

A "chimeric antibody or binding fragment thereof", as used herein, broadly refers to an antibody or binding fragment thereof comprising a first amino acid sequence linked to a second amino acid sequence with which it is not naturally linked in nature. The amino acid sequences may normally exist in separate proteins that are brought together in the fusion protein or they may normally exist in the same protein but are placed in a new arrangement in the fusion protein. A chimeric protein may be created, for example, by chemical synthesis, or by creating and translating a polynucleotide in which the peptide regions are encoded in the desired relationship. The term "chimeric antibody or binding fragment thereof" encompasses herein antibodies and binding fragment thereof in which (a) the constant region, or a portion thereof, is altered, replaced or exchanged so that the variable region is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

In one embodiment, the chimeric antibody or binding fragment thereof according to the present invention comprises a heavy chain and/or a light chain, comprising a human constant region and a murine variable region (including murine CDRs and murine FRs).

In one embodiment, the chimeric antibody or binding fragment thereof according to the present invention comprises a human heavy chain and a murine light chain; or a murine heavy chain and a human light chain.

In one embodiment, the chimeric antibody or binding fragment thereof according to the present invention comprises at least one, preferably at least two, more preferably the three HCVR's CDRs set forth in SEQ ID NOs: 1, 2 and 3; and/or at least one, preferably at least two, more preferably the three LCVR's CDRs set forth in SEQ ID NOs: 12, 13 and 14.

In a preferred embodiment, the chimeric antibody or binding fragment thereof according to the present invention comprises at least one, preferably at least two, more preferably the three HCVR's CDRs set forth in SEQ ID NOs: 1, 4 and 3; and/or at least one, preferably at least two, more preferably the three LCVR's CDRs set forth in SEQ ID NOs: 15, 16 and 17.

In a preferred embodiment, the chimeric antibody or binding fragment thereof according to the present invention comprises at least one, preferably at least two, more preferably the three HCVR's CDRs set forth in SEQ ID NOs: 1, 4 and 3; and/or at least one, preferably at least two, more preferably the three LCVR's CDRs set forth in SEQ ID NOs: 18, 111 or 120, and 17, respectively.

In a preferred embodiment, the chimeric antibody or binding fragment thereof according to the present invention may further comprise at least one, preferably at least two, more preferably at least three, even more preferably the four HCVR's FRs set forth in SEQ ID NOs: 25, 26, 27 and 28; and/or at least one, preferably at least two, more preferably at least three, even more preferably the four LCVR's FRs set forth in SEQ ID NOs: 44, 45, 46 and 47.

In a preferred embodiment, the chimeric antibody or binding fragment thereof according to the present invention may further comprise at least one, preferably at least two, more preferably at least three, even more preferably the four HCVR's FRs set forth in SEQ ID NOs: 25, 26, 27 and 28;

and/or at least one, preferably at least two, more preferably at least three, even more preferably the four LCVR's FRs set forth in SEQ ID NOs: 48, 58, 50 and 51.

In a preferred embodiment, the chimeric antibody or binding fragment thereof according to the present invention may therefore comprise a HCVR as set forth in SEQ ID NO: 61; and/or a LCVR as set forth in SEQ ID NO: 71 or 81.

In a preferred embodiment, the chimeric antibody or binding fragment thereof according to the present invention may therefore comprise a HCVR as set forth in SEQ ID NO: 61; and/or a LCVR as set forth in SEQ ID NO: 112, 113, 125, 126, 128 or 129.

In a preferred embodiment, the chimeric antibody or binding fragment thereof according to the present invention may further comprise a human HCCR as set forth in SEQ ID NO: 91, 114 or 115; and/or a human LCCR as set forth in SEQ ID NO: 92.

In a preferred embodiment, the chimeric antibody or binding fragment thereof according to the present invention may further comprise a human HCCR as set forth in SEQ ID NO: 91; and/or a human LCCR as set forth in SEQ ID NO: 92.

In a preferred embodiment, the chimeric antibody or binding fragment thereof according to the present invention may further comprise a human HCCR as set forth in SEQ ID NO: 114; and/or a human LCCR as set forth in SEQ ID NO: 92.

In a preferred embodiment, the chimeric antibody or binding fragment thereof according to the present invention may further comprise a human HCCR as set forth in SEQ ID NO: 115; and/or a human LCCR as set forth in SEQ ID NO: 92.

In a preferred embodiment, the chimeric antibody or binding fragment thereof according to the present invention may further comprise a human HCCR as set forth in SEQ ID NO: 91, 114 or 115; and/or a murine LCCR as set forth in SEQ ID NO: 94.

In a preferred embodiment, the chimeric antibody or binding fragment thereof according to the present invention may further comprise a human HCCR as set forth in SEQ ID NO: 91; and/or a murine LCCR as set forth in SEQ ID NO: 94.

In a preferred embodiment, the chimeric antibody or binding fragment thereof according to the present invention may further comprise a human HCCR as set forth in SEQ ID NO: 114; and/or a murine LCCR as set forth in SEQ ID NO: 94.

In a preferred embodiment, the chimeric antibody or binding fragment thereof according to the present invention may further comprise a human HCCR as set forth in SEQ ID NO: 115; and/or a murine LCCR as set forth in SEQ ID NO: 94.

In a preferred embodiment, the chimeric antibody or binding fragment thereof according to the present invention may further comprise a murine HCCR as set forth in SEQ ID NO: 93; and/or a human LCCR as set forth in SEQ ID NO: 92.

In a preferred embodiment, the chimeric antibody or binding fragment thereof according to the present invention may therefore comprise a heavy chain comprising a variable region as set forth in SEQ ID NO: 61; and/or constant region as set forth in SEQ ID NO: 91, 114 or 115.

In a preferred embodiment, the chimeric antibody or binding fragment thereof according to the present invention may therefore comprise a heavy chain comprising a variable region as set forth in SEQ ID NO: 61; and/or constant region as set forth in SEQ ID NO: 91.

In a preferred embodiment, the chimeric antibody or binding fragment thereof according to the present invention may therefore comprise a heavy chain comprising a variable region as set forth in SEQ ID NO: 61; and/or constant region as set forth in SEQ ID NO: 114.

In a preferred embodiment, the chimeric antibody or binding fragment thereof according to the present invention may therefore comprise a heavy chain comprising a variable region as set forth in SEQ ID NO: 61; and/or constant region as set forth in SEQ ID NO: 115.

In a preferred embodiment, the chimeric antibody or binding fragment thereof according to the present invention may therefore comprise a light chain comprising a variable region as set forth in SEQ ID NO: 71 or 81; and/or constant region as set forth in SEQ ID NO: 92.

In one embodiment, the antibody or binding fragment thereof according to the present invention is a humanized antibody or binding fragment thereof.

A "humanized antibody or binding fragment thereof", as used herein, refers to a chimeric antibody or binding fragment thereof which contains minimal sequence derived from a non-human immunoglobulin. It includes antibodies made by a non-human cell having variable and constant regions which have been altered to more closely resemble antibodies that would be made by a human cell, e.g., by altering the non-human antibody amino acid sequence to incorporate amino acids found in human germline immunoglobulin sequences. Humanized antibodies or binding fragment thereof according to the present invention may include amino acid residues not encoded by human germline immunoglobulin sequences (e.g., mutations introduced by random or site-specific mutagenesis in vitro or by somatic mutation in vivo), for example in the CDRs. The term "humanized antibody or binding fragment thereof" also includes antibodies and binding fragment thereof in which CDR sequences derived from the germline of another mammalian species, such as a mouse, have been grafted onto human framework sequences. In other words, the term "humanized antibody or binding fragment thereof" refers to an antibody or binding fragment thereof in which the CDRs of a recipient human antibody are replaced by CDRs from a donor non-human antibody, e.g., a mouse antibody. Humanized antibodies or binding fragments thereof may also comprise residues of donor origin in the framework sequences. The humanized antibody or binding fragment thereof can also comprise at least a portion of a human immunoglobulin constant region. Humanized antibodies and binding fragments thereof may also comprise residues which are found neither in the recipient antibody, nor in the imported CDR or FR sequences. Humanization can be performed using methods known in the art (e.g., Jones et al., 1986. *Nature.* 321(6069):522-5; Riechmann et al., 1988. *Nature.* 332 (6162):323-7; Verhoeyen et al., 1988. *Science.* 239(4847): 1534-6; Presta, 1992. *Curr Opin Biotechnol.* 3(4):394-8; U.S. Pat. No. 4,816,567), including techniques such as "superhumanizing" antibodies (e.g., Tan et al., 2002. *J Immunol.* 169(2):1119-25) and "resurfacing" (e.g., Staelens et al., 2006. *Mol Immunol.* 43(8):1243-57; Roguska et al., 1994. *Proc Nat Acad Sci USA.* 91(3):969-73).

Methods for humanizing the antibody or binding fragment thereof according to the present invention are well-known in the art, and will be further detailed in the Example section below. The choice of human variable domains, both light and heavy, to be used in making the humanized antibody or binding fragment thereof is very important to reduce antigenicity. According to the so-called "best-fit" method, the sequence of the variable domain of an antibody or binding fragment thereof according to the present invention is screened against the entire library of known human variable-domain sequences. The human sequence that is closest to the mouse sequence is then accepted as the human framework (FR) for the humanized antibody (Sims et al., 1993. *J Immunol.* 151(4):2296-308; Chothia & Lesk, 1987. *J Mol Biol.* 196(4):901-17).

Another method for humanizing the antibody or binding fragment thereof according to the present invention uses a particular FR from the consensus sequence of all human antibodies of a particular subgroup of light or heavy chains. The same framework can be used for several different humanized antibodies (Carter et al., 1992. *Proc Natl Acad Sci USA.* 89(10):4285-9; Presta et al., 1993. *J Immunol.* 151(5):2623-32). It is further important that antibodies be humanized with retention of high affinity for hCD45RC and other favorable biological properties. To achieve this goal, according to a preferred method, humanized antibodies and binding fragments thereof are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its epitope. In this way, CDR residues can be selected and combined from the consensus and import sequences so that the desired antibody characteristic, such as an increased affinity for hCD45RC, is achieved. In general, the CDR residues are directly and most substantially involved in influencing antigen binding.

Another method for humanizing the antibody or binding fragment thereof according to the present invention is to use a transgenic or transchromosomic animal carrying parts of the human immune system for immunization. As a host, these animals have had their immunoglobulin genes replaced by functional human immunoglobulin genes. Thus, antibodies produced by these animals or in hybridomas made from the B cells of these animals are already humanized. Examples of such transgenic or transchromosomic animal include, without limitation:

the XenoMouse (Abgenix, Fremont, CA), described in U.S. Pat. Nos. 5,939,598, 6,075,181, 6,114,598, 6,150,584 and 6,162,963;

the HuMAb Mouse® (Medarex, Inc.), described in Lonberg et al., 1994. *Nature.* 368(6474):856-859; Lonberg & Huszar, 1995. *Int Rev Immunol.* 13(1):65-93; Harding & Lonberg, 1995. *Ann N Y Acad Sci.* 764:536-46; Taylor et al., 1992. *Nucleic Acids Res.* 20(23):6287-95; Chen et al., 1993. *Int Immunol.* 5(6):647-56; Tuaillon et al., 1993. *Proc Natl Acad Sci USA.* 90(8):3720-4; Choi et al., 1993. *Nat Genet.* 4(2):117-23; Chen et al., 1993. *EMBO J.* 12(3):821-30; Tuaillon et al., 1994. *J Immunol.* 152(6):2912-20; Taylor et al., 1994. *Int Immunol.* 6(4):579-91; Fishwild et al., 1996. *Nat Biotechnol.* 14(7):845-51;

the KM Mouse®, described in Patent application WO2002043478;

the TC mice, described in Tomizuka et al., 2000. *Proc Natl Acad Sci USA.* 97(2):722-7; and the OmniRat™ (OMT, Inc.), described in Patent application WO2008151081; Geurts et al., 2009. *Science.* 325(5939):433; Menoret et al., 2010. *Eur J Immunol.* 40(10):2932-41; Osborn et al., 2013. *J Immunol.* 190(4):1481-90.

Humanized antibodies and binding fragments thereof may also be produced according to various other techniques, such as by using, for immunization, other transgenic animals that have been engineered to express a human antibody repertoire (Jakobovitz et al., 1993. *Nature.* 362(6417):255-8), or by selection of antibody repertoires using phage display methods. Such techniques are known to the skilled person and can be implemented starting from monoclonal antibodies or binding fragments thereof as disclosed in the present application.

In some embodiments, the antibody or binding fragment thereof according to the present invention comprising HCVR and LCVR (or CDRs thereof) may comprise a first constant domain ($C_H1$ and/or $C_L$), the amino acid sequence of which is fully or substantially human.

In some embodiment, especially when the antibody or binding fragment thereof according to the present invention is intended for human therapeutic uses, it is typical for the entire constant region, or at least a part thereof, to have a fully or substantially human amino acid sequence. Therefore, one or more of, or any combination of, the $C_H1$ domain, hinge region, $C_H2$ domain, $C_H3$ domain and $C_L$ domain (and $C_H4$ domain if present) may be fully or substantially human with respect to its amino acid sequence. Advantageously, the $C_H1$ domain, hinge region, $C_H2$ domain, $C_H3$ domain and $C_L$ domain (and $C_H4$ domain if present) may all have a fully or substantially human amino acid sequence.

The term "substantially human", in the context of the constant region of a humanized or chimeric antibody or binding fragment thereof, refers to an amino acid sequence identity of at least 70%, preferably at least 75%, 80%, 85%, 90%, 95%, 96%, 97%, 98%, 99% or more with a human constant region.

The term "human amino acid sequence", in this context, refers to an amino acid sequence which is encoded by a human immunoglobulin gene, which includes germline, rearranged and somatically mutated genes. The present invention also contemplates proteins comprising constant domains of "human" sequence which have been altered, by one or more amino acid additions, deletions or substitutions with respect to the human sequence, excepting those embodiments where the presence of a "fully human hinge region" is expressly required.

The presence of a "fully human hinge region" in the antibody or binding fragment thereof according to the present invention may be beneficial both to minimize immunogenicity and to optimize stability of the antibody. It is considered that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g., by addition or deletion of N- or O-linked glycosylation sites). Depending on the intended use of the antibody or binding fragment thereof, it may be desirable to modify the antibody or binding fragment thereof according to the present invention with respect to its binding properties to Fc receptors, for example to modulate effector function. For example, cysteine residue(s) may be introduced in the Fc region, thereby allowing interchain disulfide bond formation in this region. The homodimeric antibody thus generated may have improved effector function (Caron et al., 1992. *J Exp Med.* 176(4):1191-5; Shopes, 1992. *J Immunol.* 148(9): 2918-22).

In one embodiment, the humanized antibody or binding fragment thereof according to the present invention comprises at least one, preferably at least two, more preferably the three HCVR's CDRs set forth in SEQ ID NOs: 1, 2 and 3; and/or at least one, preferably at least two, more preferably the three LCVR's CDRs set forth in SEQ ID NOs: 12, 13 and 14, with, wherever applicable, $X_{12}$ being absent or being a Ser (S).

In one embodiment, the humanized antibody or binding fragment thereof according to the present invention comprises at least one, preferably at least two, more preferably the three HCVR's CDRs and/or at least one, preferably at least two, more preferably the three LCVR's CDRs, in a combination as set forth in Table 2 with, wherever applicable, $X_{12}$ being absent or being a Ser (S).

In one embodiment, the humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 selected from SEQ ID NOs: 4, 5, 6, 7, 8, 9, 10, 11, 100, 116, 117, 118, and 119; and
    a $V_H$-CDR3 with SEQ ID NO: 3; and
  a LCVR which comprises at least one, preferably at least two, more preferably the following three CDRs:
    a $V_L$-CDR1 selected from SEQ ID NOs: 15 and 18, with $X_{12}$ being absent or being a Ser (S);
    a $V_L$-CDR2 selected from SEQ ID NOs: 16, 19, 20, 22, 111 and 120; and
    a $V_L$-CDR3 selected from SEQ ID NOs: 17 and 21.

In a preferred embodiment, the humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 selected from SEQ ID NOs: 4 and 5; and
    a $V_H$-CDR3 with SEQ ID NO: 3; and
  a LCVR which comprises at least one, preferably at least two, more preferably the following three CDRs:
    a $V_L$-CDR1 with SEQ ID NO: 15, with $X_{12}$ being absent;
    a $V_L$-CDR2 with SEQ ID NO: 16; and
    a $V_L$-CDR3 with SEQ ID NO: 17.

In a preferred embodiment, the humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 selected from SEQ ID NOs: 6, 7 and 8; and
    a $V_H$-CDR3 with SEQ ID NO: 3; and
  a LCVR which comprises at least one, preferably at least two, more preferably the following three CDRs:
    a $V_L$-CDR1 with SEQ ID NO: 18, with $X_{12}$ being absent;
    a $V_L$-CDR2 selected from SEQ ID NO: 16 and 19; and
    a $V_L$-CDR3 with SEQ ID NO: 17.

In a preferred embodiment, the humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 selected from SEQ ID NOs: 9, 10 and 11; and
    a $V_H$-CDR3 with SEQ ID NO: 3; and
  a LCVR which comprises at least one, preferably at least two, more preferably the following three CDRs:
    a $V_L$-CDR1 with SEQ ID NO: 18, with $X_{12}$ being absent;
    a $V_L$-CDR2 selected from SEQ ID NO: 19, 20 and 22; and
    a $V_L$-CDR3 selected from SEQ ID NO: 17 and 21.

In a preferred embodiment, the humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 with SEQ ID NOs: 100; and
    a $V_H$-CDR3 with SEQ ID NO: 3; and
  a LCVR which comprises at least one, preferably at least two, more preferably the following three CDRs:
    a $V_L$-CDR1 with SEQ ID NO: 18, with $X_{12}$ being a Ser (S);
    a $V_L$-CDR2 with SEQ ID NO: 16; and
    a $V_L$-CDR3 with SEQ ID NO: 17.

In a preferred embodiment, the humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 selected from SEQ ID NOs: 6, 7, 8 and 100; and
    a $V_H$-CDR3 with SEQ ID NO: 3; and
  a LCVR which comprises at least one, preferably at least two, more preferably the following three CDRs:
    a $V_L$-CDR1 with SEQ ID NO: 18, with $X_{12}$ being absent or being a Ser (S);
    a $V_L$-CDR2 selected from SEQ ID NO: 16 and 19; and
    a $V_L$-CDR3 with SEQ ID NO: 17.

In a preferred embodiment, the humanized antibody or binding fragment thereof according to the present invention comprises a combination of (i) at least one, preferably at least two, more preferably three HCVR's CDRs and (ii) at least one, preferably at least two, more preferably three LCVR's CDRs, said combination being selected from combinations #1, #7, #14, #26 and #50 as set forth in Table 2 with, wherever applicable, $X_{12}$ being absent or being a Ser (S).

In one embodiment, the humanized antibody or binding fragment thereof according to the present invention may further comprise at least one, preferably at least two, more preferably at least three, even more preferably the four HCVR's FRs and/or at least one, preferably at least two, more preferably at least three, even more preferably the four LCVR's FRs, as set forth in Table 3.

In one embodiment, the humanized antibody or binding fragment thereof according to the present invention may further comprise:
  a HCVR which comprises at least one, preferably at least two, more preferably at least three, even more preferably the four following FRs:
    a $V_H$-FR1 selected from SEQ ID NOs: 29, 33, 36, 39, 40 and 42;

a V$_H$-FR2 selected from SEQ ID NOs: 30, 34, 37 and 43;
a V$_H$-FR3 selected from SEQ ID NOs: 31, 35, 38 and 41; and
a V$_H$-FR4 with SEQ ID NO: 32; and
a LCVR which comprises at least one, preferably at least two, more preferably at least three, even more preferably the four following FRs:
a V$_L$-FR1 selected from SEQ ID NOs: 48, 52 and 55;
a V$_L$-FR2 selected from SEQ ID NOs: 49, 53, 56, 58, 59 and 60;
a V$_L$-FR3 selected from SEQ ID NOs: 50, 54 and 57; and
a V$_L$-FR4 with SEQ ID NO: 51.

In one embodiment, the humanized antibody or binding fragment thereof according to the present invention may further comprise a combination of (i) at least one, preferably at least two, more preferably at least three, even more preferably the four HCVR's FRs and (ii) at least one, preferably at least two, more preferably at least three, even more preferably the four LCVR's FRs, said combination being selected from combinations #9, #10, #11, #12, #13, #14, #16, #17, #18, #19, #20, #21, #23, #24, #25, #26, #27, #28, #30, #31, #32, #33, #34, #35, #37, #38, #39, #40, #41, #42, #44, #45, #46, #47, #48, #49, #51, #52, #53, #54, #55 and #56 as set forth in Table 3.

In a preferred embodiment, the humanized antibody or binding fragment thereof according to the present invention may further comprise:
a HCVR which comprises at least one, preferably at least two, more preferably at least three, even more preferably the four following FRs:
a V$_H$-FR1 selected from SEQ ID NOs: 29, 33 and 36;
a V$_H$-FR2 selected from SEQ ID NOs: 30, 34 and 37;
a V$_H$-FR3 selected from SEQ ID NOs: 31, 35 and 38; and
a V$_H$-FR4 with SEQ ID NO: 32; and
a LCVR which comprises at least one, preferably at least two, more preferably at least three, even more preferably the four following FRs:
a V$_L$-FR1 selected from SEQ ID NOs: 48, 52 and 55;
a V$_L$-FR2 selected from SEQ ID NOs: 49, 53 and 56;
a V$_L$-FR3 selected from SEQ ID NOs: 50, 54 and 57; and
a V$_L$-FR4 with SEQ ID NO: 51.

In a preferred embodiment, the humanized antibody or binding fragment thereof according to the present invention may further comprise a combination of (i) at least one, preferably at least two, more preferably at least three, even more preferably the four HCVR's FRs and (ii) at least one, preferably at least two, more preferably at least three, even more preferably the four LCVR's FRs, said combination being selected from combinations #9, #10, #11, #16, #17, #18, #23, #24 and #25 as set forth in Table 3.

In one embodiment, the humanized antibody or binding fragment thereof according to the present invention may therefore comprise:
a HCVR selected from SEQ ID NOs: 62, 63, 64, 65, 66, 67, 68, 69, 70, 101, 121, 122, 123 and 124; and/or
a LCVR selected from SEQ ID NOs: 82, 83, 84, 85, 86, 87, 88, 89, 90, 103, 113, 126 and 129.

In one embodiment, the humanized antibody or binding fragment thereof according to the present invention may therefore comprise any combination of a HCVR selected from SEQ ID NOs: 62, 63, 64, 65, 66, 67, 68, 69, 70, 101, 121, 122, 123 and 124, and a LCVR selected from SEQ ID NOs: 82, 83, 84, 85, 86, 87, 88, 89, 90, 103, 113, 126 and 129, as detailed above.

In a preferred embodiment, the humanized antibody or binding fragment thereof according to the present invention may therefore comprise:
a HCVR selected from SEQ ID NOs: 62, 63 and 64; and/or
a LCVR selected from SEQ ID NOs: 82, 83 and 84.

In a preferred embodiment, the humanized antibody or binding fragment thereof according to the present invention may therefore comprise any combination of a HCVR selected from SEQ ID NOs: 62, 63 and 64 and a LCVR selected from SEQ ID NOs: 82, 83 and 84, as detailed above.

In a preferred embodiment, the humanized antibody or binding fragment thereof according to the present invention may therefore comprise:
a HCVR selected from SEQ ID NOs: 62, 63, 64, 65, 67 and 101; and/or
a LCVR selected from SEQ ID NOs: 82, 83, 84, 85 and 103.

In a preferred embodiment, the humanized antibody or binding fragment thereof according to the present invention may therefore comprise any combination of a HCVR selected from SEQ ID NOs: 62, 63, 64, 65, 67 and 101, and a LCVR selected from SEQ ID NOs: 82, 83, 84, 85 and 103, as detailed above.

In a preferred embodiment, the humanized antibody or binding fragment thereof according to the present invention may therefore comprise a HCVR as set forth in SEQ ID NO: 62 and a LCVR as set forth in SEQ ID NO: 82.

In a preferred embodiment, the humanized antibody or binding fragment thereof according to the present invention may therefore comprise a HCVR as set forth in SEQ ID NO: 62 and a LCVR as set forth in SEQ ID NO: 83.

In a preferred embodiment, the humanized antibody or binding fragment thereof according to the present invention may therefore comprise a HCVR as set forth in SEQ ID NO: 62 and a LCVR as set forth in SEQ ID NO: 84.

In a preferred embodiment, the humanized antibody or binding fragment thereof according to the present invention may therefore comprise a HCVR as set forth in SEQ ID NO: 63 and a LCVR as set forth in SEQ ID NO: 82.

In a preferred embodiment, the humanized antibody or binding fragment thereof according to the present invention may therefore comprise a HCVR as set forth in SEQ ID NO: 63 and a LCVR as set forth in SEQ ID NO: 83.

In a preferred embodiment, the humanized antibody or binding fragment thereof according to the present invention may therefore comprise a HCVR as set forth in SEQ ID NO: 63 and a LCVR as set forth in SEQ ID NO: 84.

In a preferred embodiment, the humanized antibody or binding fragment thereof according to the present invention may therefore comprise a HCVR as set forth in SEQ ID NO: 64 and a LCVR as set forth in SEQ ID NO: 82.

In a preferred embodiment, the humanized antibody or binding fragment thereof according to the present invention may therefore comprise a HCVR as set forth in SEQ ID NO: 64 and a LCVR as set forth in SEQ ID NO: 83.

In a preferred embodiment, the humanized antibody or binding fragment thereof according to the present invention may therefore comprise a HCVR as set forth in SEQ ID NO: 64 and a LCVR as set forth in SEQ ID NO: 84.

In a preferred embodiment, the humanized antibody or binding fragment thereof according to the present invention may therefore comprise a HCVR as set forth in SEQ ID NO: 101 and a LCVR as set forth in SEQ ID NO: 85.

In a preferred embodiment, the humanized antibody or binding fragment thereof according to the present invention may therefore comprise a HCVR as set forth in SEQ ID NO: 101 and a LCVR as set forth in SEQ ID NO: 103.

In a preferred embodiment, the humanized antibody or binding fragment thereof according to the present invention may therefore comprise a HCVR as set forth in SEQ ID NO: 65 and a LCVR as set forth in SEQ ID NO: 85.

In a preferred embodiment, the humanized antibody or binding fragment thereof according to the present invention may therefore comprise a HCVR as set forth in SEQ ID NO: 65 and a LCVR as set forth in SEQ ID NO: 103.

In a preferred embodiment, the humanized antibody or binding fragment thereof according to the present invention may therefore comprise a HCVR as set forth in SEQ ID NO: 62 and a LCVR as set forth in SEQ ID NO: 85.

In a preferred embodiment, the humanized antibody or binding fragment thereof according to the present invention may therefore comprise a HCVR as set forth in SEQ ID NO: 101 and a LCVR as set forth in SEQ ID NO: 82.

In a preferred embodiment, the humanized antibody or binding fragment thereof according to the present invention may therefore comprise a HCVR as set forth in SEQ ID NO: 121 and a LCVR as set forth in SEQ ID NO: 85.

In a preferred embodiment, the humanized antibody or binding fragment thereof according to the present invention may therefore comprise a HCVR as set forth in SEQ ID NO: 122 and a LCVR as set forth in SEQ ID NO: 85.

In a preferred embodiment, the humanized antibody or binding fragment thereof according to the present invention may therefore comprise a HCVR as set forth in SEQ ID NO: 123 and a LCVR as set forth in SEQ ID NO: 85.

In a preferred embodiment, the humanized antibody or binding fragment thereof according to the present invention may therefore comprise a HCVR as set forth in SEQ ID NO: 124 and a LCVR as set forth in SEQ ID NO: 85.

In a preferred embodiment, the humanized antibody or binding fragment thereof according to the present invention may therefore comprise a HCVR as set forth in SEQ ID NO: 63 and a LCVR as set forth in SEQ ID NO: 85.

In a preferred embodiment, the humanized antibody or binding fragment thereof according to the present invention may therefore comprise a HCVR as set forth in SEQ ID NO: 67 and a LCVR as set forth in SEQ ID NO: 85.

In a preferred embodiment, the humanized antibody or binding fragment thereof according to the present invention may therefore comprise a HCVR as set forth in SEQ ID NO: 67 and a LCVR as set forth in SEQ ID NO: 103.

In one embodiment, the humanized antibody or binding fragment thereof according to the present invention may further comprise a HCCR as set forth in SEQ ID NO: 91, 114 or 115; and/or a LCCR as set forth in SEQ ID NO: 92.

In one embodiment, the humanized antibody or binding fragment thereof according to the present invention may further comprise a HCCR as set forth in SEQ ID NO: 91; and/or a LCCR as set forth in SEQ ID NO: 92.

In one embodiment, the humanized antibody or binding fragment thereof according to the present invention may further comprise a HCCR as set forth in SEQ ID NO: 114; and/or a LCCR as set forth in SEQ ID NO: 92.

In one embodiment, the humanized antibody or binding fragment thereof according to the present invention may further comprise a HCCR as set forth in SEQ ID NO: 115; and/or a LCCR as set forth in SEQ ID NO: 92.

In one embodiment, the humanized antibody or binding fragment thereof according to the present invention may therefore comprise a heavy chain comprising a variable region as set forth in SEQ ID NOs: 62, 63, 64, 65, 66, 67, 68, 69, 70 or 101; and/or constant region as set forth in SEQ ID NO: 91, 114 or 115.

In one embodiment, the humanized antibody or binding fragment thereof according to the present invention may therefore comprise a heavy chain comprising a variable region as set forth in SEQ ID NOs: 62, 63, 64, 65, 66, 67, 68, 69, 70 or 101; and/or constant region as set forth in SEQ ID NO: 91.

In one embodiment, the humanized antibody or binding fragment thereof according to the present invention may therefore comprise a heavy chain comprising a variable region as set forth in SEQ ID NOs: 62, 63, 64, 65, 66, 67, 68, 69, 70 or 101; and/or constant region as set forth in SEQ ID NO: 114.

In one embodiment, the humanized antibody or binding fragment thereof according to the present invention may therefore comprise a heavy chain comprising a variable region as set forth in SEQ ID NOs: 62, 63, 64, 65, 66, 67, 68, 69, 70 or 101; and/or constant region as set forth in SEQ ID NO: 115.

In a preferred embodiment, the humanized antibody or binding fragment thereof according to the present invention may therefore comprise a heavy chain comprising a variable region as set forth in SEQ ID NOs: 62, 63 or 64; and/or constant region as set forth in SEQ ID NO: 91, 114 or 115.

In a preferred embodiment, the humanized antibody or binding fragment thereof according to the present invention may therefore comprise a heavy chain comprising a variable region as set forth in SEQ ID NOs: 62, 63 or 64; and/or constant region as set forth in SEQ ID NO: 91.

In a preferred embodiment, the humanized antibody or binding fragment thereof according to the present invention may therefore comprise a heavy chain comprising a variable region as set forth in SEQ ID NOs: 62, 63 or 64; and/or constant region as set forth in SEQ ID NO: 114.

In a preferred embodiment, the humanized antibody or binding fragment thereof according to the present invention may therefore comprise a heavy chain comprising a variable region as set forth in SEQ ID NOs: 62, 63 or 64; and/or constant region as set forth in SEQ ID NO: 115.

In a preferred embodiment, the humanized antibody or binding fragment thereof according to the present invention may therefore comprise a heavy chain comprising a variable region as set forth in SEQ ID NOs: 62, 63, 64, 65, 67 and 101; and/or constant region as set forth in SEQ ID NO: 91, 114 or 115.

In a preferred embodiment, the humanized antibody or binding fragment thereof according to the present invention may therefore comprise a heavy chain comprising a variable region as set forth in SEQ ID NOs: 62, 63, 64, 65, 67 and 101; and/or constant region as set forth in SEQ ID NO: 91.

In a preferred embodiment, the humanized antibody or binding fragment thereof according to the present invention may therefore comprise a heavy chain comprising a variable region as set forth in SEQ ID NOs: 62, 63, 64, 65, 67 and 101; and/or constant region as set forth in SEQ ID NO: 114.

In a preferred embodiment, the humanized antibody or binding fragment thereof according to the present invention may therefore comprise a heavy chain comprising a variable region as set forth in SEQ ID NOs: 62, 63, 64, 65, 67 and 101; and/or constant region as set forth in SEQ ID NO: 115.

In a preferred embodiment, the humanized antibody or binding fragment thereof according to the present invention may therefore comprise a heavy chain comprising a variable region as set forth in SEQ ID NO: 101; and/or constant region as set forth in SEQ ID NO: 114.

In a preferred embodiment, the humanized antibody or binding fragment thereof according to the present invention may therefore comprise a heavy chain comprising a variable region as set forth in SEQ ID NO: 101; and/or constant region as set forth in SEQ ID NO: 115.

In one embodiment, the humanized antibody or binding fragment thereof according to the present invention may therefore comprise a light chain comprising a variable region as set forth in SEQ ID NOs: 82, 83, 84, 85, 86, 87, 88, 89, 90 or 103; and/or constant region as set forth in SEQ ID NO: 92.

In a preferred embodiment, the humanized antibody or binding fragment thereof according to the present invention may therefore comprise a light chain comprising a variable region as set forth in SEQ ID NOs: 82, 83 or 84; and/or constant region as set forth in SEQ ID NO: 92.

In a preferred embodiment, the humanized antibody or binding fragment thereof according to the present invention may therefore comprise a light chain comprising a variable region as set forth in SEQ ID NOs: 82, 83, 84, 85 or 103; and/or constant region as set forth in SEQ ID NO: 92.

According to a specific embodiment, the murine, chimeric or humanized antibody or fragment thereof as previously defined hereinabove comprises a LCVR's CDR1 set forth in SEQ ID NO: 12 (preferably set forth in SEQ ID NO: 15 or 18, more preferably set forth in SEQ ID NO: 15), with $X_{12}$ being selected from Asn (N), Ser (S) and Gly (G). In this embodiment, where $X_{12}$ is not absent, the amino acid residue at Kabat position L71 of the LCVR is preferably Phe (F); in other words, the murine, chimeric or humanized antibody or fragment thereof according to the present invention preferably comprises a LCVR's FR3 set forth in SEQ ID NOs: 46, 50, 54 or 57, with $X_{15}$ being Phe (F). Upon satisfaction of these features (i.e., $X_{12}$ not being absent and preferably Kabat position L71 (i.e., $X_{15}$) further being a Phe (F)), any of the above embodiments relating to the murine, chimeric or humanized antibody or binding fragment thereof according to the present invention apply.

Therefore, according to this specific embodiment, the murine, chimeric or humanized antibody or binding fragment thereof according to the present invention comprises at least one, preferably at least two, more preferably the three HCVR's CDRs set forth in SEQ ID NOs: 1, 2 and 3; and/or at least one, preferably at least two, more preferably the three LCVR's CDRs set forth in SEQ ID NOs: 12, 13 and 14, with, wherever applicable, $X_{12}$ being selected from Asn (N), Ser (S) and Gly (G).

According to this specific embodiment, the murine, chimeric or humanized antibody or binding fragment thereof according to the present invention comprises at least one, preferably at least two, more preferably the three HCVR's CDRs and/or at least one, preferably at least two, more preferably the three LCVR's CDRs, in a combination as set forth in Table 2 with, wherever applicable, $X_{12}$ being selected from Asn (N), Ser (S) and Gly (G).

According to this specific embodiment, the murine, chimeric or humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 selected from SEQ ID NOs: 4, 5, 6, 7, 8, 9, 10, 11 and 100; and
    a $V_H$-CDR3 with SEQ ID NO: 3; and
  a LCVR which comprises at least one, preferably at least two, more preferably the following three CDRs:
    a $V_L$-CDR1 selected from SEQ ID NOs: 15 and 18, with $X_{12}$ being selected from Asn (N), Ser (S) and Gly (G);
    a $V_L$-CDR2 selected from SEQ ID NOs: 16, 19, 20, 22, 111 and 120; and
    a $V_L$-CDR3 selected from SEQ ID NOs: 17 and 21.

According to this specific embodiment, the murine, chimeric or humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 selected from SEQ ID NOs: 4, 5, 6, 8, 100, 116, 117, 118 and 119; and
    a $V_H$-CDR3 with SEQ ID NO: 3; and
  a LCVR which comprises at least one, preferably at least two, more preferably the following three CDRs:
    a $V_L$-CDR1 selected from SEQ ID NOs: 15 and 18, with $X_{12}$ being selected from Asn (N), Ser (S) and Gly (G);
    a $V_L$-CDR2 selected from SEQ ID NOs: 16, 111 and 120; and
    a $V_L$-CDR3 with SEQ ID NO: 17.

According to this specific embodiment, the murine, chimeric or humanized antibody or binding fragment thereof according to the present invention comprises:
  a HCVR which comprises at least one, preferably at least two, more preferably the following three CDRs:
    a $V_H$-CDR1 with SEQ ID NO: 1;
    a $V_H$-CDR2 selected from SEQ ID NOs: 4 and 5; and
    a $V_H$-CDR3 with SEQ ID NO: 3; and
  a LCVR which comprises at least one, preferably at least two, more preferably the following three CDRs:
    a $V_L$-CDR1 with SEQ ID NO: 15, with $X_{12}$ being selected from Asn (N), Ser (S) and Gly (G);
    a $V_L$-CDR2 with SEQ ID NO: 16; and
    a $V_L$-CDR3 with SEQ ID NO: 17.

According to this specific embodiment, the murine, chimeric or humanized antibody or binding fragment thereof according to the present invention comprises a combination of (i) at least one, preferably at least two, more preferably three HCVR's CDRs and (ii) at least one, preferably at least two, more preferably three LCVR's CDRs, said combination being selected from combinations #1, #7, #14, #26 and #50 as set forth in Table 2 with, wherever applicable, $X_{12}$ being selected from Asn (N), Ser (S) and Gly (G).

According to this specific embodiment, the humanized antibody or binding fragment thereof according to the present invention may further comprise at least one, preferably at least two, more preferably at least three, even more preferably the four HCVR's FRs and/or at least one, preferably at least two, more preferably at least three, even more preferably the four LCVR's FRs, as set forth in Table 3 with, wherever applicable, $X_{15}$ being Phe (F).

According to this specific embodiment, the murine, chimeric or humanized antibody or binding fragment thereof according to the present invention may further comprise:
  a HCVR which comprises at least one, preferably at least two, more preferably at least three, even more preferably the four following FRs:
    a $V_H$-FR1 selected from SEQ ID NOs: 25, 29, 33, 36, 39, 40 and 42;
    a $V_H$-FR2 selected from SEQ ID NOs: 26, 30, 34, 37 and 43;

a $V_H$-FR3 selected from SEQ ID NOs: 27, 31, 35, 38 and 41; and
a $V_H$-FR4 selected from SEQ ID NO: 28 and 32; and
a LCVR which comprises at least one, preferably at least two, more preferably at least three, even more preferably the four following FRs:
a $V_L$-FR1 selected from SEQ ID NOs: 44, 48, 52 and 55;
a $V_L$-FR2 selected from SEQ ID NOs: 45, 49, 53, 56, 58, 59 and 60;
a $V_L$-FR3 selected from SEQ ID NOs: 46, 50, 54 and 57 with $X_{15}$ being Phe (F); and
a $V_L$-FR4 selected from SEQ ID NO: 47 and 51.

According to this specific embodiment, the murine, chimeric or humanized antibody or binding fragment thereof according to the present invention may further comprise a combination of (i) at least one, preferably at least two, more preferably at least three, even more preferably the four HCVR's FRs and (ii) at least one, preferably at least two, more preferably at least three, even more preferably the four LCVR's FRs, said combination being selected from any of the combinations set forth in Table 3 with, wherever applicable, $X_{15}$ being Phe (F).

According to this specific embodiment, the murine, chimeric or humanized antibody or binding fragment thereof according to the present invention may further comprise:
a HCVR which comprises at least one, preferably at least two, more preferably at least three, even more preferably the four following FRs:
a $V_H$-FR1 selected from SEQ ID NOs: 29, 33, 36, 39, 40 and 42;
a $V_H$-FR2 selected from SEQ ID NOs: 30, 34, 37 and 43;
a $V_H$-FR3 selected from SEQ ID NOs: 31, 35, 38 and 41; and
a $V_H$-FR4 with SEQ ID NO: 32; and
a LCVR which comprises at least one, preferably at least two, more preferably at least three, even more preferably the four following FRs:
a $V_L$-FR1 selected from SEQ ID NOs: 48, 52 and 55;
a $V_L$-FR2 selected from SEQ ID NOs: 49, 53, 56, 58, 59 and 60;
a $V_L$-FR3 selected from SEQ ID NOs: 50, 54 and 57 with $X_{15}$ being Phe (F); and
a $V_L$-FR4 with SEQ ID NO: 51.

According to this specific embodiment, the murine, chimeric or humanized antibody or binding fragment thereof according to the present invention may further comprise a combination of (i) at least one, preferably at least two, more preferably at least three, even more preferably the four HCVR's FRs and (ii) at least one, preferably at least two, more preferably at least three, even more preferably the four LCVR's FRs, said combination being selected from combinations #9, #10, #11, #12, #13, #14, #16, #17, #18, #19, #20, #21, #23, #24, #25, #26, #27, #28, #30, #31, #32, #33, #34, #35, #37, #38, #39, #40, #41, #42, #44, #45, #46, #47, #48, #49, #51, #52, #53, #54, #55 and #56 as set forth in Table 3 with, wherever applicable, $X_{15}$ being Phe (F).

According to this specific embodiment, the murine, chimeric or humanized antibody or binding fragment thereof according to the present invention may further comprise:
a HCVR which comprises at least one, preferably at least two, more preferably at least three, even more preferably the four following FRs:
a $V_H$-FR1 selected from SEQ ID NOs: 29, 33 and 36;
a $V_H$-FR2 selected from SEQ ID NOs: 30, 34 and 37;
a $V_H$-FR3 selected from SEQ ID NOs: 31, 35 and 38; and
a $V_H$-FR4 with SEQ ID NO: 32; and
a LCVR which comprises at least one, preferably at least two, more preferably at least three, even more preferably the four following FRs:
a $V_L$-FR1 selected from SEQ ID NOs: 48, 52 and 55;
a $V_L$-FR2 selected from SEQ ID NOs: 49, 53 and 56;
a $V_L$-FR3 selected from SEQ ID NOs: 50, 54 and 57 with $X_{15}$ being Phe (F); and
a $V_L$-FR4 with SEQ ID NO: 51.

According to this specific embodiment, the murine, chimeric or humanized antibody or binding fragment thereof according to the present invention may further comprise a combination of (i) at least one, preferably at least two, more preferably at least three, even more preferably the four HCVR's FRs and (ii) at least one, preferably at least two, more preferably at least three, even more preferably the four LCVR's FRs, said combination being selected from combinations #9, #10, #11, #16, #17, #18, #23, #24 and #25 as set forth in Table 3 with, wherever applicable, $X_{15}$ being Phe (F).

According to this specific embodiment, the murine, chimeric or humanized antibody or binding fragment thereof according to the present invention may therefore comprise:
a HCVR selected from SEQ ID NOs: 61, 62, 63, 64, 65, 66, 67, 68, 69, 70, 101, 121, 122, 123 and 124; and/or
a LCVR selected from SEQ ID NOs: 71, 72, 73, 74, 75, 76, 77, 78, 79, 80, 102, 112, 125 and 128, with $X_{12}$ being selected from Asn (N), Ser (S) and Gly (G), and $X_{13}$ being any amino acid but Ala (A) or Asn (N).

According to this specific embodiment, the murine, chimeric or humanized antibody or binding fragment thereof according to the present invention may therefore comprise any combination of a HCVR selected from SEQ ID NOs: 61, 62, 63, 64, 65, 66, 67, 68, 69, 70, 101, 121, 122, 123 and 124, and a LCVR selected from SEQ ID NOs: 71, 72, 73, 74, 75, 76, 77, 78, 79, 80, 102, 112, 125 and 128, as detailed above.

According to this specific embodiment, the murine, chimeric or humanized antibody or binding fragment thereof according to the present invention may therefore comprise:
a HCVR selected from SEQ ID NOs: 61; and/or
a LCVR selected from SEQ ID NOs: 71 with $X_{12}$ being selected from Asn (N), Ser (S) and Gly (G).

According to this specific embodiment, the murine, chimeric or humanized antibody or binding fragment thereof according to the present invention may therefore comprise any combination of a HCVR selected from SEQ ID NOs: 61 and a LCVR selected from SEQ ID NOs: 71, as detailed above.

According to this specific embodiment, the murine, chimeric or humanized antibody or binding fragment thereof according to the present invention may therefore comprise:
a HCVR selected from SEQ ID NOs: 62, 63 and 64; and/or
a LCVR selected from SEQ ID NOs: 72, 73 and 74, with $X_{12}$ being selected from Asn (N), Ser (S) and Gly (G).

According to this specific embodiment, the murine, chimeric or humanized antibody or binding fragment thereof according to the present invention may therefore comprise any combination of a HCVR selected from SEQ ID NOs: 62, 63 and 64 and a LCVR selected from SEQ ID NOs: 72, 73 and 74, as detailed above.

According to this specific embodiment, the murine, chimeric or humanized antibody or binding fragment thereof according to the present invention may therefore comprise:

a HCVR selected from SEQ ID NOs: 62, 63, 64, 65, 67, 101, 121, 122, 123 and 124; and/or a LCVR selected from SEQ ID NOs: 72, 73, 74, 75 and 102.

According to this specific embodiment, the murine, chimeric or humanized antibody or binding fragment thereof according to the present invention may therefore comprise any combination of a HCVR selected from SEQ ID NOs: 62, 63, 64, 65, 67 and 101, and a LCVR selected from SEQ ID NOs: SEQ ID NOs: 72, 73, 74, 75 and 102, as detailed above.

According to this specific embodiment, the murine, chimeric or humanized antibody or binding fragment thereof according to the present invention may further comprise a HCCR as set forth in SEQ ID NO: 91, 93, 114 or 115; and/or a LCCR as set forth in SEQ ID NO: 92 or 94.

According to this specific embodiment, the murine, chimeric or humanized antibody or binding fragment thereof according to the present invention may further comprise a HCCR as set forth in SEQ ID NO: 91 or 93; and/or a LCCR as set forth in SEQ ID NO: 92 or 94.

According to this specific embodiment, the murine, chimeric or humanized antibody or binding fragment thereof according to the present invention may therefore comprise a heavy chain comprising a variable region as set forth in SEQ ID NOs: 61, 62, 63, 64, 65, 66, 67, 68, 69, 70 or 101; and/or constant region as set forth in SEQ ID NO: 91, 93, 114 or 115.

According to this specific embodiment, the murine, chimeric or humanized antibody or binding fragment thereof according to the present invention may therefore comprise a heavy chain comprising a variable region as set forth in SEQ ID NOs: 61, 62, 63, 64, 65, 66, 67, 68, 69, 70 or 101; and/or constant region as set forth in SEQ ID NO: 91 or 93.

According to this specific embodiment, the murine, chimeric or humanized antibody or binding fragment thereof according to the present invention may therefore comprise a heavy chain comprising a variable region as set forth in SEQ ID NOs: 62, 63 or 64; and/or constant region as set forth in SEQ ID NO: 91, 93, 114 or 115.

According to this specific embodiment, the murine, chimeric or humanized antibody or binding fragment thereof according to the present invention may therefore comprise a heavy chain comprising a variable region as set forth in SEQ ID NOs: 62, 63 or 64; and/or constant region as set forth in SEQ ID NO: 91 or 93.

According to this specific embodiment, the murine, chimeric or humanized antibody or binding fragment thereof according to the present invention may therefore comprise a heavy chain comprising a variable region as set forth in SEQ ID NOs: 62, 63, 64, 65, 67 and 101; and/or constant region as set forth in SEQ ID NO: 91, 93, 114 or 115.

According to this specific embodiment, the murine, chimeric or humanized antibody or binding fragment thereof according to the present invention may therefore comprise a heavy chain comprising a variable region as set forth in SEQ ID NOs: 62, 63, 64, 65, 67 and 101; and/or constant region as set forth in SEQ ID NO: 91 or 93.

According to this specific embodiment, the murine, chimeric or humanized antibody or binding fragment thereof according to the present invention may therefore comprise a light chain comprising a variable region as set forth in SEQ ID NOs: 81, 82, 83, 84, 85, 86, 87, 88, 89, 90, 103 or 113; and/or a constant region as set forth in SEQ ID NO: 92 or 94.

According to this specific embodiment, the murine, chimeric or humanized antibody or binding fragment thereof according to the present invention may therefore comprise a light chain comprising a variable region as set forth in SEQ ID NOs: 82, 83 or 84; and/or a constant region as set forth in SEQ ID NO: 92.

According to this specific embodiment, the murine, chimeric or humanized antibody or binding fragment thereof according to the present invention may therefore comprise a light chain comprising a variable region as set forth in SEQ ID NOs: 82, 83, 84, 85 or 103; and/or a constant region as set forth in SEQ ID NO: 92.

Another object of the invention is an isolated nucleic acid encoding the antibody or binding fragment thereof binding to hCD45RC according to the present invention.

An "isolated nucleic add", as used herein, is intended to refer to a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

In one embodiment, the isolated nucleic acid is purified.

In one embodiment, the isolated nucleic acid is purified to:

(1) greater than 80%, 85%, 90%, 91%, 92%, 93%, 94%, 95% or more by weight of nucleic acid as determined by absorbance methods or fluorescence methods (such as, e.g., by measuring the ratio of absorbance at 260 and 280 nm (A262so)), and most preferably more than 96%, 97%, 98% or 99% by weight; or (2) homogeneity as shown by agarose gel electrophoresis and using an intercalating agent such as ethidium bromide, SYBR Green, GelGreen or the like.

In one embodiment, the nucleic acid according to the present invention comprises or consists of a sequence encoding the HCVR of the antibody or binding fragment thereof according to the invention.

In one embodiment, the nucleic acid according to the present invention comprises or consists of a sequence SEQ ID NO: 95 or any sequence sharing at least 70%, 75%, 80%, 85%, 90%, 95%, 96%, 97%, 98%, 99% or more identity with SEQ ID NO: 95, encoding the HCVR of the murine or chimeric antibody or binding fragment thereof with SEQ ID NO: 61.

```
                                          SEQ ID NO: 95
CAGGTCCAGCTGCAACAGTCTGGCGCTGAGCTGGTTAGGCCTGGGACTTC

AGTGAAGATGTCCTGCAAGGCCGCTGGATACACCTTCACTAACTACTACA

TAGGTTGGGTAAAGCAGAGGCCTGGACATGGCCTTGAGTGGATCGGAGAT

ATTTTCCCTGGAGGTGACTATGCCAACAGCAATGAGAAGTTCAAGGGCAA

AGCCiACACTGACTGCAGACACATCCTCCAGCACAGCCTACATGCAGCTC

AGCAGCCTGACATCTGAGGACTCTGCCATCTATTACTGTGTGAGAAGGAA

CTTTGACTACTGGGGCCAAGGCACCACTCTCACAGTGTCCTCA
```

In one embodiment, the nucleic acid according to the present invention comprises or consists of a sequence encoding the LCVR of the antibody or binding fragment thereof according to the invention.

In one embodiment, the nucleic acid according to the present invention comprises or consists of a sequence SEQ ID NO: 96 or any sequence sharing at least 70%, 75%, 80%, 85%, 90%, 95%, 96%, 97%, 98%, 99% or more identity with SEQ ID NO: 96, encoding the LCVR of the murine or chimeric antibody or binding fragment thereof with SEQ ID NO: 81.

SEQ ID NO: 96
CAAATTGTTCTCACCCAGTCTCCAACAATCATGTCTGCATCTCCAGGGGA

GAAGGTGACCATAACCTGCAGTGCCAGCTCAAGTGTAAGTTACATGCACT

GGTTCCAGCAGAAGACAGGCACTTCTCCCAGACTCTGGATTTATAACACA

TCCA1ACCTGCCTTCTGGAGTCCCCGCTCGCTTCAGTGGCAGTGGATCTG

GGACCTCTTACTCTCTCACAATCAGCCGAATGGAGGCTGAAGATGCTGCC

ACTTATTACTGCCAGCAAAGGAGTAGTTACCCACTCACGTTCGGTGCTGG

GACCAAGCTGGAGCTGAAA

In one embodiment, the nucleic acid according to the present invention comprises or consists of:
a sequence encoding the HCVR of the antibody or binding fragment thereof according to the invention, and
a sequence encoding the LCVR of the antibody or binding fragment thereof according to the invention.

In one embodiment, the nucleic acid according to the present invention comprises or consists of:
a sequence SEQ ID NO: 95 or any sequence sharing at least 70%, 75%, 80%, 85%, 90%, 95%, 96%, 97%, 98%, 99% or more identity with SEQ ID NO: 995 and
a sequence SEQ ID NO: 96 or any sequence sharing at least 70%, 75%, 80%, 85%, 90%, 95%, 96%, 97%, 98%, 99% or more identity with SEQ ID NO: 96.

It will be readily understood that the one skilled in the art can design nucleic acid sequences encoding all other HCVRs and LCVRs herein disclosed, in particular for the humanized antibodies or binding fragment thereof according to the invention.

It is further understood that the one skilled in the art is familiar with molecular biology methods aiming at modifying a nucleic acid sequence in order to improve, e.g., recombinant production rates, such as by codon optimization. Ultimately, the present application encompasses any nucleic acid encoding any HCVRs and/or LCVRs as herein disclosed.

In one embodiment, the nucleic acid according to the present invention comprises or consists of a sequence encoding a fully or substantially fully human HCCR of the antibody or binding fragment thereof according to the invention.

In one embodiment, the nucleic acid according to the present invention comprises or consists of a sequence SEQ ID NO: 97 or any sequence sharing at least 70%, 75%, 80%, 85%, 90%, 95%, 96%, 97%, 98%, 99% or more identity with SEQ ID NO: 97, encoding the HCCR of the chimeric or humanized antibody or binding fragment thereof with SEQ ID NO: 91.

SEQ ID NO: 97
GCCTCCACCAAGGGCCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAGAGTTGAGCCC

AAATCTTGTGACAAAACTCACACATGCCCACCGTGCCCAGCACCTGAACT

CCTGGGGGGACCGTCAGTCTTCCTCTTCCCCCCAAAACCCAAGGACACCC

TCATGATCTCCCGGACCCCTGAGGTCACATGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACAACAGCACGTACC

GTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAA

AACCATCTCCAAAGCCAAAGGGCAGCCCCGAGAACCACAGGTGTACACCC

TGCCCCCATCCCGGGAGGAGATGACCAAGAACCAGGTCAGCCTGACCTGC

CTGGTCAAAGGCTTCTATCCCAGCGACATCGCCGTGGAGTGGGAGAGCAA

TGGGCAGCCGGAGAACAACTACAAGACCACGCCTCCCGTGCTGGACTCCG

ACGGCTCCTTCTTCCTCTATAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCCCCGGGTAAA

In one embodiment, the nucleic acid according to the present invention comprises or consists of a sequence encoding a fully or substantially fully human LCCR of the antibody or binding fragment thereof according to the invention.

In one embodiment, the nucleic acid according to the present invention comprises or consists of a sequence SEQ ID NO: 98 or any sequence sharing at least 70%, 75%, 80%, 85%, 90%, 95%, 96%, 97%, 98%, 99% or more identity with SEQ ID NO: 98, encoding the HCCR of the chimeric or humanized antibody or binding fragment thereof with SEQ ID NO: 92.

SEQ ID NO: 98
CGAACTGTGGCTGCACCATCTGTCTTCATCTTCCCGCCATCTGATGAGC

AGTTGAAATCTGGAACTGCCTCTGTTGTGTGCCTGCTGAATAACTTCTA

TCCCAGAGAGGCCAAAGTACAGTGGAAGGTGGATAACGCCCTCCAATCG

GGTAACTCCCAGGAGAGTGTCACAGAGCAGGACAGCAAGGACAGCACCT

ACAGCCTCAGCAGCACCCTGACGCTGAGCAAAGCAGACTACGAGAAACA

CAAAGTCTACGCCTGCGAAGTCACCCATCAGGGCCTGAGCTCGCCCGTC

ACAAAGAGCTTCAACAGGGGAGAGTGT

In one embodiment, the nucleic acid according to the present invention comprises or consists of:
a sequence encoding a fully or substantially fully human HCCR of the antibody or binding fragment thereof according to the invention, and
a sequence encoding a fully or substantially fully human LCCR of the antibody or binding fragment thereof according to the invention.

In one embodiment, the nucleic acid according to the present invention comprises or consists of:
a sequence SEQ ID NO: 97 or any sequence sharing at least 70%, 75%, 80%, 85%, 90%, 95%, 96%, 97%, 98%, 99% or more identity with SEQ ID NO: 97, and a sequence SEQ ID NO: 98 or any sequence sharing at least 70%, 75%, 80%, 85%, 90%, 95%, 96%, 97%, 98%, 99% or more identity with SEQ ID NO: 98.

Another object of the present invention is an expression vector comprising the nucleic acid encoding the antibody or binding fragment thereof binding to hCD45RC according to the present invention.

In one embodiment, the expression vector according to the present invention comprises a sequence encoding the HCVR of the antibody or binding fragment thereof according to the invention, preferably operably linked to regulatory elements.

In one embodiment, the expression vector according to the present invention comprises a sequence SEQ ID NO: 95 or any sequence sharing at least 70%, 75%, 80%, 85%, 90%, 95%, 96%, 97%, 98%, 99% or more identity with SEQ ID NO: 95, preferably operably linked to regulatory elements.

In one embodiment, the expression vector according to the present invention comprises a sequence encoding the LCVR of the antibody or binding fragment thereof according to the invention, preferably operably linked to regulatory elements.

In one embodiment, the expression vector according to the present invention comprises a sequence SEQ ID NO: 96 or any sequence sharing at least 70%, 75%, 80%, 85%, 90%, 95%, 96%, 97%, 98%, 99% or more identity with SEQ ID NO: 96, preferably operably linked to regulatory elements.

In one embodiment, the expression vector according to the present invention comprises:
  a sequence encoding the HCVR of the antibody or binding fragment thereof according to the invention, preferably operably linked to regulatory elements, and
  a sequence encoding the LCVR of the antibody or binding fragment thereof according to the invention, preferably operably linked to regulatory elements.

In one embodiment, the expression vector according to the present invention comprises:
  a sequence SEQ ID NO: 95 or any sequence sharing at least 70%, 75%, 80%, 85%, 90%, 95%, 96%, 97%, 98%, 99% or more identity with SEQ ID NO: 95, preferably operably linked to regulatory elements, and
  a sequence SEQ ID NO: 96 or any sequence sharing at least 70%, 75%, 80%, 85%, 90%, 95%, 96%, 97%, 98%, 99% or more identity with SEQ ID NO: 96, preferably operably linked to regulatory elements.

In one embodiment, the expression vector according to the present invention comprises a sequence encoding the HCCR of the antibody or binding fragment thereof according to the invention, preferably operably linked to regulatory elements.

In one embodiment, the expression vector according to the present invention comprises a sequence SEQ ID NO: 97 or any sequence sharing at least 70%, 75%, 80%, 85%, 90%, 95%, 96%, 97%, 98%, 99% or more identity with SEQ ID NO: 97, preferably operably linked to regulatory elements.

In one embodiment, the expression vector according to the present invention comprises a sequence encoding the LCCR of the antibody or binding fragment thereof according to the invention, preferably operably linked to regulatory elements.

In one embodiment, the expression vector according to the present invention comprises a sequence SEQ ID NO: 98 or any sequence sharing at least 70%, 75%, 80%, 85%, 90%, 95%, 96%, 97%, 98%, 99% or more identity with SEQ ID NO: 98, preferably operably linked to regulatory elements.

In one embodiment, the expression vector according to the present invention comprises:
  a sequence encoding the HCCR of the antibody or binding fragment thereof according to the invention, preferably operably linked to regulatory elements, and
  a sequence encoding the LCCR of the antibody or binding fragment thereof according to the invention, preferably operably linked to regulatory elements.

In one embodiment, the expression vector according to the present invention comprises:
  a sequence SEQ ID NO: 97 or any sequence sharing at least 70%, 75%, 80%, 85%, 90%, 95%, 96%, 97%, 98%, 99% or more identity with SEQ ID NO: 97, preferably operably linked to regulatory elements, and
  a sequence SEQ ID NO: 98 or any sequence sharing at least 70%, 75%, 80%, 85%, 90%, 95%, 96%, 97%, 98%, 99% or more identity with SEQ ID NO: 98, preferably operably linked to regulatory elements.

In one embodiment, the expression vector according to the present invention comprises a sequence encoding the heavy chain of the antibody or binding fragment thereof according to the invention, preferably operably linked to regulatory elements.

In one embodiment, the expression vector according to the present invention comprises a sequence encoding the light chain of the antibody or binding fragment thereof according to the invention, preferably operably linked to regulatory elements.

In one embodiment, the expression vector according to the present invention comprises:
  a sequence encoding the heavy chain of the antibody or binding fragment thereof according to the invention, preferably operably linked to regulatory elements, and
  a sequence encoding the light chain of the antibody or binding fragment thereof according to the invention, preferably operably linked to regulatory elements.

In one embodiment, the expression vector according to the present invention is monocistronic.

By "monocistronic", it is meant that a single nucleic acid encoding a single protein is expressed in a single expression vector.

In one embodiment, the expression vector according to the present invention is polycistronic.

By "polycistronic", it is meant that at least two or more nucleic acids, each encoding a single protein, are expressed in a single expression vector.

Another object of the present invention is a cell comprising the nucleic acid encoding the antibody or binding fragment thereof binding to hCD45RC according to the present invention, or the expression vector comprising the nucleic acid encoding the antibody or binding fragment thereof binding to hCD45RC according to the present invention.

Another object of the present invention is a method of producing and purifying the isolated antibody or a binding fragment thereof, binding to hCD45RC according to the present invention.

In one embodiment, the method comprises:
  culturing host cells transformed with the nucleic acid or expression vector according to the present invention, under conditions suitable for expression of the antibody or binding fragment thereof, and
  recovering the expressed antibody or binding fragment thereof.

This recombinant process can be used for large scale production of antibodies or binding fragments thereof, including monoclonal antibodies intended for in vitro, ex vivo and/or in vivo therapeutic and/or diagnostic uses.

These processes are well-known in the art (Subramanian (Ed.), 2004. *Antibodies* (1st ed., Vol. 1: Production and Purification). New York, NY: Springer US).

In an embodiment, the expressed antibody or binding fragment thereof is further purified.

Methods to purify the antibody or binding fragment thereof according to the present invention are well-known in the art (Subramanian (Ed.), 2004. *Antibodies* (1st ed., Vol. 1: Production and Purification). New York, NY: Springer US), and include, without limitation, chromatography, preferably by affinity chromatography, more preferably by affinity chromatography on protein L agarose.

In one embodiment, the antibody according to the present invention can be modified to enhance antibody-dependent cell-mediated cytotoxicity (ADCC), complement dependent cytotoxicity (CDC) and/or antibody-dependent phagocytosis. Such modifications are well-known in the art.

For example, antibodies comprising a low fucose content are known to enhance ADCC response via the FcγRIII receptor (International patent publication WO2014140322).

Thus, the antibody according to the present invention may comprise a low fucose content. The term "fucose content", as used herein, refers to the percentage of fucosylated forms within the N-glycans attached to the N297 residue of the Fc fragment of each heavy chain of each antibody (corresponding to N180 of SEQ ID NO: 91 or SEQ ID NO: 114; or N174 of SEQ ID NO: 93).

The term "low fucose content", as used herein, refers to a fucose content of less than, or equal to, 65%. Advantageously, the fucose content is less than or equal to 65%, preferably less than or equal to 60%, 55% or 50%, or even less than or equal to 45%, 40%, 35%, 30%, 25% or 20%. However, it is not necessary that the fucose content be zero, and it may for example be greater than or equal to 5%, 10%, 15% or 20%.

In one embodiment, the antibody according to the present invention may further comprises different types of glycosylation (N-glycans of the oligomannose or biantennary complex type, with a variable proportion of bisecting N-acetylglucosamine (GlcNAc) residues or galactose residues in the case of N-glycans of the biantennary complex type), provided that they have a low fucose content (International patent publication WO2007048077). For example, antibodies having slightly fucosylated N-glycans can be obtained as described in European patent publication EP1176195 or in International patent publications WO2001077181 or WO2012041768.

The N-glycans of the oligomannose type have reduced half-life in vivo as compared to N-glycans of the biantennary complex type. Consequently, advantageously, the antibodies according to the present invention have on their N-glycosylation sites of the Fc fragment glycan structures of the biantennary complex type, with a low fucose content, as defined above.

In some embodiments, the antibody according to the present invention is conjugated to a therapeutic moiety, i.e., a drug. In one embodiment, the therapeutic moiety is selected from a cytotoxin, a chemotherapeutic agent, a cytokine, an immunosuppressant, an immune stimulator, a lytic peptide and a radioisotope. Such conjugates are referred to herein as an "antibody drug conjugates" or "ADCs".

In some embodiments, the antibody of the present invention is conjugated to a cytotoxic moiety. In one embodiment, the cytotoxic moiety is selected from taxol; cytochalasin B; gramicidin D; ethidium bromide; emetine; mitomycin; etoposide; tenoposide; vincristine; vinblastine; colchicin; doxorubicin; daunorubicin; dihydroxyanthracin dione; tubulin-inhibitors (such as, e.g., maytansine or an analog or derivative thereof); antimitotic agents (such as, e.g., monomethyl auristatin E or F or an analog or derivative thereof); dolastatin or an analogue thereof; irinotecan or an analogue thereof; mitoxantrone; mithramycin; actinomycin D; 1-dehydrotestosterone; glucocorticoids; procaine; tetracaine; lidocaine; propranolol; puromycin; calicheamicin or an analog or derivative thereof; antimetabolites (such as, e.g., methotrexate, mercaptopurine, 6-thioguanine, cytarabine, fludarabin, 5-fluorouracil, decarbazine, hydroxyurea, asparaginase, gemcitabine, or cladribine); an alkylating agent (such as, e.g., mechlorethamine, thioepa, chlorambucil, melphalan, carmustine, lomustine, cyclophosphamide, busulfan, dibromomannitol, streptozotocin, dacarbazine, procarbazine or mitomycin C); platinum derivatives (such as, e.g., cisplatin or carboplatin); duocarmycin A, duocarmycin SA, rachelmycin, or an analog or derivative thereof; antibiotics (such as, e.g., dactinomycin, bleomycin, daunorubicin, doxorubicin, idarubicin, mithramycin, mitomycin, mitoxantrone, plicamycin or anthramycin); pyrrolo[2,1-c][1,4]-benzodiazepines (such as, e.g., anthramycin); diphtheria toxin and related molecules (such as, e.g., diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alphasarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins); ribonucleases; DNase I; Staphylococcal enterotoxin A; pokeweed antiviral protein; diphtherin toxin; and *Pseudomonas* endotoxin.

In some embodiments, the antibody according to the present invention is conjugated to an auristatin or a peptide analog, derivative or prodrug thereof. Auristatins have been shown to interfere with microtubule dynamics, GTP hydrolysis and nuclear and cellular division (Woyke et al., 2001. *Antimicrob Agents Chemother.* 46(12):3802-8) and have anti-cancer (U.S. Pat. No. 5,663,149) and antifungal activity (Pettit et al., 1998. *Antimicrob Agents Chemother.* 42(11): 2961-5). For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to antibodies, are described in, e.g., U.S. Pat. Nos. 5,635,483, 5,780,588 and 6,214,345 and in International patent publications WO2002088172, WO2004010957, WO2005081711, WO2005084390, WO2006132670, WO2003026577, WO200700860, WO2007011968 and WO2005082023.

In some embodiments, the antibody according to the present invention is conjugated to pyrrolo[2,1-c][1,4]-benzodiazepine (PDB) (such as, e.g., anthramycin) or an analog, derivative or prodrug thereof. Suitable PDBs and PDB derivatives, and related technologies are described in the art.

In some embodiments, the antibody according to the present invention is conjugated to a cytotoxic moiety selected from anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In some embodiments, the antibody according to the present invention is conjugated to an anthracycline or an analog, derivative or prodrug thereof.

In some embodiments, the antibody according to the present invention is conjugated to maytansine or an analog, derivative or prodrug thereof.

In some embodiments, the antibody according to the present invention is conjugated to calicheamicin or an analog, derivative or prodrug thereof.

In some embodiments, the antibody according to the present invention is conjugated to duocarmycin or an analog, derivative or prodrug thereof.

In some embodiments, the antibody according to the present invention is conjugated to rachelmycin (CC-1065) or an analog, derivative or prodrug thereof.

In some embodiments, the antibody according to the present invention is conjugated to dolastatin or an analog, derivative or prodrug thereof.

In some embodiments, the antibody according to the present invention is conjugated to monomethyl auristatin E or an analog, derivative or prodrug thereof.

In some embodiments, the antibody according to the present invention is conjugated to monomethyl auristatin F or an analog, derivative or prodrug thereof.

In some embodiments, the antibody according to the present invention is conjugated to irinotecan or an analog, derivative or prodrug thereof.

In some embodiments, the antibody according to the present invention is labelled.

By "labeled", it is meant that the isolated antibody or binding fragment thereof has at least one element, isotope or chemical compound conjugated or attached to it, enabling for example the detection of said isolated antibody or binding fragment thereof.

Examples of labels include, but are not limited to, luminescent dyes (also termed fluorophores or photodetectable labels), isotopic labels (also termed radioactive labels, radiolabels or heavy isotopes), contrast agents, magnetic labels, electric labels, thermal labels, and colored labels.

Examples of luminescent dyes include, but are not limited to, Alexa Fluor® dyes, BODIPY® dyes, fluorescein, 5-carboxyfluorescein, 5-(4,6-dichlorotriazin-2-yl) aminofluorescein, 2'7'-dimethoxy-4'5'-dichloro-6-carboxyfluorescein, fluorescein isothiocyanate (FITC), QFITC, Oregon Green® 488, Oregon Green® 514, rhodamine and derivatives thereof (such as, e.g., rhodamine green, rhodamine green-X, rhodamine red-X, X-rhodanine, 6-carboxy-X-rhodanine (ROX), 6-carboxyrhodanmine (R6G), N,N,N',N'-tetramethyl-6-carboxyrhodamine (TAMRA), lissamine rhodamine B, rhodamine 123, rhodamine X isothiocyanate, sulforhodamine B, sulforhodamine 101 (Texas Red), tetramethyl rhodamine, tetramethyl rhodamine isothiocyanate (TRITC), eosin, eosin isothiocyanate, erythrosine, erythrosine B, erythrosin isothiocyanate, Texas Red®, Texas Red®-X, naphthofluorescein, malachite green, malachite green isothiocyanate, coumarin derivatives, Pacific Orange, cascade blue, cascade yellow, dansyl chloride, dapoxyl dye, 1-dimethylamine-N(2-azido-ethyl)naphthalene-5-sulfonamide, 6-(6-amino-2-(2-azidoethyl)-1,3-dioxo-1H-benzo(de)-2 (3H)isoquinoline, 6-(6-amino-2-(2-propinyl)-1,3-dioxo-1H-benzo(de)-2(3H)isoquinoline, 8-(4-azidoethyloxyphenyl)-2,6-dietlhyl-1,3,5,7-tetramethyl-4,4-difluoro-4-bora-3a,4a-diaza-s-indacene, 8-(4-propynyloxyphenyl)-2,6-diethyl-1,3, 5,7-tetramethyl-4,4-difluoro-4-bora-3a,4a-diaza-s-indacene, 1-(3-azido-propoxy)-7-methylamino-phenoxazin-3-one, 1-(2-propynyl)-7-methylamino-phenoxazm-3-one, N-(5-(3-azidopropylamino)-9H-benzo(a)-phenoxa-2-in-9-ylidene)-N-methyl-methanaminium chloride, N-(5-(3-propynyl-amino)-91-benzo(an)-phenoxazin-9-ylene)-N-methyl-methanaminium chloride, (9-(3-azido-propoxy)-7-piperidin-1-yl-phenoxazin-3-ylidene)-dimethyl-ammonium perchlorate, 4-acetanido-4'-isothiocyanatostilbene-2,2'-disulfonic acid, acridine, acridine isothiocyanate, 5-(2'-aminoethyl)aminonaphthalene-1-sulfonic acid, 4-amino-N-[3-vinylsulfonyl)phenyl]naphthalimide-3,5 disulfonate, N-(4-anilino-1-naphtyl)maleimide, anthranilamide, Brilliant Yellow, coumarin, coumarin derivatives, 7-amino-4-methylcoumarin, 7-amino-trifluoromethylcouluarin, cyanosine, 4',6-diaminidino-2-phenylindole, 5',5"-dibromopyrogallol-sulfonephthalein, 7-diethylamino-3-(4' isothiocyanatophenyl)-4-methylcoumarin-4,4'-diisothiocyanatodihydro-stilbene-2,2'-disulfonic acid, 4,4'-diisothiocyanatostilbene-2,2'-disulfonic acid, ethidium, IR 144, IR 1446, 4-methylumbelliferone, o-cresolphthalein, nitrotyrosine, pararosaniline, Phenol Red, B-pbycoerythrin, o-pbthaldialdehyde, pyrene, pyrene butyrate, succinimidyl 1-pyrene butyrate, Reactive Red 4, riboflavin, rosolic acid, lanthanide chelates, quantum dots, cyanines, pyrelium dyes, and squaraines.

Examples of isotopic labels include, but are not limited to, $^{99m}$Tc compounds (such as, e.g., exametazime, medronic acid, macroaggregated albumin, sestamibi, tetrofosmin, exametazime, sulesomab, tilmanocept, arcitumomab, votumumab, hynic-octreotide, and the like): $^{123}$I, $^{125}$I or $^{131}$I compounds (such as, e.g., iotlupane, iofetamine, iomazenil, sodium iodohippurate, iobenguane, iodocholesterol, minretumomah, tositumomab, and the like); $^{18}$F compounds (such as, e.g., florbetapir, tlutemetamol, fluciclovine, fludeoxyglucose, fluoroethyltyrosine, sodium fluoride, and the like); $^{64}$Cu compounds (such as, e.g., Cu-ETS2, and the like): $^{75}$Se compounds (such as, e.g., SeHCAT); $^{111}$In compounds (such as, e.g., imeiromah, capromah pendetide, satumomab pendetide, and the like): $^{82}$Rb compounds (such as, e.g., rubidium chloride); $^{153}$Sm compounds (such as, e.g., lexidronam, and the like): $^{89}$Sr compounds (such as, e.g., strontium-89 chloride, and the like); $^{90}$Y compounds (such as, e.g., ibritumomab tiuxetan, and the like); $^{223}$Ra compounds (such as, e.g., radium-223 chloride, and the like); $^{177}$Lu compounds (such as, e.g., oxodotreotide, and the like); and any compounds comprising at least one $^{2}$H, $^{3}$H, $^{11}$C, $^{13}$N, $^{14}$C, $^{13}$O, $^{18}$F, $^{22}$Na, $^{24}$Na, $^{32}$P, $^{47}$Ca, $^{51}$Cr, $^{57}$Co, $^{58}$Co, $^{59}$Fe, $^{64}$Cu, $^{67}$Ga, $^{68}$Ga, $^{75}$Se, $^{81}$mKr, $^{82}$Rb, $^{89}$Sr, $^{90}$Y, $^{99m}$Tc, $^{111}$In, $^{123}$I, $^{125}$I, $^{131}$I, $^{133}$Xe, $^{153}$Sm, $^{165}$Dy, $^{169}$Er, $^{177}$Lu, $^{186}$Re, $^{198}$Au, $^{201}$Tl and/or $^{223}$Ra atom.

Examples of contrast agents include, but are not limited to, diatrizoic acid, metrizoic acid, iodamide, iotalamic acid, ioxitalamic acid, ioglicic acid, acetrizoic acid, iocarmic acid, methiodal, diodone, metrizamide, iohexol, ioxaglic acid, iopamidol, iopromide, iotrolan, ioversol, iopentol, iodixanol, iomeprol, iobitridol, ioxilan, iodoxamic acid, iotroxic acid, ioglycamic acid, adipiodone, iobenzamic acid, iopanoic acid, iocetamic acid, sodium iopodate, tyropanoic acid, calcium iopodate, iopydol, propyliodone, iofendylate, lipiodol, barium sulfate, gadobenic acid, gadobutrol, gadodiamide, gadofosveset, gadolinium, gadopentetic acid, gadoteric acid, gadoteridol, gadoversetamide, gadoxetic acid, ferric ammonium citrate, mangafodipir, ferumoxsil, ferristene, perflubron, microspheres of human albumin. microparticles of galactose, perflenapent, microspheres of phospholipids, sulfur hexafluoride, and the like.

A further object of the present invention is a composition comprising the antibody or a binding fragment thereof, binding to hCD45RC according to the present invention.

A further object of the present invention is a composition comprising at least one nucleic acid encoding the antibody or binding fragment thereof binding to hCD45RC according to the present invention.

A further object of the present invention is a composition comprising at least one expression vector comprising at least one nucleic acid encoding the antibody or binding fragment thereof binding to hCD45RC according to the present invention.

A further object of the present invention is a pharmaceutical composition comprising the antibody or a binding fragment thereof, binding to hCD45RC according to the present invention; and at least one pharmaceutically acceptable excipient.

A further object of the present invention is a pharmaceutical composition comprising at least one nucleic acid encoding the antibody or binding fragment thereof binding to hCD45RC according to the present invention; and at least one pharmaceutically acceptable excipient.

A further object of the present invention is a pharmaceutical composition comprising at least one expression vector comprising at least one nucleic acid encoding the antibody or binding fragment thereof binding to hCD45RC according to the present invention; and at least one pharmaceutically acceptable excipient or vehicle.

The term "pharmaceutically acceptable excipient" includes any and all solvents, dispersion media, coatings, antibacterial and antifungal agents, isotonic and absorption delaying agents and the like. Said excipient does not produce an adverse, allergic or other untoward reaction when administered to an animal, preferably a human. For human administration, preparations should meet sterility, pyrogenicity, and general safety and purity standards as required by regulatory offices, such as, for example, FDA Office or EMA.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In one embodiment, the pharmaceutical compositions according to the present invention comprise vehicles which are pharmaceutically acceptable for a formulation capable of being injected to a subject. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

A further object of the present invention is a medicament comprising the antibody or a binding fragment thereof, binding to hCD45RC according to the present invention.

A further object of the present invention is a medicament comprising at least one nucleic acid encoding the antibody or binding fragment thereof binding to hCD45RC according to the present invention.

A further object of the present invention is a medicament comprising at least one expression vector comprising at least one nucleic acid encoding the antibody or binding fragment thereof binding to hCD45RC according to the present invention.

The present invention further relates to methods of inducing immune tolerance in a subject in need thereof, by administering the isolated antibody or binding fragment thereof, nucleic acid, expression vector, composition, pharmaceutical composition or medicament according to the present invention. It also relates to the isolated antibody or binding fragment thereof, nucleic acid, expression vector, composition, pharmaceutical composition or medicament according to the present invention, for use in inducing immune tolerance in a subject in need thereof.

The term "immune tolerance", as used herein, relates to a state of unresponsiveness of the immune system to specific substances or tissues that have the capacity to elicit an immune response while preserving immune response against other substances or tissues.

The term "immune response", as used herein, includes T cell-mediated and/or B cell-mediated immune responses. Exemplary immune responses include, but are not limited to, T cell responses (e.g., cytokine production and cellular cytotoxicity), but also immune responses that are indirectly effected by T cell activation (e.g., macrophages). Immune cells involved in the immune response include lymphocytes (such as B cells and T cells, including $CD4^+$, $CD8^+$, $T_h1$ and $T_h2$ cells), antigen presenting cells (e.g., professional antigen presenting cells such as dendritic cells), natural killer cells, myeloid cells (such as macrophages, eosinophils, mast cells, basophils, and granulocytes).

The present invention further relates to methods of depleting $CD45RC^{high}$ cells in a subject in need thereof, by administering the isolated antibody or binding fragment thereof, nucleic acid, expression vector, composition, pharmaceutical composition or medicament according to the present invention. It also relates to the isolated antibody or binding fragment thereof, nucleic acid, expression vector, composition, pharmaceutical composition or medicament according to the present invention, for use in depleting $CD45RC^{high}$ cells in a subject in need thereof.

The relative level of expression of hCD45RC is measured using cytometry. Three types of cells can be distinguished: cells presenting a high, intermediary or negative level of hCD45RC expression.

In one embodiment, the isolated antibody or binding fragment thereof, nucleic acid, expression vector, composition, pharmaceutical composition or medicament according to the present invention depletes $CD45RC^{high}$ T cells. "$CD45RC^{high}$ T cells" are T cells that express the CD45RC marker at a high level, as defined above. It is readily understood by the one skilled in the art that the isolated antibody or binding fragment thereof, nucleic acid, expression vector, composition, pharmaceutical composition or medicament according to the present invention that depletes $CD45RC^{high}$ T cells may also be able to deplete other types of $CD45RC^{high}$ cells, such as $CD45RC^{high}$ NK cells or $CD45RC^{high}$ B cells.

As used herein, the terms "deplete" or "depleting", with respect to cells expressing CD45RC, refer to a measurable decrease in the number of cells in the subject. The reduction can be at least about 10%, e.g., at least about 20%, 30%, 40%, 50%, 60%, 70%, 80%, 90%, 95%, 96%, 97%, 98%, 99%, or more. In some embodiments, the terms refer to a decrease in the number of CD45RC$^{high}$ cells in a subject or in a sample to an amount below detectable limits. According to the present invention, the isolated antibody or binding fragment thereof, nucleic acid, expression vector, composition, pharmaceutical composition or medicament specifically mediates depletion of the effector cells strongly expressing CD45RC, in particular those designed as CD45RC$^{high}$ Terr.

In particular, said isolated antibody or binding fragment thereof, nucleic acid, expression vector, composition, pharmaceutical composition or medicament according to the present invention depletes CD45RC$^{high}$ T cells by binding to hCD45RC and transducing pro-apoptotic signals and/or by activating antibody-dependent cell mediated cytotoxicity (ADCC), complement dependent cytotoxicity (CDC) or antibody dependent phagocytosis.

As used herein, the term "antibody-dependent cell-mediated cytotoxicity" or "ADCC" refers to a form of cytotoxicity in which secreted antibodies bound onto Fc receptors (FcRs) present on certain cytotoxic cells (e.g., NK cells, neutrophils, monocytes and macrophages) enable these cytotoxic effector cells to bind specifically to an antigen-bearing target cell and subsequently to kill the target cell. To assess ADCC activity of a molecule of interest, an in vitro ADCC assay, such as that described in U.S. Pat. No. 5,500,362 or 5,821,337, may be performed.

In some embodiments, the isolated antibody or binding fragment thereof, nucleic acid, expression vector, composition, pharmaceutical composition or medicament according to the present invention mediates complement dependent cytotoxicity.

The term "complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay such as, e.g., the one described in Gazzano-Santoro et al., 1997. *J Immunol Methods*. 202(2):163-71, may be performed.

In a particular embodiment, the isolated antibody or binding fragment thereof according to the present invention may be conjugated to a cytotoxic agent or a growth inhibitory agent.

The present invention further relates to methods of expanding and/or potentiating regulatory T cells in a subject in need thereof, by administering the isolated antibody or binding fragment thereof, nucleic acid, expression vector, composition, pharmaceutical composition or medicament according to the present invention. It also relates to the isolated antibody or binding fragment thereof, nucleic acid, expression vector, composition, pharmaceutical composition or medicament according to the present invention, for use in expanding and/or potentiating regulatory T cells in a subject in need thereof.

As used herein, the term "expand" refers to the process of converting and/or amplifying a given population of cells (e.g., immune cells such as Tregs). Expansion of a population of cells can occur in vivo, in vitro or ex vivo.

As used herein, the term "potentiate" refers to the process of increasing the function of a given population of cells (e.g., increasing the suppressive capacity of Tregs cells).

Potentiation of a population of cells can occur in vivo, in vitro or ex vivo.

"Regulatory T cells" or "Tregs" are T cells that suppress an abnormal or excessive immune response and play a role in immune tolerance. Tregs are typically "forkhead box P3 (Foxp3$^+$) regulatory T cells" and/or "CD45RC$^{low/-}$ cells".

As used herein, the terms "forkhead box P3 (Foxp3$^+$) regulatory T cells" and "CD45RC$^{low/-}$ cells" refer to 0.1-10% of CD4$^+$ and/or CD8$^+$ T cells in humans and rodents whose characteristic marker is the transcription factor Foxp3.

In one embodiment, the methods and uses are for expanding and/or potentiating Foxp3$^+$ and/or CD45RC$^{low/-}$ Tregs.

In one embodiment, CD45RC$^{low/-}$ Tregs are expanded by stimulation. In one embodiment, CD45RC$^{low/-}$ Tregs are expanded by stimulation in the presence of IL-2 and IL-15. In one embodiment, CD45RC$^{low/-}$ Tregs are expanded by stimulation with anti-CD3/anti-CD28 antibodies and/or allogeneic antigen-presenting cells (APCs) and/or specific antigens.

Additionally or alternatively, the invention relates to in vitro or ex vivo methods of purifying CD45RC$^{low/-}$ Tregs.

In one embodiment, CD45RC$^{low/-}$ Tregs are CD8$^+$/CD4$^+$ T cells. In one embodiment, CD45RC$^{low/-}$ Tregs are CD8$^+$/CD4$^-$ T cells. In one embodiment, CD45RC$^{low/-}$ Tregs are CD8$^-$/CD4$^+$ T cells.

In one embodiment, purified CD45RC$^{low/-}$ Tregs can be further expanded and/or potentiated prior to, concomitantly with or after administration to a subject in need thereof.

The present invention further relates to methods of preventing and/or reducing transplant rejections, by administering to a subject in need thereof the isolated antibody or binding fragment thereof, nucleic acid, expression vector, composition, pharmaceutical composition or medicament according to the present invention. It also relates to the isolated antibody or binding fragment thereof, nucleic acid, expression vector, composition, pharmaceutical composition or medicament according to the present invention, for use in preventing and/or reducing transplant rejections in a subject in need thereof.

The terms "preventing transplant rejections" and "reducing transplant rejections" are meant to encompass prevention or inhibition of immune transplant rejection, as well as delaying the onset or the progression of immune transplant rejection. The terms are also meant to encompass prolonging survival of a transplant in a subject, or reversing failure of a transplant in a subject. Further, the terms are meant to encompass ameliorating a symptom of an immune transplant rejection, including, for example, ameliorating an immunological complication associated with immune rejection, such as, e.g., interstitial fibrosis, chronic graft arteriosclerosis, or vasculitis.

The term "transplantation" and variations thereof refer to the insertion of a transplant (also called graft) into a recipient, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins.

In another scenario, the graft is derived from a species different from that into which it is transplanted, including animals from phylogenically widely separated species, for example, a baboon heart being transplanted into a human host.

The term "transplant rejection", as used herein, encompasses both acute and chronic transplant rejection.

"Acute rejection" is the rejection by the immune system of a tissue transplant-recipient when the transplanted tissue is immunologically foreign. Acute rejection is characterized by infiltration of the transplant tissue by immune cells of the recipient, which carry out their effector function and destroy the transplant tissue. The onset of acute rejection is rapid and generally occurs in humans within a few weeks after transplant surgery. Generally, acute rejection can be inhibited or suppressed with immunosuppressive drugs such as rapamycin, cyclosporin, anti-CD40L monoclonal antibody and the like.

"Chronic rejection" generally occurs in humans within several months to years after engraftment, even in the presence of successful immunosuppression of acute rejection. Fibrosis is a common factor in chronic rejection of all types of organ transplants.

In one embodiment, the transplant rejection is an allogeneic transplant rejection. Accordingly, in one embodiment, the donor of the transplant is a human. The donor of the transplant can be a living donor or a deceased donor, namely a cadaveric donor.

In one embodiment, the transplant is an organ, a tissue or cells.

As used herein, the term "organ" refers to a solid vascularized organ that performs a specific function or group of functions within an organism. The term organ includes, but is not limited to, heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus.

As used herein, the term "tissue" refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

As used herein, the term "cells" refers to a composition enriched for cells of interest, preferably a composition comprising at least 30%, preferably at least 50%, even more preferably at least 65% of said cells.

In one embodiment, the "cells" are selected from the group comprising or consisting of: multipotent hematopoietic stem cells derived from bone marrow, peripheral blood, or umbilical cord blood; or pluripotent (i.e., embryonic stem cells [ES] or induced pluripotent stem cells [iPS]) or multipotent stem cell-derived differentiated cells of different cell lineages, including, but not limited to, cardiomyocytes, β-pancreatic cells, hepatocytes, neurons and the like.

In one embodiment where the transplantation is an allogeneic hematopoietic stem cell transplantation (HSCT), the "cells" are selected from the group comprising or consisting of: multipotent hematopoietic stem cells, usually derived from bone marrow, peripheral blood, or umbilical cord blood.

"HSCT" or "hematopoletic stem cell transplantation" is a transplantation therapy which can be curative for patients affected with leukemia and lymphomas (including, without limitation, acute myeloid leukemia (AML), acute lymphoid leukemia (ALL), chronic myeloid leukemia (CML), myelodysplasia syndrome (MDS), myeloproliferative syndrome, Hodgkin lymphomas, non-Hodgkin lymphomas, chronic lymphatic leukemia (CLL) and multiple myeloma). However, an important limitation of allogeneic HSCT is the development of graft-versus-host-disease (GVHD), which occurs in a severe form in about 30-50% of humans who receive this therapy.

Therefore, in one embodiment, the isolated antibody or binding fragment thereof, nucleic acid, expression vector, composition, pharmaceutical composition or medicament according to the present invention is used to prevent and/or reduce GVHD.

In a further embodiment, the isolated antibody or binding fragment thereof, nucleic acid, expression vector, composition, pharmaceutical composition or medicament according to the present invention may be used in combination with multipotent hematopoietic stem cells to prevent and/or treat leukemia and/or lymphomas (including, without limitation, acute myeloid leukemia (AML), acute lymphoid leukemia (ALL), chronic myeloid leukemia (CML), myelodysplasia syndrome (MDS), myeloproliferative syndrome, Hodgkin lymphomas, non-Hodgkin lymphomas, chronic lymphatic leukemia (CLL) and multiple myeloma).

Additionally or alternatively, the isolated antibody or binding fragment thereof, nucleic acid, expression vector, composition, pharmaceutical composition or medicament according to the present invention may be used may be used for graft engineering.

In one embodiment, the transplant to be grafted is treated with the isolated antibody or binding fragment thereof, nucleic acid, expression vector, composition, pharmaceutical composition or medicament according to the present invention prior to transplantation, to deplete $CD45RC^{high}$ cells.

In a preferred embodiment, the transplant is bone marrow, and is treated with the isolated antibody or binding fragment thereof, nucleic acid, expression vector, composition, pharmaceutical composition or medicament according to the present invention prior to transplantation to deplete $CD45RC^{high}$ T cells. In one embodiment, the bone marrow comprises $CD34^+$ cells containing $CD45RC^{high}$ T cells and $CD45RC^{low/-}$ T cells.

The present invention further relates to methods of preventing, reducing and/or treating $hCD45RC^{high}$-related diseases, disorders or conditions, by administering to a subject in need thereof the isolated antibody or binding fragment thereof, nucleic acid, expression vector, composition, pharmaceutical composition or medicament according to the present invention. It also relates to the isolated antibody or binding fragment thereof, nucleic acid, expression vector, composition, pharmaceutical composition or medicament according to the present invention, for use in preventing and/or treating $hCD45RC^{high}$-related diseases, disorders or conditions.

As used herein, the term "$hCD45RC^{high}$-related diseases, disorders or conditions" refers to diseases, disorders or conditions caused by or potentialized by an increased proportion of cells expressing hCD45RC cells in a subject and/or by an increased level of expression of hCD45RC in cells of the subject.

By "increased proportion of $CD45RC^{high}$ cells in a subject" is meant an increase of about 5%, preferably about 10%, 15%, 20%, 25%, 30%, 35%, 40%, 45%, 50%, 60%, 70%, 80%, 90%, 100% or more of the number of cells expressing CD45RC (i.e., $CD45RC^{high}$ cells) in a given subject as compared to a reference, such as, e.g., the number of $CD45RC^{high}$ cells in a substantially healthy subject.

By "increased level of expression of hCD45RC in cells of the subject" is meant an increase of about 5%, preferably about 10%, 15%, 20%, 25%, 30%, 35%, 40%, 45%, 50%, 60%, 70%, 80%, 90%, 100% or more of the expression level of hCD45RC, whether at the mRNA level or at the protein level, in cells of a given subject as compared to a reference, such as, e.g., the expression level of hCD45RC in cells of a substantially healthy subject.

In one embodiment, hCD45RC$^{high}$-related diseases, disorders or conditions are selected from the group comprising or consisting of autoimmune diseases, undesired immune responses, monogenic diseases and lymphoma or cancer.

In one embodiment, hCD45RC$^{high}$-related diseases, disorders or conditions are selected from the group comprising or consisting of autoimmune diseases, undesired immune responses and monogenic diseases.

As used herein, the term "autoimmune disease" refers to a disease in which the immune system produces an immune response (e.g., a B cell or a T cell response) against an antigen that is part of the normal host (that is an autoantigen), with consequent injury to tissues. In an autoimmune disease, the immune system of the host fails to recognize a particular antigen as "self" and an immune reaction is mounted against the host's tissues expressing the antigen.

Exemplary autoimmune diseases contemplated in the present invention include, but are not limited to, rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (including Crohn's disease and ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, acquired hemophilia, thrombotic thrombocytopenic purpura, uveitis, IgG4-associated autoimmune diseases (such as, e.g., diseases listed in Table 1 of Kleger et al., 2015. *Dtsch Arztebl Int.* 112(8):128-135, which Table is incorporated by reference) and the like.

In a preferred embodiment, the autoimmune disease is systemic lupus erythematosis.

In a preferred embodiment, the autoimmune disease is inflammatory bowel disease, including Crohn's disease and ulcerative colitis. In a preferred embodiment, the autoimmune disease is Crohn's disease. In a preferred embodiment, the autoimmune disease is ulcerative colitis.

As used herein, the term "undesired immune response" refers to any unwanted immune reaction, preferably any unwanted immune reaction directed to (i) proteins expressed in the course of gene therapy, (ii) vectors (such as, e.g., viral vectors) used in the course of gene therapy and/or (iii) therapeutic proteins. Such proteins include for example factor VIII (hemophilia A) and other coagulation factors, enzyme replacement therapies, monoclonal antibodies (e.g., natalizumab, rituximab, infliximab), polyclonal antibodies, enzymes and cytokines (e.g., IFNβ). The term "undesired immune response" also refers to allergies and allergic reactions.

In one embodiment, the isolated antibody or binding fragment thereof, nucleic acid, expression vector, composition, pharmaceutical composition or medicament according to the present invention may be administered to a subject in order to suppress an immune response, especially to prevent immune reactions to specific proteins when their expression is restored by gene therapy in those subjects with corresponding genetic deficiencies. Thus, the isolated antibody or binding fragment thereof, nucleic acid, expression vector, composition, pharmaceutical composition or medicament according to the present invention may be used to prevent immune reactivity towards proteins normally absent in the subject due to mutations, while their reconstitution is achieved by gene therapy. Moreover, protein therapy is an area of medical innovation that is becoming more widespread, and involves the application of proteins, such as enzymes, antibodies or cytokines, directly to subjects as therapeutic products. One of the major hurdles in delivery of such medicaments involves the immune responses directed against the therapeutic protein themselves. Administration of protein-based therapeutics is often accompanied by administration of immune suppressants, which are used in order to facilitate a longer lifetime of the protein and therefore increased uptake of the protein into the cells and tissues of the organism. General immune suppressants can however be disadvantageous due to the unspecific nature of the immune suppression that is carried out, resulting in unwanted side effects in the patient. Therefore, this approach can be applied to suppress an immune response against therapeutic proteins and peptides, such as therapeutic antibodies, cytokines, enzymes or any other protein administered to a patient.

In one embodiment, the isolated antibody or binding fragment thereof, nucleic acid, expression vector, composition, pharmaceutical composition or medicament according to the present invention may be administered to a subject in order to suppress an immune response, especially to prevent immune reactions to vectors used in gene therapy, in particular viral vectors used in gene therapy. Such viral vectors include, e.g., adeno-associated virus (AAV) vectors, adenoviral (Ad) vectors, lentiviral vectors and the like. For a review, see Nayak & Herzog, 2010. *Gene Ther.* 17(3):295-304.

As used herein, the term "allergy" or "allergies" refers to an improper reaction of the immune system. Allergic reactions occur to normally harmless environmental substances known as allergens; these reactions are acquired, predictable and rapid. Strictly, allergy is one of four forms of hypersensitivity and is called type I (or immediate) hypersensitivity. It is characterized by excessive activation of certain white blood cells called mast cells and basophils by a type of antibody known as IgE, resulting in an extreme inflammatory response. Common allergic reactions include eczema, hives, hay fever, asthma, food allergies, and reactions to the venom of stinging insects such as wasps and bees.

The term "monogenic diseases", as used herein, refers to diseases resulting from a mutation in a single gene selected among the following genes:
  (i) genes which are not associated with immune function but whose deficiency is associated with inflammation and/or immune reactions, such as genes deficient in the following diseases: Duchenne muscular dystrophy (DMD), cystic fibrosis, lysosomal diseases and al-antitrypsin deficiency; and
  (ii) genes involved in the immune system and whose deficiency generates inflammation and/or autoimmune reactions, such as genes deficient in the following diseases: T cell primary immunodeficiency such as IPEX (immunodysregulation polyendocrinopathy enteropathy X-linked syndrome), APECED (autoimmune polyendocrinopathy-candidiasis-ectodermal dystrophy), B cell primary immunodeficiencies, Muckle-Wells syndrome, mixed autoinflammatory and autoimmune syndrome, NLRP12-associated hereditary periodic fever syndrome, and tumor necrosis factor receptor 1 associated periodic syndrome.

In a preferred embodiment, the autoimmune disease is APECED (autoimmune polyendocrinopathy-candidiasis-ectodermal dystrophy).

In a preferred embodiment, the autoimmune disease is Duchenne muscular dystrophy (DMD).

The term "lymphoma or cancer", as used herein, encompass lymphoma or cancer which are associated with $CD45RC^{high}$ cells. Exemplary lymphoma or cancer associated with $CD45RC^{high}$ cells include, but are not limited to, acute myeloid leukemia (AML), acute lymphoid leukemia (ALL), chronic myeloid leukemia (CML), myelodysplasia syndrome (MDS)/myeloproliferative syndrome, lymphomas (such as, e.g., Hodgkin and non-Hodgkin lymphomas), chronic lymphatic leukemia (CLL) and multiple myeloma. The present invention relates therefore to a method of depleting $CD45RC^{high}$ cells in a subject in need thereof, thereby expending and/or potentiating regulatory T cells, preferably Foxp3+ and/or $CD45RC^{low}$ Tregs, thereby preventing and/or reducing transplant rejections; or preventing, reducing and/or treating $hCD45RC^{high}$-related diseases, disorders or conditions, by administering the isolated antibody or binding fragment thereof, nucleic acid, expression vector, composition, pharmaceutical composition or medicament according to the present invention.

In a preferred embodiment, the $hCD45RC^{high}$-related disease, disorder or condition is systemic lupus erythematosis, inflammatory bowel disease (including Crohn's disease and ulcerative colitis), APECED (autoimmune polyendocrinopathy-candidiasis-ectodermal dystrophy), or Duchenne muscular dystrophy (DMD).

In a preferred embodiment, the $hCD45RC^{high}$-related disease, disorder or condition is systemic lupus erythematosis, inflammatory bowel disease (including Crohn's disease and ulcerative colitis), or APECED (autoimmune polyendocrinopathy-candidiasis-ectodermal dystrophy).

It also relates to the isolated antibody or binding fragment thereof, nucleic acid, expression vector, composition, pharmaceutical composition or medicament according to the present invention for use in depleting $CD45RC^{high}$ cells in a subject in need thereof, thereby expending and/or potentiating regulatory T cells, preferably Foxp3+ and/or $CD45RC^{low}$ Tregs, thereby preventing and/or reducing transplant rejections; or preventing, reducing and/or treating $hCD45RC^{high}$-related diseases, disorders or conditions.

In one embodiment, the isolated antibody or binding fragment thereof, nucleic acid, expression vector, composition, pharmaceutical composition or medicament according to the present invention will be formulated for administration to the subject.

In one embodiment, the isolated antibody or binding fragment thereof, nucleic acid, expression vector, composition, pharmaceutical composition or medicament according to the present invention is to be administered systemically or locally.

In one embodiment, the isolated antibody or binding fragment thereof, nucleic acid, expression vector, composition, pharmaceutical composition or medicament according to the present invention is to be administered by injection, orally, topically, nasally, buccally, rectally, vaginally, intratracheally, by endoscopy, transmucosally, or by percutaneous administration.

In one embodiment, the isolated antibody or binding fragment thereof, nucleic acid, expression vector, composition, pharmaceutical composition or medicament according to the present invention is to be injected, preferably systemically injected.

Examples of formulations adapted for injection include, but are not limited to, solutions, such as, for example, sterile aqueous solutions, gels, dispersions, emulsions, suspensions, solid forms suitable for using to prepare solutions or suspensions upon the addition of a liquid prior to use, such as, for example, powder, liposomal forms and the like.

Examples of systemic injections include, but are not limited to, intravenous (iv), subcutaneous, intramuscular (im), intradermal (id), intraperitoneal (ip) injection and perfusion.

In one embodiment, when injected, the isolated antibody or binding fragment thereof, nucleic acid, expression vector, composition, pharmaceutical composition or medicament according to the present invention is sterile. Methods for obtaining a sterile composition include, but are not limited to, GMP synthesis (where GMP stands for "Good manufacturing practice").

Sterile injectable forms of a composition may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution.

In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

It will be understood that other suitable routes of administration are also contemplated in the present invention, and the administration mode will ultimately be decided by the attending physician within the scope of sound medical judgment. Apart from administration by injection (iv, ip, im and the like), other routes are available, such as nebulization (Respaud et al., 2014. *MAbs.* 6(5):1347-55; Guilleminault et al., 2014. *J Control Release.* 196:344-54; Respaud et al., 2015. *Expert Opin Drug Deliv.* 12(6):1027-39) or subcutaneous administration (Jackisch et al., 2014. *Geburtshilfe Frauenheilkd.* 74(4):343-349; Solal-Celigny, 2015. *Expert Rev Hematol.* 8(2):147-53).

In one embodiment, the isolated antibody or binding fragment thereof, nucleic acid, expression vector, composition, pharmaceutical composition or medicament according to the present invention is to be administered to the subject in need thereof in a therapeutically effective amount.

The term "therapeutically effective amount", as used herein, refers to an amount effective, at dosages and for periods of time necessary, to achieve a desired preventive and/or therapeutic result.

It will be however understood that the total daily usage of the isolated antibody or binding fragment thereof, nucleic acid, expression vector, composition, pharmaceutical composition or medicament according to the present invention will be decided by the attending physician within the scope of sound medical judgment. The specific therapeutically effective dose level for any particular patient will depend upon a variety of factors including the disease being treated and the severity of the disease; activity of the isolated antibody or binding fragment thereof, nucleic acid, expression vector, composition, pharmaceutical composition or medicament employed; the age, body weight, general health, sex and diet of the subject; the time of administration, route of administration, and rate of excretion of the specific isolated antibody or binding fragment thereof, nucleic acid, expression vector, composition, pharmaceutical composition or medicament employed; the duration of the treatment; drugs used in combination or coincidental with the specific isolated antibody or binding fragment thereof, nucleic acid, expression vector, composition, pharmaceutical composition or medicament employed; and like factors well known in the medical arts. For example, it is well within the skill of the art to start doses of the compound at levels lower than those required to achieve the desired therapeutic effect and to gradually increase the dosage until the desired effect is achieved. The total dose required for each treatment may be administered by multiple doses or in a single dose.

In one embodiment, a therapeutically effective amount of the isolated antibody or binding fragment thereof, nucleic acid, expression vector, composition, pharmaceutical composition or medicament according to the present invention ranges from about 0.1 mg/kg to about 5 mg/kg, from about 0.2 mg/kg to about 4 mg/kg, from about 0.3 mg/kg to about 3 mg/kg, from about 0.4 mg/kg to about 2.5 mg/kg, from about 0.5 mg/kg to about 2 mg/kg.

In one embodiment, a therapeutically effective amount of the isolated antibody or binding fragment thereof, nucleic acid, expression vector, composition, pharmaceutical composition or medicament according to the present invention ranges from about 10 µg/kg to about 400 µg/kg, from about 20 µg/kg to about 300 µg/kg, from about 30 µg/kg to about 250 µg/kg, from about 35 µg/kg to about 200 µg/kg, from about 40 µg/kg to about 160 µg/kg.

In one embodiment, a therapeutically effective amount of the isolated antibody or binding fragment thereof, nucleic acid, expression vector, composition, pharmaceutical composition or medicament according to the present invention is to be administered once a day, twice a day, three times a day or more.

In one embodiment, a therapeutically effective amount of the isolated antibody or binding fragment thereof, nucleic acid, expression vector, composition, pharmaceutical composition or medicament according to the present invention is to be administered every day, every two days, every three days, every four days, every five days, every six days.

In one embodiment, a therapeutically effective amount of the isolated antibody or binding fragment thereof, nucleic acid, expression vector, composition, pharmaceutical composition or medicament according to the present invention is to be administered every week, every two weeks, every three weeks.

In one embodiment, a therapeutically effective amount of the isolated antibody or binding fragment thereof, nucleic acid, expression vector, composition, pharmaceutical composition or medicament according to the present invention is to be administered every month, every two months, every three months, every four months, every five months, every six months.

In a preferred embodiment, a therapeutically effective amount of the isolated antibody or binding fragment thereof, nucleic acid, expression vector, composition, pharmaceutical composition or medicament according to the present invention is to be administered every 12 hours, every 24 hours, every 36 hours, every 48 hours, every 60 hours, every 72 hours, every 96 hours.

In a preferred embodiment, a therapeutically effective amount of the isolated antibody or binding fragment thereof, nucleic acid, expression vector, composition, pharmaceutical composition or medicament according to the present invention is to be administered every 60 hours.

In one embodiment, the isolated antibody or binding fragment thereof, nucleic acid, expression vector, composition, pharmaceutical composition or medicament according to the present invention is for acute administration. In one embodiment, the isolated antibody or binding fragment thereof, nucleic acid, expression vector, composition, pharmaceutical composition or medicament according to the present invention is for chronic administration.

In one embodiment, a therapeutically effective amount of the isolated antibody or binding fragment thereof, nucleic acid, expression vector, composition, pharmaceutical composition or medicament according to the present invention is to be administered for about 5 days, 7 days, 10 days, 14 days, 21 days, 28 days, 1 month, 2 months, 3 months, 6 months, 1 year or more.

In one embodiment, a therapeutically effective amount of the isolated antibody or binding fragment thereof, nucleic acid, expression vector, composition, pharmaceutical composition or medicament according to the present invention is to be administered for a period of time ranging from about one week to about eight weeks, from about two weeks to about seven weeks, from about two weeks to about six weeks, from about two weeks to about five weeks.

In a preferred embodiment, a therapeutically effective amount of the isolated antibody or binding fragment thereof, nucleic acid, expression vector, composition, pharmaceutical composition or medicament according to the present invention is to be administered for a period of time ranging from about 10 days to about 40 days, from about 15 days to about 35 days, from about 20 days to about 30 days.

In one embodiment, the isolated antibody or binding fragment thereof, nucleic acid, expression vector, composition, pharmaceutical composition or medicament according to the present invention is to be administered before, concomitantly with or after a therapeutic drug.

Some examples of therapeutic drugs suitable for co-administration with the isolated antibody or binding fragment thereof, nucleic acid, expression vector, composition, pharmaceutical composition or medicament according to the present invention include, without limitation, immunosuppressants, cytotoxins, chemotherapeutic agents, cytokines, immune stimulators, lytic peptides and radioisotopes.

It will be understood by the one skilled in the art that the co-administration of the isolated antibody or binding fragment thereof, nucleic acid, expression vector, composition, pharmaceutical composition or medicament according to the present invention with a particular therapeutic drug, which may be chosen among those recited herein but without being limited thereto, will depend on the disease or condition to be prevented and/or treated.

Examples of immunosuppressants include, without limitation, mTOR inhibitors such as, e.g., sirolimus, everolimus, ridaforolimus, temsirolimus, umirolimus and zotarolimus; IL-1 receptor antagonists such as, e.g., anakinra; antimetabolites such as, e.g., azathioprine, leflunomide, methotrexate, mycophenolic acid and teriflunomide; IMiDs such as, e.g., apremilast, lenalidomide, pomalidomide and thalidomide; and antibodies such as, e.g., eculizumab, adalimumab, afelimomab, certolizumab pegol, golimumab, infliximab, nerelimomab, mepolizumab, omalizumab, faralimomab, elsilimomab, lebrikizumab, ustekinumab, secukinumab, muromonab-CD3, otelixizumab, teplizumab, visilizumab, clenoliximab, keliximab, zanolimumab, efalizumab, erlizumab, obinutuzumab, rituximab, ocrelizumab, pascolizumab, gomiliximab, lumiliximab, teneliximab, toralizumab, aselizumab, galiximab, gavilimomab, ruplizumab, belimumab, blisibimod, ipilimumab, tremelimumab, bertilimumab, lerdelimumab, metelimumab, natalizumab, tocilizumab, odulimomab, basiliximab, daclizumab, inolimomab, zolimomab aritox, atorolimumab, cedelizumab, fontolizumab, maslimomab, morolimumab, pexelizumab, reslizumab, rovelizumab, siplizumab, talizumab, telimomab aritox, vapaliximab, vepalimomab, abatacept, belatacept, etanercept, pegsunercept, aflibercept, alefacept and rilonacept.

Examples of cytotoxins include, without limitation, radionuclides (e.g., $^{35}$S, $^{14}$C, $^{32}$P, $^{125}$I, $^{131}$I, $^{90}$Y, $^{89}$Zr, $^{201}$Tl, $^{186}$Re, $^{188}$Re, $^{57}$Cu, $^{213}$Bi, and $^{211}$At), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU) etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), *Pseudomonas* exotoxin (PE) A. PE40, abrin, saporin, pokeweed viral protein, ethidium bromide, glucocorticoid, anthrax toxin and others.

Examples of chemotherapeutic agents include, without limitation, platinum coordination compounds (such as, e.g., cisplatin, carboplatin or oxalyplatin); taxane compounds (such as, e.g., paclitaxel or docetaxel); topoisomerase I inhibitors (such as, e.g., irinotecan or topotecan); topoisomerase II inhibitors (such as, e.g., etoposide or teniposide); vinca alkaloids (such as, e.g., vinblastine, vincristine or vinorelbine); anti-tumor nucleoside derivatives (such as, e.g., 5-fluorouracil, gemcitabine or capecitabine); alkylating agents (such as, e.g., nitrogen mustard or nitrosourea, cyclophosphamide, chlorambucil, carmustine or lomustine; anti-tumor anthracycline derivatives (suc has, e.g., daunorubicin, doxorubicin, idarubicin or mitoxantrone); anti-HER2 antibodies (such as, e.g., trastuzumab); estrogen receptor antagonists or selective estrogen receptor modulators (such as, e.g., tamoxifen, toremifene, droloxifene, faslodex or raloxifene); aromatase inhibitors (such as, e.g., exemestane, anastrozole, letrazole or vorozole); differentiating agents (such as, e.g., retinoids, vitamin D and retinoic acid metabolism blocking agents [RAMBA] such as accutane); DNA methyl transferase inhibitors (such as, e.g., azacytidine); kinase inhibitors (such as, e.g., flavoperidol, imatinib mesylate or gefitinib); farnesyltransferase inhibitors; and HDAC inhibitors.

Examples of cytokines include, without limitation, chemokines (such as, e.g., CCL1, CCL2/MCP1, CCL3/MIP1α, CCL4/MIP1β, CCL5/RANTES, CCL6, CCL7, CCL8, CCL9, CCL11, CCL12, CCL13, CCL14, CCL15, CCL16, CCL17, CCL18/PARC/DCCK1/AMAC1/MIP4, CCL19, CCL20, CCL21, CCL22, CCL23, CCL24, CCL25, CCL26, CCL27, CCL28, CXCL1/KC, CXCL2, CXCL3, CXCL4, CXCL5, CXCL6, CXCL7, CXCL8/IL8, CXCL9, CXCL10, CXCL11, CXCL12, CXCL13, CXCL14, CXCL15, CXCL16, CXCL17, CX3CL1, XCL1 and XCL2), tumor necrosis factors (such as, e.g., TNFA, Lymphotoxin, TNFSF4, TNFSF5/CD40LG, TNFSF6, TNFSF7, TNFSF8, TNFSF9, TNFSF10, TNFSF11, TNFSF13, TNFSF13B and EDA) and interleukins (such as, e.g., IL-1α, IL-1β, IL-1Ra, IL-2, IL-3, IL-4, IL-5, IL-6, IL-7, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36α, IL-36β, IL-36γ, IL-36Ra, IL-37, IL-38, IFNα, IFNβ, IFNκ, IFNω and GM-CSF).

Examples of immune stimulators include, without limitation, flgrastim, pegfilgrastim, lenograstim, molgramostim, sargramostim, ancestim, albinterferon, interferon alfa, peginterferon alfa, interferon beta, peginterferon beta, interferon gamma, aldesleukin, oprelvekin, growth hormone, immunocyanin, pegademase, prolactin, tasonermin, histamine dihydrochloride, poly ICLC, vitamin D, lentinan, plerixafor, roquinimex, mifamurtide, glatiramer acetate, thymopentin, thymosin a1, thymulin, polyinosinic:polycytidylic acid, pidotimod, Bacillus Calmette-Guérin vaccine, melanoma vaccine and sipuleucel-T vaccine.

Examples of lytic peptides include, without limitation, toxins (such as, e.g., Diptheria toxin or *Pseudomonas* exotoxin).

Examples of radioisotopes include, without limitation, the radionuclides of technetium (e.g., Tc-99 and Tc-97), potassium (e.g., K-40), rubidium (e.g., Rb-82), iodine (e.g., I-123, I-124, I-125, I-129, I-131), cesium (e.g., Cs-135, Cs-137), cobalt (e.g., Co-60), palladium (e.g., Pd-103, Pd-107), cadmium (e.g., Cd-113), strontium (e.g., Sr-89, Sr-90), europium (e.g., Eu-55), tin (e.g., Sn-121, Sn-126), phosphorus (e.g., P-32, P-33), thallium (e.g., T1-201), indium (e.g., In-111), gallium (e.g., Ga-67, Ga-68), yttrium (e.g., Y-90), iridium (e.g., Ir-192), bismuth (e.g., Bi-213), radium (e.g., Ra-223, Ra-225), and ruthenium (e.g., Ru-106).

The invention further relates to the use of the isolated antibody or binding fragment thereof according to the present invention, for detecting or quantifying hCD45RC in a sample, cell, tissue or organ; and to methods for detecting or quantifying hCD45RC in a sample, cell, tissue or organ, comprising contacting said sample, cell, tissue or organ with the isolated antibody or binding fragment thereof according to the present invention.

In one embodiment, the uses and methods for detecting or quantifying hCD45RC may be in vitro or in vivo.

In one embodiment, the isolated antibody or binding fragment thereof according to the present invention is labeled, as described hereinabove, for detection or diagnostic purposes.

Assays suitable for detecting or quantifying hCD45RC using the isolated antibody or binding fragment thereof according to the present invention are well-known in the art, and include, without limitation, ELISA, sandwich ELISA, RIA, FACS, tissue immunohistochemistry, Western-blot and immunoprecipitation.

In one embodiment, the sample is a biological sample. Examples of biological samples include, but are not limited to, bodily fluids (preferably blood, more preferably blood serum), plasma, synovial fluid, bronchoalveolar lavage fluid, sputum, lymph, ascitic fluids, urine, amniotic fluid, peritoneal fluid, cerebrospinal fluid, pleural fluid, pericardial fluid, and alveolar macrophages, tissue lysates, biopsies and extracts prepared from diseased tissues.

In one embodiment, the sample is taken or retrieved from a subject prior to any analysis. Accordingly, in this embodiment, the uses and methods for detecting or quantifying hCD45RC are in vitro uses and methods.

The invention further relates to the use of the isolated antibody or binding fragment thereof according to the present invention, for diagnosing hCD45RC-related diseases in a subject; and to methods for diagnosing hCD45RC-related diseases in a subject comprising contacting a sample from said subject with the isolated antibody or binding fragment thereof according to the present invention.

Assays suitable for detecting or quantifying hCD45RC using the isolated antibody or binding fragment thereof according to the present invention are well-known in the art, and include, without limitation, ELISA, sandwich ELISA, RIA, FACS, tissue immunohistochemistry, Western-blot and immunoprecipitation.

In one embodiment, the sample is a biological sample. Examples of biological samples include, but are not limited to, bodily fluids (preferably blood, more preferably blood serum), plasma, synovial fluid, bronchoalveolar lavage fluid, sputum, lymph, ascitic fluids, urine, amniotic fluid, peritoneal fluid, cerebrospinal fluid, pleural fluid, pericardial fluid, and alveolar macrophages, tissue lysates, biopsies and extracts prepared from diseased tissues.

In one embodiment, the sample is taken or retrieved from a subject prior to any analysis. Accordingly, in this embodiment, the uses and methods for diagnosing hCD45RC-related diseases are in vitro uses and methods.

In one embodiment, the hCD45RC-related diseases are hCD45RC$^{high}$-related diseases, as defined hereinabove. According to this embodiment, the subject may be diagnosed as affected with or suffering from a hCD45RC-related disease if hCD45RC is detected in a sample from said subject at a level, amount or concentration higher than in a reference subject (e.g., in a substantially healthy subject, or in a subject who is known not to be affected with or suffering from a hCD45RC-related disease).

In one embodiment, the uses and methods for diagnosing hCD45RC-related diseases further comprise a step of treating the subject if said subject is diagnosed as being affected with or suffering from a hCD45RC-related disease.

The present application discloses an isolated anti-human CD45RC antibody or binding fragment thereof, wherein said antibody or binding fragment thereof binds to human CD45RC with:
 (i) an equilibrium dissociation constant ($K_D$) of $5 \times 10^{-7}$ M or less;
 (ii) an association rate ($K_{on}$) of $1 \times 10^4$ M$^{-1}$ sec$^{-1}$ or more; and/or
 (iii) a dissociation rate ($K_{off}$) of $5 \times 10^{-2}$ sec$^{-1}$ or less;
preferably wherein the $K_D$, $K_{on}$ and/or $K_{off}$ are determined by surface plasmon resonance.

The antibody or binding fragment thereof binds to at least one epitope displayed in the C determinant of hCD45RC.

The antibody or binding fragment thereof binds to at least one epitope comprising at least amino acids of SEQ ID NO: 23 or a fragment thereof; or of a sequence sharing at least about 70% identity with SEQ ID NO: 23 or a fragment thereof.

The antibody is monoclonal.
The antibody is murine, chimeric or humanized.

a) The variable region of the heavy chain (HCVR) of the antibody or binding fragment thereof comprises the following three complementary-determining regions (CDRs):

```
VH-CDR1:
                                            (SEQ ID NO: 1)
NYYIG;

VH-CDR2:
                                            (SEQ ID NO: 2)
X1-IF-X2-GG-X3-Y-X4-N-X5-X6-X7-X8-X9-X10-G;
and

VH-CDR3:
                                            (SEQ ID NO: 3)
RNFDY,
``` and
b) the variable region of the light chain (LCVR) of said antibody or binding fragment thereof comprises the following three CDRs:

```
VL-CDR1:
                                            (SEQ ID NO: 12)
X11-ASSSVS-X12-YMH;

VL-CDR2:
                                            (SEQ ID NO: 13)
X13-TSN-X14-X15-X16;
and VL-CDR3:
                                            (SEQ ID NO: 14)
X17-QRSSYPLTF;
``` wherein:
 $X_1$ is selected from Asp (D), Ile (I) and Arg (R);
 $X_2$ is selected from Pro (P) and Ser (S);
 $X_3$ is selected from Asp (D), Ser (S) and Gly (G);
 $X_4$ is selected from Thr (T) and Ala (A);
 $X_5$ is selected from Tyr (Y) and Ser (S);
 $X_6$ is selected from Ala (A), Asn (N) and Ser (S);
 $X_7$ is selected from Glu (E), Asp (D), Pro (P) and Gln (Q);
 $X_8$ is selected from Lys (K) and Ser (S);
 $X_9$ is selected from Phe (F) and Val (V);
 $X_{10}$ is selected from Lys (K) and Gln (Q);
 $X_{11}$ is selected from Arg (R) and Ser (S);
 $X_{12}$ is selected from Asn (N), Ser (S), Gly (G) and an empty position;
 $X_{13}$ is selected from Asn (N) and Ala (A); or $X_{13}$ being any amino acid but Ala (A) or Asn (N);
 $X_{14}$ is selected from Leu (L), Ser (S) and Arg (R);
 $X_{15}$ is selected from Pro (P), Ala (A) and Gln (Q);
 $X_{16}$ is selected from Ser (S) and Thr (T); and
 $X_{17}$ is selected from Gln (Q) and His (H).

The antibody or binding fragment thereof comprises a combination of CDRs as set forth in Table 2.

The antibody or binding fragment thereof comprises:
 a) a HCVR selected from SEQ ID NOs: 61-70; and
 b) a LCVR selected from SEQ ID NOs: 71-90.

The antibody or binding fragment thereof comprises a combination of HCVR and LCVR selected from:
 SEQ ID NOs: 61 and 71; SEQ ID NOs: 61 and 81; SEQ ID NOs: 62 and 72; SEQ ID NOs: 62 and 73; SEQ ID NOs: 62 and 74; SEQ ID NOs: 62 and 82; SEQ ID NOs: 62 and 83; SEQ ID NOs: 62 and 84; SEQ ID NOs: 63 and 72; SEQ ID NOs: 63 and 73; SEQ ID NOs: 63 and 74; SEQ ID NOs: 63 and 82; SEQ ID NOs: 63 and 83; SEQ ID NOs: 63 and 84; SEQ ID NOs: 64 and 72; SEQ ID NOs: 64 and 73; SEQ ID NOs: 64 and 74; SEQ ID NOs: 64 and 82; SEQ ID NOs: 64 and 83; and SEQ ID NOs: 64 and 84.

wherein $X_{12}$ in SEQ ID NOs 71-74 is selected from Asn (N), Ser (S) and Gly (G).

The present application also discloses nucleic acid encoding the isolated antibody or binding fragment thereof described above.

The present application also discloses an expression vector comprising the nucleic acid described above.

The present application also discloses a composition comprising the isolated antibody or binding fragment thereof described above, the nucleic acid described above, or the expression vector described above.

The present application also discloses a pharmaceutical composition comprising the isolated antibody or binding fragment thereof described above, the nucleic acid described above, or the expression vector described above, and at least one pharmaceutically acceptable excipient.

The present application also discloses the isolated antibody or binding fragment thereof described above, the nucleic acid described above, the expression vector described above, the composition described above or the pharmaceutical composition described above, for use as a medicament.

The isolated antibody or binding fragment thereof described above, the nucleic acid described above, the expression vector described above, the composition described above or the pharmaceutical composition described above is/are for use in:
  inducing immune tolerance in a subject in need thereof;
  preventing and/or reducing transplant rejections; and/or
  preventing, reducing and/or treating CD45RChigh-related conditions, preferably selected from autoimmune diseases, undesired immune responses, monogenic diseases and lymphoma or cancer.

The isolated antibody or binding fragment thereof described above, the nucleic acid described above, the expression vector described above, the composition described above or the pharmaceutical composition described above is/are for use in preventing and/or treating graft-versus-host disease (GVHD).

EXAMPLES

The present invention is further illustrated by the following examples.

Throughout the examples, the following nomenclature applies:

"ABIS-45RC": the murine anti-hCD45RC antibody of the invention, comprising:
  a heavy chain variable region with SEQ ID NO: 61;
  a heavy chain constant region with SEQ ID NO: 93;
  a light chain variable region with SEQ ID NO: 81; and
  a light chain constant region with SEQ ID NO: 94.

"Anti-45RC Variant A": a humanized variant of ABIS-45RC, comprising:
  a heavy chain variable region with SEQ ID NO: 62;
  a heavy chain constant region with SEQ ID NO: 91;
  a light chain variable region with SEQ ID NO: 82; and
  a light chain constant region with SEQ ID NO: 92.

"Anti-45RC Variant B": a humanized variant of ABIS-45RC, comprising:
  a heavy chain variable region with SEQ ID NO: 62;
  a heavy chain constant region with SEQ ID NO: 91;
  a light chain variable region with SEQ ID NO: 83; and
  a light chain constant region with SEQ ID NO: 92.

"Anti-45RC Variant C": a humanized variant of ABIS-45RC, comprising:
  a heavy chain variable region with SEQ ID NO: 62;
  a heavy chain constant region with SEQ ID NO: 91;
  a light chain variable region with SEQ ID NO: 84; and
  a light chain constant region with SEQ ID NO: 92.

"Anti-45RC Variant D": a humanized variant of ABIS-45RC, comprising:
  a heavy chain variable region with SEQ ID NO: 63;
  a heavy chain constant region with SEQ ID NO: 91;
  a light chain variable region with SEQ ID NO: 82; and
  a light chain constant region with SEQ ID NO: 92.

"Anti-45RC Variant E": a humanized variant of ABIS-45RC, comprising:
  a heavy chain variable region with SEQ ID NO: 63;
  a heavy chain constant region with SEQ ID NO: 91;
  a light chain variable region with SEQ ID NO: 83; and
  a light chain constant region with SEQ ID NO: 92.

"Anti-45RC Variant F": a humanized variant of ABIS-45RC, comprising:
  a heavy chain variable region with SEQ ID NO: 63;
  a heavy chain constant region with SEQ ID NO: 91;
  a light chain variable region with SEQ ID NO: 84; and
  a light chain constant region with SEQ ID NO: 92.

"Anti-45RC Variant G": a humanized variant of ABIS-45RC, comprising:
  a heavy chain variable region with SEQ ID NO: 64;
  a heavy chain constant region with SEQ ID NO: 91;
  a light chain variable region with SEQ ID NO: 83; and
  a light chain constant region with SEQ ID NO: 92.

"Anti-45RC Variant H": a humanized variant of ABIS-45RC, comprising:
  a heavy chain variable region with SEQ ID NO: 64;
  a heavy chain constant region with SEQ ID NO: 91;
  a light chain variable region with SEQ ID NO: 84; and
  a light chain constant region with SEQ ID NO: 92.

"Anti-45RC Variant I": a humanized variant of ABIS-45RC, comprising:
  a heavy chain variable region with SEQ ID NO: 64;
  a heavy chain constant region with SEQ ID NO: 91;
  a light chain variable region with SEQ ID NO: 82; and
  a light chain constant region with SEQ ID NO: 92.

"Anti-45RC Variant A1": a humanized variant of ABIS-45RC, comprising:
  a heavy chain variable region with SEQ ID NO: 101;
  a heavy chain constant region with SEQ ID NO: 91;
  a light chain variable region with SEQ ID NO: 85; and
  a light chain constant region with SEQ ID NO: 92.

"Anti-45RC Variant A2": a humanized variant of ABIS-45RC, comprising:
  a heavy chain variable region with SEQ ID NO: 101;
  a heavy chain constant region with SEQ ID NO: 91;
  a light chain variable region with SEQ ID NO: 103; and
  a light chain constant region with SEQ ID NO: 92.

"Anti-45RC Variant A3": a humanized variant of ABIS-45RC, comprising:
  a heavy chain variable region with SEQ ID NO: 65;
  a heavy chain constant region with SEQ ID NO: 91;
  a light chain variable region with SEQ ID NO: 85; and
  a light chain constant region with SEQ ID NO: 92.

"Anti-45RC Variant A4": a humanized variant of ABIS-45RC, comprising:
  a heavy chain variable region with SEQ ID NO: 65;
  a heavy chain constant region with SEQ ID NO: 91;
  a light chain variable region with SEQ ID NO: 103; and
  a light chain constant region with SEQ ID NO: 92.

"Anti-45RC Variant A5": a humanized variant of ABIS-45RC, comprising:
  a heavy chain variable region with SEQ ID NO: 62;
  a heavy chain constant region with SEQ ID NO: 91;
  a light chain variable region with SEQ ID NO: 85; and
  a light chain constant region with SEQ ID NO: 92.

"Anti-45RC Variant A6": a humanized variant of ABIS-45RC, comprising:
  a heavy chain variable region with SEQ ID NO: 101;
  a heavy chain constant region with SEQ ID NO: 91;
  a light chain variable region with SEQ ID NO: 82; and
  a light chain constant region with SEQ ID NO: 92.

"Anti-45RC Variant A7": a humanized variant of ABIS-45RC, comprising:
  a heavy chain variable region with SEQ ID NO: 121;
  a heavy chain constant region with SEQ ID NO: 91;
  a light chain variable region with SEQ ID NO: 85; and
  a light chain constant region with SEQ ID NO: 92.

"Anti-45RC Variant A8": a humanized variant of ABIS-45RC, comprising:
  a heavy chain variable region with SEQ ID NO: 122;
  a heavy chain constant region with SEQ ID NO: 91;
  a light chain variable region with SEQ ID NO: 85; and
  a light chain constant region with SEQ ID NO: 92.

"Anti-45RC Variant A9": a humanized variant of ABIS-45RC, comprising:
  a heavy chain variable region with SEQ ID NO: 123;
  a heavy chain constant region with SEQ ID NO: 91;
  a light chain variable region with SEQ ID NO: 85; and
  a light chain constant region with SEQ ID NO: 92.

"Anti-45RC Variant A10": a humanized variant of ABIS-45RC, comprising:
  a heavy chain variable region with SEQ ID NO: 124;
  a heavy chain constant region with SEQ ID NO: 91;
  a light chain variable region with SEQ ID NO: 85; and
  a light chain constant region with SEQ ID NO: 92.

"Anti-45RC Variant D1": a humanized variant of ABIS-45RC, comprising:
  a heavy chain variable region with SEQ ID NO: 63;
  a heavy chain constant region with SEQ ID NO: 91;
  a light chain variable region with SEQ ID NO: 85; and
  a light chain constant region with SEQ ID NO: 92.

"Anti-45RC Variant I1": a humanized variant of ABIS-45RC, comprising:
  a heavy chain variable region with SEQ ID NO: 67;
  a heavy chain constant region with SEQ ID NO: 91;
  a light chain variable region with SEQ ID NO: 85; and
  a light chain constant region with SEQ ID NO: 92.

"Anti-45RC Variant I2": a humanized variant of ABIS-45RC, comprising:
  a heavy chain variable region with SEQ ID NO: 67;
  a heavy chain constant region with SEQ ID NO: 91;
  a light chain variable region with SEQ ID NO: 103; and
  a light chain constant region with SEQ ID NO: 92.

"MT2": a murine anti-hCD45RC antibody commercially available at OriGene, under Ref. AM39022PU-N.

"Engineered Asn/Phe ABIS-45RC": the murine ABIS-45RC, chimerized by engineering its LCVR by insertion of one residue in the CDR1 and substitution of one residue in the FR3 (as described in Example 8). Engineered Asn/Phe ABIS-45RC comprises:
  a heavy chain variable region with SEQ ID NO: 61;
  a heavy chain constant region with SEQ ID NO: 93;
  a light chain variable region with SEQ ID NO: 71 with $X_{12}$ being Asn (N); and
  a light chain constant region with SEQ ID NO: 94.

"Engineered Ser/Phe ABIS-45RC": the murine ABIS-45RC, chimerized by engineering its LCVR by insertion of one residue in the CDR1 and substitution of one residue in the FR3 (as described in Example 8). Engineered Ser/Phe ABIS-45RC comprises:
  a heavy chain variable region with SEQ ID NO: 61;
  a heavy chain constant region with SEQ ID NO: 93;
  a light chain variable region with SEQ ID NO: 71 with $X_{12}$ being Ser (S); and
  a light chain constant region with SEQ ID NO: 94.

"Engineered Gly/Phe ABIS-45RC": the murine ABIS-45RC, chimerized by engineering its LCVR by insertion of one residue in the CDR1 and substitution of one residue in the FR3 (as described in Example 8). Engineered Gly/Phe ABIS-45RC comprises:
  a heavy chain variable region with SEQ ID NO: 61;
  a heavy chain constant region with SEQ ID NO: 93;
  a light chain variable region with SEQ ID NO: 71 with $X_{12}$ being Gly (G); and
  a light chain constant region with SEQ ID NO: 94.

"Chimeric N50A ABIS-45RC": a chimeric variant of the murine ABIS-45RC, comprising the murine ABIS-45RC light chain and a humanized heavy chain. Chimeric N50A ABIS-45RC comprises:
  a heavy chain variable region with SEQ ID NO: 61;
  a heavy chain constant region with SEQ ID NO: 93;
  a light chain variable region with SEQ ID NO: 113; and
  a light chain constant region with SEQ ID NO: 92.

"Chimeric S52A ABIS-45RC": a chimeric variant of the murine ABIS-45RC, comprising the murine ABIS-45RC light chain and a humanized heavy chain. Chimeric S52A ABIS-45RC comprises:
  a heavy chain variable region with SEQ ID NO: 61;
  a heavy chain constant region with SEQ ID NO: 93;
  a light chain variable region with SEQ ID NO: 126; and
  a light chain constant region with SEQ ID NO: 92.

"Chimeric N50X ABIS-45RC": a chimeric variant of the murine ABIS-45RC, comprising the murine ABIS-45RC light chain and a humanized heavy chain. Chimeric N50X ABIS-45RC comprises:
  a heavy chain variable region with SEQ ID NO: 61;
  a heavy chain constant region with SEQ ID NO: 93;
  a light chain variable region with SEQ ID NO: 129, with $X_{13}$ being any amino acid but Ala (A) or Asn (N); and
  a light chain constant region with SEQ ID NO: 92.

Example 1

Reactivity of ABIS-45RC

Material and Methods

PBMC Staining and Data Acquisition

50 µL or 100 µL of fresh EDTA whole blood were stained with combinations of appropriate monoclonal antibodies (Abs) followed by erythrocyte lysis (versalyse, Beckman Coulter). After washing, cells were analyzed on a Navios flow cytometer and data analyzed using Kaluza software (Beckman Coulter, Marseille, France) and FlowJo Software (Tree Star Inc).

Antibodies and Flow Cytometry

TABLE 6

Antibodies used for flow cytometry analysis. For each
antibody in the left column, the clone used is given in the right column.

| Antibody (specificity) | Clone |
|---|---|
| CD117 | 104D2D1 |
| CD11c | BUI5 |
| CD123 | 9F5 |
| CD127 | R34.34 |
| CD14 | RMO52 |
| CD16 | 3G8 |
| CD161 | 191B8 |
| CD19 | SJ25C1 |
| CD25 | 2A3 |
| CD3 | SK7 |
| CD3 | UCHT1 |
| CD336 | Z231 |
| CD4 | 13B8.2 |
| CD45 | J.33 |
| CD56 | N901 |
| CD56 | NCAM162 |
| CD8 | B9.11 |
| CD8 | SK1 |
| Cocktail ILCs | — |
| CRTH2 | BM16 |
| HLADR | L243 |
| Lineage1 DCs | — |
| TCRab | IP26A |
| TCRgd | IMMU510 |
| Va24 | 6B11 |
| Va7,2 | REA179 |
| CD45RC | MT2 |
| CD45RC | ABIS |
| Streptavidine | Alexa fluor 405 |

Results

As a first screening, ABIS-45RC did not react against CD45RC− cells sorted using the commercial anti-CD45RC mAb MT2 clone suggesting that ABIS45RC could recognize CD45RC (data not shown).

Figure 1:
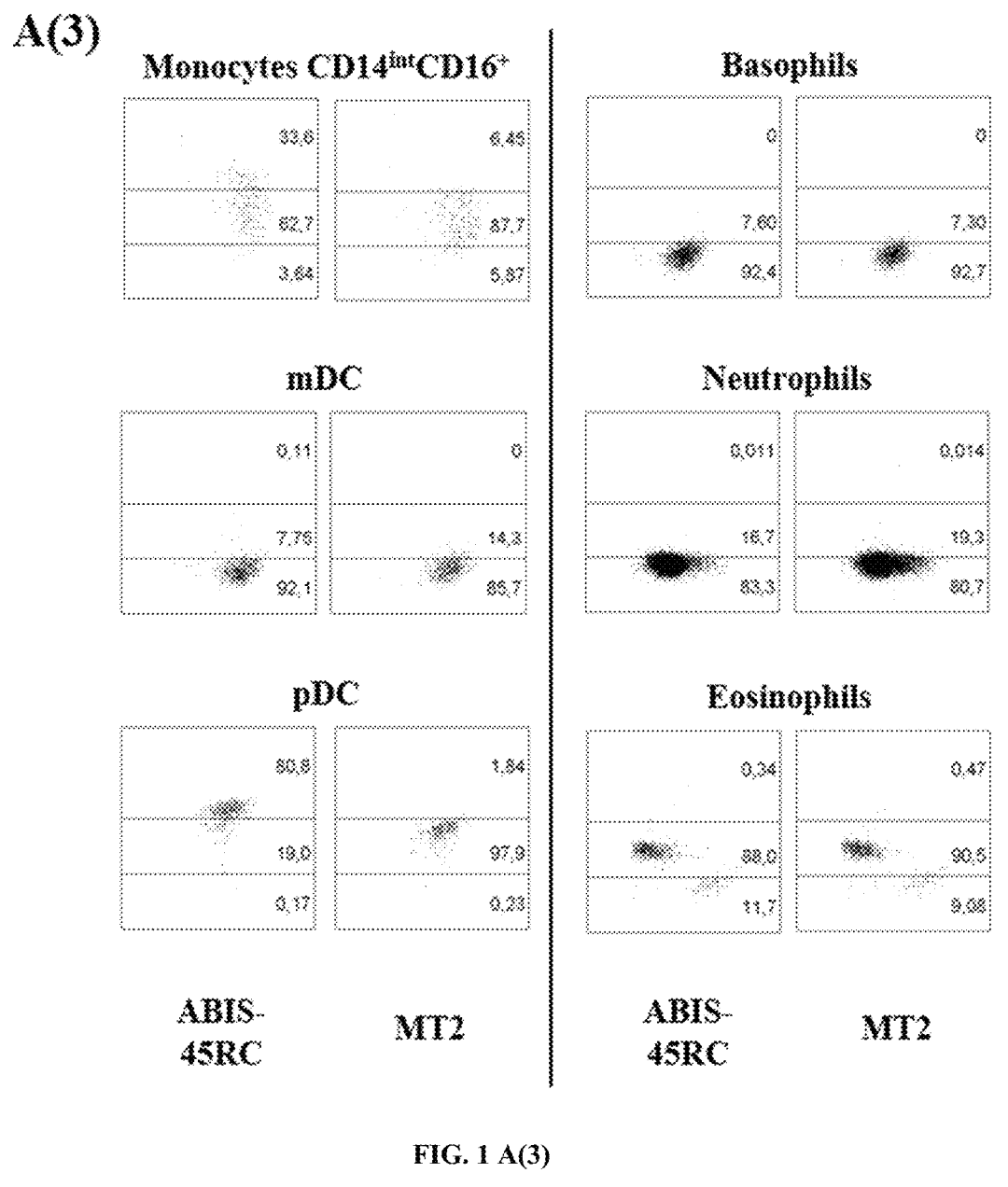

To further characterize ABIS-45RC, we analyzed its reactivity with human PBMCs. As shown in FIGS. 1A and B, a fraction of T CD4$^+$ and T CD8$^+$ cells is ABIS-45RC$^{high}$ whereas the rest is ABIS-45RC$^{low}$ or ABIS-45RC. Most B and NK cells as well as pDCs were ABIS-45RC$^{high}$. Most of NKT, iNKT MAIT, ILC2, ILC3 and of CD14$^{int}$CD16$^+$ monocytes were ABIS-45RC$^{high}$ or ABIS-45RC$^{low}$. CD14$^{high}$CD16$^-$ monocytes, mDC, basophils and neutrophils were predominantly ABIS-45RC$^-$. CD4$^+$ Treg and CD8$^+$Foxp3$^+$ Treg were largely ABIS-45RC$^{low/-}$.

The analysis of the major PBMCs populations showed that ABIS-45RC had a pattern of reactivity comparable to the commercial anti-CD45RC mouse MT2 antibody (FIG. 1 and Picarda et al., 2017. *JCI Insight.* 2(3):e90088).

Example 2

Comparison of ABIS-45RC and the Commercial Anti-CD45RC Antibody "MT2"

Material and Methods

PBMC Isolation

Blood healthy volunteers is collected and peripheral blood mononuclear cells (PBMC) were isolated by Ficoll gradient centrifugation, which enables removal of unwanted fractions of blood products such as granulocytes, platelets and reaming red blood cell contaminants.

Antibodies and Flow Cytometry

Human PBMC were labeled with the ABIS-45RC antibody (at the indicated concentrations), an anti-CD3 antibody and an anti-CD45RC (mouse clone MT2, Biolegend)-FITC labeled at 1.33 mg/mL. The ABIS-45RC reactivity was revealed using a biotin donkey anti-human IgG$^+$ Streptavidin PercpCy 5.5 secondary antibody.

A Canto II cytometer (BD Biosciences) was used to measure fluorescence intensity and data were analyzed using the FLOWJO software (Tree Star Inc.). Cells were first gated by their morphology and dead cells were excluded by selecting DAPI-negative cells.

Cytotoxicity Analysis

Human PBMCs were incubated with medium at 37° C., isotype control antibody (Ms IgG1, clone 107.3, 10 µg/ml), ABIS-45RC or anti-CD45RC (mouse clone MT2) at 2.5 or µg/ml for 10 minutes to 18 hours. Then, cells were stained with anti-CD3 (clone SK7, BD Biosciences), Annexin-V, and DAPI. Percentage of apoptosis was obtained by gating on Annexin V$^+$ and DAPI$^+$ cells among T or non-T cells by flow cytometry.

Results

Both ABIS-45RC and Commercial Anti-CD45RC M72 Antibodies Compete for the Same Epitope A shown in FIG. 2, co-labelling with the commercial anti-CD45RC MT2 clone showed that both antibodies competed and thus recognized the same or close epitope of human CD45RC.

Cytotoxicity Induced by ABIS-45RC is Higher Compared to Commercial Anti-CD45RC

Figure 3:
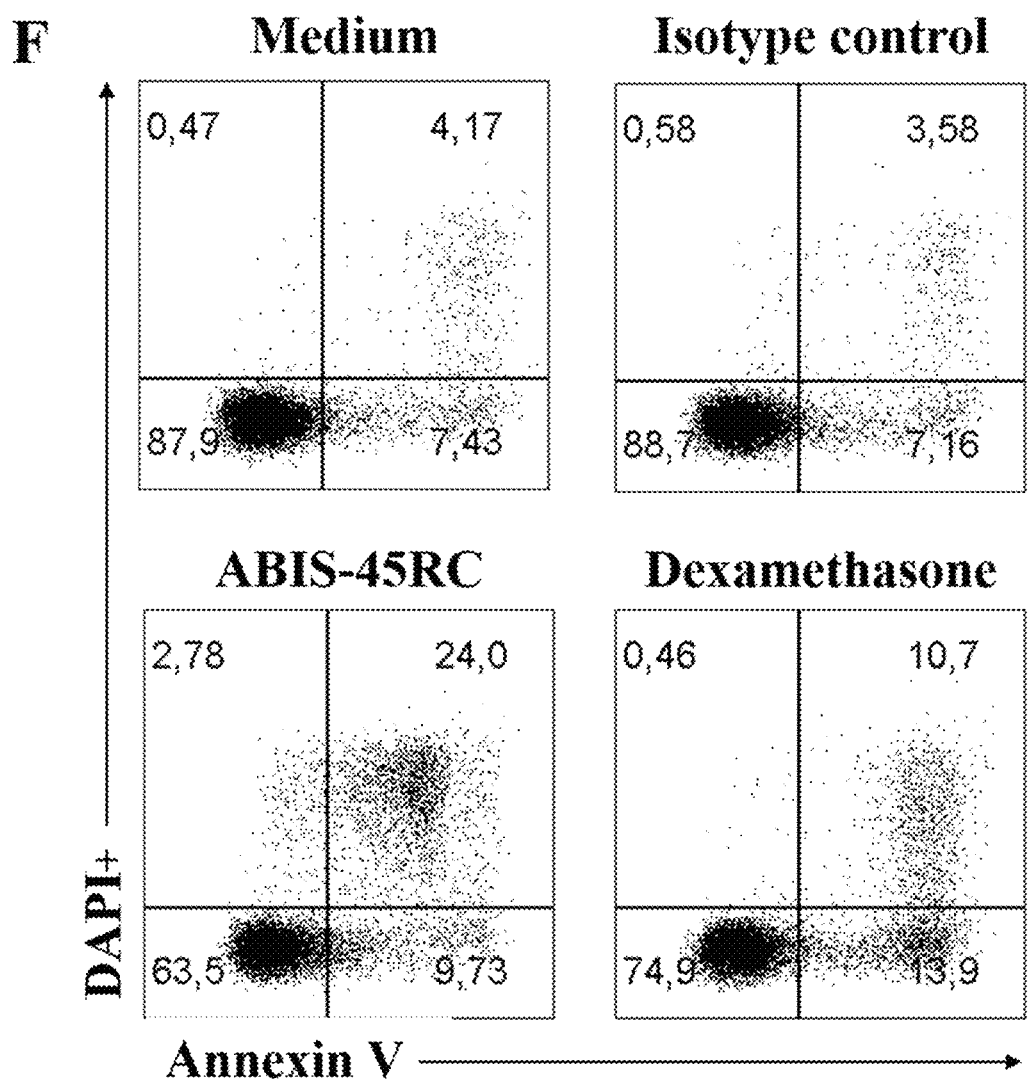
FIGS. 3A-E and 3F show that cytotoxicity induced by ABIS-45RC is higher compared to commercial anti-CD45RC MT2. PBMCs from healthy volunteers (n=3) were incubated at 37° C. with medium, isotype negative control (2.5 or 10 mg/mL), ABIS-CD45RC (2.5 or 10 mg/mL) or dexamethasone (10 mg/mL) as a positive control for the indicated time points and then cells were labeled with an anti-CD3-FITC mouse antibody and apoptotic cells by labeling with Annexin-V-PE. (A-E) Graphs indicate % of Annexin $V^+$ cells in indicated cell populations. (F) Representative dot plots of Annexin $V^+$ (early apoptotic) and $DAPI^+$ (late apoptotic) cells. Numbers indicate the percentage of cells in each category.

As shown in FIG. 3, ABIS-45RC was cytotoxic to T cells but not non-T cells.

Moreover, the T cells cytotoxicity was directly correlated to the level of CD45RC expression and importantly, ABIS-45RC performed better at 2.5 µg/mL as compared to the MT2 clone at 10 µg/mL.

Example 3

Affinity of ABIS-45RC

Material and Methods

Briefly, 1×10$^7$ CD45RC$^{high}$ PBMCs or CHO cells expressing CD45RC after plasmid transfection were solubilized using the Mem-PER membrane isolation kit (Thermo-fisher). ABIS-45RC was immobilized on a biochip CM5 and cell membranes were incubated at 25° C. to measure affinity constants using single cycle kinetics and calibration free concentration analysis on a BIAcore 3000 and a BIAcore T200.

Results

Measurement of the affinity of CD45RC antibody was assessed by surface Plasmon Resonance (SPR), a technology for characterizing antibody-antigen interactions, and revealed an affinity ($K_D$) of 5×10$^{-8}$ M, with a $K_{on}$ of 2.91×10$^5$ M$^{-1}$·sec$^{-1}$ and a $K_{off}$ of 1.44×10$^{-2}$ sec$^{-1}$.

Example 4

Treatment of Graft-Versus-Host-Disease (GVHD) with ABIS-45RC

Material and Methods

PBMC Isolation

Blood was collected at the Établissement Français du Sang (Nantes, France) from healthy individuals. Written informed consent was provided according to institutional guidelines. PBMC were isolated by Ficoll-Paque density-gradient centrifugation (Eurobio, Courtaboeuf, France). Remaining red cells and platelets were eliminated with a hypotonic solution and centrifugation.

Animals 8- to 12-week-old NOD/SCID/IL2Rγ$^{-/-}$ (NSG) mice were bred in our own animal facilities in SPF conditions (accreditation number C44-278).

GVHD Model

Adult NSG immunodeficient mice were whole-body sublethaly irradiated (irradiation dose of 2 Gy at day −1) to induce lesions in tissues that will favor the development of GVHD. The following day (day 0), 1.5×10$^7$ PBMCs (including CD45RC$^{high}$ and CD45RC$^{low/-}$ T cells) from healthy volunteers were injected intravenously in these mice.

Human PBMCs, and in particular T cells, react against and attack mouse tissues inducing lesions. These T cells and the lesions observed in liver, intestine, lungs and skin mimic the GVHD observed following bone marrow transplantation in humans or other GVHD experimental systems using rodents as donors and recipients. In particular, these tissue lesions typically induce a body weight loss that begins—depending on the number of PBMCs injected and in our experimental system—around day 13 after injection of the PBMCs. Body weight loss is monitored daily and animals are sacrificed when it drops to 20% of the original body weight to avoid unnecessary suffering.

Treatment

NSG mice were treated intraperitoneally with purified ABIS-45RC, with MT2 anti-CD45RC antibody or with an irrelevant control (an IVIg preparation used clinically comprising human purified IgG, and containing predominantly IgG1 antibodies) at 0.8 mg/kg from day 0 and every 2.5 days during 20 days.

NSG mice treated with ABIS-45RC or control antibodies also received intraperitoneally rapamycin from day 0 to day 10 at a suboptimal dose of 0.4 mg/day.

The experimental procedure is summarized in FIG. 4A.

Results

Figure 4:
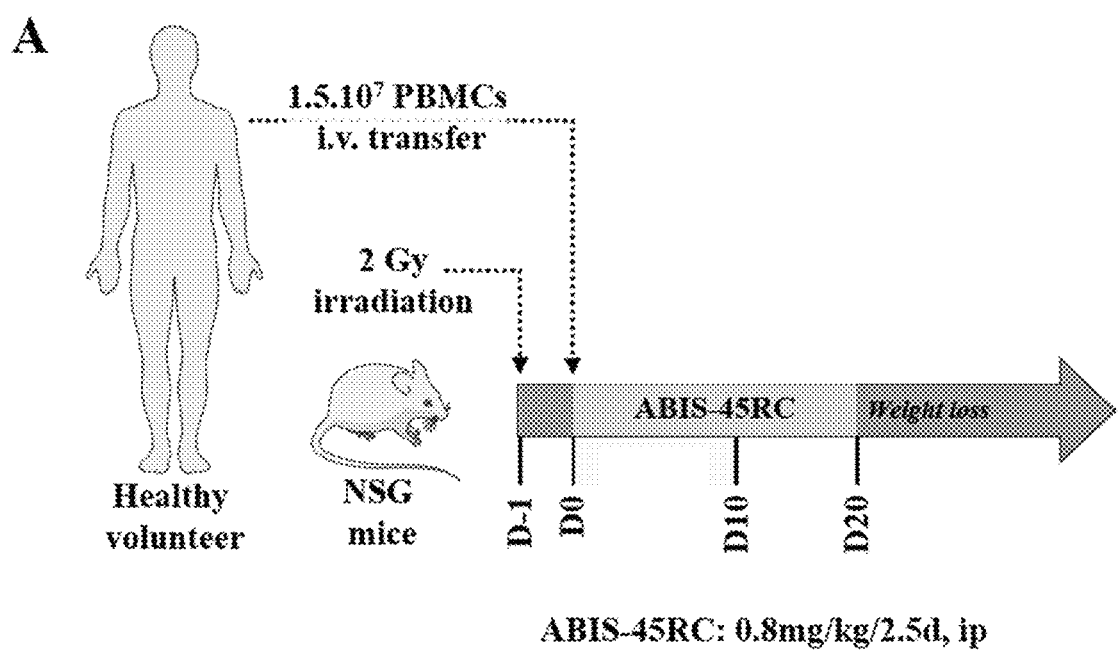
FIGS. 4A and 4B-C show the use of ABIS-45RC to treat GVHD in immune humanized NSG immunodeficient mice. (A) Experimental procedure showing that peripheral blood mononuclear cells (PBMCs) from healthy donor volunteers were infused intravenously (iv) (day 0) into previously (day −1) sublethaly (2 Gy) irradiated NSG immunodeficient mice. ABIS-45RC was administered intraperitoneally (ip) with the indicated protocol between day 0 to 20. Isotype control were human IgG (IVIg preparation) and was administered using the same protocol as ABIS-45RC. (B-C) Survival curves for NSG mice and statistics were analyzed using a Kaplan-Meier analysis (* $p<0.01$, ** $p<0.001$).

Treatment with PBMCs only induced weight loss, initiated around day 14, and, as shown in FIG. 4, death of all mice by day 33 (median survival: 11 days (FIG. 4B) to 15 days (FIG. 4C) days).

Treatment with control antibody and rapamycin only prolonged survival without reaching statistical significance (median survival: 21 days (FIG. 4C)).

While treatment with MT2 significantly prolonged survival of the mice (median survival: 19 days (FIG. 4B)), treatment with ABIS-45RC significantly increased this prolongation of survival of the mice up to 72 days (median survival: 35 days (FIG. 4B)).

Finally, combinatorial administration of ABIS-45RC with rapamycin completely prevented death as a consequence of GVHD (100% survival, FIG. 4C).

Example 5

Humanization of ABIS-45RC

The design for the humanization of ABIS-45RC by grafting of the CDRs into human germline antibody sequences was undertaken. ABIS-45RC was humanized by grafting the three CDRs from the LCVR (with SEQ ID NOs: 15, 16 and 17) into a human germline LCVR that was as homologous as possible to ABIS-45RC's LCVR. Similarly, the three CDRs from the HCVR (with SEQ ID NOs: 1, 4 and 3) were grafted into a human germline HCVR that was as homologous as possible to ABIS-45RC's HCVR.

In addition, a few amino acid residues in the framework regions (FR) of the selected human germline variable regions were changed to the amino acid residues that were present in the murine variable regions (so called back-mutations). Based upon information on the structure of immunoglobulin variable regions, and with the guidance of an homology molecular model of the Fv of ABIS-45RC, these few residues in the FRs were identified as having key roles in either maintaining the CDRs in the right conformation or in HCVR/LCVR packing, and thus they were retained in a first humanized version (version A) or substituted with their human germline counterparts, if possible, in subsequent humanized version (versions B and C). Under guidance of the homology molecular model, in versions B and C, when judged possible, the CDR residues were also substituted for their human germline counterparts.

Homology Model Building

A model of ABIS-45RC was constructed according to established protocols (Ramos, 2012. *Methods Mol Biol.* 907:39-55).

Light Chain

In this Section, Unless Specified Otherwise, Amino Acid Numbering is Based on SEQ ID NO: 81.

The LCVR's framework residues were used to search the sequences of solved antibody structures via protein BLAST. The top hits were Protein Data Bank (PDB) ID: 4NCC (2.50 Å resolution) having 83 of 89 FR residues identical, and 85 out of 89 FR residues similar, to those of ABIS-45RC's LCVR, and PDB ID: 1QOK (2.40 Å resolution) having 83 of 87 framework residues identical, and 84 out of 87 similar, to those of ABIS-45RC's LCVR.

The sequences of these two structures both differed from that of ABIS-45RC's LCVR (with SEQ ID NO: 81) with the substitutions T9A, T39P, R44K, N49S and P54A. In addition, PDB ID: 4NCC differed in sequence from ABIS-45RC's LCVR with the substitutions L95F, A99G and L105I.

A comparison of the two structures showed high homology. However, the carbon chains adopted slightly different conformations in the regions A13-E17 and E104-K106.

Based upon the results of the subsequent CDR searches, and the presence of the two N-terminal residues, the LCVR of the structure of PDB ID: 4NCC was selected as the LCVR framework template, and the rotameric conformation of L105I was selected (in PyMol) with reference to PDB ID: 1QOK.

Subsequently, the sequences of ABIS-45RC LCVR's CDR1, CDR2 and CDR3, with the addition of two residues on each end, were used to search the sequences of solved antibody structures via protein BLAST.

For CDR1, the top hits consisted of a cluster of sequences having 9 out of 9 identical residues. Amongst these were PDB ID: 4NCC and PDB ID: 1QOK. Thus, the PDB ID: 4NCC structure was adopted as the template for CDR1.

For CDR2, the top hits consisted of a cluster of sequences having 6 out of 7 identical residues. Amongst these were again PDB ID: 4NCC and PDB ID: 1QOK. The PDB ID: 4NCC structure was therefore also adopted as the template for CDR2.

For CDR3, the top hit, containing no gaps, was PDB ID: 1QOK, having 13 out of 13 identical residues. PDB ID: 4NCC was however a close second, having 12 out of 13 identical residues. A comparison of the two structures showed essentially identical conformations, excepting for the L95F substitution. Thus, the PDB ID: 4NCC structure was adopted as the template for CDR3, and the rotameric conformation of L95F was selected (in PyMol) with reference to PDB ID: 1QOK.

It was thus not necessary to fit any CDR templates to the LCVR framework template because PDB ID: 4NCC was selected as the primary template for all of the LCVR's CDRs.

Finally, the LCVR partial model was manually subjected to mutagenesis at 8 positions (in PyMol), with selection of optimal rotamers, in order to match the ABIS-45RC LCVR sequence.

Heavy Chain

In this Section, Unless Specified Otherwise, Amino Acid Numbering is Based on SEQ ID NO: 61.

Next, the HCVR's framework residues were used to search the sequences of solved antibody structures via protein BLAST. The top hit was PDB ID: 3OPZ (3.40 Å resolution), having 84 out of 90 framework residues identical, and 85 out of 90 similar, to those of ABIS-45RC's HCVR.

Since PDB ID: 3OPZ was missing the N terminal residue, and was resolved with fairly poor resolution, additional hits with the highest identity/similarity scores were also surveyed. The top amongst these were PDB ID: 4CAD (2.50 Å resolution), having 78 out of 91 framework residues identical, and 87 out of 91 similar, to those of ABIS-45RC's HCVR; and PDB ID: 1RUR (1.50 Å resolution), having 75 out of 91 framework residues identical, and 87 out of 91 similar, to those of ABIS-45RC's HCVR.

A comparison of the PDB ID: 3OPZ and PDB ID: 4CAD structures showed high homology with alternative residue rotamers being the principal differences.

A comparison of the PDB ID: 3OPZ and PDB ID: 1RUR structures similarly showed high homology; however, there was a significant conformational change in the $V_H$-FR2 loop L45-G49 relative to the PDB ID: 3OPZ and PDB ID: 4CAD structures.

Further, based upon sequence, ABIS-45RC's HCVR and PDB ID: 4CAD were predicted to exhibit the Honegger Type III (Honegger & Pluckthun, 2001. *J Mol Biol.* 309(3): 687-99) conformation of the N-terminal strand 5-12 because of the presence of a glutamine in position 6. However, PDB ID: 1RUR was predicted to exhibit the Honegger Type I conformation, due to the presence of a glutamic acid in position 6. Nevertheless, the three structures exhibited the identical conformation of the 5-12 strand. Also, the sequences of ABIS-45RC's HCVR, PDB ID: 4CAD and PDB ID: 1RUR were predicted to adopt the K-form (kinked base conformation) defined by the revised Shirai's rules for HCVR's CDR3 (Kuroda et al., 2008. *Proteins.* 73(3):608-20).

Based upon the results of the subsequent CDR searches, higher overall sequence similarity, structural concordance with PDB ID: 3OPZ, and higher experimental resolution, the HCVR of the structure PDB ID: 1RUR was selected as the HCVR framework template; however, the 45-49 loop of PDB ID: 4CAD (having the same conformation as that of PDB ID: 3OPZ) was substituted for that of PDB ID: 1RUR in the HCVR template using two residues N and C-terminal overhangs on the 45-49 ends to anchor the loop template fragment to the framework template.

Subsequently, the sequences of HCVR's CDR1, CDR2 and CDR3, with the addition of two residues on each end, were used to search the sequences of solved antibody structures via protein BLAST.

For CDR1, there was a cluster of sequence hits having 9 out of 12 identical residues. Amongst these was PDB ID: 1RUR. Thus, the PDB ID: 1RUR structure was selected as the template for CDR1.

For CDR2, the top hit was PDB ID: 3NTC (1.55 Å resolution) having 8 out of 12 residues identical, and 9 out of 12 similar, to those of ABIS-45RC's HCVR. However, PDB ID: 1RUR was a close second having 7 of 12 residues identical, and 9 out of 12 similar, to those of ABIS-45RC's HCVR. Comparison of the two structures showed essentially identical conformations, and the higher identity of PDB ID: 3NTC was due to 2 C terminal residues added to the CDR2 sequence for purposes of BLAST search. Thus, the PDB ID: 1RUR structure was preferred as the template for CDR2.

For CDR3, the top two hits, containing no gaps, were PDB ID: iNGY (2.20 Å resolution) and PDB ID: 1NGZ (1.60 Å resolution), both having 8 out of 11 residues identical, and 9 out of 11 similar, to those of ABIS-45RC's HCVR. A comparison of the two structures showed a significantly different mainchain conformation. Without willing to be bound to a theory, the Inventors hypothesized that this difference might be due to the residue in position 101. In PDB ID: iNGY, a larger methionine cannot adopt the orientation of the smaller serine of PDB ID: 1NGZ, which directs its sidechain into the core of the protein. Since the desired substitution to match the ABIS-45RC's HCVR sequence is F101, the PDB ID: iNGY structure was adopted as the template for CDR3. Next, in order to complete the HCVR partial model, the CDR3 template was grafted onto the modified PDB ID: 1RUR HCVR template using the two residue overhang on its ends to anchor the CDR template fragment to the framework template (in PyMol).

Finally, the HCVR partial model was manually subjected to mutagenesis at 23 positions (in PyMol), with selection of optimal rotamers, in order to match the ABIS-45RC's HCVR sequence.

Final Model Assembly

Subsequently, the best tertiary arrangement of the HCVR and LCVR partial models were selected to assemble the final model. The HCVR and LCVR template sequences were submitted to the Packing Angle Prediction Server (PAPS) (Abhinandan & Martin, 2010. *Protein Eng Des Sel.* 23(9): 689-97) to find a predicted best-fit tertiary arrangement. The PAPS server predicted that the solved antibody structure PDB ID: 1MNU, with a relative packing angle of −45.6°, would provide the best tertiary arrangement of HCVR and LCVR. Thus, the final model was assembled by fitting the backbone coordinates of the conserved anchor segments of the HCVR and LCVR partial models to PDB ID: 1MNU (in PyMol).

Lastly, the coordinates of this final model were subjected to a round of energy minimization employing GROMACS (Van der Spoel et al., 2005. *J Comput Chem.* 26(16):1701-18) with the GROMOS96 force-field (Scott et al., 1999. *J Phys Chem A.* 103(19):3596-3607).

Human Germlines

For the design of CDR-grafted versions of ABIS-45RC's HCVR and LCVR, two times three human germlines were selected:

IGHV1-2*01, IGHV5-51*01 and IGHV3-11*05 for the HCVR; and

IGKV1-9*01, IGKV6-21*02 and IGKV3-11*01 for the LCVR.

Design of Humanized HCVR and LCVR

The humanized versions A for both HCVR and LCVR are conservative versions that explicitly minimize and/or avoid alteration of CDR residues. These versions are thus expected to give a similar or better binding and/or potency activity as a chimeric antibody (ABIS-45RC's HCVR [SEQ ID NO: 61] and LCVR [SEQ ID NO: 81] fused to human constant regions [SEQ ID NOs: 91 and 92]).

The humanized versions B for both HCVR and LCVR are designed to reach a percentage of sequence identity with the closest human germline of at least 85%. This can be achieved by germlining (i.e., substituting the mouse residue with the corresponding human germline residue) FR and/or CDR amino acid residues. 85% is the cut-off percentage identity necessary to get the substem -zu- for "humanized", denomination according to the 2014 World Health Organization (WHO) guidance on antibody International Nonproprietary Names (INN).

The humanized versions C for both HCVR and LCVR are designed to reach the highest degree of humanness (i.e., the highest degree of sequence identity with the corresponding human germline). Following inspection of the homology molecular model, a number of residues have been identified as candidates for germlining. Therefore, all the residues that could reasonably be germlined have been taken into consideration.

HCVR, Using IGHV1-2*01

To design humanized HCVR version A from IGHV1-2*01, the murine CDRs (with SEQ ID NOs: 1, 4 and 3) were grafted into IGHV1-2*01 and 4 residues in FR2 and FR3 were back-mutated to the parental murine residues, to maintain the full activity of the antibody. These residues are I48, L70, A72 and V97 in SEQ ID NO: 61. The resulting HCVR is as set forth in SEQ ID NO: 62 and shares 81.6% sequence identity with IGHV1-2*01 human germline.

To design humanized HCVR version B from IGHV1-2*01, in addition to version A, 5 amino acid residues in the CDR2 were further germlined (i.e., substituted by the corresponding IGHV1-2*01 human germline residues). These residues are D56G, A58T, S60Y, N61A and K65Q in SEQ ID NO: 61. The resulting HCVR is as set forth in SEQ ID NO: 65 and shares 86.7% sequence identity with IGHV1-2*01 human germline.

To design humanized HCVR version C from IGHV1-2*01, in addition to version B, 2 amino acid residues in the CDR2 were further germlined. These residues are D50R and E62Q in SEQ ID NO: 61. The resulting HCVR is as set forth in SEQ ID NO: 68 and shares 88.8% sequence identity with IGHV1-2*01 human germline.

Various other humanized versions of the HCVR from IGHV1-2*01 were further designed, starting from version B. Indeed, to get a well humanized monoclonal antibody, 85% is supposed to be sufficient (version B from IGHV1-2*01 shares 86.7% sequence identity with IGHV1-2*01 human germline). In order to reduce the risk of introducing mutations, versions D, E, F, G and H were thus designed to reach 85% and no more.

The resulting HCVR versions D, E, F, G and H from IGHV1-2*01 are as set forth in SEQ ID NOs: 101, 121, 122, 123 and 124, respectively, and all share 85.7% sequence identity with IGHV1-2*01 human germline.

HCVR, Using IGHV5-51*01

To design humanized HCVR version A from IGHV5-51*01, the murine CDRs (with SEQ ID NOs: 1, 4 and 3) were grafted into IGHV5-51*01 and 6 residues in FR1, FR2 and FR3 were back-mutated to the parental murine residues, to maintain the full activity of the antibody. These residues are A24, T28, I48, L70, L83 and V97 in SEQ ID NO: 61. The resulting HCVR is as set forth in SEQ ID NO: 63 and shares 79.6% sequence identity with IGHV5-51*01 human germline.

To design humanized HCVR version B from IGHV5-51*01, in addition to version A, 1 amino acid residue in the FR1 and 6 amino acid residues in the CDR2 were further germlined. These residues are A24G, D56S, A58T, S60Y, N61S, K63S and K65Q in SEQ ID NO: 61. The resulting HCVR is as set forth in SEQ ID NO: 66 and shares 86.7% sequence identity with IGHV5-51*01 human germline.

To design humanized HCVR version C from IGHV5-51*01, in addition to version B, 1 amino acid residue in the FR1 and 2 amino acid residues in the CDR2 were further germlined. These residues are T28S, D50I and E62P in SEQ ID NO: 61. The resulting HCVR is as set forth in SEQ ID NO: 69 and shares 89.8% sequence identity with IGHV5-51*01 human germline.

HCVR, Using IGHV3-11*05

To design humanized HCVR version A from IGHV3-11*05, the murine CDRs (with SEQ ID NOs: 1, 4 and 3) were grafted into IGHV3-11*05 and 9 residues in FR1, FR2 and FR3 were back-mutated to the parental murine residues, to maintain the full activity of the antibody. These residues are Y27, T30, I48, G49, L70, A72, T74, A79 and V97 in SEQ ID NO: 61. The resulting HCVR is as set forth in SEQ ID NO: 64 and shares 76.5% sequence identity with IGHV3-11*05 human germline.

To design humanized HCVR version B from IGHV3-11*05, in addition to version A, 2 amino acid residues in the FR1, 6 amino acid residues in the CDR2 and 1 amino acid residue in the FR3 were further germlined. These residues are Y27F, T30S, D56S, A58T, S60Y, N61A, E62D, K63S and A79L in SEQ ID NO: 61. The resulting HCVR is as set forth in SEQ ID NO: 67 and shares 89.8% sequence identity with IGHV3-11*05 human germline.

To design humanized HCVR version C from IGHV3-11*05, in addition to version B, 1 amino acid residue in the FR2 and 1 amino acid residue in the CDR2 were further germlined. These residues are I48V and P53S in SEQ ID NO: 61. The resulting HCVR is as set forth in SEQ ID NO: 70 and shares 87.8% sequence identity with IGHV3-11*05 human germline.

LCVR, using IGKV1-9*01

To design humanized LCVR version A from IGKV1-9*01, the murine CDRs (with SEQ ID NOs: 15, 16 and 17 with $X_{12}$ being absent) were grafted into IGKV1-9*01 and 3 residues in FR2 and FR3 were back-mutated to the parental murine residues, to maintain the full activity of the antibody. These residues are F35, W46 and Y70 in SEQ ID NO: 81. The resulting LCVR is as set forth in SEQ ID NO: 82 and shares 83.2% sequence identity with IGKV1-9*01 human germline.

To design humanized LCVR version B from IGKV1-9*01, in addition to version A, 1 amino acid residue in the CDR1 and 1 amino acid residue in the FR2 were further germlined. These residues are S24R and F35Y in SEQ ID NO: 81. The resulting LCVR is as set forth in SEQ ID NO: 85 and shares 85.3% sequence identity with IGKV1-9*01 human germline.

To design humanized LCVR version C from IGKV1-9*01, in addition to version B, 2 amino acid residues in the CDR2 and 1 amino acid residue in the FR3 were further germlined. These residues are N49A, P54Q and Y70F in SEQ ID NO: 81. The resulting LCVR is as set forth in SEQ ID NO: 88 and shares 88.4% sequence identity with IGKV1-9*01 human germline.

A LCVR version D from IGKV1-9*01 was further designed, in order to introduce an extra residue (Ser, S) in the CDR1 as found in the human germline IGKV1-9*01. The introduction of the extra residue in the CDR1 loop has shown that the binding activity was conserved (data not shown). The introduction of a serine residue in the CDR1 of version B brings the sequence identity to 86.3%, so in order to reduce the risk of introducing mutations, version D was designed where Kabat residue L36 was reverted to the original mouse residue Phe (F). The resulting LCVR is as set forth in SEQ ID NO: 103.

LCVR, Using IGKV6-21*02

To design humanized LCVR version A from IGKV6-21*02, the murine CDRs (with SEQ ID NOs: 15, 16 and 17 with $X_{12}$ being absent) were grafted into IGKV6-21*02 and 4 residues in FR2 and FR3 were back-mutated to the parental murine residues, to maintain the full activity of the antibody. These residues are F35, W46, Y48 and Y70 in SEQ ID NO: 81. The resulting LCVR is as set forth in SEQ ID NO: 83 and shares 81.1% sequence identity with IGKV6-21*02 human germline.

To design humanized LCVR version B from IGKV6-21*02, in addition to version A, 1 amino acid residue in the CDR1, 1 amino acid residue in the FR2, 1 amino acid residue in the CDR2 and 1 amino acid residue in the FR3 were further germlined. These residues are S24R, F35Y, L53S and Y70F in SEQ ID NO: 81. The resulting LCVR is as set forth in SEQ ID NO: 86 and shares 85.3% sequence identity with IGKV6-21*02 human germline.

To design humanized LCVR version C from IGKV6-21*02, in addition to version B, 1 amino acid residue in the CDR3 was further germlined. This residue is Q88H in SEQ ID NO: 81. The resulting LCVR is as set forth in SEQ ID NO: 89 and shares 86.3% sequence identity with IGKV6-21*02 human germline.

LCVR, Using IGKV3-11*01

To design humanized LCVR version A from IGKV3-11*01, the murine CDRs (with SEQ ID NOs: 15, 16 and 17 with $X_{12}$ being absent) were grafted into IGKV3-11*01 and 3 residues in FR2 and FR3 were back-mutated to the parental murine residues, to maintain the full activity of the antibody. These residues are F35, W46 and Y70 in SEQ ID NO: 81. The resulting LCVR is as set forth in SEQ ID NO: 84 and shares 84.2% sequence identity with IGKV3-11*01 human germline.

To design humanized LCVR version B from IGKV3-11*01, in addition to version A, 1 amino acid residue in the CDR1 was further germlined. This residue is S24R in SEQ ID NO: 81. The resulting LCVR is as set forth in SEQ ID NO: 87 and shares 85.3% sequence identity with IGKV3-11*01 human germline.

To design humanized LCVR version C from IGKV3-11*01, in addition to version B, 1 amino acid residue in the FR2, 3 amino acid residues in the CDR2 and 1 amino acid residue in the FR3 were further germlined. These residues are F35Y, L53R, P54A, S55 and Y70F in SEQ ID NO: 81. The resulting LCVR is as set forth in SEQ ID NO: 90 and shares 90.5% sequence identity with IGKV3-11*01 human germline.

Example 6

Production, Purification and Characterization of Humanized Anti-45RC Antibodies

Analytical size exclusion chromatography (SEC-HPLC) and differential scanning calorimetry (DSC) were used to compare the profile and the thermal stability, respectively, of 9 humanized anti-45RC variants A to I. These variants correspond to antibody comprising the "versions A" HCVR and LCVR described in Example 5.

Analytical size exclusion chromatography (SEC-HPLC) and differential scanning calorimetry (DSC) were also used to compare the profile and the thermal stability, respectively, of 4 other humanized anti-45RC variants A1, A2, I1 and I2.

Material and Methods

SEC-HPLC

A Shimadzu Prominence HPLC system was used, with a Superdex 200 Increase 5/150 GL column (GE Healthcare). The column was previously calibrated in the same buffer and conditions used during sample analysis (using the Molecular Weight SEC Calibration kits from GE Healthcare, in PBS 1×, at 0.25 mL/min, with the column oven set to 30° C.).

All samples were centrifuged (20.000 g, 5 minutes, 4° C.) and had their protein content quantitated by Nanodrop ND-1000 spectrophotometer with IgG analysis program, prior to SEC analysis.

The isocratic program was set to inject about 15 µg of each sample, at 0.25 mL/min during 18 minutes. After SEC analysis, 280 nm chromatogram was extracted from the raw data, and analyzed by peak integration.

DSC

A Microcal™ VP-Capillary DSC system was used to perform differential scanning calorimetry experiments.

Samples in 1×PBS buffer were centrifuged (20.000 g, 5 minutes, 4° C.), and had their protein content quantitated Nanodrop ND-1000 spectrophotometer with IgG analysis program, prior to DSC analysis. Samples were then diluted in PBS to a final concentration of 1 mg/mL.

The pre-equilibration time was 3 minutes and the thermograms that followed were acquired between 20 and 110° C. with a scanning rate of 60° C./hour, a filtering period of seconds and medium feedback.

Prior to sample analysis, 5 buffer/buffer scans were measured to stabilize the instrument, and a buffer/buffer scan was performed between each protein/buffer scan.

The data was fitted to a non-2-state unfolding model, with the pre- and post-transition adjusted baseline subtracted. The calorimetric enthalpy (ΔH) is determined as the area under the peak of the transition, whereas the van't Hoff enthalpy (ΔHv) is determined from the model used.

Results

SEC-HPLC

A summary of the SEC parameters is given in Table 7 below.

TABLE 7

SEC parameters of the humanized ABIS-45RC variants A-I, A1, A2; I1 and I2.

| ABIS-45RC variant | Peak # | RT | Area | Area % | Calculated MW |
|---|---|---|---|---|---|
| A | 1 | 4.939 | 373336 | 10.62 | 510 |
|  | 2 | 5.212 | 790998 | 22.50 | 404 |
|  | 3 | 6.099 | 2351531 | 66.88 | 190 |
| B | 1 | 4.671 | 1305266 | 26.47 | 640 |
|  | 2 | 5.013 | 1451918 | 29.44 | 478 |
|  | 3 | 5.899 | 2174527 | 44.10 | 225 |
| C | 1 | 4.896 | 405089 | 14.04 | 529 |
|  | 2 | 5.148 | 527782 | 18.29 | 426 |
|  | 3 | 5.980 | 1788411 | 61.97 | 210 |
|  | 4 | 7.708 | 164621 | 5.70 | 48 |

TABLE 7-continued

SEC parameters of the humanized ABIS-45RC variants A-I, A1, A2; I1 and I2.

| ABIS-45RC variant | Peak # | RT | Area | Area % | Calculated MW |
|---|---|---|---|---|---|
| D | 1 | 4.939 | 126757 | 5.38 | 510 |
|   | 2 | 5.268 | 430061 | 18.25 | 385 |
|   | 3 | 6.137 | 1799214 | 76.37 | 184 |
| E | 1 | 4.738 | 607732 | 18.87 | 605 |
|   | 2 | 5.039 | 686150 | 21.31 | 468 |
|   | 3 | 5.925 | 1925975 | 59.82 | 220 |
| F | 1 | 4.811 | 791680 | 13.93 | 568 |
|   | 2 | 5.124 | 1306598 | 22.99 | 435 |
|   | 3 | 5.977 | 3585434 | 63.08 | 211 |
| G | 1 | 4.768 | 185266 | 3.54 | 589 |
|   | 2 | 5.092 | 889883 | 16.99 | 447 |
|   | 3 | 5.893 | 4159958 | 79.46 | 226 |
| H | 1 | 4.896 | 105313 | 1.90 | 529 |
|   | 2 | 5.158 | 506367 | 9.11 | 423 |
|   | 3 | 5.962 | 4941812 | 88.99 | 213 |
| I | 1 | 5.142 | 123472 | 3.16 | 429 |
|   | 2 | 6.081 | 3783288 | 96.84 | 193 |
| A1 | 1 | 5.074 | 129770 | 2.65 | 478 |
|   | 2 | 6.098 | 4775239 | 97.35 | 189 |
| A2 | 1 | 5.074 | 129770 | 2.65 | 478 |
|   | 2 | 6.098 | 4775239 | 97.35 | 189 |
| I1 | 1 | 4.885 | 131671 | 2.5 | 567 |
|   | 2 | 5.146 | 355754 | 6.78 | 447 |
|   | 3 | 6.142 | 4760685 | 90.7 | 181 |
| I2 | 1 | 4.864 | 32276 | 0.73 | 578 |
|   | 2 | 5.150 | 168687 | 3.79 | 446 |
|   | 3 | 6.181 | 4246352 | 95.48 | 175 |

RT: retention time (in minutes)
MW: molecular weight (in kDa)

Table 7 above shows in bold the peaks corresponding to the anti-CD45RC antibodies (peak 3 for each of variants A to H, I1 and I2; and peak 2 for each of variants I, A1 and A2), with RT and calculated MW expected for a monomeric, non-precipitated and non-dissociated antibody.

DSC

A summary of the DSC parameters is given in Table 8 below.

TABLE 8

DSC parameters of the humanized ABIS-45RC variants A-I, A1, A2; I1 and I2. Denaturation of the antibody happens in two steps, hence two melting temperatures are given, one of each step.

| ABIS-45RC variant | Conc. | $T_{1/2}$ | $\Delta H$ | $T_{onset}$ | $T_{m1}$ | $T_{m2}$ |
|---|---|---|---|---|---|---|
| A | 0.0035 | 7.09 | 763 | 55.59 | 66.44 | 80.64 |
| B | 0.0056 | 7.09 | 776 | 55.96 | 64.73 | 81.01 |
| C | 0.0031 | 7.93 | 596 | 55.95 | 63.05 | 79.74 |
| D | 0.0023 | 5.83 | 863 | 60.09 | 70.91 | 80.10 |
| E | 0.0042 | 5.83 | 762 | 57.09 | 71.28 | 80.05 |
| F | 0.0099 | 5.41 | 867 | 58.63 | 71.15 | 80.34 |
| G | 0.0087 | 5.01 | 824 | 60.76 | 69.93 | 80.79 |
| H | 0.0093 | 4.59 | 877 | 59.79 | 68.14 | 80.24 |
| I | 0.0055 | 5.42 | 809 | 62.07 | 70.83 | 81.27 |
| A1 | 0.0049 | 3.32 | 969 | 61.09 | 68.17 | 81.91 |
| A2 | 0.0070 | 5.83 | 1150 | 60.21 | 66.92 | 81.94 |
| I1 | 0.0067 | 3.75 | 1080 | 63.08 | 73.08 | 81.84 |
| I2 | 0.0055 | 4.16 | 1030 | 63.68 | 72.43 | 82.02 |

Conc.: concentration, in mM.
$T_{1/2}$: width of transition at half height of the peak, in °C.
$\Delta H$: calorimetric enthalpy of unfolding, in cal/M.
$T_{onset}$: temperature at which the unfolding transition begins, in °C.
$T_{m1}$: denaturing/melting temperature of the first step, in °C.
$T_{m2}$: denaturing/melting temperature of the second step, in °C.

Example 7

Reactivity of Humanized ABIS-45RC Variants A-I

Material and Methods

PBMC Isolation

Blood healthy volunteers is collected and peripheral blood mononuclear cells (PBMC) were isolated by Ficoll gradient centrifugation, which enables removal of unwanted fractions of blood products such as granulocytes, platelets and reaming red blood cell contaminants.

Antibodies and Flow Cytometry

Human PBMC were labeled with the murine ABIS-45RC antibody or each of the humanized ABIS-45RC antibodies variants A-I (at 2 μg/mL and 1 μg/mL); and an anti-CD3 antibody. The murine and humanized ABIS-45RC antibodies reactivity was revealed using a biotin donkey anti-human IgG$^+$ Streptavidin PercpCy 5.5 secondary antibody.

A Canto II cytometer (BD Biosciences) was used to measure fluorescence intensity and data were analyzed using the FLOWJO software (Tree Star Inc.). Cells were first gated by their morphology and dead cells were excluded by selecting DAPI-negative cells.

Results

Both ABIS-45RC and Commercial Anti-CD45RC M72 Antibodies Compete for the Same Epitope Labelling with either of the humanized ABIS-45RC antibodies (variant A, FIG. 5A; variant B, FIG. 5B; variant C, FIG. 5C; variant D, FIG. 5D; variant E, FIG. 5E; variant F, FIG. 5F; variant G, FIG. 5G; variant H, FIG. 5H; variant I, FIG. 5I) or the murine ABIS-45RC (FIG. 5J) shows that the antibodies recognized human CD45RC in a similar manner.

Example 8

Engineered Antibodies

The CDR1 of ABIS-45RC's LCVR has a canonical structure unique to mouse antibodies, with a length of 10 amino acid residues (SEQ ID NO: 15 with $X_{12}$ being absent, i.e., SASSSVSYMH).

For the design of humanized versions A, B and C of the LCVR described in Example 5, this 10-amino-acid-residue CDR1 was grafted into the human germlines, with backmutation and/or germlining but no addition or deletion of any residue. However, in human germlines, the LCVR's CDR1 has a minimum length of 11 amino acid residues.

Therefore, to increase the humanness of the humanized antibodies, the Inventors have sought to engineer ABIS-45RC VL-CDR1 "SASSSVSYMH" to extend it by one extra residue. One candidate position is position 8 in SEQ ID NO: 15 (designated as $X_{12}$), i.e., between S30 and Y31 in SEQ ID NO: 81. In all of the candidate germlines for the humanization design, this position is occupied with Asn (N), Ser (S) or Gly (G), while in the murine germline, this position is empty.

In order to investigate the structural relevance and stability of such insertion, ABIS-45RC VL-CDR1 was expanded by insertion of an asparagine, i.e., SEQ ID NO: 15 with $X_{12}$ being Asn (N), i.e., SASSSVS<u>N</u>YMH. A search of the sequences of solved antibody structures via protein BLAST was then conducted. The top hit was the LCVR CDR1 of the structure PDB ID: 5CMA. Subsequently, this structural segment was grafted onto the ABIS-45RC model using the two-residue overhang on its ends to anchor the CDR template fragment to the model. It was observed that, in order to accommodate the additional residue, there was a conformational change that shifted the neighboring residue, thereby presenting a slight steric clash with Y70. However, in all of the human germlines, this residue is a more accommodating phenylalanine.

Engineered Mouse Antibody

Based on the above, the Inventors have engineered the ABIS-RC45 antibody, by inserting an asparagine residue (Asn, N) in the VL-CDR1, and further mutating Y70 of SEQ ID NO: 81 into a phenylalanine (Phe, F). The resulting "engineered Asn/Phe ABIS-RC45" LCVR is set forth in SEQ ID NO: 71, with $X_{12}$ being Asn (N).

Two other mouse antibodies have also been produced on the same basis, by inserting a serine residue (Ser, S) or a glycine residue (Gly, G) in the VL-CDR1, and further mutating Y70 of SEQ ID NO: 81 into a phenylalanine (Phe, F). The two resulting "engineered Ser/Phe ABIS-RC45" and "engineered Gly/Phe ABIS-RC45" LCVR are set forth in SEQ ID NO: 71, with $X_{12}$ being Ser (S) or Gly (G), respectively.

Engineered Humanized Antibodies

Based on the above, engineered humanized LCVR versions A, B and C (as described in Example 5) can be further designed, as set forth in SEQ ID NOs: 72-80 where $X_{12}$ is Asn (N), Ser (S) or Gly (G) and the residue in position 70 is a Phe (F).

Example 9

Reactivity of Engineered Asn/Phe ABIS-45RC

Material and Methods

Blood from healthy volunteers was collected and peripheral blood mononuclear cells (PBMC) were isolated by Ficoll gradient centrifugation, which enables removal of unwanted fractions of blood products such as granulocytes, platelets and reaming red blood cell contaminants.

Human PBMCs were labeled with ABIS-45RC or with engineered Asn/Phe ABIS-45RC and an anti-CD3 antibody. The reactivity was revealed using a biotin donkey anti-human IgG$^+$ Streptavidin PercpCy 5.5 secondary antibody.

A Canto II cytometer (BD Biosciences) was used to measure fluorescence intensity and data were analyzed using the FLOWJO software (Tree Star Inc.). Cells were first gated by their morphology and dead cells were excluded by selecting DAPI-negative cells.

Results

Figure 6:
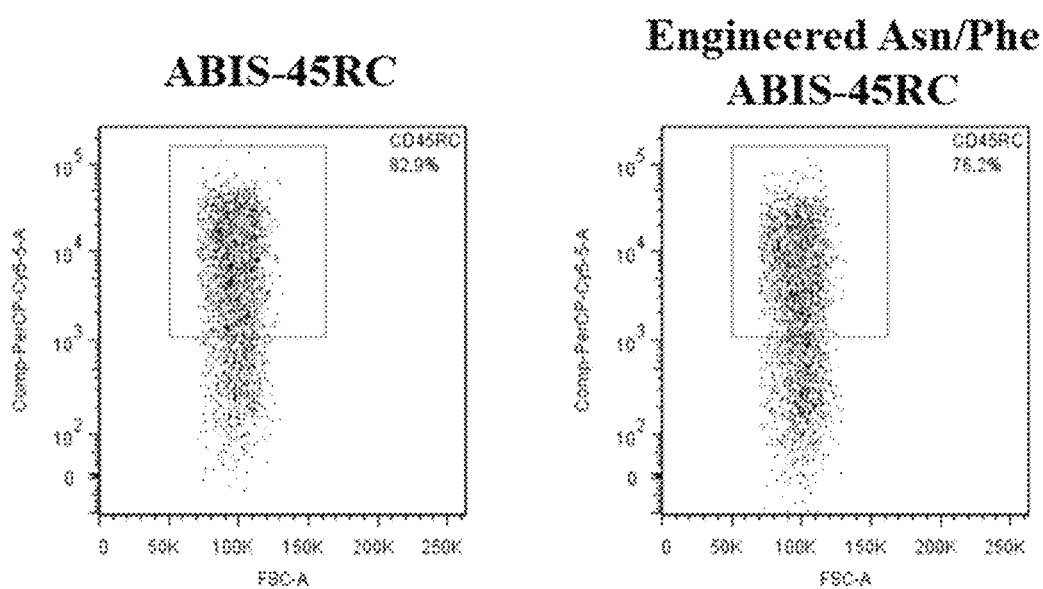
FIG. 6 shows two dot plots of flow cytometry showing that both ABIS-45RC (left panel) and engineered Asn/Phe ABIS-45RC (right panel) have an equivalent pattern of reactivity against human T cells.

As shown in FIG. 6, labelling with either ABIS-45RC (left panel) or the engineered Asn/Phe ABIS-45RC (right panel) shows that both antibodies recognized human CD45RC in a similar manner.

Example 10

Reactivity of Humanized ABIS-45RC

Material and Methods

Blood from healthy volunteers was collected and peripheral blood mononuclear cells (PBMC) were isolated by Ficoll gradient centrifugation, which enables removal of unwanted fractions of blood products such as granulocytes, platelets and reaming red blood cell contaminants.

Human PBMCs were labeled with ABIS-45RC or with humanized ABIS-45RC at 20, 5, 1.25 or 0.3 µg/mL and an anti-CD3 antibody. The reactivity was revealed using a biotin donkey anti-human IgG$^+$ Streptavidin PercpCy 5.5 secondary antibody.

A Canto II cytometer (BD Biosciences) was used to measure fluorescence intensity and data were analyzed using the FLOWJO software (Tree Star Inc.). Cells were first gated by their morphology and dead cells were excluded by selecting DAPI-negative cells.

Results

Figure 7A:
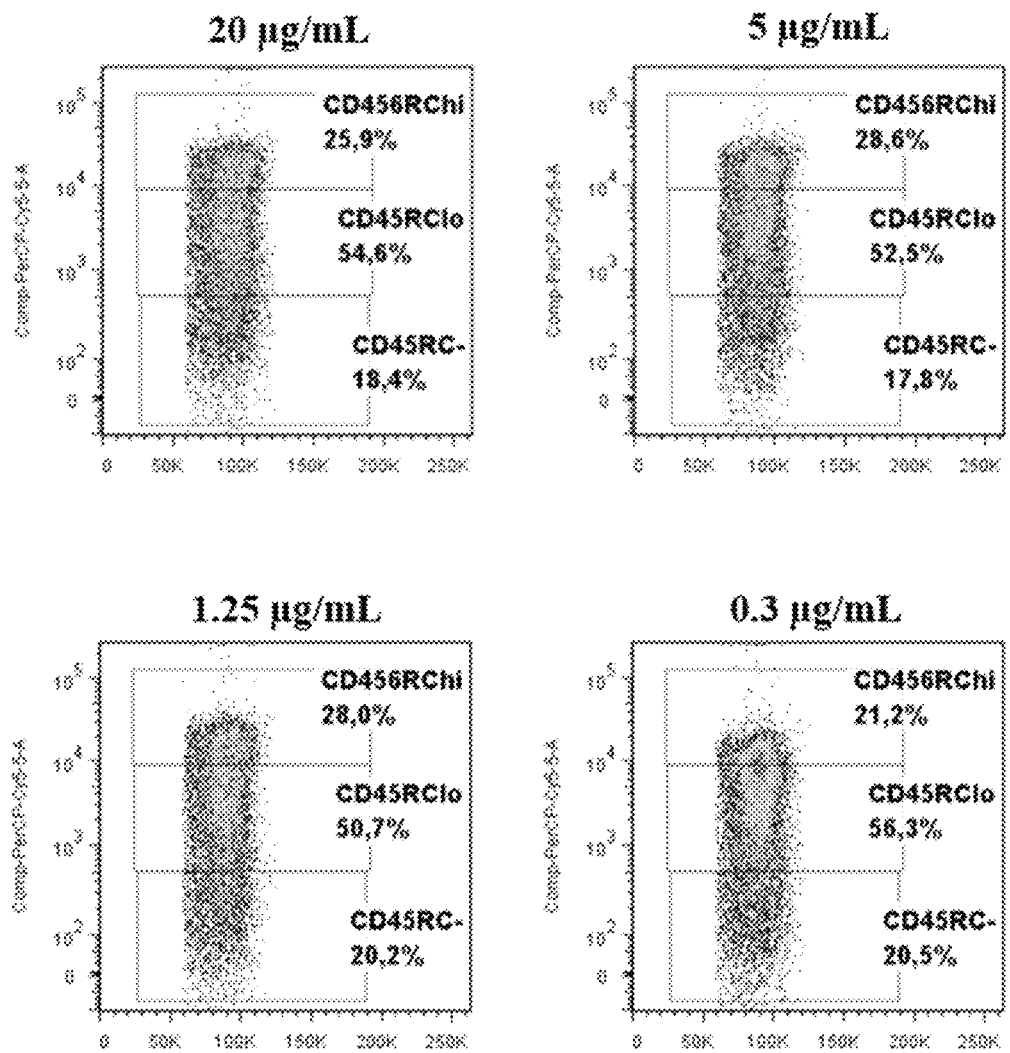
FIGS. 7A, 7B, and 7C show the expression level of CD45RC on $CD3^+$ leukocyte in human blood from three healthy volunteers. Cells were first gated on morphology, doublet cells and lived cells. (A) representative dot plot analysis of CD45RC expression detected by murine ABIS-45RC from one out of three healthy volunteers analyzed; (B) representative dot plot analysis of CD45RC expression detected by humanized ABIS-45RC variant A1 from one out of three healthy volunteers analyzed; (C) representative dot plot analysis of CD45RC expression detected by humanized ABIS-45RC variant A3 from one out of three healthy volunteers analyzed. x-axis shows the FSC; y-axis represents the fluorescence intensity of anti-CD45RC antibody labelling. The squares define cells with high, intermediate/low and negative levels of CD45RC expression as indicated and numbers represent the percentage of cells in each category.
Figure 7B:
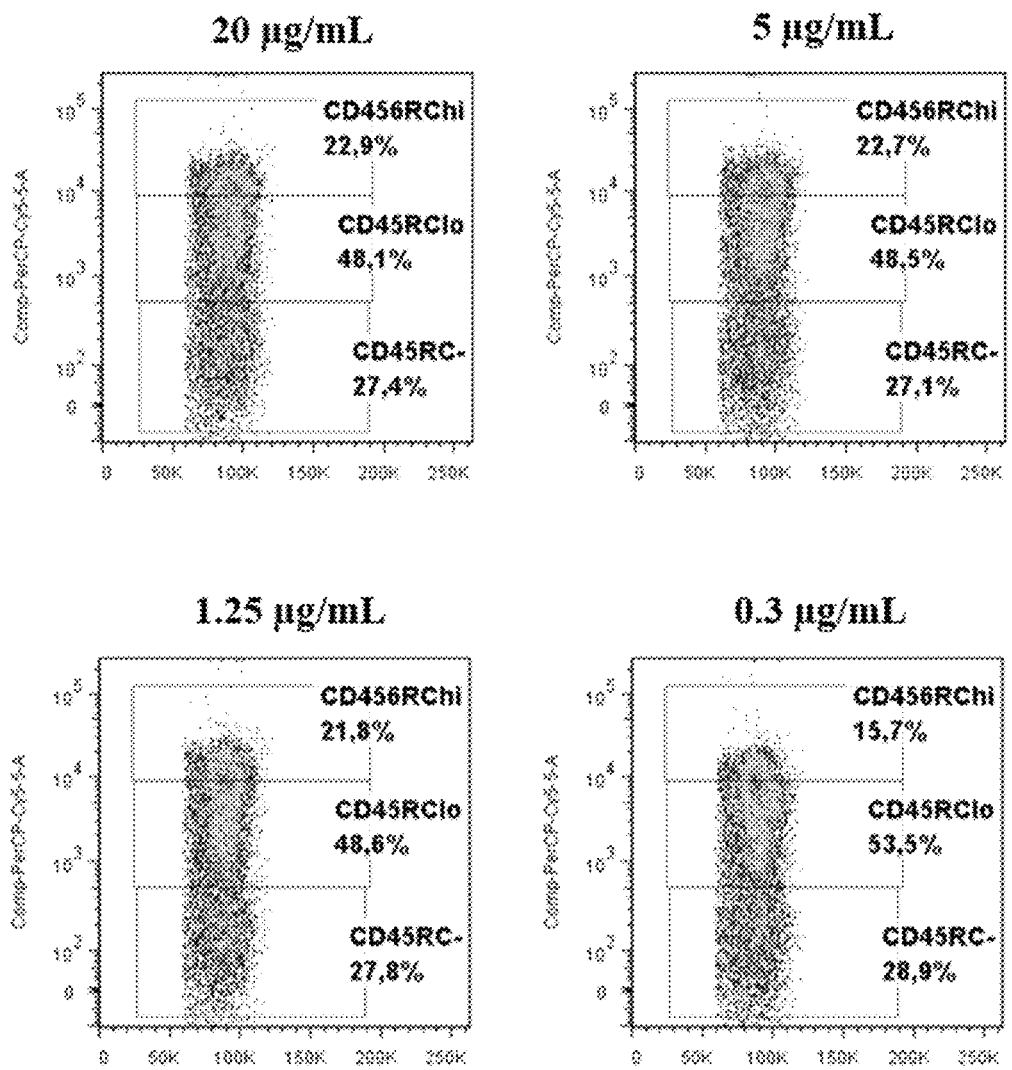
Figure 7C:
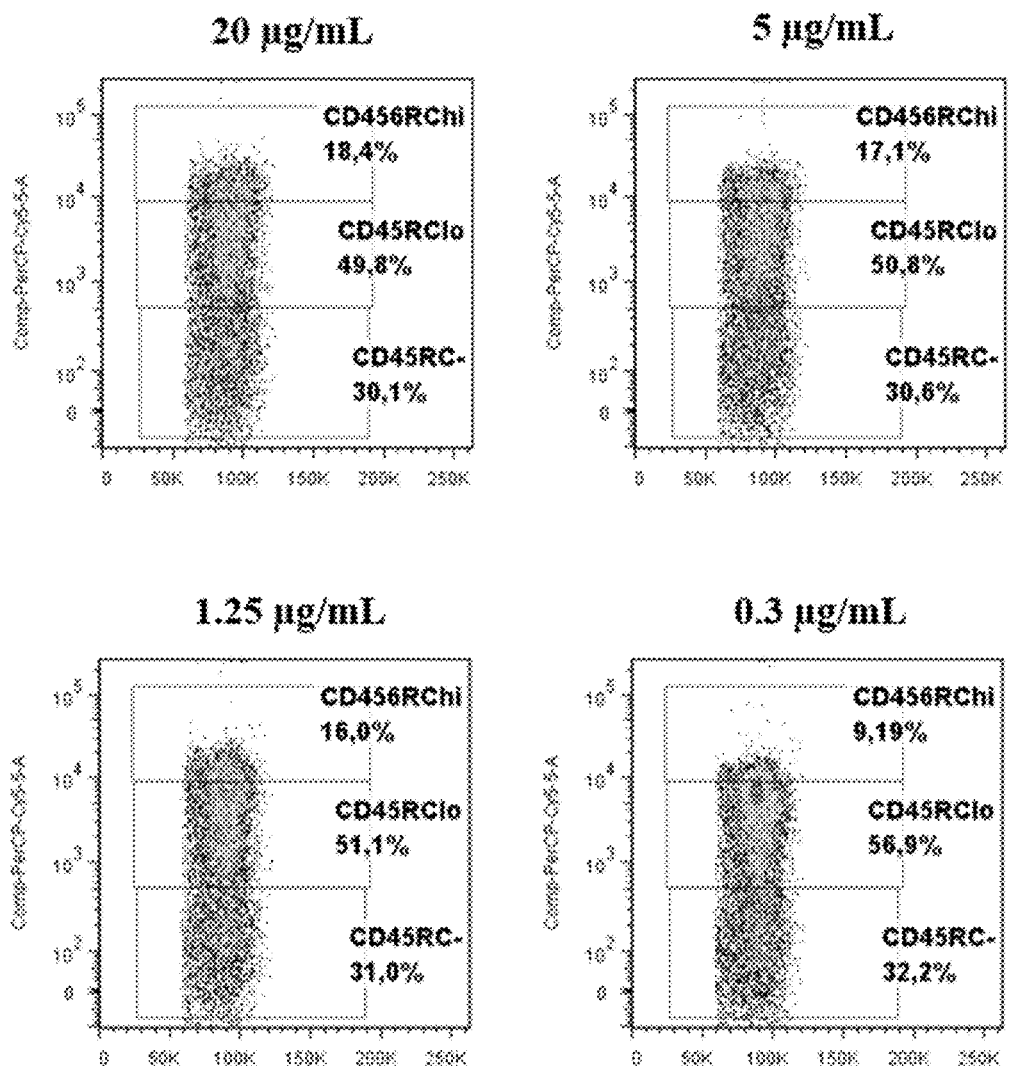

Labelling with either murine ABIS-45RC (FIG. 7A) or the humanized ABIS-45RC variant A1 (FIG. 7B) or variant A3 (FIG. 7C), at various concentrations, shows that both antibodies recognized human CD45RC in a similar manner.

Example 11

Cell Death Induction by Humanized ABIS-45RC Variants

Material and Methods

Human PBMCs were incubated with medium, isotype control Ab or anti-CD45RC variants (10 µg/mL) for 6 hours. Then, cells were stained with anti-CD3 and anti-CD45RA, annexin V and DAPI. Percentage of total apoptosis was obtained by gating on DAPI$^+$ Annexin V$^+$+DAPI$^-$ Annexin V$^+$ cells among T or non-T cells by flow cytometry.

Results

Figure 8A:
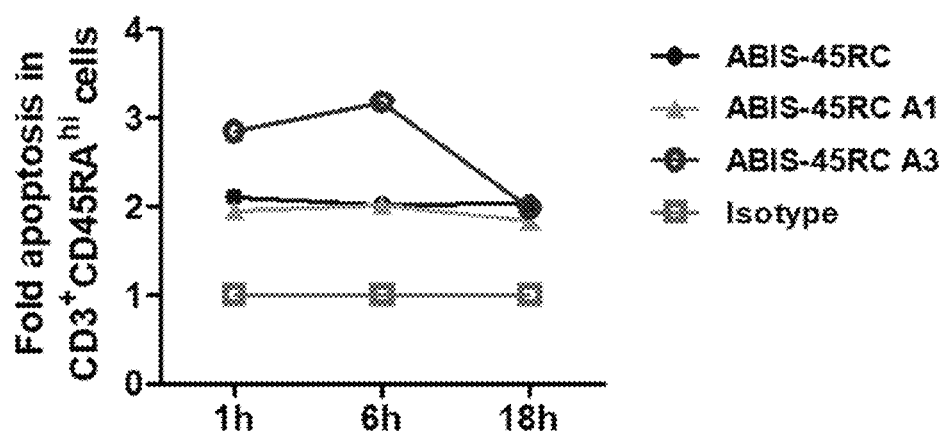
FIGS. 8A and 8B show that cytotoxicity induced by ABIS-45RC or by the humanized variants A1 and A3 is comparable. PBMCs from healthy volunteers were incubated at 37° C. with an isotype negative control (10 µg/mL), with murine ABIS-CD45RC (10 µg/mL), with the humanized variant A1 (10 µg/mL) or with the humanized variant A3 (10 µg/mL) for the indicated time points, and cells were then labeled with anti-CD3 and anti-CD45RA antibodies and apoptotic cells by labeling with Annexin-V-PE. The graphs indicate fold apoptosis in $CD3^+CD45RA^{hi}$ cells (A) and in CD3-cells (B), compared to the isotype control condition.
Figure 8B:
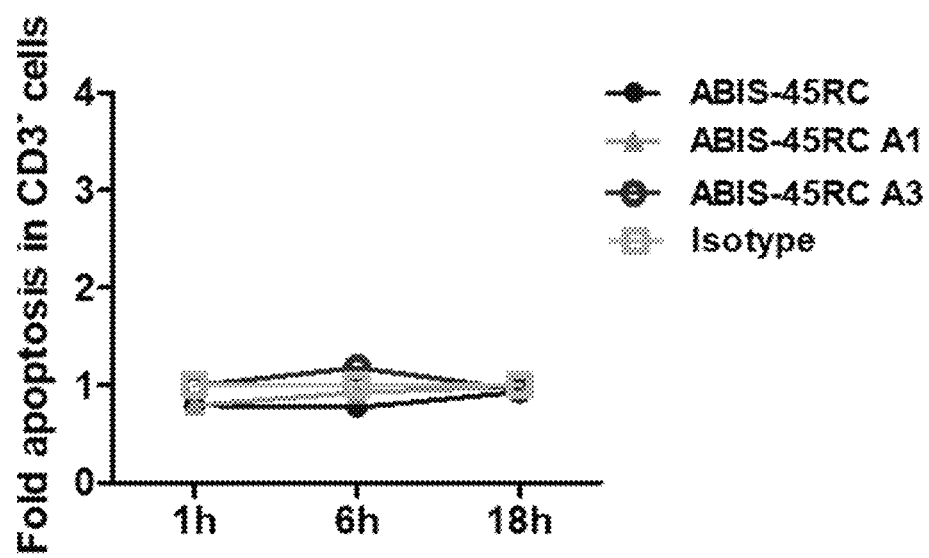

ABIS-45RC or the humanized variants A1 or A3 efficiently induced cell death of CD3$^+$ cells (FIG. 8A) but not CD3$^-$ cells (FIG. 8B).

Example 12

Cross-Reactivity of Humanized ABIS-45RC with Primate

Material and Methods

Blood from cynomolgus macaque was collected and peripheral blood mononuclear cells (PBMC) were isolated by Ficoll gradient centrifugation. PBMCs were labeled with ABIS-45RC or with humanized ABIS-45RC at 10 µg/ml and an anti-CD3 antibody. The reactivity was revealed using a biotin donkey anti-human IgG+ Streptavidin PercpCy 5.5 secondary antibody.

A Canto II cytometer (BD Biosciences) was used to measure fluorescence intensity and data were analyzed using the FLOWJO software (Tree Star Inc.). Cells were first gated by their morphology and dead cells were excluded by selecting DAPI-negative cells.

Results

Figure 9A:
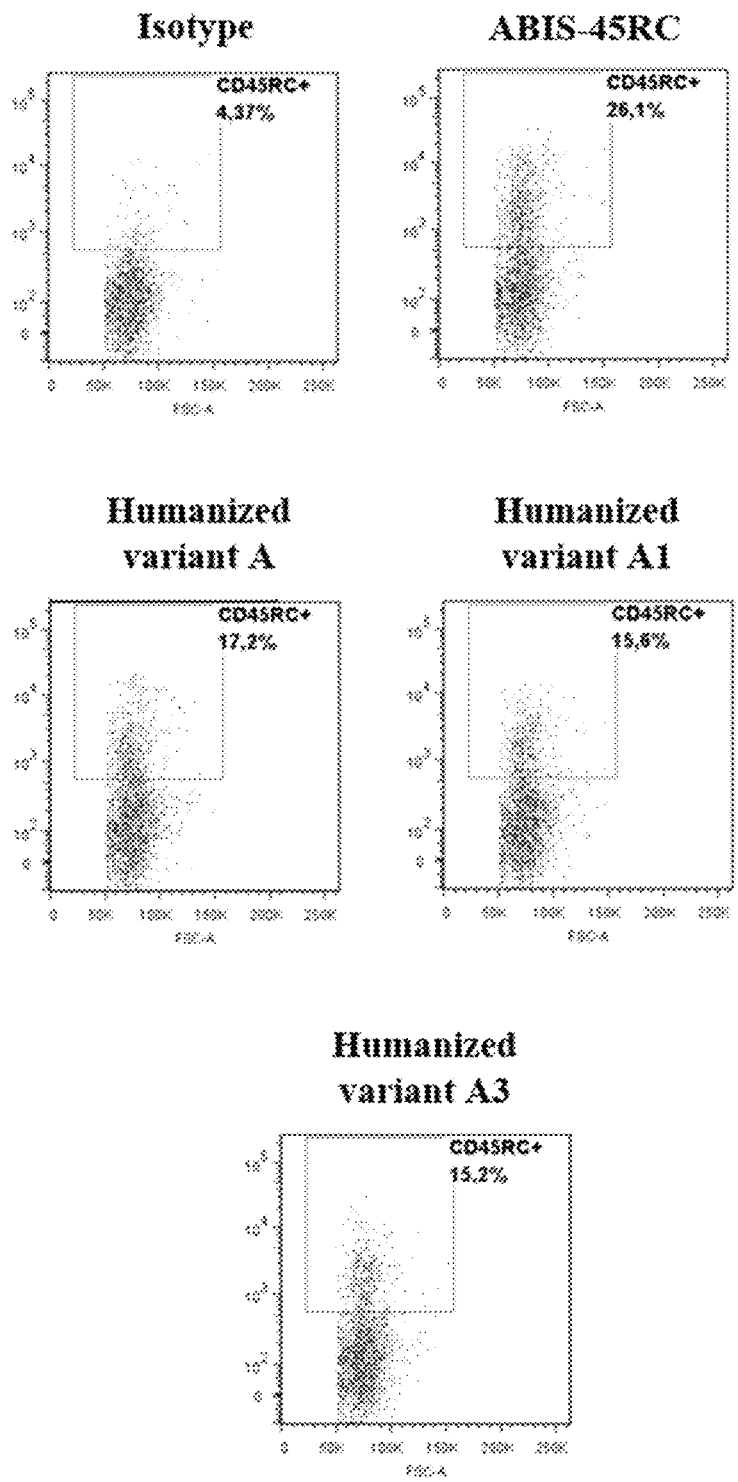
Figure 10:
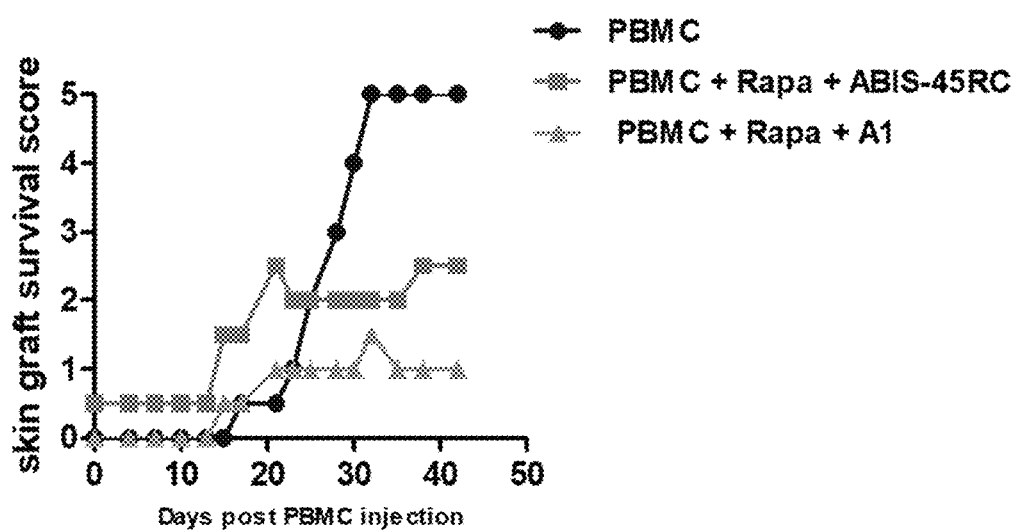
FIG. 10 shows the skin graft survival of treated humanized mice with anti-human CD45RC treatment. NSG mice transferred with total human PBMCs to induce human skin rejection were treated with murine ABIS-45RC or humanized variant A1, together with rapamycin (Rapa). Results are expressed in skin graft survival score.

Labelling with either ABIS-45RC or the humanized variants A, A1 or A3 showed that all antibodies recognized macaque CD45RC in a similar manner in CD3+ cells (FIG. 9A) and CD3− cells (FIG. 9B).

Example 13

Treatment of Human Skin Rejection with ABIS-45RC and Humanized Variant A1

Material and Methods

PBMC Isolation

Blood was collected at the Établissement Français du Sang (Nantes, France) from healthy individuals. Written informed consent was provided according to institutional guidelines. PBMC were isolated by Ficoll-Paque density-gradient centrifugation (Eurobio, Courtaboeuf, France). Remaining red cells and platelets were eliminated with a hypotonic solution and centrifugation.

Animals 8- to 12-week-old NOD/SCID/IL2Ry (NSG) mice were bred in our own animal facilities in SPF conditions (accreditation number C44-278).

Human Skin Transplantation Model

Human skins were obtained from healthy volunteers from abdominoplasty surgery and transplantation was performed as previously described (Bézie et al., 2018. *Front Immunol.* 8:2014). One month later, $5 \times 10^6$ PBMCs from allogeneic healthy volunteers were intravenously injected with or without antibodies.

Graft rejection was scored from 0 to 5 based on dryness (score 1), rigidity (score 2), scab (score 3), partial loss (score 4) and complete loss of the skin (score 5) by macroscopic observation.

Human PBMCs engraftment was monitored in blood by flow cytometry.

Treatment

NSG mice were treated intraperitoneally with purified ABIS-45RC or humanized variant A1 antibodies at 0.8 mg/kg from day 0 and every 2.5 days during 20 days, together with intraperitoneal administration of rapamycin from day 0 to day 10 at a suboptimal dose of 0.4 mg/day.

Results

Treatment with PBMCs only induced weight loss, initiated around day 14, and, as shown in Sure 10, death of all mice by day 33.

We previously showed that treatment with rapamycin only did not prolonged survival (median survival: 21 days (Bézie et al., 2018. *Front Immunol.* 8:2014)). Here, treatment with ABIS-45RC or the humanized variant A1 completely abrogated the skin graft rejection.

The invention claimed is:
1. An isolated anti-human CD45RC antibody or binding fragment thereof, wherein said antibody or binding fragment thereof comprises:
   (a) a heavy chain variable region (HCVR) which comprises the following three complementary-determining regions (CDRs):
      (i) V$_H$-CDR1 of sequence SEQ ID NO: 1;
      (ii) V$_H$-CDR2 with a sequence selected from the group consisting of sequences SEQ ID NOs: 4, 5, 6, 7, 8, 9, 10, 11, 100, 116, 117, 118 and 119; and
      (iii) V$_H$-CDR3 of sequence SEQ ID NO: 3; and
   (b) a light chain variable region (LCVR) which comprises the following three CDRs:
      (i) V$_L$-CDR1 with a sequence selected from the group consisting of sequences SEQ ID NO: 15 (SASSSVS-X-YMH) and SEQ ID NO: 18 (RASSSVS-X-YMH), wherein X is absent or is selected from the group consisting of Asn (N), Ser(S) and Gly (G);
      (ii) V$_L$-CDR2 with a sequence selected from the group consisting of sequences SEQ ID NOs: 16, 19, 20, 22, 111, 120 and 127; and
      (iii) V$_L$-CDR3 with a sequence selected from the group consisting of sequences SEQ ID NOs: 17 and 21.

2. The isolated antibody or binding fragment thereof according to claim 1, wherein said antibody or binding fragment thereof comprises a combination of 3 HCVR's CDRs and 3 LCVR's CDRs as set forth the table below:

| CDRs' combination # | V$_H$-CDR1 | V$_H$-CDR2 | V$_H$-CDR3 | V$_L$-CDR1 | V$_L$-CDR2 | V$_L$-CDR3 |
|---|---|---|---|---|---|---|
| #1  | 1 | 4  | 3 | 15 | 16 | 17 |
| #2  | 1 | 4  | 3 | 18 | 16 | 17 |
| #3  | 1 | 4  | 3 | 18 | 19 | 17 |
| #4  | 1 | 4  | 3 | 18 | 20 | 17 |
| #5  | 1 | 4  | 3 | 18 | 19 | 21 |
| #6  | 1 | 4  | 3 | 18 | 22 | 17 |
| #7  | 1 | 5  | 3 | 15 | 16 | 17 |
| #8  | 1 | 5  | 3 | 18 | 16 | 17 |
| #9  | 1 | 5  | 3 | 18 | 19 | 17 |
| #10 | 1 | 5  | 3 | 18 | 20 | 17 |
| #11 | 1 | 5  | 3 | 18 | 19 | 21 |
| #12 | 1 | 5  | 3 | 18 | 22 | 17 |
| #13 | 1 | 6  | 3 | 15 | 16 | 17 |
| #14 | 1 | 6  | 3 | 18 | 16 | 17 |
| #15 | 1 | 6  | 3 | 18 | 19 | 17 |
| #16 | 1 | 6  | 3 | 18 | 20 | 17 |
| #17 | 1 | 6  | 3 | 18 | 19 | 21 |
| #18 | 1 | 6  | 3 | 18 | 22 | 17 |
| #19 | 1 | 7  | 3 | 15 | 16 | 17 |
| #20 | 1 | 7  | 3 | 18 | 16 | 17 |
| #21 | 1 | 7  | 3 | 18 | 19 | 17 |
| #22 | 1 | 7  | 3 | 18 | 20 | 17 |
| #23 | 1 | 7  | 3 | 18 | 19 | 21 |
| #24 | 1 | 7  | 3 | 18 | 22 | 17 |
| #25 | 1 | 8  | 3 | 15 | 16 | 17 |
| #26 | 1 | 8  | 3 | 18 | 16 | 17 |
| #27 | 1 | 8  | 3 | 18 | 19 | 17 |
| #28 | 1 | 8  | 3 | 18 | 20 | 17 |
| #29 | 1 | 8  | 3 | 18 | 19 | 21 |
| #30 | 1 | 8  | 3 | 18 | 22 | 17 |
| #31 | 1 | 9  | 3 | 15 | 16 | 17 |
| #32 | 1 | 9  | 3 | 18 | 16 | 17 |
| #33 | 1 | 9  | 3 | 18 | 19 | 17 |
| #34 | 1 | 9  | 3 | 18 | 20 | 17 |
| #35 | 1 | 9  | 3 | 18 | 19 | 21 |
| #36 | 1 | 9  | 3 | 18 | 22 | 17 |
| #37 | 1 | 10 | 3 | 15 | 16 | 17 |
| #38 | 1 | 10 | 3 | 18 | 16 | 17 |
| #39 | 1 | 10 | 3 | 18 | 19 | 17 |
| #40 | 1 | 10 | 3 | 18 | 20 | 17 |
| #41 | 1 | 10 | 3 | 18 | 19 | 21 |
| #42 | 1 | 10 | 3 | 18 | 22 | 17 |
| #43 | 1 | 11 | 3 | 15 | 16 | 17 |
| #44 | 1 | 11 | 3 | 18 | 16 | 17 |
| #45 | 1 | 11 | 3 | 18 | 19 | 17 |
| #46 | 1 | 11 | 3 | 18 | 20 | 17 |
| #47 | 1 | 11 | 3 | 18 | 19 | 21 |
| #48 | 1 | 11 | 3 | 18 | 22 | 17 |
| #49 | 1 | 100 | 3 | 15 | 16 | 17 |
| #50 | 1 | 100 | 3 | 18 | 16 | 17 |
| #51 | 1 | 100 | 3 | 18 | 19 | 17 |
| #52 | 1 | 100 | 3 | 18 | 20 | 17 |
| #53 | 1 | 100 | 3 | 18 | 19 | 21 |
| #54 | 1 | 100 | 3 | 18 | 22 | 17 |
| #55 | 1 | 4  | 3 | 18 | 111 | 17 |
| #56 | 1 | 5  | 3 | 18 | 111 | 17 |
| #57 | 1 | 6  | 3 | 18 | 111 | 17 |
| #58 | 1 | 7  | 3 | 18 | 111 | 17 |
| #59 | 1 | 8  | 3 | 18 | 111 | 17 |
| #60 | 1 | 9  | 3 | 18 | 111 | 17 |
| #61 | 1 | 10 | 3 | 18 | 111 | 17 |
| #62 | 1 | 11 | 3 | 18 | 111 | 17 |
| #63 | 1 | 100 | 3 | 18 | 111 | 17 |
| #64 | 1 | 116 | 3 | 15 | 16 | 17 |
| #65 | 1 | 116 | 3 | 18 | 16 | 17 |
| #66 | 1 | 116 | 3 | 18 | 19 | 17 |
| #67 | 1 | 116 | 3 | 18 | 20 | 17 |
| #68 | 1 | 116 | 3 | 18 | 19 | 21 |
| #69 | 1 | 116 | 3 | 18 | 22 | 17 |
| #70 | 1 | 116 | 3 | 18 | 111 | 17 |
| #71 | 1 | 117 | 3 | 15 | 16 | 17 |
| #72 | 1 | 117 | 3 | 18 | 16 | 17 |
| #73 | 1 | 117 | 3 | 18 | 19 | 17 |
| #74 | 1 | 117 | 3 | 18 | 20 | 17 |
| #75 | 1 | 117 | 3 | 18 | 19 | 21 |
| #76 | 1 | 117 | 3 | 18 | 22 | 17 |
| #77 | 1 | 117 | 3 | 18 | 111 | 17 |
| #78 | 1 | 118 | 3 | 15 | 16 | 17 |
| #79 | 1 | 118 | 3 | 18 | 16 | 17 |
| #80 | 1 | 118 | 3 | 18 | 19 | 17 |
| #81 | 1 | 118 | 3 | 18 | 20 | 17 |
| #82 | 1 | 118 | 3 | 18 | 19 | 21 |
| #83 | 1 | 118 | 3 | 18 | 22 | 17 |
| #84 | 1 | 118 | 3 | 18 | 111 | 17 |
| #85 | 1 | 119 | 3 | 15 | 16 | 17 |
| #86 | 1 | 119 | 3 | 18 | 16 | 17 |
| #87 | 1 | 119 | 3 | 18 | 19 | 17 |
| #88 | 1 | 119 | 3 | 18 | 20 | 17 |
| #89 | 1 | 119 | 3 | 18 | 19 | 21 |
| #90 | 1 | 119 | 3 | 18 | 22 | 17 |
| #91 | 1 | 119 | 3 | 18 | 111 | 17 |
| #92 | 1 | 4  | 3 | 15 | 120 | 17 |
| #93 | 1 | 5  | 3 | 15 | 120 | 17 |
| #94 | 1 | 6  | 3 | 15 | 120 | 17 |
| #95 | 1 | 7  | 3 | 15 | 120 | 17 |
| #96 | 1 | 8  | 3 | 15 | 120 | 17 |
| #97 | 1 | 9  | 3 | 15 | 120 | 17 |
| #98 | 1 | 10 | 3 | 15 | 120 | 17 |
| #99 | 1 | 11 | 3 | 15 | 120 | 17 |
| #100 | 1 | 100 | 3 | 15 | 120 | 17 |
| #101 | 1 | 116 | 3 | 15 | 120 | 17 |
| #102 | 1 | 117 | 3 | 15 | 120 | 17 |
| #103 | 1 | 118 | 3 | 15 | 120 | 17 |
| #104 | 1 | 119 | 3 | 15 | 120 | 17 |
| #105 | 1 | 4  | 3 | 15 | 127 | 17 |
| #106 | 1 | 5  | 3 | 15 | 127 | 17 |
| #107 | 1 | 6  | 3 | 15 | 127 | 17 |
| #108 | 1 | 7  | 3 | 15 | 127 | 17 |
| #109 | 1 | 8  | 3 | 15 | 127 | 17 |
| #110 | 1 | 9  | 3 | 15 | 127 | 17 |
| #111 | 1 | 10 | 3 | 15 | 127 | 17 |
| #112 | 1 | 11 | 3 | 15 | 127 | 17 |
| #113 | 1 | 100 | 3 | 15 | 127 | 17 |
| #114 | 1 | 116 | 3 | 15 | 127 | 17 |
| #115 | 1 | 117 | 3 | 15 | 127 | 17 |
| #116 | 1 | 118 | 3 | 15 | 127 | 17 |
| #117 | 1 | 119 | 3 | 15 | 127 | 17. |

3. The isolated antibody or binding fragment thereof according to claim 1, wherein said antibody or binding fragment thereof comprises:
   (a) a HCVR which comprises the following three CDRs:
      (i) $V_H$-CDR1 of sequence SEQ ID NO: 1;
      (ii) $V_H$-CDR2 with a sequence selected from the group consisting of sequences SEQ ID NOs: 4 and 5; and
      (iii) $V_H$-CDR3 of sequence SEQ ID NO: 3; and
   (b) a LCVR which comprises the following three CDRs:
      (i) $V_L$-CDR1 of sequence SEQ ID NO: 15, wherein X is absent;
      (ii) $V_L$-CDR2 of sequence SEQ ID NO: 16; and
      (iii) $V_L$-CDR3 of sequence SEQ ID NO: 17.

4. The isolated antibody or binding fragment thereof according to claim 1, wherein said antibody or binding fragment thereof comprises:
   (a) a HCVR which comprises the following three CDRs:
      (i) $V_H$-CDR1 of sequence SEQ ID NO: 1;
      (ii) $V_H$-CDR2 of sequence SEQ ID NO: 4; and
      (iii) $V_H$-CDR3 of sequence SEQ ID NO: 3; and
   (b) a LCVR which comprises the following three CDRs:
      (i) $V_L$-CDR1 of sequence SEQ ID NO: 15, wherein X is absent;
      (ii) $V_L$-CDR2 of sequence SEQ ID NO: 16; and
      (iii) $V_L$-CDR3 of sequence SEQ ID NO: 17.

5. The isolated antibody or binding fragment thereof according to claim 1, wherein said antibody or binding fragment thereof comprises:
   (a) a HCVR which comprises the following three CDRs:
      (i) $V_H$-CDR1 of sequence SEQ ID NO: 1;
      (ii) $V_H$-CDR2 with a sequence selected from the group consisting of sequences SEQ ID NOs: 4, 6, and 100; and
      (iii) $V_H$-CDR3 of sequence SEQ ID NO: 3; and
   (b) a LCVR which comprises the following three CDRs:
      (i) $V_L$-CDR1 with a sequence selected from the group consisting of sequences SEQ ID NOs: 15 and 18, wherein X is absent;
      (ii) $V_L$-CDR2 of sequence SEQ ID NO: 16; and
      (iii) $V_L$-CDR3 of sequence SEQ ID NO: 17.

6. The isolated antibody or binding fragment thereof according to claim 1, wherein said antibody or binding fragment thereof comprises:
   1) a HCVR of sequence SEQ ID NO: 61 and a LCVR of sequence SEQ ID NO: 81;
   2) a HCVR of sequence SEQ ID NO: 62 and a LCVR of sequence SEQ ID NO: 82;
   3) a HCVR of sequence SEQ ID NO: 62 and a LCVR of sequence SEQ ID NO: 83;
   4) a HCVR of sequence SEQ ID NO: 62 and a LCVR of sequence SEQ ID NO: 84;
   5) a HCVR of sequence SEQ ID NO: 63 and a LCVR of sequence SEQ ID NO: 82;
   6) a HCVR of sequence SEQ ID NO: 63 and a LCVR of sequence SEQ ID NO: 83;
   7) a HCVR of sequence SEQ ID NO: 63 and a LCVR of sequence SEQ ID NO: 84;
   8) a HCVR of sequence SEQ ID NO: 64 and a LCVR of sequence SEQ ID NO: 82;
   9) a HCVR of sequence SEQ ID NO: 64 and a LCVR of sequence SEQ ID NO: 83;
   10) a HCVR of sequence SEQ ID NO: 64 and a LCVR of sequence SEQ ID NO: 84;
   11) a HCVR of sequence SEQ ID NO: 101 and a LCVR of sequence SEQ ID NO: 85;
   12) a HCVR of sequence SEQ ID NO: 101 and a LCVR of sequence SEQ ID NO: 103;
   13) a HCVR of sequence SEQ ID NO: 65 and a LCVR of sequence SEQ ID NO: 85;
   14) a HCVR of sequence SEQ ID NO: 65 and a LCVR of sequence SEQ ID NO: 103;
   15) a HCVR of sequence SEQ ID NO: 62 and a LCVR of sequence SEQ ID NO: 85;
   16) a HCVR of sequence SEQ ID NO: 101 and a LCVR of sequence SEQ ID NO: 82;
   17) a HCVR of sequence SEQ ID NO: 121 and a LCVR of sequence SEQ ID NO: 85;
   18) a HCVR of sequence SEQ ID NO: 122 and a LCVR of sequence SEQ ID NO: 85;
   19) a HCVR of sequence SEQ ID NO: 123 and a LCVR of sequence SEQ ID NO: 85;
   20) a HCVR of sequence SEQ ID NO: 124 and a LCVR of sequence SEQ ID NO: 85;
   21) a HCVR of sequence SEQ ID NO: 63 and a LCVR of sequence SEQ ID NO: 85;
   22) a HCVR of sequence SEQ ID NO: 67 and a LCVR of sequence SEQ ID NO: 85;
   23) a HCVR of sequence SEQ ID NO: 67 and a LCVR of sequence SEQ ID NO: 103; or
   24) a HCVR of sequence SEQ ID NO: 61 and a LCVR of sequence SEQ ID NO: 113; or
   25) a HCVR of sequence SEQ ID NO: 61 and a LCVR of sequence SEQ ID NO: 126; or
   26) a HCVR and a LCVR comprising a sequence of the non-CDR regions sharing at least 70% of identity with the sequence of the non-CDR regions of the HCVR and LCVR according to 1) to 25).

7. The isolated antibody or binding fragment thereof according to claim 1, wherein said antibody or binding fragment thereof comprises:
   (a) a HCVR which comprises the following three CDRs:
      (i) $V_H$-CDR1 of sequence SEQ ID NO: 1;
      (ii) $V_H$-CDR2 with a sequence selected from the group consisting of sequences SEQ ID NOs: 4, 5, 6, 7, 8, 9, 10, 11, 100, 116, 117, 118 and 119; and
      (iii) $V_H$-CDR3 of sequence SEQ ID NO: 3; and
   (b) a LCVR which comprises the following three CDRs:
      (i) $V_L$-CDR1 with a sequence selected from the group consisting of sequences SEQ ID NOs: 15 and 18, wherein X in SEQ ID NOs: 15 and 18 is selected from the group consisting of Asn (N), Ser(S) and Gly (G);
      (ii) $V_L$-CDR2 with a sequence selected from the group consisting of sequences SEQ ID NOs: 16, 19, 20, 22, 111, 120 and 127; and
      (iii) $V_L$-CDR3 with a sequence selected from the group consisting of sequences SEQ ID NOs: 17 and 21.

8. The isolated antibody or binding fragment thereof according to claim 7, wherein the amino acid residue at Kabat position L71 of the LCVR is Phe (F).

9. A nucleic acid encoding the isolated antibody or binding fragment thereof according to claim 1.

10. An expression vector comprising the nucleic acid according to claim 9.

11. A cell comprising the nucleic acid according to claim 9 or an expression vector comprising the nucleic acid.

12. A pharmaceutical composition comprising the isolated antibody or binding fragment thereof according to claim 1, a nucleic acid encoding the isolated antibody or binding fragment thereof, an expression vector comprising the nucleic acid, or a cell comprising the nucleic acid or the expression vector, and at least one pharmaceutically acceptable excipient.

13. A method of inducing immune tolerance in a subject in need thereof, comprising administering to said subject the isolated antibody or binding fragment thereof according to claim 1, a nucleic acid encoding the isolated antibody or binding fragment thereof, an expression vector comprising the nucleic acid, or a cell comprising the nucleic acid or the expression vector.

14. A method of preventing and/or reducing transplant rejections in a subject in need thereof, comprising administering to said subject the isolated antibody or binding fragment thereof according to claim 1, a nucleic acid encoding the isolated antibody or binding fragment thereof, an expression vector comprising the nucleic acid, or a cell comprising the nucleic acid or the expression vector.

15. A method of reducing and/or treating $CD45RC^{high}$-related conditions in a subject in need thereof, comprising administering to said subject the isolated antibody or binding fragment thereof according to claim 1, a nucleic acid encoding the isolated antibody or binding fragment thereof, an expression vector comprising the nucleic acid, or a cell comprising the nucleic acid or the expression vector.

16. The method of reducing and/or treating $CD45RC^{high}$ related conditions according to claim 15, wherein the $CD45RC^{high}$-related condition is selected from the group consisting of autoimmune diseases, undesired immune responses, monogenic diseases, lymphoma and cancer.

17. A method of preventing and/or treating graft-versus-host disease (GVHD) in a subject in need thereof, comprising administering to said subject the isolated antibody or binding fragment thereof according to claim 1, a nucleic acid encoding the isolated antibody or binding fragment thereof, an expression vector comprising the nucleic acid, or a cell comprising the nucleic acid or the expression vector.

18. A method for detecting or quantifying hCD45RC in a sample, cell, tissue or organ, comprising contacting said sample, cell, tissue or organ with the isolated antibody or binding fragment thereof according to claim 1.

19. The method for detecting or quantifying hCD45RC according to claim 18, wherein the isolated antibody or binding fragment thereof is labelled.

20. The isolated antibody or binding fragment thereof according to claim 1, wherein said antibody or binding fragment thereof comprises:
 (a) a HCVR which comprises the following three CDRs:
  (i) $V_H$-CDR1 of sequence SEQ ID NO: 1;
  (ii) $V_H$-CDR2 with a sequence selected from the group consisting of sequences SEQ ID NOs: 4 and 118; and
  (iii) $V_H$-CDR3 of sequence SEQ ID NO: 3; and
 (b) a LCVR which comprises the following three CDRs:
  (i) $V_L$-CDR1 of sequence SEQ ID NO: 15, wherein X is absent;
  (ii) $V_L$-CDR2 of sequence SEQ ID NO: 120; and
  (iii) $V_L$-CDR3 of sequence SEQ ID NO: 17.

* * * * *

SEQUENCE LISTING

```
<160> NUMBER OF SEQ ID NOS: 129

<210> SEQ ID NO 1
<211> LENGTH: 5
<212> TYPE: PRT
<213> ORGANISM: Artificial Sequence
<220> FEATURE:
<223> OTHER INFORMATION: VH-CDR1

<400> SEQUENCE: 1

Asn Tyr Tyr Ile Gly
1               5

<210> SEQ ID NO 2
<211> LENGTH: 17
<212> TYPE: PRT
<213> ORGANISM: Artificial Sequence
<220> FEATURE:
<221> NAME/KEY: SITE
<222> LOCATION: 1
<223> OTHER INFORMATION: Xaa is selected from Asp (D), Ile (I) and Arg
      (R)
<220> FEATURE:
<223> OTHER INFORMATION: VH-CDR2
<220> FEATURE:
<221> NAME/KEY: SITE
<222> LOCATION: 4
<223> OTHER INFORMATION: Xaa is selected from Pro and Ser (S)
<220> FEATURE:
<221> NAME/KEY: SITE
<222> LOCATION: 7
<223> OTHER INFORMATION: Xaa is selected from Asp (D), Ser (S) and Gly
      (G)
<220> FEATURE:
<221> NAME/KEY: SITE
<222> LOCATION: 9
<223> OTHER INFORMATION: Xaa is selected from Ala (A) and Thr (T)
```

```
<220> FEATURE:
<221> NAME/KEY: SITE
<222> LOCATION: 11
<223> OTHER INFORMATION: Xaa is selected from Ser (S) and Tyr (Y)
<220> FEATURE:
<221> NAME/KEY: SITE
<222> LOCATION: 12
<223> OTHER INFORMATION: Xaa is selected from Asn (N), Ala (A) and Ser
      (S)
<220> FEATURE:
<221> NAME/KEY: SITE
<222> LOCATION: 13
<223> OTHER INFORMATION: Xaa is selected from Glu (E), Asp (D), Pro (P)
      and Gln (Q)
<220> FEATURE:
<221> NAME/KEY: SITE
<222> LOCATION: 14
<223> OTHER INFORMATION: Xaa is selected from Lys (K) and Ser (S)
<220> FEATURE:
<221> NAME/KEY: SITE
<222> LOCATION: 15
<223> OTHER INFORMATION: Xaa is selected from Phe (F) and Val (V)
<220> FEATURE:
<221> NAME/KEY: SITE
<222> LOCATION: 16
<223> OTHER INFORMATION: Xaa is selected from Lys (K) and Gln (Q)

<400> SEQUENCE: 2

Xaa Ile Phe Xaa Gly Gly Xaa Tyr Xaa Asn Xaa Xaa Xaa Xaa Xaa Xaa
1               5                   10                  15

Gly

<210> SEQ ID NO 3
<211> LENGTH: 5
<212> TYPE: PRT
<213> ORGANISM: Artificial Sequence
<220> FEATURE:
<223> OTHER INFORMATION: VH-CDR3

<400> SEQUENCE: 3

Arg Asn Phe Asp Tyr
1               5

<210> SEQ ID NO 4
<211> LENGTH: 17
<212> TYPE: PRT
<213> ORGANISM: Artificial Sequence
<220> FEATURE:
<223> OTHER INFORMATION: VH-CDR2

<400> SEQUENCE: 4

Asp Ile Phe Pro Gly Gly Asp Tyr Ala Asn Ser Asn Glu Lys Phe Lys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: VH-CDR2

<400> SEQUENCE: 5

Asp Ile Phe Pro Gly Gly Asp Tyr Ala Asn Ser Asn Glu Lys Val Lys
1               5                   10                  15

Gly

<210> SEQ ID NO 6
```

```
<211> LENGTH: 17
<212> TYPE: PRT
<213> ORGANISM: Artificial Sequence
<220> FEATURE:
<223> OTHER INFORMATION: VH-CDR2

<400> SEQUENCE: 6

Asp Ile Phe Pro Gly Gly Gly Tyr Thr Asn Tyr Ala Glu Lys Phe Gln
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: VH-CDR2

<400> SEQUENCE: 7

Asp Ile Phe Pro Gly Gly Ser Tyr Thr Asn Tyr Ser Glu Ser Phe Gln
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: VH-CDR2

<400> SEQUENCE: 8

Asp Ile Phe Pro Gly Gly Ser Tyr Thr Asn Tyr Ala Asp Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: VH-CDR2

<400> SEQUENCE: 9

Arg Ile Phe Pro Gly Gly Gly Tyr Thr Asn Tyr Ala Gln Lys Phe Gln
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: VH-CDR2

<400> SEQUENCE: 10

Ile Ile Phe Pro Gly Gly Ser Tyr Thr Asn Tyr Ser Pro Ser Phe Gln
1               5                   10                  15

Gly

<210> SEQ ID NO 11
<211> LENGTH: 17
<212> TYPE: PRT
<213> ORGANISM: Artificial Sequence
<220> FEATURE:
```

```
<223> OTHER INFORMATION: VH-CDR2

<400> SEQUENCE: 11

Asp Ile Phe Ser Gly Gly Ser Tyr Thr Asn Tyr Ala Asp Ser Val Lys
1               5                   10                  15
Gly

<210> SEQ ID NO 12
<211> LENGTH: 11
<212> TYPE: PRT
<213> ORGANISM: Artificial Sequence
<220> FEATURE:
<221> NAME/KEY: SITE
<222> LOCATION: 1
<223> OTHER INFORMATION: Xaa is selected from Ser (S) and Arg (R)
<220> FEATURE:
<223> OTHER INFORMATION: VL-CDR1
<220> FEATURE:
<221> NAME/KEY: SITE
<222> LOCATION: 8
<223> OTHER INFORMATION: Xaa is absent, or is selected from Asn (N), Ser
      (S) and Gly (G)

<400> SEQUENCE: 12

Xaa Ala Ser Ser Ser Val Ser Xaa Tyr Met His
1               5                   10

<210> SEQ ID NO 13
<211> LENGTH: 7
<212> TYPE: PRT
<213> ORGANISM: Artificial Sequence
<220> FEATURE:
<221> NAME/KEY: SITE
<222> LOCATION: 1
<223> OTHER INFORMATION: Xaa is selected from Asn (N) and Ala (A); or
      Xaa is any amino acid but Ala (A) or Asn (N)
<220> FEATURE:
<223> OTHER INFORMATION: VL-CDR2
<220> FEATURE:
<221> NAME/KEY: SITE
<222> LOCATION: 5
<223> OTHER INFORMATION: Xaa is selected from Leu (L), Ser (S) and Arg
      (R)
<220> FEATURE:
<221> NAME/KEY: SITE
<222> LOCATION: 6
<223> OTHER INFORMATION: Xaa is selected from Pro (P), Ala (A) and Gln
      (Q)
<220> FEATURE:
<221> NAME/KEY: SITE
<222> LOCATION: 7
<223> OTHER INFORMATION: Xaa is selected from Ser (S) and Thr (T)

<400> SEQUENCE: 13

Xaa Thr Ser Asn Xaa Xaa Xaa
1               5

<210> SEQ ID NO 14
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Xaa is selected from Gln (Q) and His (H)
<220> FEATURE:
<223> OTHER INFORMATION: VL-CDR3

<400> SEQUENCE: 14

Xaa Gln Arg Ser Ser Tyr Pro Leu Thr Phe
1               5                   10
```

```
<210> SEQ ID NO 15
<211> LENGTH: 11
<212> TYPE: PRT
<213> ORGANISM: Artificial Sequence
<220> FEATURE:
<223> OTHER INFORMATION: VL-CDR1
<220> FEATURE:
<221> NAME/KEY: SITE
<222> LOCATION: 8
<223> OTHER INFORMATION: Xaa is absent or is selected from Asn (N), Ser
      (S) and Gly (G)

<400> SEQUENCE: 15

Ser Ala Ser Ser Ser Val Ser Xaa Tyr Met His
1               5                   10

<210> SEQ ID NO 16
<211> LENGTH: 7
<212> TYPE: PRT
<213> ORGANISM: Artificial Sequence
<220> FEATURE:
<223> OTHER INFORMATION: VL-CDR2

<400> SEQUENCE: 16

Asn Thr Ser Asn Leu Pro Ser
1               5

<210> SEQ ID NO 17
<211> LENGTH: 10
<212> TYPE: PRT
<213> ORGANISM: Artificial Sequence
<220> FEATURE:
<223> OTHER INFORMATION: VL-CDR3

<400> SEQUENCE: 17

Gln Gln Arg Ser Ser Tyr Pro Leu Thr Phe
1               5                   10

<210> SEQ ID NO 18
<211> LENGTH: 11
<212> TYPE: PRT
<213> ORGANISM: Artificial Sequence
<220> FEATURE:
<223> OTHER INFORMATION: VL-CDR1
<220> FEATURE:
<221> NAME/KEY: SITE
<222> LOCATION: 8
<223> OTHER INFORMATION: Xaa is absent or is selected from Asn (N), Ser
      (S) and Gly (G)

<400> SEQUENCE: 18

Arg Ala Ser Ser Ser Val Ser Xaa Tyr Met His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: VL-CDR2

<400> SEQUENCE: 19

Asn Thr Ser Asn Ser Pro Ser
1               5

<210> SEQ ID NO 20
<211> LENGTH: 7
```

```
<212> TYPE: PRT
<213> ORGANISM: Artificial Sequence
<220> FEATURE:
<223> OTHER INFORMATION: VL-CDR2

<400> SEQUENCE: 20

Ala Thr Ser Asn Leu Gln Ser
1               5

<210> SEQ ID NO 21
<211> LENGTH: 10
<212> TYPE: PRT
<213> ORGANISM: Artificial Sequence
<220> FEATURE:
<223> OTHER INFORMATION: VL-CDR3

<400> SEQUENCE: 21

His Gln Arg Ser Ser Tyr Pro Leu Thr Phe
1               5                   10

<210> SEQ ID NO 22
<211> LENGTH: 7
<212> TYPE: PRT
<213> ORGANISM: Artificial Sequence
<220> FEATURE:
<223> OTHER INFORMATION: VL-CDR2

<400> SEQUENCE: 22

Asn Thr Ser Asn Arg Ala Thr
1               5

<210> SEQ ID NO 23
<211> LENGTH: 48
<212> TYPE: PRT
<213> ORGANISM: Homo sapiens
<220> FEATURE:
<223> OTHER INFORMATION: C determinant of hCD45RC

<400> SEQUENCE: 23

Asp Val Pro Gly Glu Arg Ser Thr Ala Ser Thr Phe Pro Thr Asp Pro
1               5                   10                  15

Val Ser Pro Leu Thr Thr Thr Leu Ser Leu Ala His His Ser Ser Ala
            20                  25                  30

Ala Leu Pro Ala Arg Thr Ser Asn Thr Thr Ile Thr Ala Asn Thr Ser
        35                  40                  45

<210> SEQ ID NO 24
<211> LENGTH: 144
<212> TYPE: DNA
<213> ORGANISM: Homo sapiens
<220> FEATURE:
<223> OTHER INFORMATION: Exon 6 of hCD45RC

<400> SEQUENCE: 24
gatgtcccag gagagaggag tacagccagc acctttccta cagacccagt ttccccattg      60
acaaccaccc tcagccttgc acaccacagc tctgctgcct tacctgcacg cacctccaac    120
accaccatca cagcgaacac ctca                                            144

<210> SEQ ID NO 25
<211> LENGTH: 30
<212> TYPE: PRT
<213> ORGANISM: Artificial Sequence
<220> FEATURE:
<223> OTHER INFORMATION: VH-FR1
```

<400> SEQUENCE: 25

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr
                20                  25                  30

<210> SEQ ID NO 26
<211> LENGTH: 14
<212> TYPE: PRT
<213> ORGANISM: Artificial Sequence
<220> FEATURE:
<223> OTHER INFORMATION: VH-FR2

<400> SEQUENCE: 26

Trp Val Lys Gln Arg Pro Gly His Gly Leu Glu Trp Ile Gly
1               5                   10

<210> SEQ ID NO 27
<211> LENGTH: 32
<212> TYPE: PRT
<213> ORGANISM: Artificial Sequence
<220> FEATURE:
<223> OTHER INFORMATION: VH-FR3

<400> SEQUENCE: 27

Lys Ala Thr Leu Thr Ala Asp Thr Ser Ser Thr Ala Tyr Met Gln
1               5                   10                  15

Leu Ser Ser Leu Thr Ser Glu Asp Ser Ala Ile Tyr Tyr Cys Val Arg
                20                  25                  30

<210> SEQ ID NO 28
<211> LENGTH: 11
<212> TYPE: PRT
<213> ORGANISM: Artificial Sequence
<220> FEATURE:
<223> OTHER INFORMATION: VH-FR4

<400> SEQUENCE: 28

Trp Gly Gln Gly Thr Thr Leu Thr Val Ser Ser
1               5                   10

<210> SEQ ID NO 29
<211> LENGTH: 30
<212> TYPE: PRT
<213> ORGANISM: Artificial Sequence
<220> FEATURE:
<223> OTHER INFORMATION: VH-FR1

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
                20                  25                  30

<210> SEQ ID NO 30
<211> LENGTH: 14
<212> TYPE: PRT
<213> ORGANISM: Artificial Sequence
<220> FEATURE:
<223> OTHER INFORMATION: VH-FR2

<400> SEQUENCE: 30

Trp Val Arg Gln Ala Pro Gly Gln Gly Leu Glu Trp Ile Gly
1               5                   10

```
<210> SEQ ID NO 31
<211> LENGTH: 32
<212> TYPE: PRT
<213> ORGANISM: Artificial Sequence
<220> FEATURE:
<223> OTHER INFORMATION: VH-FR3

<400> SEQUENCE: 31

Arg Val Thr Leu Thr Ala Asp Thr Ser Ile Ser Thr Ala Tyr Met Glu
1               5                   10                  15

Leu Ser Arg Leu Arg Ser Asp Asp Thr Val Val Tyr Tyr Cys Val Arg
            20                  25                  30

<210> SEQ ID NO 32
<211> LENGTH: 11
<212> TYPE: PRT
<213> ORGANISM: Artificial Sequence
<220> FEATURE:
<223> OTHER INFORMATION: VH-FR4

<400> SEQUENCE: 32

Trp Gly Gln Gly Thr Leu Val Thr Val Ser Ser
1               5                   10

<210> SEQ ID NO 33
<211> LENGTH: 30
<212> TYPE: PRT
<213> ORGANISM: Artificial Sequence
<220> FEATURE:
<223> OTHER INFORMATION: VH-FR1

<400> SEQUENCE: 33

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr
            20                  25                  30

<210> SEQ ID NO 34
<211> LENGTH: 14
<212> TYPE: PRT
<213> ORGANISM: Artificial Sequence
<220> FEATURE:
<223> OTHER INFORMATION: VH-FR2

<400> SEQUENCE: 34

Trp Val Arg Gln Met Pro Gly Lys Gly Leu Glu Trp Ile Gly
1               5                   10

<210> SEQ ID NO 35
<211> LENGTH: 32
<212> TYPE: PRT
<213> ORGANISM: Artificial Sequence
<220> FEATURE:
<223> OTHER INFORMATION: VH-FR3

<400> SEQUENCE: 35

Gln Val Thr Leu Ser Ala Asp Lys Ser Ile Ser Thr Ala Tyr Leu Gln
1               5                   10                  15

Leu Ser Ser Leu Lys Ala Ser Asp Thr Ala Met Tyr Tyr Cys Val Arg
            20                  25                  30

<210> SEQ ID NO 36
<211> LENGTH: 30
<212> TYPE: PRT
<213> ORGANISM: Artificial Sequence
```

<220> FEATURE:
<223> OTHER INFORMATION: VH-FR1

<400> SEQUENCE: 36

Gln Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr
            20                  25                  30

<210> SEQ ID NO 37
<211> LENGTH: 14
<212> TYPE: PRT
<213> ORGANISM: Artificial Sequence
<220> FEATURE:
<223> OTHER INFORMATION: VH-FR2

<400> SEQUENCE: 37

Trp Ile Arg Gln Ala Pro Gly Lys Gly Leu Glu Trp Ile Gly
1               5                   10

<210> SEQ ID NO 38
<211> LENGTH: 32
<212> TYPE: PRT
<213> ORGANISM: Artificial Sequence
<220> FEATURE:
<223> OTHER INFORMATION: VH-FR3

<400> SEQUENCE: 38

Arg Phe Thr Leu Ser Ala Asp Thr Ala Lys Asn Ser Ala Tyr Leu Gln
1               5                   10                  15

Met Asn Ser Leu Arg Ala Glu Asp Thr Ala Val Tyr Tyr Cys Val Arg
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: VH-FR1

<400> SEQUENCE: 39

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: VH-FR1

<400> SEQUENCE: 40

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: VH-FR3

```
<400> SEQUENCE: 41

Arg Phe Thr Leu Ser Ala Asp Thr Ala Lys Asn Ser Leu Tyr Leu Gln
1               5                   10                  15

Met Asn Ser Leu Arg Ala Glu Asp Thr Ala Val Tyr Tyr Cys Val Arg
                20                  25                  30

<210> SEQ ID NO 42
<211> LENGTH: 30
<212> TYPE: PRT
<213> ORGANISM: Artificial Sequence
<220> FEATURE:
<223> OTHER INFORMATION: VH-FR1

<400> SEQUENCE: 42

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
                20                  25                  30

<210> SEQ ID NO 43
<211> LENGTH: 14
<212> TYPE: PRT
<213> ORGANISM: Artificial Sequence
<220> FEATURE:
<223> OTHER INFORMATION: VH-FR2

<400> SEQUENCE: 43

Trp Ile Arg Gln Ala Pro Gly Lys Gly Leu Glu Trp Val Gly
1               5                   10

<210> SEQ ID NO 44
<211> LENGTH: 23
<212> TYPE: PRT
<213> ORGANISM: Artificial Sequence
<220> FEATURE:
<223> OTHER INFORMATION: VL-FR1

<400> SEQUENCE: 44

Gln Ile Val Leu Thr Gln Ser Pro Thr Ile Met Ser Ala Ser Pro Gly
1               5                   10                  15

Glu Lys Val Thr Ile Thr Cys
                20

<210> SEQ ID NO 45
<211> LENGTH: 15
<212> TYPE: PRT
<213> ORGANISM: Artificial Sequence
<220> FEATURE:
<223> OTHER INFORMATION: VL-FR2

<400> SEQUENCE: 45

Trp Phe Gln Gln Lys Thr Gly Thr Ser Pro Arg Leu Trp Ile Tyr
1               5                   10                  15

<210> SEQ ID NO 46
<211> LENGTH: 32
<212> TYPE: PRT
<213> ORGANISM: Artificial Sequence
<220> FEATURE:
<223> OTHER INFORMATION: VL-FR3
<220> FEATURE:
<221> NAME/KEY: SITE
<222> LOCATION: 15
<223> OTHER INFORMATION: Xaa is selected from Tyr (Y) and Phe (F)
```

<400> SEQUENCE: 46

Gly Val Pro Ala Arg Phe Ser Gly Ser Gly Ser Gly Thr Ser Xaa Ser
1               5                   10                  15

Leu Thr Ile Ser Arg Met Glu Ala Glu Asp Ala Ala Thr Tyr Tyr Cys
            20                  25                  30

<210> SEQ ID NO 47
<211> LENGTH: 9
<212> TYPE: PRT
<213> ORGANISM: Artificial Sequence
<220> FEATURE:
<223> OTHER INFORMATION: VL-FR4

<400> SEQUENCE: 47

Gly Ala Gly Thr Lys Leu Glu Leu Lys
1               5

<210> SEQ ID NO 48
<211> LENGTH: 23
<212> TYPE: PRT
<213> ORGANISM: Artificial Sequence
<220> FEATURE:
<223> OTHER INFORMATION: VL-FR1

<400> SEQUENCE: 48

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 49
<211> LENGTH: 15
<212> TYPE: PRT
<213> ORGANISM: Artificial Sequence
<220> FEATURE:
<223> OTHER INFORMATION: VL-FR2

<400> SEQUENCE: 49

Trp Phe Gln Gln Lys Pro Gly Lys Ala Pro Lys Leu Trp Ile Tyr
1               5                   10                  15

<210> SEQ ID NO 50
<211> LENGTH: 32
<212> TYPE: PRT
<213> ORGANISM: Artificial Sequence
<220> FEATURE:
<223> OTHER INFORMATION: VL-FR3
<220> FEATURE:
<221> NAME/KEY: SITE
<222> LOCATION: 15
<223> OTHER INFORMATION: Xaa is selected from Tyr (Y) and Phe (F)

<400> SEQUENCE: 50

Gly Val Pro Ser Arg Phe Ser Gly Ser Gly Ser Gly Thr Glu Xaa Thr
1               5                   10                  15

Leu Thr Ile Ser Ser Leu Gln Pro Glu Asp Phe Ala Thr Tyr Tyr Cys
            20                  25                  30

<210> SEQ ID NO 51
<211> LENGTH: 9
<212> TYPE: PRT
<213> ORGANISM: Artificial Sequence
<220> FEATURE:
<223> OTHER INFORMATION: VL-FR4

<400> SEQUENCE: 51

Gly Gly Gly Thr Lys Val Glu Ile Lys
1               5

<210> SEQ ID NO 52
<211> LENGTH: 23
<212> TYPE: PRT
<213> ORGANISM: Artificial Sequence
<220> FEATURE:
<223> OTHER INFORMATION: VL-FR1

<400> SEQUENCE: 52

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 53
<211> LENGTH: 15
<212> TYPE: PRT
<213> ORGANISM: Artificial Sequence
<220> FEATURE:
<223> OTHER INFORMATION: VL-FR2

<400> SEQUENCE: 53

Trp Phe Gln Gln Lys Pro Asp Gln Ser Pro Lys Leu Trp Ile Tyr
1               5                   10                  15

<210> SEQ ID NO 54
<211> LENGTH: 32
<212> TYPE: PRT
<213> ORGANISM: Artificial Sequence
<220> FEATURE:
<223> OTHER INFORMATION: VL-FR3
<220> FEATURE:
<221> NAME/KEY: SITE
<222> LOCATION: 15
<223> OTHER INFORMATION: Xaa is selected from Tyr (Y) and Phe (F)

<400> SEQUENCE: 54

Gly Val Pro Ser Arg Phe Ser Gly Ser Gly Ser Gly Thr Asp Xaa Thr
1               5                   10                  15

Leu Thr Ile Asn Ser Leu Glu Ala Glu Asp Ala Ala Thr Tyr Tyr Cys
            20                  25                  30

<210> SEQ ID NO 55
<211> LENGTH: 23
<212> TYPE: PRT
<213> ORGANISM: Artificial Sequence
<220> FEATURE:
<223> OTHER INFORMATION: VL-FR1

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 56
<211> LENGTH: 15
<212> TYPE: PRT
<213> ORGANISM: Artificial Sequence
<220> FEATURE:
<223> OTHER INFORMATION: VL-FR2

<400> SEQUENCE: 56

```
Trp Phe Gln Gln Lys Pro Gly Gln Ala Pro Arg Leu Trp Ile Tyr
1               5                   10                  15
```

<210> SEQ ID NO 57
<211> LENGTH: 32
<212> TYPE: PRT
<213> ORGANISM: Artificial Sequence
<220> FEATURE:
<223> OTHER INFORMATION: VL-FR3
<220> FEATURE:
<221> NAME/KEY: SITE
<222> LOCATION: 15
<223> OTHER INFORMATION: Xaa is selected from Tyr (Y) and Phe (F)

<400> SEQUENCE: 57

```
Gly Ile Pro Ala Arg Phe Ser Gly Ser Gly Ser Gly Thr Asp Xaa Thr
1               5                   10                  15

Leu Thr Ile Ser Ser Leu Glu Pro Glu Asp Phe Ala Val Tyr Tyr Cys
            20                  25                  30
```

<210> SEQ ID NO 58
<211> LENGTH: 15
<212> TYPE: PRT
<213> ORGANISM: Artificial Sequence
<220> FEATURE:
<223> OTHER INFORMATION: VL-FR2

<400> SEQUENCE: 58

```
Trp Tyr Gln Gln Lys Pro Gly Lys Ala Pro Lys Leu Trp Ile Tyr
1               5                   10                  15
```

<210> SEQ ID NO 59
<211> LENGTH: 15
<212> TYPE: PRT
<213> ORGANISM: Artificial Sequence
<220> FEATURE:
<223> OTHER INFORMATION: VL-FR2

<400> SEQUENCE: 59

```
Trp Tyr Gln Gln Lys Pro Asp Gln Ser Pro Lys Leu Trp Ile Tyr
1               5                   10                  15
```

<210> SEQ ID NO 60
<211> LENGTH: 15
<212> TYPE: PRT
<213> ORGANISM: Artificial Sequence
<220> FEATURE:
<223> OTHER INFORMATION: VL-FR2

<400> SEQUENCE: 60

```
Trp Tyr Gln Gln Lys Pro Gly Gln Ala Pro Arg Leu Trp Ile Tyr
1               5                   10                  15
```

<210> SEQ ID NO 61
<211> LENGTH: 114
<212> TYPE: PRT
<213> ORGANISM: Artificial Sequence
<220> FEATURE:
<223> OTHER INFORMATION: Murine HCVR

<400> SEQUENCE: 61

```
Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Tyr Ile Gly Trp Val Lys Gln Arg Pro Gly His Gly Leu Glu Trp Ile
```

```
                35                  40                  45
Gly Asp Ile Phe Pro Gly Gly Asp Tyr Ala Asn Ser Asn Glu Lys Phe
 50                  55                  60
Lys Gly Lys Ala Thr Leu Thr Ala Asp Thr Ser Ser Thr Ala Tyr
 65                  70                  75                  80
Met Gln Leu Ser Ser Leu Thr Ser Glu Asp Ser Ala Ile Tyr Tyr Cys
                 85                  90                  95
Val Arg Arg Asn Phe Asp Tyr Trp Gly Gln Gly Thr Thr Leu Thr Val
                100                 105                 110
Ser Ser

<210> SEQ ID NO 62
<211> LENGTH: 114
<212> TYPE: PRT
<213> ORGANISM: Artificial Sequence
<220> FEATURE:
<223> OTHER INFORMATION: Humanized HCVR

<400> SEQUENCE: 62

Gln Val Gln Leu Val Gln Ser Gly Ala Glu Val Lys Lys Pro Gly Ala
 1                   5                  10                  15
Ser Val Lys Val Ser Cys Lys Ala Ser Gly Tyr Thr Phe Thr Asn Tyr
                 20                  25                  30
Tyr Ile Gly Trp Val Arg Gln Ala Pro Gly Gln Gly Leu Glu Trp Ile
                 35                  40                  45
Gly Asp Ile Phe Pro Gly Gly Asp Tyr Ala Asn Ser Asn Glu Lys Phe
 50                  55                  60
Lys Gly Arg Val Thr Leu Thr Ala Asp Thr Ser Ile Ser Thr Ala Tyr
 65                  70                  75                  80
Met Glu Leu Ser Arg Leu Arg Ser Asp Asp Thr Val Val Tyr Tyr Cys
                 85                  90                  95
Val Arg Arg Asn Phe Asp Tyr Trp Gly Gln Gly Thr Leu Val Thr Val
                100                 105                 110
Ser Ser

<210> SEQ ID NO 63
<211> LENGTH: 114
<212> TYPE: PRT
<213> ORGANISM: Artificial Sequence
<220> FEATURE:
<223> OTHER INFORMATION: Humanized HCVR

<400> SEQUENCE: 63

Glu Val Gln Leu Val Gln Ser Gly Ala Glu Val Lys Lys Pro Gly Glu
 1                   5                  10                  15
Ser Leu Lys Ile Ser Cys Lys Ala Ser Gly Tyr Thr Phe Thr Asn Tyr
                 20                  25                  30
Tyr Ile Gly Trp Val Arg Gln Met Pro Gly Lys Gly Leu Glu Trp Ile
                 35                  40                  45
Gly Asp Ile Phe Pro Gly Gly Asp Tyr Ala Asn Ser Asn Glu Lys Phe
 50                  55                  60
Lys Gly Gln Val Thr Leu Ser Ala Asp Lys Ser Ile Ser Thr Ala Tyr
 65                  70                  75                  80
Leu Gln Leu Ser Ser Leu Lys Ala Ser Asp Thr Ala Met Tyr Tyr Cys
                 85                  90                  95
Val Arg Arg Asn Phe Asp Tyr Trp Gly Gln Gly Thr Leu Val Thr Val
                100                 105                 110
```

Ser Ser

<210> SEQ ID NO 64
<211> LENGTH: 114
<212> TYPE: PRT
<213> ORGANISM: Artificial Sequence
<220> FEATURE:
<223> OTHER INFORMATION: Humanized HCVR

<400> SEQUENCE: 64

Gln Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Tyr Ile Gly Trp Ile Arg Gln Ala Pro Gly Lys Gly Leu Glu Trp Ile
        35                  40                  45

Gly Asp Ile Phe Pro Gly Gly Asp Tyr Ala Asn Ser Asn Glu Lys Val
    50                  55                  60

Lys Gly Arg Phe Thr Leu Ser Ala Asp Thr Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Val Arg Arg Asn Phe Asp Tyr Trp Gly Gln Gly Thr Leu Val Thr Val
            100                 105                 110

Ser Ser

<210> SEQ ID NO 65
<211> LENGTH: 114
<212> TYPE: PRT
<213> ORGANISM: Artificial Sequence
<220> FEATURE:
<223> OTHER INFORMATION: Humanized HCVR

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile Gly Trp Val Arg Gln Ala Pro Gly Gln Gly Leu Glu Trp Ile
        35                  40                  45

Gly Asp Ile Phe Pro Gly Gly Tyr Thr Asn Tyr Ala Glu Lys Phe
    50                  55                  60

Gln Gly Arg Val Thr Leu Thr Ala Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Val Arg Arg Asn Phe Asp Tyr Trp Gly Gln Gly Thr Leu Val Thr Val
            100                 105                 110

Ser Ser

<210> SEQ ID NO 66
<211> LENGTH: 114
<212> TYPE: PRT
<213> ORGANISM: Artificial Sequence
<220> FEATURE:
<223> OTHER INFORMATION: Humanized HCVR

<400> SEQUENCE: 66

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Tyr Ile Gly Trp Val Arg Gln Met Pro Gly Lys Gly Leu Glu Trp Ile
        35                  40                  45

Gly Asp Ile Phe Pro Gly Gly Ser Tyr Thr Asn Tyr Ser Glu Ser Phe
    50                  55                  60

Gln Gly Gln Val Thr Leu Ser Ala Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Arg Asn Phe Asp Tyr Trp Gly Gln Gly Thr Leu Val Thr Val
            100                 105                 110

Ser Ser
```

<210> SEQ ID NO 67
<211> LENGTH: 114
<212> TYPE: PRT
<213> ORGANISM: Artificial Sequence
<220> FEATURE:
<223> OTHER INFORMATION: Humanized HCVR

<400> SEQUENCE: 67

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Tyr Ile Gly Trp Ile Arg Gln Ala Pro Gly Lys Gly Leu Glu Trp Ile
        35                  40                  45

Gly Asp Ile Phe Pro Gly Gly Ser Tyr Thr Asn Tyr Ala Asp Ser Val
    50                  55                  60

Lys Gly Arg Phe Thr Leu Ser Ala Asp Thr Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Arg Asn Phe Asp Tyr Trp Gly Gln Gly Thr Leu Val Thr Val
            100                 105                 110

Ser Ser
```

<210> SEQ ID NO 68
<211> LENGTH: 114
<212> TYPE: PRT
<213> ORGANISM: Artificial Sequence
<220> FEATURE:
<223> OTHER INFORMATION: Humanized HCVR

<400> SEQUENCE: 68

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile Gly Trp Val Arg Gln Ala Pro Gly Gln Gly Leu Glu Trp Ile
        35                  40                  45

Gly Arg Ile Phe Pro Gly Gly Gly Tyr Thr Asn Tyr Ala Gln Lys Phe
    50                  55                  60

Gln Gly Arg Val Thr Leu Thr Ala Asp Thr Ser Ile Ser Thr Ala Tyr
```

```
                65                  70                  75                  80
Met Glu Leu Ser Arg Leu Arg Ser Asp Thr Val Val Tyr Tyr Cys
                    85                  90                  95

Val Arg Arg Asn Phe Asp Tyr Trp Gly Gln Gly Thr Leu Val Thr Val
                100                 105                 110

Ser Ser
```

<210> SEQ ID NO 69
<211> LENGTH: 114
<212> TYPE: PRT
<213> ORGANISM: Artificial Sequence
<220> FEATURE:
<223> OTHER INFORMATION: Humanized HCVR

<400> SEQUENCE: 69

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile Gly Trp Val Arg Gln Met Pro Gly Lys Gly Leu Glu Trp Ile
            35                  40                  45

Gly Ile Ile Phe Pro Gly Gly Ser Tyr Thr Asn Tyr Ser Pro Ser Phe
        50                  55                  60

Gln Gly Gln Val Thr Leu Ser Ala Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Arg Asn Phe Asp Tyr Trp Gly Gln Gly Thr Leu Val Thr Val
                100                 105                 110

Ser Ser
```

<210> SEQ ID NO 70
<211> LENGTH: 114
<212> TYPE: PRT
<213> ORGANISM: Artificial Sequence
<220> FEATURE:
<223> OTHER INFORMATION: Humanized HCVR

<400> SEQUENCE: 70

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
                20                  25                  30

Tyr Ile Gly Trp Ile Arg Gln Ala Pro Gly Lys Gly Leu Glu Trp Val
            35                  40                  45

Gly Asp Ile Phe Ser Gly Gly Ser Tyr Thr Asn Tyr Ala Asp Ser Val
        50                  55                  60

Lys Gly Arg Phe Thr Leu Ser Ala Asp Thr Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Arg Asn Phe Asp Tyr Trp Gly Gln Gly Thr Leu Val Thr Val
                100                 105                 110

Ser Ser
```

<210> SEQ ID NO 71
<211> LENGTH: 107

```
<212> TYPE: PRT
<213> ORGANISM: Artificial Sequence
<220> FEATURE:
<223> OTHER INFORMATION: Murine LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 71

Gln Ile Val Leu Thr Gln Ser Pro Thr Ile Met Ser Ala Ser Pro Gly
1               5                   10                  15

Glu Lys Val Thr Ile Thr Cys Ser Ala Ser Ser Val Ser Xaa Tyr
            20                  25                  30

Met His Trp Phe Gln Gln Lys Thr Gly Thr Ser Pro Arg Leu Trp Ile
        35                  40                  45

Tyr Asn Thr Ser Asn Leu Pro Ser Gly Val Pro Ala Arg Phe Ser Gly
    50                  55                  60

Ser Gly Ser Gly Thr Ser Phe Ser Leu Thr Ile Ser Arg Met Glu Ala
65                  70                  75                  80

Glu Asp Ala Ala Thr Tyr Tyr Cys Gln Gln Arg Ser Ser Tyr Pro Leu
                85                  90                  95

Thr Phe Gly Ala Gly Thr Lys Leu Glu Leu Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 72

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Val Ser Xaa Tyr
            20                  25                  30

Met His Trp Phe Gln Gln Lys Pro Gly Lys Ala Pro Lys Leu Trp Ile
        35                  40                  45

Tyr Asn Thr Ser Asn Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Arg Ser Ser Tyr Pro Leu
                85                  90                  95

Thr Phe Gly Gly Gly Thr Lys Val Glu Ile Lys
            100                 105

<210> SEQ ID NO 73
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
```

```
<223> OTHER INFORMATION: Xaa is selected from Asn (N), Ser (S) and Gly
      (G)

<400> SEQUENCE: 73

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Val Ser Xaa Tyr
            20                  25                  30

Met His Trp Phe Gln Gln Lys Pro Asp Gln Ser Pro Lys Leu Trp Ile
            35                  40                  45

Tyr Asn Thr Ser Asn Leu Pro Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Arg Ser Ser Tyr Pro Leu
                85                  90                  95

Thr Phe Gly Gly Gly Thr Lys Val Glu Ile Lys
            100                 105

<210> SEQ ID NO 74
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Xaa Tyr
            20                  25                  30

Met His Trp Phe Gln Gln Lys Pro Gly Gln Ala Pro Arg Leu Trp Ile
            35                  40                  45

Tyr Asn Thr Ser Asn Leu Pro Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Tyr Pro Leu
                85                  90                  95

Thr Phe Gly Gly Gly Thr Lys Val Glu Ile Lys
            100                 105

<210> SEQ ID NO 75
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 75

Asp Ile Gln Leu Thr Gln Ser Pro Ser Phe Leu Ser Ala Ser Val Gly
1               5                   10                  15
```

Asp Arg Val Thr Ile Thr Cys Arg Ala Ser Ser Val Ser Xaa Tyr
            20                  25                  30

Met His Trp Tyr Gln Gln Lys Pro Gly Lys Ala Pro Lys Leu Trp Ile
        35                  40                  45

Tyr Asn Thr Ser Asn Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Arg Ser Ser Tyr Pro Leu
                85                  90                  95

Thr Phe Gly Gly Gly Thr Lys Val Glu Ile Lys
            100                 105

<210> SEQ ID NO 76
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 76

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Val Ser Xaa Tyr
            20                  25                  30

Met His Trp Tyr Gln Gln Lys Pro Asp Gln Ser Pro Lys Leu Trp Ile
        35                  40                  45

Tyr Asn Thr Ser Asn Ser Pro Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Arg Ser Ser Tyr Pro Leu
                85                  90                  95

Thr Phe Gly Gly Gly Thr Lys Val Glu Ile Lys
            100                 105

<210> SEQ ID NO 77
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Xaa Tyr
            20                  25                  30

Met His Trp Phe Gln Gln Lys Pro Gly Gln Ala Pro Arg Leu Trp Ile
        35                  40                  45

```
Tyr Asn Thr Ser Asn Leu Pro Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Tyr Pro Leu
                85                  90                  95

Thr Phe Gly Gly Gly Thr Lys Val Glu Ile Lys
                100                 105

<210> SEQ ID NO 78
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 78

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Xaa Tyr
                20                  25                  30

Met His Trp Tyr Gln Gln Lys Pro Gly Lys Ala Pro Lys Leu Trp Ile
        35                  40                  45

Tyr Ala Thr Ser Asn Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Arg Ser Ser Tyr Pro Leu
                85                  90                  95

Thr Phe Gly Gly Gly Thr Lys Val Glu Ile Lys
                100                 105

<210> SEQ ID NO 79
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 79

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Val Ser Xaa Tyr
                20                  25                  30

Met His Trp Tyr Gln Gln Lys Pro Asp Gln Ser Pro Lys Leu Trp Ile
        35                  40                  45

Tyr Asn Thr Ser Asn Ser Pro Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Arg Ser Ser Tyr Pro Leu
```

```
                    85                  90                  95

Thr Phe Gly Gly Gly Thr Lys Val Glu Ile Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 80

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Xaa Tyr
            20                  25                  30

Met His Trp Tyr Gln Gln Lys Pro Gly Gln Ala Pro Arg Leu Trp Ile
            35                  40                  45

Tyr Asn Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Tyr Pro Leu
                85                  90                  95

Thr Phe Gly Gly Gly Thr Lys Val Glu Ile Lys
            100                 105

<210> SEQ ID NO 81
<211> LENGTH: 106
<212> TYPE: PRT
<213> ORGANISM: Artificial Sequence
<220> FEATURE:
<223> OTHER INFORMATION: Murine LCVR

<400> SEQUENCE: 81

Gln Ile Val Leu Thr Gln Ser Pro Thr Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Thr Gly Thr Ser Pro Arg Leu Trp Ile Tyr
            35                  40                  45

Asn Thr Ser Asn Leu Pro Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 82
<211> LENGTH: 106
<212> TYPE: PRT
<213> ORGANISM: Artificial Sequence
<220> FEATURE:
<223> OTHER INFORMATION: Humanized LCVR
```

<400> SEQUENCE: 82

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Val Ser Tyr Met
            20                  25                  30

His Trp Phe Gln Gln Lys Pro Gly Lys Ala Pro Lys Leu Trp Ile Tyr
            35                  40                  45

Asn Thr Ser Asn Leu Pro Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Arg Ser Ser Tyr Pro Leu Thr
                85                  90                  95

Phe Gly Gly Gly Thr Lys Val Glu Ile Lys
            100                 105

<210> SEQ ID NO 83
<211> LENGTH: 106
<212> TYPE: PRT
<213> ORGANISM: Artificial Sequence
<220> FEATURE:
<223> OTHER INFORMATION: Humanized LCVR

<400> SEQUENCE: 83

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Val Ser Tyr Met
            20                  25                  30

His Trp Phe Gln Gln Lys Pro Asp Gln Ser Pro Lys Leu Trp Ile Tyr
            35                  40                  45

Asn Thr Ser Asn Leu Pro Ser Gly Val Pro Ser Arg Phe Ser Gly Ser
        50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys Gln Gln Arg Ser Ser Tyr Pro Leu Thr
                85                  90                  95

Phe Gly Gly Gly Thr Lys Val Glu Ile Lys
            100                 105

<210> SEQ ID NO 84
<211> LENGTH: 106
<212> TYPE: PRT
<213> ORGANISM: Artificial Sequence
<220> FEATURE:
<223> OTHER INFORMATION: Humanized LCVR

<400> SEQUENCE: 84

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Phe Gln Gln Lys Pro Gly Gln Ala Pro Arg Leu Trp Ile Tyr
            35                  40                  45

Asn Thr Ser Asn Leu Pro Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys
            100                 105

<210> SEQ ID NO 85
<211> LENGTH: 106
<212> TYPE: PRT
<213> ORGANISM: Artificial Sequence
<220> FEATURE:
<223> OTHER INFORMATION: Humanized LCVR

<400> SEQUENCE: 85

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Trp Ile Tyr
            35                  40                  45

Asn Thr Ser Asn Leu Pro Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Arg Ser Ser Tyr Pro Leu Thr
                85                  90                  95

Phe Gly Gly Gly Thr Lys Val Glu Ile Lys
            100                 105

<210> SEQ ID NO 86
<211> LENGTH: 106
<212> TYPE: PRT
<213> ORGANISM: Artificial Sequence
<220> FEATURE:
<223> OTHER INFORMATION: Humanized LCVR

<400> SEQUENCE: 86

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Val Ser Tyr Met
            20                  25                  30

His Trp Tyr Gln Gln Lys Pro Asp Gln Ser Pro Lys Leu Trp Ile Tyr
            35                  40                  45

Asn Thr Ser Asn Ser Pro Ser Gly Val Pro Ser Arg Phe Ser Gly Ser
        50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Arg Ser Ser Tyr Pro Leu Thr
                85                  90                  95

Phe Gly Gly Gly Thr Lys Val Glu Ile Lys
            100                 105

<210> SEQ ID NO 87
<211> LENGTH: 106
<212> TYPE: PRT
<213> ORGANISM: Artificial Sequence
<220> FEATURE:
<223> OTHER INFORMATION: Humanized LCVR

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Phe Gln Gln Lys Pro Gly Gln Ala Pro Arg Leu Trp Ile Tyr
            35                  40                  45

Asn Thr Ser Asn Leu Pro Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys
            100                 105

<210> SEQ ID NO 88
<211> LENGTH: 106
<212> TYPE: PRT
<213> ORGANISM: Artificial Sequence
<220> FEATURE:
<223> OTHER INFORMATION: Humanized LCVR

<400> SEQUENCE: 88

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Trp Ile Tyr
            35                  40                  45

Ala Thr Ser Asn Leu Gln Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Arg Ser Ser Tyr Pro Leu Thr
                85                  90                  95

Phe Gly Gly Gly Thr Lys Val Glu Ile Lys
            100                 105

<210> SEQ ID NO 89
<211> LENGTH: 106
<212> TYPE: PRT
<213> ORGANISM: Artificial Sequence
<220> FEATURE:
<223> OTHER INFORMATION: Humanized LCVR

<400> SEQUENCE: 89

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Val Ser Tyr Met
            20                  25                  30

His Trp Tyr Gln Gln Lys Pro Asp Gln Ser Pro Lys Leu Trp Ile Tyr
            35                  40                  45

Asn Thr Ser Asn Ser Pro Ser Gly Val Pro Ser Arg Phe Ser Gly Ser
        50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys His Gln Arg Ser Ser Tyr Pro Leu Thr
                85                  90                  95

```
Phe Gly Gly Gly Thr Lys Val Glu Ile Lys
            100                 105

<210> SEQ ID NO 90
<211> LENGTH: 106
<212> TYPE: PRT
<213> ORGANISM: Artificial Sequence
<220> FEATURE:
<223> OTHER INFORMATION: Humanized LCVR

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Leu Trp Ile Tyr
        35                  40                  45

Asn Thr Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gly Gly Thr Lys Val Glu Ile Lys
            100                 105

<210> SEQ ID NO 91
<211> LENGTH: 330
<212> TYPE: PRT
<213> ORGANISM: Artificial Sequence
<220> FEATURE:
<223> OTHER INFORMATION: Human HCCR

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
                180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 92
<211> LENGTH: 107
<212> TYPE: PRT
<213> ORGANISM: Artificial Sequence
<220> FEATURE:
<223> OTHER INFORMATION: Human LCCR

<400> SEQUENCE: 92

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 93
<211> LENGTH: 323
<212> TYPE: PRT
<213> ORGANISM: Artificial Sequence
<220> FEATURE:
<223> OTHER INFORMATION: Murine HCCR

<400> SEQUENCE: 93

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45
```

-continued

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly

<210> SEQ ID NO 94
<211> LENGTH: 107
<212> TYPE: PRT
<213> ORGANISM: Artificial Sequence
<220> FEATURE:
<223> OTHER INFORMATION: Murine LCCR

<400> SEQUENCE: 94

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser

```
                85                  90                  95
Pro Ile Val Lys Ser Phe Asn Arg Asn Glu Cys
                100                 105
```

<210> SEQ ID NO 95
<211> LENGTH: 342
<212> TYPE: DNA
<213> ORGANISM: Artificial Sequence
<220> FEATURE:
<223> OTHER INFORMATION: Murine HCVR

<400> SEQUENCE: 95

```
caggtccagc tgcaacagtc tggcgctgag ctggttaggc ctgggacttc agtgaagatg    60
tcctgcaagg ccgctggata caccttcact aactactaca taggttgggt aaagcagagg   120
cctggacatg gccttgagtg gatcggagat atttttcctg aggtgactat tgccaacagc   180
aatgagaagt tcaagggcaa agccacactg actgcagaca catcctccag cacagcctac   240
atgcagctca gcagcctgac atctgaggac tctgccatct attactgtgt gagaaggaac   300
tttgactact ggggccaagg caccactctc acagtgtcct ca                      342
```

<210> SEQ ID NO 96
<211> LENGTH: 318
<212> TYPE: DNA
<213> ORGANISM: Artificial Sequence
<220> FEATURE:
<223> OTHER INFORMATION: Murine LCVR

<400> SEQUENCE: 96

```
caaattgttc tcacccagtc tccaacaatc atgtctgcat ctccagggga gaaggtgacc    60
ataacctgca gtgccagctc aagtgtaagt tacatgcact ggttccagca gaagacaggc   120
acttctccca gactctggat ttataacaca tccaacctgc cttctggagt ccccgctcgc   180
ttcagtggca gtggatctgg gacctcttac tctctcacaa tcagccgaat ggaggctgaa   240
gatgctgcca cttattactg ccagcaaagg agtagttacc cactcacgtt cggtgctggg   300
accaagctgg agctgaaa                                                 318
```

<210> SEQ ID NO 97
<211> LENGTH: 990
<212> TYPE: DNA
<213> ORGANISM: Artificial Sequence
<220> FEATURE:
<223> OTHER INFORMATION: Human HCCR

<400> SEQUENCE: 97

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggggga  360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
```

```
gagtacaagt gcaaggtctc caacaaagcc ctcccagccc ccatcgagaa aaccatctcc      660
aaagccaaag ggcagccccg agaaccacag gtgtacaccc tgcccccatc ccggaggag       720 atgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctat agcaagctca ccgtggacaa gagcaggtgg      900
cagcagggga acgtcttctc atgctccgtg atgcatgagg ctctgcacaa ccactacacg      960
cagaagagcc tctccctgtc cccgggtaaa                                       990
```

<210> SEQ ID NO 98
<211> LENGTH: 321
<212> TYPE: DNA
<213> ORGANISM: Artificial Sequence
<220> FEATURE:
<223> OTHER INFORMATION: Human LCCR

<400> SEQUENCE: 98

```
cgaactgtgg ctgcaccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg t                                                321
```

<210> SEQ ID NO 99
<211> LENGTH: 1306
<212> TYPE: PRT
<213> ORGANISM: Homo sapiens
<220> FEATURE:
<223> OTHER INFORMATION: hCD45
<300> PUBLICATION INFORMATION:
<308> DATABASE ACCESSION NUMBER: UniProt Accession P08575-3
<309> DATABASE ENTRY DATE: 2018 03 28

<400> SEQUENCE: 99

```
Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
        115                 120                 125

Gly Ser Ala Ala Asn Ala Lys Leu Asn Pro Thr Pro Gly Ser Asn Ala
    130                 135                 140

Ile Ser Asp Val Pro Gly Glu Arg Ser Thr Ala Ser Thr Phe Pro Thr
145                 150                 155                 160
```

-continued

```
Asp Pro Val Ser Pro Leu Thr Thr Thr Leu Ser Leu Ala His His Ser
            165                 170                 175

Ser Ala Ala Leu Pro Ala Arg Thr Ser Asn Thr Thr Ile Thr Ala Asn
        180                 185                 190

Thr Ser Asp Ala Tyr Leu Asn Ala Ser Glu Thr Thr Thr Leu Ser Pro
        195                 200                 205

Ser Gly Ser Ala Val Ile Ser Thr Thr Thr Ile Ala Thr Thr Pro Ser
        210                 215                 220

Lys Pro Thr Cys Asp Glu Lys Tyr Ala Asn Ile Thr Val Asp Tyr Leu
225                 230                 235                 240

Tyr Asn Lys Glu Thr Lys Leu Phe Thr Ala Lys Leu Asn Val Asn Glu
                245                 250                 255

Asn Val Glu Cys Gly Asn Asn Thr Cys Thr Asn Asn Glu Val His Asn
                260                 265                 270

Leu Thr Glu Cys Lys Asn Ala Ser Val Ser Ile Ser His Asn Ser Cys
            275                 280                 285

Thr Ala Pro Asp Lys Thr Leu Ile Leu Asp Val Pro Pro Gly Val Glu
        290                 295                 300

Lys Phe Gln Leu His Asp Cys Thr Gln Val Glu Lys Ala Asp Thr Thr
305                 310                 315                 320

Ile Cys Leu Lys Trp Lys Asn Ile Glu Thr Phe Thr Cys Asp Thr Gln
                325                 330                 335

Asn Ile Thr Tyr Arg Phe Gln Cys Gly Asn Met Ile Phe Asp Asn Lys
                340                 345                 350

Glu Ile Lys Leu Glu Asn Leu Glu Pro Glu His Glu Tyr Lys Cys Asp
        355                 360                 365

Ser Glu Ile Leu Tyr Asn Asn His Lys Phe Thr Asn Ala Ser Lys Ile
        370                 375                 380

Ile Lys Thr Asp Phe Gly Ser Pro Gly Glu Pro Gln Ile Ile Phe Cys
385                 390                 395                 400

Arg Ser Glu Ala Ala His Gln Gly Val Ile Thr Trp Asn Pro Pro Gln
                405                 410                 415

Arg Ser Phe His Asn Phe Thr Leu Cys Tyr Ile Lys Glu Thr Glu Lys
                420                 425                 430

Asp Cys Leu Asn Leu Asp Lys Asn Leu Ile Lys Tyr Asp Leu Gln Asn
        435                 440                 445

Leu Lys Pro Tyr Thr Lys Tyr Val Leu Ser Leu His Ala Tyr Ile Ile
        450                 455                 460

Ala Lys Val Gln Arg Asn Gly Ser Ala Ala Met Cys His Phe Thr Thr
465                 470                 475                 480

Lys Ser Ala Pro Pro Ser Gln Val Trp Asn Met Thr Val Ser Met Thr
                485                 490                 495

Ser Asp Asn Ser Met His Val Lys Cys Arg Pro Arg Asp Arg Asn
                500                 505                 510

Gly Pro His Glu Arg Tyr His Leu Glu Val Glu Ala Gly Asn Thr Leu
        515                 520                 525

Val Arg Asn Glu Ser His Lys Asn Cys Asp Phe Arg Val Lys Asp Leu
        530                 535                 540

Gln Tyr Ser Thr Asp Tyr Thr Phe Lys Ala Tyr Phe His Asn Gly Asp
545                 550                 555                 560

Tyr Pro Gly Glu Pro Phe Ile Leu His His Ser Thr Ser Tyr Asn Ser
                565                 570                 575

Lys Ala Leu Ile Ala Phe Leu Ala Phe Leu Ile Ile Val Thr Ser Ile
```

```
              580                 585                 590
Ala Leu Leu Val Val Leu Tyr Lys Ile Tyr Asp Leu His Lys Lys Arg
            595                 600                 605

Ser Cys Asn Leu Asp Glu Gln Gln Glu Leu Val Glu Arg Asp Asp Glu
610                 615                 620

Lys Gln Leu Met Asn Val Glu Pro Ile His Ala Asp Ile Leu Leu Glu
625                 630                 635                 640

Thr Tyr Lys Arg Lys Ile Ala Asp Glu Gly Arg Leu Phe Leu Ala Glu
                645                 650                 655

Phe Gln Ser Ile Pro Arg Val Phe Ser Lys Phe Pro Ile Lys Glu Ala
                660                 665                 670

Arg Lys Pro Phe Asn Gln Asn Lys Asn Arg Tyr Val Asp Ile Leu Pro
                675                 680                 685

Tyr Asp Tyr Asn Arg Val Glu Leu Ser Glu Ile Asn Gly Asp Ala Gly
            690                 695                 700

Ser Asn Tyr Ile Asn Ala Ser Tyr Ile Asp Gly Phe Lys Glu Pro Arg
705                 710                 715                 720

Lys Tyr Ile Ala Ala Gln Gly Pro Arg Asp Glu Thr Val Asp Asp Phe
                725                 730                 735

Trp Arg Met Ile Trp Glu Gln Lys Ala Thr Val Ile Val Met Val Thr
                740                 745                 750

Arg Cys Glu Glu Gly Asn Arg Asn Lys Cys Ala Glu Tyr Trp Pro Ser
                755                 760                 765

Met Glu Glu Gly Thr Arg Ala Phe Gly Asp Val Val Lys Ile Asn
770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
                805                 810                 815

Thr Ser Trp Pro Asp His Gly Val Pro Glu Asp Pro His Leu Leu Leu
                820                 825                 830

Lys Leu Arg Arg Arg Val Asn Ala Phe Ser Asn Phe Phe Ser Gly Pro
                835                 840                 845

Ile Val Val His Cys Ser Ala Gly Val Gly Arg Thr Gly Thr Tyr Ile
                850                 855                 860

Gly Ile Asp Ala Met Leu Glu Gly Leu Glu Ala Glu Asn Lys Val Asp
865                 870                 875                 880

Val Tyr Gly Tyr Val Val Lys Leu Arg Arg Gln Arg Cys Leu Met Val
                885                 890                 895

Gln Val Glu Ala Gln Tyr Ile Leu Ile His Gln Ala Leu Val Glu Tyr
                900                 905                 910

Asn Gln Phe Gly Glu Thr Glu Val Asn Leu Ser Glu Leu His Pro Tyr
                915                 920                 925

Leu His Asn Met Lys Lys Arg Asp Pro Pro Ser Glu Pro Ser Pro Leu
            930                 935                 940

Glu Ala Glu Phe Gln Arg Leu Pro Ser Tyr Arg Ser Trp Arg Thr Gln
945                 950                 955                 960

His Ile Gly Asn Gln Glu Glu Asn Lys Ser Lys Asn Arg Asn Ser Asn
                965                 970                 975

Val Ile Pro Tyr Asp Tyr Asn Arg Val Pro Leu Lys His Glu Leu Glu
                980                 985                 990

Met Ser Lys Glu Ser Glu His Asp Ser Asp Glu Ser Ser Asp Asp Asp
            995                 1000                1005
```

```
Ser Asp Ser Glu Glu Pro Ser Lys Tyr Ile Asn Ala Ser Phe Ile Met
    1010                1015                1020

Ser Tyr Trp Lys Pro Glu Val Met Ile Ala Ala Gln Gly Pro Leu Lys
1025                1030                1035                1040

Glu Thr Ile Gly Asp Phe Trp Gln Met Ile Phe Gln Arg Lys Val Lys
                1045                1050                1055

Val Ile Val Met Leu Thr Glu Leu Lys His Gly Asp Gln Glu Ile Cys
            1060                1065                1070

Ala Gln Tyr Trp Gly Glu Gly Lys Gln Thr Tyr Gly Asp Ile Glu Val
        1075                1080                1085

Asp Leu Lys Asp Thr Asp Lys Ser Ser Thr Tyr Thr Leu Arg Val Phe
    1090                1095                1100

Glu Leu Arg His Ser Lys Arg Lys Asp Ser Arg Thr Val Tyr Gln Tyr
1105                1110                1115                1120

Gln Tyr Thr Asn Trp Ser Val Glu Gln Leu Pro Ala Glu Pro Lys Glu
                1125                1130                1135

Leu Ile Ser Met Ile Gln Val Val Lys Gln Lys Leu Pro Gln Lys Asn
            1140                1145                1150

Ser Ser Glu Gly Asn Lys His His Lys Ser Thr Pro Leu Leu Ile His
        1155                1160                1165

Cys Arg Asp Gly Ser Gln Gln Thr Gly Ile Phe Cys Ala Leu Leu Asn
    1170                1175                1180

Leu Leu Glu Ser Ala Glu Thr Glu Glu Val Val Asp Ile Phe Gln Val
1185                1190                1195                1200

Val Lys Ala Leu Arg Lys Ala Arg Pro Gly Met Val Ser Thr Phe Glu
                1205                1210                1215

Gln Tyr Gln Phe Leu Tyr Asp Val Ile Ala Ser Thr Tyr Pro Ala Gln
            1220                1225                1230

Asn Gly Gln Val Lys Lys Asn His Gln Glu Asp Lys Ile Glu Phe
        1235                1240                1245

Asp Asn Glu Val Asp Lys Val Lys Gln Asp Ala Asn Cys Val Asn Pro
    1250                1255                1260

Leu Gly Ala Pro Glu Lys Leu Pro Glu Ala Lys Glu Gln Ala Glu Gly
1265                1270                1275                1280

Ser Glu Pro Thr Ser Gly Thr Glu Gly Pro Glu His Ser Val Asn Gly
                1285                1290                1295

Pro Ala Ser Pro Ala Leu Asn Gln Gly Ser
        1300                1305

<210> SEQ ID NO 100
<211> LENGTH: 17
<212> TYPE: PRT
<213> ORGANISM: Artificial Sequence
<220> FEATURE:
<223> OTHER INFORMATION: VH-CDR2

<400> SEQUENCE: 100

Asp Ile Phe Pro Gly Gly Asp Tyr Thr Asn Tyr Ala Glu Lys Phe Gln
1               5                   10                  15

Gly

<210> SEQ ID NO 101
<211> LENGTH: 114
<212> TYPE: PRT
<213> ORGANISM: Artificial Sequence
<220> FEATURE:
```

<223> OTHER INFORMATION: Humanized HCVR

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile Gly Trp Val Arg Gln Ala Pro Gly Gln Gly Leu Glu Trp Ile
        35                  40                  45

Gly Asp Ile Phe Pro Gly Gly Asp Tyr Thr Asn Tyr Ala Glu Lys Phe
    50                  55                  60

Gln Gly Arg Val Thr Leu Thr Ala Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Val Arg Arg Asn Phe Asp Tyr Trp Gly Gln Gly Thr Leu Val Thr Val
            100                 105                 110

Ser Ser

<210> SEQ ID NO 102
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 102

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Xaa Tyr
            20                  25                  30

Met His Trp Phe Gln Gln Lys Pro Gly Lys Ala Pro Lys Leu Trp Ile
        35                  40                  45

Tyr Asn Thr Ser Asn Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Arg Ser Ser Tyr Pro Leu
                85                  90                  95

Thr Phe Gly Gly Gly Thr Lys Val Glu Ile Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: Humanized LCVR

<400> SEQUENCE: 103

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Ser Tyr
            20                  25                  30

```
Met His Trp Phe Gln Gln Lys Pro Gly Lys Ala Pro Lys Leu Trp Ile
             35                  40                  45

Tyr Asn Thr Ser Asn Leu Pro Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Arg Ser Ser Tyr Pro Leu
                 85                  90                  95

Thr Phe Gly Gly Gly Thr Lys Val Glu Ile Lys
                100                 105
```

<210> SEQ ID NO 104
<211> LENGTH: 1193
<212> TYPE: PRT
<213> ORGANISM: Homo sapiens
<220> FEATURE:
<223> OTHER INFORMATION: hCD45RC
<300> PUBLICATION INFORMATION:
<308> DATABASE ACCESSION NUMBER: UniProt Accession P08575-10
<309> DATABASE ENTRY DATE: 2018 03 28

<400> SEQUENCE: 104

```
Met Thr Met Tyr Leu Trp Leu Lys Leu Leu Ala Phe Gly Phe Ala Phe
 1               5                  10                  15

Leu Asp Thr Glu Val Phe Val Thr Gly Gln Ser Pro Thr Pro Ser Pro
                 20                  25                  30

Thr Asp Val Pro Gly Glu Arg Ser Thr Ala Ser Thr Phe Pro Thr Asp
                 35                  40                  45

Pro Val Ser Pro Leu Thr Thr Thr Leu Ser Leu Ala His His Ser Ser
 50                  55                  60

Ala Ala Leu Pro Ala Arg Thr Ser Asn Thr Thr Ile Thr Ala Asn Thr
 65                  70                  75                  80

Ser Asp Ala Tyr Leu Asn Ala Ser Glu Thr Thr Thr Leu Ser Pro Ser
                 85                  90                  95

Gly Ser Ala Val Ile Ser Thr Thr Thr Ile Ala Thr Thr Pro Ser Lys
                100                 105                 110

Pro Thr Cys Asp Glu Lys Tyr Ala Asn Ile Thr Val Asp Tyr Leu Tyr
            115                 120                 125

Asn Lys Glu Thr Lys Leu Phe Thr Ala Lys Leu Asn Val Asn Glu Asn
    130                 135                 140

Val Glu Cys Gly Asn Asn Thr Cys Thr Asn Asn Glu Val His Asn Leu
145                 150                 155                 160

Thr Glu Cys Lys Asn Ala Ser Val Ser Ile Ser His Asn Ser Cys Thr
                165                 170                 175

Ala Pro Asp Lys Thr Leu Ile Leu Asp Val Pro Pro Gly Val Glu Lys
            180                 185                 190

Phe Gln Leu His Asp Cys Thr Gln Val Glu Lys Ala Asp Thr Thr Ile
    195                 200                 205

Cys Leu Lys Trp Lys Asn Ile Glu Thr Phe Thr Cys Asp Thr Gln Asn
    210                 215                 220

Ile Thr Tyr Arg Phe Gln Cys Gly Asn Met Ile Phe Asp Asn Lys Glu
225                 230                 235                 240

Ile Lys Leu Glu Asn Leu Glu Pro Glu His Glu Tyr Lys Cys Asp Ser
                245                 250                 255

Glu Ile Leu Tyr Asn Asn His Lys Phe Thr Asn Ala Ser Lys Ile Ile
            260                 265                 270
```

```
Lys Thr Asp Phe Gly Ser Pro Gly Glu Pro Gln Ile Ile Phe Cys Arg
            275                 280                 285

Ser Glu Ala Ala His Gln Gly Val Ile Thr Trp Asn Pro Pro Gln Arg
290                 295                 300

Ser Phe His Asn Phe Thr Leu Cys Tyr Ile Lys Glu Thr Glu Lys Asp
305                 310                 315                 320

Cys Leu Asn Leu Asp Lys Asn Leu Ile Lys Tyr Asp Leu Gln Asn Leu
                325                 330                 335

Lys Pro Tyr Thr Lys Tyr Val Leu Ser Leu His Ala Tyr Ile Ile Ala
            340                 345                 350

Lys Val Gln Arg Asn Gly Ser Ala Ala Met Cys His Phe Thr Thr Lys
            355                 360                 365

Ser Ala Pro Pro Ser Gln Val Trp Asn Met Thr Val Ser Met Thr Ser
370                 375                 380

Asp Asn Ser Met His Val Lys Cys Arg Pro Pro Arg Asp Arg Asn Gly
385                 390                 395                 400

Pro His Glu Arg Tyr His Leu Glu Val Glu Ala Gly Asn Thr Leu Val
            405                 410                 415

Arg Asn Glu Ser His Lys Asn Cys Asp Phe Arg Val Lys Asp Leu Gln
            420                 425                 430

Tyr Ser Thr Asp Tyr Thr Phe Lys Ala Tyr Phe His Asn Gly Asp Tyr
            435                 440                 445

Pro Gly Glu Pro Phe Ile Leu His His Ser Thr Ser Tyr Asn Ser Lys
            450                 455                 460

Ala Leu Ile Ala Phe Leu Ala Phe Leu Ile Ile Val Thr Ser Ile Ala
465                 470                 475                 480

Leu Leu Val Val Leu Tyr Lys Ile Tyr Asp Leu His Lys Lys Arg Ser
            485                 490                 495

Cys Asn Leu Asp Glu Gln Gln Glu Leu Val Glu Arg Asp Asp Glu Lys
            500                 505                 510

Gln Leu Met Asn Val Glu Pro Ile His Ala Asp Ile Leu Leu Glu Thr
            515                 520                 525

Tyr Lys Arg Lys Ile Ala Asp Glu Gly Arg Leu Phe Leu Ala Glu Phe
530                 535                 540

Gln Ser Ile Pro Arg Val Phe Ser Lys Phe Pro Ile Lys Glu Ala Arg
545                 550                 555                 560

Lys Pro Phe Asn Gln Asn Lys Asn Arg Tyr Val Asp Ile Leu Pro Tyr
            565                 570                 575

Asp Tyr Asn Arg Val Glu Leu Ser Glu Ile Asn Gly Asp Ala Gly Ser
            580                 585                 590

Asn Tyr Ile Asn Ala Ser Tyr Ile Asp Gly Phe Lys Glu Pro Arg Lys
            595                 600                 605

Tyr Ile Ala Ala Gln Gly Pro Arg Asp Glu Thr Val Asp Asp Phe Trp
610                 615                 620

Arg Met Ile Trp Glu Gln Lys Ala Thr Val Ile Val Met Val Thr Arg
625                 630                 635                 640

Cys Glu Glu Gly Asn Arg Asn Lys Cys Ala Glu Tyr Trp Pro Ser Met
            645                 650                 655

Glu Glu Gly Thr Arg Ala Phe Gly Asp Val Val Val Lys Ile Asn Gln
            660                 665                 670

His Lys Arg Cys Pro Asp Tyr Ile Ile Gln Lys Leu Asn Ile Val Asn
            675                 680                 685

Lys Lys Glu Lys Ala Thr Gly Arg Glu Val Thr His Ile Gln Phe Thr
```

```
                690             695             700
Ser Trp Pro Asp His Gly Val Pro Glu Asp Pro His Leu Leu Leu Lys
705                 710             715                 720

Leu Arg Arg Arg Val Asn Ala Phe Ser Asn Phe Phe Ser Gly Pro Ile
                725             730             735

Val Val His Cys Ser Ala Gly Val Gly Arg Thr Gly Thr Tyr Ile Gly
                740             745             750

Ile Asp Ala Met Leu Glu Gly Leu Glu Ala Glu Asn Lys Val Asp Val
            755             760             765

Tyr Gly Tyr Val Val Lys Leu Arg Arg Gln Arg Cys Leu Met Val Gln
        770             775             780

Val Glu Ala Gln Tyr Ile Leu Ile His Gln Ala Leu Val Glu Tyr Asn
785             790             795             800

Gln Phe Gly Glu Thr Glu Val Asn Leu Ser Glu Leu His Pro Tyr Leu
                805             810             815

His Asn Met Lys Lys Arg Asp Pro Pro Ser Glu Pro Ser Pro Leu Glu
                820             825             830

Ala Glu Phe Gln Arg Leu Pro Ser Tyr Arg Ser Trp Arg Thr Gln His
            835             840             845

Ile Gly Asn Gln Glu Glu Asn Lys Ser Lys Asn Arg Asn Ser Asn Val
850             855             860

Ile Pro Tyr Asp Tyr Asn Arg Val Pro Leu Lys His Glu Leu Glu Met
865             870             875             880

Ser Lys Glu Ser Glu His Asp Ser Asp Glu Ser Ser Asp Asp Asp Ser
                885             890             895

Asp Ser Glu Glu Pro Ser Lys Tyr Ile Asn Ala Ser Phe Ile Met Ser
            900             905             910

Tyr Trp Lys Pro Glu Val Met Ile Ala Ala Gln Gly Pro Leu Lys Glu
        915             920             925

Thr Ile Gly Asp Phe Trp Gln Met Ile Phe Gln Arg Lys Val Lys Val
        930             935             940

Ile Val Met Leu Thr Glu Leu Lys His Gly Asp Gln Glu Ile Cys Ala
945             950             955             960

Gln Tyr Trp Gly Glu Gly Lys Gln Thr Tyr Gly Asp Ile Glu Val Asp
                965             970             975

Leu Lys Asp Thr Asp Lys Ser Ser Thr Tyr Thr Leu Arg Val Phe Glu
            980             985             990

Leu Arg His Ser Lys Arg Lys Asp Ser Arg Thr Val Tyr Gln Tyr Gln
        995             1000            1005

Tyr Thr Asn Trp Ser Val Glu Gln Leu Pro Ala Glu Pro Lys Glu Leu
        1010            1015            1020

Ile Ser Met Ile Gln Val Val Lys Gln Lys Leu Pro Gln Lys Asn Ser
1025            1030            1035            1040

Ser Glu Gly Asn Lys His His Lys Ser Thr Pro Leu Leu Ile His Cys
                1045            1050            1055

Arg Asp Gly Ser Gln Gln Thr Gly Ile Phe Cys Ala Leu Leu Asn Leu
                1060            1065            1070

Leu Glu Ser Ala Glu Thr Glu Glu Val Val Asp Ile Phe Gln Val Val
            1075            1080            1085

Lys Ala Leu Arg Lys Ala Arg Pro Gly Met Val Ser Thr Phe Glu Gln
        1090            1095            1100

Tyr Gln Phe Leu Tyr Asp Val Ile Ala Ser Thr Tyr Pro Ala Gln Asn
1105            1110            1115            1120
```

Gly Gln Val Lys Lys Asn Asn His Gln Glu Asp Lys Ile Glu Phe Asp
            1125                1130                1135

Asn Glu Val Asp Lys Val Lys Gln Asp Ala Asn Cys Val Asn Pro Leu
            1140                1145                1150

Gly Ala Pro Glu Lys Leu Pro Glu Ala Lys Glu Gln Ala Glu Gly Ser
            1155                1160                1165

Glu Pro Thr Ser Gly Thr Glu Gly Pro Glu His Ser Val Asn Gly Pro
            1170                1175                1180

Ala Ser Pro Ala Leu Asn Gln Gly Ser
1185                1190

<210> SEQ ID NO 105
<211> LENGTH: 66
<212> TYPE: PRT
<213> ORGANISM: Homo sapiens
<220> FEATURE:
<223> OTHER INFORMATION: A determinant of hCD45

<400> SEQUENCE: 105

Gly Leu Thr Thr Ala Lys Met Pro Ser Val Pro Leu Ser Ser Asp Pro
1               5                   10                  15

Leu Pro Thr His Thr Thr Ala Phe Ser Pro Ala Ser Thr Phe Glu Arg
            20                  25                  30

Glu Asn Asp Phe Ser Glu Thr Thr Thr Ser Leu Ser Pro Asp Asn Thr
        35                  40                  45

Ser Thr Gln Val Ser Pro Asp Ser Leu Asp Asn Ala Ser Ala Phe Asn
    50                  55                  60

Thr Thr
65

<210> SEQ ID NO 106
<211> LENGTH: 47
<212> TYPE: PRT
<213> ORGANISM: Homo sapiens
<220> FEATURE:
<223> OTHER INFORMATION: B determinant of hCD45

<400> SEQUENCE: 106

Gly Val Ser Ser Val Gln Thr Pro His Leu Pro Thr His Ala Asp Ser
1               5                   10                  15

Gln Thr Pro Ser Ala Gly Thr Asp Thr Gln Thr Phe Ser Gly Ser Ala
            20                  25                  30

Ala Asn Ala Lys Leu Asn Pro Thr Pro Gly Ser Asn Ala Ile Ser
        35                  40                  45

<210> SEQ ID NO 107
<211> LENGTH: 1211
<212> TYPE: PRT
<213> ORGANISM: Homo sapiens
<220> FEATURE:
<223> OTHER INFORMATION: hCD45RA
<300> PUBLICATION INFORMATION:
<308> DATABASE ACCESSION NUMBER: UniProt Accession P08575-8
<309> DATABASE ENTRY DATE: 2018 03 28

<400> SEQUENCE: 107

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

-continued

Thr Gly Leu Thr Thr Ala Lys Met Pro Ser Val Pro Leu Ser Ser Asp
            35                  40                  45

Pro Leu Pro Thr His Thr Thr Ala Phe Ser Pro Ala Ser Thr Phe Glu
 50                  55                  60

Arg Glu Asn Asp Phe Ser Glu Thr Thr Thr Ser Leu Ser Pro Asp Asn
 65                  70                  75                  80

Thr Ser Thr Gln Val Ser Pro Asp Ser Leu Asp Asn Ala Ser Ala Phe
                85                  90                  95

Asn Thr Thr Asp Ala Tyr Leu Asn Ala Ser Glu Thr Thr Thr Leu Ser
                100                 105                 110

Pro Ser Gly Ser Ala Val Ile Ser Thr Thr Thr Ile Ala Thr Thr Pro
            115                 120                 125

Ser Lys Pro Thr Cys Asp Glu Lys Tyr Ala Asn Ile Thr Val Asp Tyr
 130                 135                 140

Leu Tyr Asn Lys Glu Thr Lys Leu Phe Thr Ala Lys Leu Asn Val Asn
 145                 150                 155                 160

Glu Asn Val Glu Cys Gly Asn Asn Thr Cys Thr Asn Asn Glu Val His
                165                 170                 175

Asn Leu Thr Glu Cys Lys Asn Ala Ser Val Ser Ile Ser His Asn Ser
            180                 185                 190

Cys Thr Ala Pro Asp Lys Thr Leu Ile Leu Asp Val Pro Pro Gly Val
            195                 200                 205

Glu Lys Phe Gln Leu His Asp Cys Thr Gln Val Glu Lys Ala Asp Thr
 210                 215                 220

Thr Ile Cys Leu Lys Trp Lys Asn Ile Glu Thr Phe Thr Cys Asp Thr
225                 230                 235                 240

Gln Asn Ile Thr Tyr Arg Phe Gln Cys Gly Asn Met Ile Phe Asp Asn
                245                 250                 255

Lys Glu Ile Lys Leu Glu Asn Leu Glu Pro Glu His Glu Tyr Lys Cys
            260                 265                 270

Asp Ser Glu Ile Leu Tyr Asn Asn His Lys Phe Thr Asn Ala Ser Lys
            275                 280                 285

Ile Ile Lys Thr Asp Phe Gly Ser Pro Gly Glu Pro Gln Ile Ile Phe
 290                 295                 300

Cys Arg Ser Glu Ala Ala His Gln Gly Val Ile Thr Trp Asn Pro Pro
305                 310                 315                 320

Gln Arg Ser Phe His Asn Phe Thr Leu Cys Tyr Ile Lys Glu Thr Glu
                325                 330                 335

Lys Asp Cys Leu Asn Leu Asp Lys Asn Leu Ile Lys Tyr Asp Leu Gln
            340                 345                 350

Asn Leu Lys Pro Tyr Thr Lys Tyr Val Leu Ser Leu His Ala Tyr Ile
            355                 360                 365

Ile Ala Lys Val Gln Arg Asn Gly Ser Ala Ala Met Cys His Phe Thr
 370                 375                 380

Thr Lys Ser Ala Pro Pro Ser Gln Val Trp Asn Met Thr Val Ser Met
385                 390                 395                 400

Thr Ser Asp Asn Ser Met His Val Lys Cys Arg Pro Pro Arg Asp Arg
                405                 410                 415

Asn Gly Pro His Glu Arg Tyr His Leu Glu Val Glu Ala Gly Asn Thr
            420                 425                 430

Leu Val Arg Asn Glu Ser His Lys Asn Cys Asp Phe Arg Val Lys Asp
            435                 440                 445

Leu Gln Tyr Ser Thr Asp Tyr Thr Phe Lys Ala Tyr Phe His Asn Gly

-continued

```
            450                 455                 460
Asp Tyr Pro Gly Glu Pro Phe Ile Leu His His Ser Thr Ser Tyr Asn
465                 470                 475                 480

Ser Lys Ala Leu Ile Ala Phe Leu Ala Phe Leu Ile Ile Val Thr Ser
                485                 490                 495

Ile Ala Leu Leu Val Val Leu Tyr Lys Ile Tyr Asp Leu His Lys Lys
                500                 505                 510

Arg Ser Cys Asn Leu Asp Glu Gln Gln Glu Leu Val Glu Arg Asp Asp
                515                 520                 525

Glu Lys Gln Leu Met Asn Val Glu Pro Ile His Ala Asp Ile Leu Leu
            530                 535                 540

Glu Thr Tyr Lys Arg Lys Ile Ala Asp Glu Gly Arg Leu Phe Leu Ala
545                 550                 555                 560

Glu Phe Gln Ser Ile Pro Arg Val Phe Ser Lys Phe Pro Ile Lys Glu
                565                 570                 575

Ala Arg Lys Pro Phe Asn Gln Asn Lys Asn Arg Tyr Val Asp Ile Leu
                580                 585                 590

Pro Tyr Asp Tyr Asn Arg Val Glu Leu Ser Glu Ile Asn Gly Asp Ala
            595                 600                 605

Gly Ser Asn Tyr Ile Asn Ala Ser Tyr Ile Asp Gly Phe Lys Glu Pro
            610                 615                 620

Arg Lys Tyr Ile Ala Ala Gln Gly Pro Arg Asp Glu Thr Val Asp Asp
625                 630                 635                 640

Phe Trp Arg Met Ile Trp Glu Gln Lys Ala Thr Val Ile Val Met Val
                645                 650                 655

Thr Arg Cys Glu Glu Gly Asn Arg Asn Lys Cys Ala Glu Tyr Trp Pro
                660                 665                 670

Ser Met Glu Glu Gly Thr Arg Ala Phe Gly Asp Val Val Val Lys Ile
            675                 680                 685

Asn Gln His Lys Arg Cys Pro Asp Tyr Ile Ile Gln Lys Leu Asn Ile
            690                 695                 700

Val Asn Lys Lys Glu Lys Ala Thr Gly Arg Glu Val Thr His Ile Gln
705                 710                 715                 720

Phe Thr Ser Trp Pro Asp His Gly Val Pro Glu Asp Pro His Leu Leu
                725                 730                 735

Leu Lys Leu Arg Arg Arg Val Asn Ala Phe Ser Asn Phe Phe Ser Gly
                740                 745                 750

Pro Ile Val Val His Cys Ser Ala Gly Val Gly Arg Thr Gly Thr Tyr
            755                 760                 765

Ile Gly Ile Asp Ala Met Leu Glu Gly Leu Glu Ala Glu Asn Lys Val
            770                 775                 780

Asp Val Tyr Gly Tyr Val Lys Leu Arg Arg Gln Arg Cys Leu Met
785                 790                 795                 800

Val Gln Val Glu Ala Gln Tyr Ile Leu Ile His Gln Ala Leu Val Glu
                805                 810                 815

Tyr Asn Gln Phe Gly Glu Thr Glu Val Asn Leu Ser Glu Leu His Pro
                820                 825                 830

Tyr Leu His Asn Met Lys Lys Arg Asp Pro Ser Glu Pro Ser Pro
            835                 840                 845

Leu Glu Ala Glu Phe Gln Arg Leu Pro Ser Tyr Arg Ser Trp Arg Thr
            850                 855                 860

Gln His Ile Gly Asn Gln Glu Glu Asn Lys Ser Lys Asn Arg Asn Ser
865                 870                 875                 880
```

Asn Val Ile Pro Tyr Asp Tyr Asn Arg Val Pro Leu Lys His Glu Leu
            885                 890                 895

Glu Met Ser Lys Glu Ser Glu His Asp Ser Asp Glu Ser Ser Asp Asp
            900                 905                 910

Asp Ser Asp Ser Glu Glu Pro Ser Lys Tyr Ile Asn Ala Ser Phe Ile
            915                 920                 925

Met Ser Tyr Trp Lys Pro Glu Val Met Ile Ala Ala Gln Gly Pro Leu
            930                 935                 940

Lys Glu Thr Ile Gly Asp Phe Trp Gln Met Ile Phe Gln Arg Lys Val
945                 950                 955                 960

Lys Val Ile Val Met Leu Thr Glu Leu Lys His Gly Asp Gln Glu Ile
            965                 970                 975

Cys Ala Gln Tyr Trp Gly Glu Gly Lys Gln Thr Tyr Gly Asp Ile Glu
            980                 985                 990

Val Asp Leu Lys Asp Thr Asp Lys Ser Ser Thr Tyr Thr Leu Arg Val
            995                 1000                1005

Phe Glu Leu Arg His Ser Lys Arg Lys Asp Ser Arg Thr Val Tyr Gln
        1010                1015                1020

Tyr Gln Tyr Thr Asn Trp Ser Val Glu Gln Leu Pro Ala Glu Pro Lys
1025                1030                1035                1040

Glu Leu Ile Ser Met Ile Gln Val Val Lys Gln Lys Leu Pro Gln Lys
        1045                1050                1055

Asn Ser Ser Glu Gly Asn Lys His His Lys Ser Thr Pro Leu Leu Ile
        1060                1065                1070

His Cys Arg Asp Gly Ser Gln Gln Thr Gly Ile Phe Cys Ala Leu Leu
        1075                1080                1085

Asn Leu Leu Glu Ser Ala Glu Thr Glu Glu Val Val Asp Ile Phe Gln
        1090                1095                1100

Val Val Lys Ala Leu Arg Lys Ala Arg Pro Gly Met Val Ser Thr Phe
1105                1110                1115                1120

Glu Gln Tyr Gln Phe Leu Tyr Asp Val Ile Ala Ser Thr Tyr Pro Ala
        1125                1130                1135

Gln Asn Gly Gln Val Lys Lys Asn Asn His Gln Glu Asp Lys Ile Glu
        1140                1145                1150

Phe Asp Asn Glu Val Asp Lys Val Lys Gln Asp Ala Asn Cys Val Asn
        1155                1160                1165

Pro Leu Gly Ala Pro Glu Lys Leu Pro Glu Ala Lys Glu Gln Ala Glu
        1170                1175                1180

Gly Ser Glu Pro Thr Ser Gly Thr Glu Gly Pro Glu His Ser Val Asn
1185                1190                1195                1200

Gly Pro Ala Ser Pro Ala Leu Asn Gln Gly Ser
            1205                1210

<210> SEQ ID NO 108
<211> LENGTH: 1192
<212> TYPE: PRT
<213> ORGANISM: Homo sapiens
<220> FEATURE:
<223> OTHER INFORMATION: hCD45RB
<300> PUBLICATION INFORMATION:
<308> DATABASE ACCESSION NUMBER: UniProt Accession P08575-9
<309> DATABASE ENTRY DATE: 2018 03 28

<400> SEQUENCE: 108

Met Thr Met Tyr Leu Trp Leu Lys Leu Leu Ala Phe Gly Phe Ala Phe
1               5                   10                  15

```
Leu Asp Thr Glu Val Phe Val Thr Gly Gln Ser Pro Thr Pro Ser Pro
            20                  25                  30

Thr Gly Val Ser Ser Val Gln Thr Pro His Leu Pro Thr His Ala Asp
        35                  40                  45

Ser Gln Thr Pro Ser Ala Gly Thr Asp Thr Gln Thr Phe Ser Gly Ser
50                  55                  60

Ala Ala Asn Ala Lys Leu Asn Pro Thr Pro Gly Ser Asn Ala Ile Ser
65                  70                  75                  80

Asp Ala Tyr Leu Asn Ala Ser Glu Thr Thr Thr Leu Ser Pro Ser Gly
                85                  90                  95

Ser Ala Val Ile Ser Thr Thr Thr Ile Ala Thr Thr Pro Ser Lys Pro
            100                 105                 110

Thr Cys Asp Glu Lys Tyr Ala Asn Ile Thr Val Asp Tyr Leu Tyr Asn
        115                 120                 125

Lys Glu Thr Lys Leu Phe Thr Ala Lys Leu Asn Val Asn Glu Asn Val
130                 135                 140

Glu Cys Gly Asn Asn Thr Cys Thr Asn Asn Glu Val His Asn Leu Thr
145                 150                 155                 160

Glu Cys Lys Asn Ala Ser Val Ser Ile Ser His Asn Ser Cys Thr Ala
                165                 170                 175

Pro Asp Lys Thr Leu Ile Leu Asp Val Pro Pro Gly Val Glu Lys Phe
            180                 185                 190

Gln Leu His Asp Cys Thr Gln Val Glu Lys Ala Asp Thr Thr Ile Cys
        195                 200                 205

Leu Lys Trp Lys Asn Ile Glu Thr Phe Thr Cys Asp Thr Gln Asn Ile
210                 215                 220

Thr Tyr Arg Phe Gln Cys Gly Asn Met Ile Phe Asp Asn Lys Glu Ile
225                 230                 235                 240

Lys Leu Glu Asn Leu Glu Pro Glu His Glu Tyr Lys Cys Asp Ser Glu
                245                 250                 255

Ile Leu Tyr Asn Asn His Lys Phe Thr Asn Ala Ser Lys Ile Ile Lys
            260                 265                 270

Thr Asp Phe Gly Ser Pro Gly Glu Pro Gln Ile Ile Phe Cys Arg Ser
        275                 280                 285

Glu Ala Ala His Gln Gly Val Ile Thr Trp Asn Pro Pro Gln Arg Ser
290                 295                 300

Phe His Asn Phe Thr Leu Cys Tyr Ile Lys Glu Thr Glu Lys Asp Cys
305                 310                 315                 320

Leu Asn Leu Asp Lys Asn Leu Ile Lys Tyr Asp Leu Gln Asn Leu Lys
                325                 330                 335

Pro Tyr Thr Lys Tyr Val Leu Ser Leu His Ala Tyr Ile Ile Ala Lys
            340                 345                 350

Val Gln Arg Asn Gly Ser Ala Ala Met Cys His Phe Thr Thr Lys Ser
        355                 360                 365

Ala Pro Pro Ser Gln Val Trp Asn Met Thr Val Ser Met Thr Ser Asp
370                 375                 380

Asn Ser Met His Val Lys Cys Arg Pro Pro Arg Asp Arg Asn Gly Pro
385                 390                 395                 400

His Glu Arg Tyr His Leu Glu Val Glu Ala Gly Asn Thr Leu Val Arg
                405                 410                 415

Asn Glu Ser His Lys Asn Cys Asp Phe Arg Val Lys Asp Leu Gln Tyr
            420                 425                 430
```

```
Ser Thr Asp Tyr Thr Phe Lys Ala Tyr Phe His Asn Gly Asp Tyr Pro
        435                 440                 445

Gly Glu Pro Phe Ile Leu His His Ser Thr Ser Tyr Asn Ser Lys Ala
450                 455                 460

Leu Ile Ala Phe Leu Ala Phe Leu Ile Ile Val Thr Ser Ile Ala Leu
465                 470                 475                 480

Leu Val Val Leu Tyr Lys Ile Tyr Asp Leu His Lys Lys Arg Ser Cys
                485                 490                 495

Asn Leu Asp Glu Gln Gln Glu Leu Val Glu Arg Asp Asp Glu Lys Gln
                500                 505                 510

Leu Met Asn Val Glu Pro Ile His Ala Asp Ile Leu Leu Glu Thr Tyr
        515                 520                 525

Lys Arg Lys Ile Ala Asp Glu Gly Arg Leu Phe Leu Ala Glu Phe Gln
530                 535                 540

Ser Ile Pro Arg Val Phe Ser Lys Phe Pro Ile Lys Glu Ala Arg Lys
545                 550                 555                 560

Pro Phe Asn Gln Asn Lys Asn Arg Tyr Val Asp Ile Leu Pro Tyr Asp
                565                 570                 575

Tyr Asn Arg Val Glu Leu Ser Glu Ile Asn Gly Asp Ala Gly Ser Asn
                580                 585                 590

Tyr Ile Asn Ala Ser Tyr Ile Asp Gly Phe Lys Glu Pro Arg Lys Tyr
        595                 600                 605

Ile Ala Ala Gln Gly Pro Arg Asp Glu Thr Val Asp Asp Phe Trp Arg
        610                 615                 620

Met Ile Trp Glu Gln Lys Ala Thr Val Ile Val Met Val Thr Arg Cys
625                 630                 635                 640

Glu Glu Gly Asn Arg Asn Lys Cys Ala Glu Tyr Trp Pro Ser Met Glu
                645                 650                 655

Glu Gly Thr Arg Ala Phe Gly Asp Val Val Lys Ile Asn Gln His
                660                 665                 670

Lys Arg Cys Pro Asp Tyr Ile Ile Gln Lys Leu Asn Ile Val Asn Lys
        675                 680                 685

Lys Glu Lys Ala Thr Gly Arg Glu Val Thr His Ile Gln Phe Thr Ser
690                 695                 700

Trp Pro Asp His Gly Val Pro Glu Asp Pro His Leu Leu Lys Leu
705                 710                 715                 720

Arg Arg Arg Val Asn Ala Phe Ser Asn Phe Ser Gly Pro Ile Val
                725                 730                 735

Val His Cys Ser Ala Gly Val Gly Arg Thr Gly Thr Tyr Ile Gly Ile
                740                 745                 750

Asp Ala Met Leu Glu Gly Leu Glu Ala Glu Asn Lys Val Asp Val Tyr
        755                 760                 765

Gly Tyr Val Val Lys Leu Arg Arg Gln Arg Cys Leu Met Val Gln Val
        770                 775                 780

Glu Ala Gln Tyr Ile Leu Ile His Gln Ala Leu Val Glu Tyr Asn Gln
785                 790                 795                 800

Phe Gly Glu Thr Glu Val Asn Leu Ser Glu Leu His Pro Tyr Leu His
                805                 810                 815

Asn Met Lys Lys Arg Asp Pro Pro Ser Glu Pro Ser Pro Leu Glu Ala
                820                 825                 830

Glu Phe Gln Arg Leu Pro Ser Tyr Arg Ser Trp Arg Thr Gln His Ile
                835                 840                 845

Gly Asn Gln Glu Glu Asn Lys Ser Lys Asn Arg Asn Ser Asn Val Ile
```

```
                850                 855                 860
Pro Tyr Asp Tyr Asn Arg Val Pro Leu Lys His Glu Leu Glu Met Ser
865                 870                 875                 880

Lys Glu Ser Glu His Asp Ser Asp Glu Ser Asp Asp Asp Ser Asp
                885                 890                 895

Ser Glu Glu Pro Ser Lys Tyr Ile Asn Ala Ser Phe Ile Met Ser Tyr
                900                 905                 910

Trp Lys Pro Glu Val Met Ile Ala Ala Gln Gly Pro Leu Lys Glu Thr
            915                 920                 925

Ile Gly Asp Phe Trp Gln Met Ile Phe Gln Arg Lys Val Lys Val Ile
        930                 935                 940

Val Met Leu Thr Glu Leu Lys His Gly Asp Gln Glu Ile Cys Ala Gln
945                 950                 955                 960

Tyr Trp Gly Glu Gly Lys Gln Thr Tyr Gly Asp Ile Glu Val Asp Leu
                965                 970                 975

Lys Asp Thr Asp Lys Ser Ser Thr Tyr Thr Leu Arg Val Phe Glu Leu
            980                 985                 990

Arg His Ser Lys Arg Lys Asp Ser Arg Thr Val Tyr Gln Tyr Gln Tyr
        995                 1000                1005

Thr Asn Trp Ser Val Glu Gln Leu Pro Ala Glu Pro Lys Glu Leu Ile
    1010                1015                1020

Ser Met Ile Gln Val Val Lys Gln Lys Leu Pro Gln Lys Asn Ser Ser
1025                1030                1035                1040

Glu Gly Asn Lys His His Lys Ser Thr Pro Leu Leu Ile His Cys Arg
                1045                1050                1055

Asp Gly Ser Gln Gln Thr Gly Ile Phe Cys Ala Leu Leu Asn Leu Leu
                1060                1065                1070

Glu Ser Ala Glu Thr Glu Glu Val Val Asp Ile Phe Gln Val Val Lys
            1075                1080                1085

Ala Leu Arg Lys Ala Arg Pro Gly Met Val Ser Thr Phe Glu Gln Tyr
        1090                1095                1100

Gln Phe Leu Tyr Asp Val Ile Ala Ser Thr Tyr Pro Ala Gln Asn Gly
1105                1110                1115                1120

Gln Val Lys Lys Asn Asn His Gln Glu Asp Lys Ile Glu Phe Asp Asn
                1125                1130                1135

Glu Val Asp Lys Val Lys Gln Asp Ala Asn Cys Val Asn Pro Leu Gly
                1140                1145                1150

Ala Pro Glu Lys Leu Pro Glu Ala Lys Glu Gln Ala Glu Gly Ser Glu
            1155                1160                1165

Pro Thr Ser Gly Thr Glu Gly Pro Glu His Ser Val Asn Gly Pro Ala
        1170                1175                1180

Ser Pro Ala Leu Asn Gln Gly Ser
1185                1190

<210> SEQ ID NO 109
<211> LENGTH: 1258
<212> TYPE: PRT
<213> ORGANISM: Homo sapiens
<220> FEATURE:
<223> OTHER INFORMATION: hCD45RAB
<300> PUBLICATION INFORMATION:
<308> DATABASE ACCESSION NUMBER: UniProt Accession P08575-5
<309> DATABASE ENTRY DATE: 2018 03 28

<400> SEQUENCE: 109

Met Thr Met Tyr Leu Trp Leu Lys Leu Leu Ala Phe Gly Phe Ala Phe
```

-continued

```
1               5                   10                  15
Leu Asp Thr Glu Val Phe Val Thr Gly Gln Ser Pro Thr Pro Ser Pro
                20                  25                  30
Thr Gly Leu Thr Thr Ala Lys Met Pro Ser Val Pro Leu Ser Ser Asp
                35                  40                  45
Pro Leu Pro Thr His Thr Thr Ala Phe Ser Pro Ala Ser Thr Phe Glu
 50                  55                  60
Arg Glu Asn Asp Phe Ser Glu Thr Thr Thr Ser Leu Ser Pro Asp Asn
 65                  70                  75                  80
Thr Ser Thr Gln Val Ser Pro Asp Ser Leu Asp Asn Ala Ser Ala Phe
                85                  90                  95
Asn Thr Thr Gly Val Ser Ser Val Gln Thr Pro His Leu Pro Thr His
                100                 105                 110
Ala Asp Ser Gln Thr Pro Ser Ala Gly Thr Asp Thr Gln Thr Phe Ser
                115                 120                 125
Gly Ser Ala Ala Asn Ala Lys Leu Asn Pro Thr Pro Gly Ser Asn Ala
                130                 135                 140
Ile Ser Asp Ala Tyr Leu Asn Ala Ser Glu Thr Thr Thr Leu Ser Pro
 145                 150                 155                 160
Ser Gly Ser Ala Val Ile Ser Thr Thr Thr Ile Ala Thr Thr Pro Ser
                165                 170                 175
Lys Pro Thr Cys Asp Glu Lys Tyr Ala Asn Ile Thr Val Asp Tyr Leu
                180                 185                 190
Tyr Asn Lys Glu Thr Lys Leu Phe Thr Ala Lys Leu Asn Val Asn Glu
                195                 200                 205
Asn Val Glu Cys Gly Asn Asn Thr Cys Thr Asn Asn Glu Val His Asn
                210                 215                 220
Leu Thr Glu Cys Lys Asn Ala Ser Val Ser Ile Ser His Asn Ser Cys
 225                 230                 235                 240
Thr Ala Pro Asp Lys Thr Leu Ile Leu Asp Val Pro Pro Gly Val Glu
                245                 250                 255
Lys Phe Gln Leu His Asp Cys Thr Gln Val Glu Lys Ala Asp Thr Thr
                260                 265                 270
Ile Cys Leu Lys Trp Lys Asn Ile Glu Thr Phe Thr Cys Asp Thr Gln
                275                 280                 285
Asn Ile Thr Tyr Arg Phe Gln Cys Gly Asn Met Ile Phe Asp Asn Lys
                290                 295                 300
Glu Ile Lys Leu Glu Asn Leu Glu Pro Glu His Glu Tyr Lys Cys Asp
 305                 310                 315                 320
Ser Glu Ile Leu Tyr Asn Asn His Lys Phe Thr Asn Ala Ser Lys Ile
                325                 330                 335
Ile Lys Thr Asp Phe Gly Ser Pro Gly Glu Pro Gln Ile Ile Phe Cys
                340                 345                 350
Arg Ser Glu Ala Ala His Gln Gly Val Ile Thr Trp Asn Pro Pro Gln
                355                 360                 365
Arg Ser Phe His Asn Phe Thr Leu Cys Tyr Ile Lys Glu Thr Glu Lys
                370                 375                 380
Asp Cys Leu Asn Leu Asp Lys Asn Leu Ile Lys Tyr Asp Leu Gln Asn
 385                 390                 395                 400
Leu Lys Pro Tyr Thr Lys Tyr Val Leu Ser Leu His Ala Tyr Ile Ile
                405                 410                 415
Ala Lys Val Gln Arg Asn Gly Ser Ala Ala Met Cys His Phe Thr Thr
                420                 425                 430
```

```
Lys Ser Ala Pro Pro Ser Gln Val Trp Asn Met Thr Val Ser Met Thr
            435                 440                 445

Ser Asp Asn Ser Met His Val Lys Cys Arg Pro Pro Arg Asp Arg Asn
    450                 455                 460

Gly Pro His Glu Arg Tyr His Leu Glu Val Glu Ala Gly Asn Thr Leu
465                 470                 475                 480

Val Arg Asn Glu Ser His Lys Asn Cys Asp Phe Arg Val Lys Asp Leu
                485                 490                 495

Gln Tyr Ser Thr Asp Tyr Thr Phe Lys Ala Tyr Phe His Asn Gly Asp
            500                 505                 510

Tyr Pro Gly Glu Pro Phe Ile Leu His His Ser Thr Ser Tyr Asn Ser
            515                 520                 525

Lys Ala Leu Ile Ala Phe Leu Ala Phe Leu Ile Ile Val Thr Ser Ile
    530                 535                 540

Ala Leu Leu Val Val Leu Tyr Lys Ile Tyr Asp Leu His Lys Lys Arg
545                 550                 555                 560

Ser Cys Asn Leu Asp Glu Gln Gln Glu Leu Val Glu Arg Asp Asp Glu
                565                 570                 575

Lys Gln Leu Met Asn Val Glu Pro Ile His Ala Asp Ile Leu Leu Glu
            580                 585                 590

Thr Tyr Lys Arg Lys Ile Ala Asp Glu Gly Arg Leu Phe Leu Ala Glu
            595                 600                 605

Phe Gln Ser Ile Pro Arg Val Phe Ser Lys Phe Pro Ile Lys Glu Ala
    610                 615                 620

Arg Lys Pro Phe Asn Gln Asn Lys Asn Arg Tyr Val Asp Ile Leu Pro
625                 630                 635                 640

Tyr Asp Tyr Asn Arg Val Glu Leu Ser Glu Ile Asn Gly Asp Ala Gly
                645                 650                 655

Ser Asn Tyr Ile Asn Ala Ser Tyr Ile Asp Gly Phe Lys Glu Pro Arg
            660                 665                 670

Lys Tyr Ile Ala Ala Gln Gly Pro Arg Asp Glu Thr Val Asp Asp Phe
    675                 680                 685

Trp Arg Met Ile Trp Glu Gln Lys Ala Thr Val Ile Val Met Val Thr
690                 695                 700

Arg Cys Glu Glu Gly Asn Arg Asn Lys Cys Ala Glu Tyr Trp Pro Ser
705                 710                 715                 720

Met Glu Glu Gly Thr Arg Ala Phe Gly Asp Val Val Lys Ile Asn
                725                 730                 735

Gln His Lys Arg Cys Pro Asp Tyr Ile Ile Gln Lys Leu Asn Ile Val
            740                 745                 750

Asn Lys Lys Glu Lys Ala Thr Gly Arg Glu Val Thr His Ile Gln Phe
    755                 760                 765

Thr Ser Trp Pro Asp His Gly Val Pro Glu Asp Pro His Leu Leu Leu
    770                 775                 780

Lys Leu Arg Arg Arg Val Asn Ala Phe Ser Asn Phe Phe Ser Gly Pro
785                 790                 795                 800

Ile Val Val His Cys Ser Ala Gly Val Gly Arg Thr Gly Thr Tyr Ile
                805                 810                 815

Gly Ile Asp Ala Met Leu Glu Gly Leu Glu Ala Glu Asn Lys Val Asp
            820                 825                 830

Val Tyr Gly Tyr Val Val Lys Leu Arg Arg Gln Arg Cys Leu Met Val
            835                 840                 845
```

-continued

Gln Val Glu Ala Gln Tyr Ile Leu Ile His Gln Ala Leu Val Glu Tyr
850                 855                 860

Asn Gln Phe Gly Glu Thr Glu Val Asn Leu Ser Glu Leu His Pro Tyr
865                 870                 875                 880

Leu His Asn Met Lys Lys Arg Asp Pro Pro Ser Glu Pro Ser Pro Leu
                885                 890                 895

Glu Ala Glu Phe Gln Arg Leu Pro Ser Tyr Arg Ser Trp Arg Thr Gln
            900                 905                 910

His Ile Gly Asn Gln Glu Glu Asn Lys Ser Lys Asn Arg Asn Ser Asn
        915                 920                 925

Val Ile Pro Tyr Asp Tyr Asn Arg Val Pro Leu Lys His Glu Leu Glu
930                 935                 940

Met Ser Lys Glu Ser Glu His Asp Ser Asp Glu Ser Ser Asp Asp Asp
945                 950                 955                 960

Ser Asp Ser Glu Glu Pro Ser Lys Tyr Ile Asn Ala Ser Phe Ile Met
                965                 970                 975

Ser Tyr Trp Lys Pro Glu Val Met Ile Ala Ala Gln Gly Pro Leu Lys
            980                 985                 990

Glu Thr Ile Gly Asp Phe Trp Gln Met Ile Phe Gln Arg Lys Val Lys
        995                 1000                1005

Val Ile Val Met Leu Thr Glu Leu Lys His Gly Asp Gln Glu Ile Cys
1010                1015                1020

Ala Gln Tyr Trp Gly Glu Gly Lys Gln Thr Tyr Gly Asp Ile Glu Val
1025                1030                1035                1040

Asp Leu Lys Asp Thr Asp Lys Ser Ser Thr Tyr Thr Leu Arg Val Phe
                1045                1050                1055

Glu Leu Arg His Ser Lys Arg Lys Asp Ser Arg Thr Val Tyr Gln Tyr
            1060                1065                1070

Gln Tyr Thr Asn Trp Ser Val Glu Gln Leu Pro Ala Glu Pro Lys Glu
        1075                1080                1085

Leu Ile Ser Met Ile Gln Val Val Lys Gln Lys Leu Pro Gln Lys Asn
1090                1095                1100

Ser Ser Glu Gly Asn Lys His His Lys Ser Thr Pro Leu Leu Ile His
1105                1110                1115                1120

Cys Arg Asp Gly Ser Gln Gln Thr Gly Ile Phe Cys Ala Leu Leu Asn
                1125                1130                1135

Leu Leu Glu Ser Ala Glu Thr Glu Glu Val Val Asp Ile Phe Gln Val
            1140                1145                1150

Val Lys Ala Leu Arg Lys Ala Arg Pro Gly Met Val Ser Thr Phe Glu
        1155                1160                1165

Gln Tyr Gln Phe Leu Tyr Asp Val Ile Ala Ser Thr Tyr Pro Ala Gln
1170                1175                1180

Asn Gly Gln Val Lys Lys Asn His Gln Glu Asp Lys Ile Glu Phe
1185                1190                1195                1200

Asp Asn Glu Val Asp Lys Val Lys Gln Asp Ala Asn Cys Val Asn Pro
                1205                1210                1215

Leu Gly Ala Pro Glu Lys Leu Pro Glu Ala Lys Glu Gln Ala Glu Gly
            1220                1225                1230

Ser Glu Pro Thr Ser Gly Thr Glu Gly Pro Glu His Ser Val Asn Gly
        1235                1240                1245

Pro Ala Ser Pro Ala Leu Asn Gln Gly Ser
1250                1255

```
<210> SEQ ID NO 110
<211> LENGTH: 1145
<212> TYPE: PRT
<213> ORGANISM: Homo sapiens
<220> FEATURE:
<223> OTHER INFORMATION: hCD45R0
<300> PUBLICATION INFORMATION:
<308> DATABASE ACCESSION NUMBER: UniProt Accession P08575-4
<309> DATABASE ENTRY DATE: 2018 03 28

<400> SEQUENCE: 110

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Asp Ala Tyr Leu Asn Ala Ser Glu Thr Thr Thr Leu Ser Pro Ser
        35                  40                  45

Gly Ser Ala Val Ile Ser Thr Thr Ile Ala Thr Thr Pro Ser Lys
    50                  55                  60

Pro Thr Cys Asp Glu Lys Tyr Ala Asn Ile Thr Val Asp Tyr Leu Tyr
65                  70                  75                  80

Asn Lys Glu Thr Lys Leu Phe Thr Ala Lys Leu Asn Val Asn Glu Asn
                85                  90                  95

Val Glu Cys Gly Asn Asn Thr Cys Thr Asn Asn Glu Val His Asn Leu
            100                 105                 110

Thr Glu Cys Lys Asn Ala Ser Val Ser Ile Ser His Asn Ser Cys Thr
        115                 120                 125

Ala Pro Asp Lys Thr Leu Ile Leu Asp Val Pro Pro Gly Val Glu Lys
    130                 135                 140

Phe Gln Leu His Asp Cys Thr Gln Val Glu Lys Ala Asp Thr Thr Ile
145                 150                 155                 160

Cys Leu Lys Trp Lys Asn Ile Glu Thr Phe Thr Cys Asp Thr Gln Asn
                165                 170                 175

Ile Thr Tyr Arg Phe Gln Cys Gly Asn Met Ile Phe Asp Asn Lys Glu
            180                 185                 190

Ile Lys Leu Glu Asn Leu Glu Pro Glu His Glu Tyr Lys Cys Asp Ser
        195                 200                 205

Glu Ile Leu Tyr Asn Asn His Lys Phe Thr Asn Ala Ser Lys Ile Ile
    210                 215                 220

Lys Thr Asp Phe Gly Ser Pro Gly Glu Pro Gln Ile Ile Phe Cys Arg
225                 230                 235                 240

Ser Glu Ala Ala His Gln Gly Val Ile Thr Trp Asn Pro Pro Gln Arg
                245                 250                 255

Ser Phe His Asn Phe Thr Leu Cys Tyr Ile Lys Glu Thr Glu Lys Asp
            260                 265                 270

Cys Leu Asn Leu Asp Lys Asn Leu Ile Lys Tyr Asp Leu Gln Asn Leu
        275                 280                 285

Lys Pro Tyr Thr Lys Tyr Val Leu Ser Leu His Ala Tyr Ile Ile Ala
    290                 295                 300

Lys Val Gln Arg Asn Gly Ser Ala Ala Met Cys His Phe Thr Thr Lys
305                 310                 315                 320

Ser Ala Pro Pro Ser Gln Val Trp Asn Met Thr Val Ser Met Thr Ser
                325                 330                 335

Asp Asn Ser Met His Val Lys Cys Arg Pro Pro Arg Asp Arg Asn Gly
            340                 345                 350

Pro His Glu Arg Tyr His Leu Glu Val Glu Ala Gly Asn Thr Leu Val
```

-continued

```
            355                 360                 365
Arg Asn Glu Ser His Lys Asn Cys Asp Phe Arg Val Lys Asp Leu Gln
    370                 375                 380
Tyr Ser Thr Asp Tyr Thr Phe Lys Ala Tyr Phe His Asn Gly Asp Tyr
385                 390                 395                 400
Pro Gly Glu Pro Phe Ile Leu His His Ser Thr Ser Tyr Asn Ser Lys
                405                 410                 415
Ala Leu Ile Ala Phe Leu Ala Phe Leu Ile Val Thr Ser Ile Ala
                420                 425                 430
Leu Leu Val Val Leu Tyr Lys Ile Tyr Asp Leu His Lys Lys Arg Ser
            435                 440                 445
Cys Asn Leu Asp Glu Gln Gln Glu Leu Val Glu Arg Asp Asp Glu Lys
    450                 455                 460
Gln Leu Met Asn Val Glu Pro Ile His Ala Asp Ile Leu Leu Glu Thr
465                 470                 475                 480
Tyr Lys Arg Lys Ile Ala Asp Glu Gly Arg Leu Phe Leu Ala Glu Phe
                485                 490                 495
Gln Ser Ile Pro Arg Val Phe Ser Lys Phe Pro Ile Lys Glu Ala Arg
                500                 505                 510
Lys Pro Phe Asn Gln Asn Lys Asn Arg Tyr Val Asp Ile Leu Pro Tyr
            515                 520                 525
Asp Tyr Asn Arg Val Glu Leu Ser Glu Ile Asn Gly Asp Ala Gly Ser
    530                 535                 540
Asn Tyr Ile Asn Ala Ser Tyr Ile Asp Gly Phe Lys Glu Pro Arg Lys
545                 550                 555                 560
Tyr Ile Ala Ala Gln Gly Pro Arg Asp Glu Thr Val Asp Asp Phe Trp
                565                 570                 575
Arg Met Ile Trp Glu Gln Lys Ala Thr Val Ile Val Met Val Thr Arg
                580                 585                 590
Cys Glu Glu Gly Asn Arg Asn Lys Cys Ala Glu Tyr Trp Pro Ser Met
            595                 600                 605
Glu Glu Gly Thr Arg Ala Phe Gly Asp Val Val Lys Ile Asn Gln
    610                 615                 620
His Lys Arg Cys Pro Asp Tyr Ile Ile Gln Lys Leu Asn Ile Val Asn
625                 630                 635                 640
Lys Lys Glu Lys Ala Thr Gly Arg Glu Val Thr His Ile Gln Phe Thr
                645                 650                 655
Ser Trp Pro Asp His Gly Val Pro Glu Asp Pro His Leu Leu Leu Lys
                660                 665                 670
Leu Arg Arg Arg Val Asn Ala Phe Ser Asn Phe Phe Ser Gly Pro Ile
            675                 680                 685
Val Val His Cys Ser Ala Gly Val Gly Arg Thr Gly Thr Tyr Ile Gly
    690                 695                 700
Ile Asp Ala Met Leu Glu Gly Leu Glu Ala Glu Asn Lys Val Asp Val
705                 710                 715                 720
Tyr Gly Tyr Val Val Lys Leu Arg Arg Gln Arg Cys Leu Met Val Gln
                725                 730                 735
Val Glu Ala Gln Tyr Ile Leu Ile His Gln Ala Leu Val Glu Tyr Asn
            740                 745                 750
Gln Phe Gly Glu Thr Glu Val Asn Leu Ser Glu Leu His Pro Tyr Leu
        755                 760                 765
His Asn Met Lys Lys Arg Asp Pro Pro Ser Glu Pro Ser Pro Leu Glu
    770                 775                 780
```

Ala Glu Phe Gln Arg Leu Pro Ser Tyr Arg Ser Trp Arg Thr Gln His
785                 790                 795                 800

Ile Gly Asn Gln Glu Glu Asn Lys Ser Lys Asn Arg Asn Ser Asn Val
            805                 810                 815

Ile Pro Tyr Asp Tyr Asn Arg Val Pro Leu Lys His Glu Leu Glu Met
        820                 825                 830

Ser Lys Glu Ser Glu His Asp Ser Asp Glu Ser Ser Asp Asp Asp Ser
            835                 840                 845

Asp Ser Glu Glu Pro Ser Lys Tyr Ile Asn Ala Ser Phe Ile Met Ser
        850                 855                 860

Tyr Trp Lys Pro Glu Val Met Ile Ala Ala Gln Gly Pro Leu Lys Glu
865                 870                 875                 880

Thr Ile Gly Asp Phe Trp Gln Met Ile Phe Gln Arg Lys Val Lys Val
            885                 890                 895

Ile Val Met Leu Thr Glu Leu Lys His Gly Asp Gln Glu Ile Cys Ala
        900                 905                 910

Gln Tyr Trp Gly Glu Gly Lys Gln Thr Tyr Gly Asp Ile Glu Val Asp
            915                 920                 925

Leu Lys Asp Thr Asp Lys Ser Ser Thr Tyr Thr Leu Arg Val Phe Glu
930                 935                 940

Leu Arg His Ser Lys Arg Lys Asp Ser Arg Thr Val Tyr Gln Tyr Gln
945                 950                 955                 960

Tyr Thr Asn Trp Ser Val Glu Gln Leu Pro Ala Glu Pro Lys Glu Leu
            965                 970                 975

Ile Ser Met Ile Gln Val Val Lys Gln Lys Leu Pro Gln Lys Asn Ser
        980                 985                 990

Ser Glu Gly Asn Lys His His Lys Ser Thr Pro Leu Leu Ile His Cys
            995                 1000                1005

Arg Asp Gly Ser Gln Gln Thr Gly Ile Phe Cys Ala Leu Leu Asn Leu
        1010                1015                1020

Leu Glu Ser Ala Glu Thr Glu Glu Val Val Asp Ile Phe Gln Val Val
1025                1030                1035                1040

Lys Ala Leu Arg Lys Ala Arg Pro Gly Met Val Ser Thr Phe Glu Gln
                1045                1050                1055

Tyr Gln Phe Leu Tyr Asp Val Ile Ala Ser Thr Tyr Pro Ala Gln Asn
                1060                1065                1070

Gly Gln Val Lys Lys Asn Asn His Gln Glu Asp Lys Ile Glu Phe Asp
                1075                1080                1085

Asn Glu Val Asp Lys Val Lys Gln Asp Ala Asn Cys Val Asn Pro Leu
        1090                1095                1100

Gly Ala Pro Glu Lys Leu Pro Glu Ala Lys Glu Gln Ala Glu Gly Ser
1105                1110                1115                1120

Glu Pro Thr Ser Gly Thr Glu Gly Pro Glu His Ser Val Asn Gly Pro
                1125                1130                1135

Ala Ser Pro Ala Leu Asn Gln Gly Ser
            1140                1145

<210> SEQ ID NO 111
<211> LENGTH: 7
<212> TYPE: PRT
<213> ORGANISM: Artificial Sequence
<220> FEATURE:
<223> OTHER INFORMATION: VL-CDR2

<400> SEQUENCE: 111

Ala Thr Ser Asn Leu Pro Ser
1               5

<210> SEQ ID NO 112
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)

<400> SEQUENCE: 112

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Ser Xaa Tyr
            20                  25                  30

Met His Trp Tyr Gln Gln Lys Pro Gly Lys Ala Pro Lys Leu Trp Ile
            35                  40                  45

Tyr Ala Thr Ser Asn Leu Pro Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Arg Ser Ser Tyr Pro Leu
                85                  90                  95

Thr Phe Gly Gly Gly Thr Lys Val Glu Ile Lys
                100                 105

<210> SEQ ID NO 113
<211> LENGTH: 106
<212> TYPE: PRT
<213> ORGANISM: Artificial Sequence
<220> FEATURE:
<223> OTHER INFORMATION: Humanized LCVR

<400> SEQUENCE: 113

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Trp Ile Tyr
            35                  40                  45

Ala Thr Ser Asn Leu Pro Ser Gly Val Pro Ser Arg Phe Ser Gly Ser
50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Arg Ser Ser Tyr Pro Leu Thr
                85                  90                  95

Phe Gly Gly Gly Thr Lys Val Glu Ile Lys
                100                 105

<210> SEQ ID NO 114
<211> LENGTH: 330
<212> TYPE: PRT
<213> ORGANISM: Artificial Sequence
<220> FEATURE:
<223> OTHER INFORMATION: Human HCCR

<400> SEQUENCE: 114

| Ala | Ser | Thr | Lys | Gly | Pro | Ser | Val | Phe | Pro | Leu | Ala | Pro | Ser | Ser | Lys |
|---|---|---|---|---|---|---|---|---|---|---|---|---|---|---|---|
| 1 | | | | 5 | | | | | 10 | | | | | 15 | |

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 115
<211> LENGTH: 113
<212> TYPE: PRT
<213> ORGANISM: Artificial Sequence
<220> FEATURE:
<223> OTHER INFORMATION: Human HCCR

<400> SEQUENCE: 115

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Val Ala Ala Ala His His His His
            100                 105                 110
His
```

```
<210> SEQ ID NO 116
<211> LENGTH: 17
<212> TYPE: PRT
<213> ORGANISM: Artificial Sequence
<220> FEATURE:
<223> OTHER INFORMATION: VH-CDR2

<400> SEQUENCE: 116

Asp Ile Phe Pro Gly Gly Gly Tyr Ala Asn Tyr Ala Glu Lys Phe Gln
1               5                   10                  15
Gly
```

```
<210> SEQ ID NO 117
<211> LENGTH: 17
<212> TYPE: PRT
<213> ORGANISM: Artificial Sequence
<220> FEATURE:
<223> OTHER INFORMATION: VH-CDR2

<400> SEQUENCE: 117

Asp Ile Phe Pro Gly Gly Gly Tyr Thr Asn Tyr Ala Glu Lys Phe Lys
1               5                   10                  15
Gly
```

```
<210> SEQ ID NO 118
<211> LENGTH: 17
<212> TYPE: PRT
<213> ORGANISM: Artificial Sequence
<220> FEATURE:
<223> OTHER INFORMATION: VH-CDR2

<400> SEQUENCE: 118

Asp Ile Phe Pro Gly Gly Gly Tyr Thr Asn Tyr Asn Glu Lys Phe Gln
1               5                   10                  15
Gly
```

```
<210> SEQ ID NO 119
<211> LENGTH: 17
<212> TYPE: PRT
<213> ORGANISM: Artificial Sequence
<220> FEATURE:
<223> OTHER INFORMATION: VH-CDR2

<400> SEQUENCE: 119

Asp Ile Phe Pro Gly Gly Gly Tyr Thr Asn Ser Ala Glu Lys Phe Gln
1               5                   10                  15
Gly
```

```
<210> SEQ ID NO 120
<211> LENGTH: 7
<212> TYPE: PRT
<213> ORGANISM: Artificial Sequence
<220> FEATURE:
<223> OTHER INFORMATION: VL-CDR2

<400> SEQUENCE: 120

Asn Thr Ala Asn Leu Pro Ser
1               5

<210> SEQ ID NO 121
<211> LENGTH: 114
<212> TYPE: PRT
<213> ORGANISM: Artificial Sequence
<220> FEATURE:
<223> OTHER INFORMATION: Humanized HCVR

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile Gly Trp Val Arg Gln Ala Pro Gly Gln Gly Leu Glu Trp Ile
            35                  40                  45

Gly Asp Ile Phe Pro Gly Gly Gly Tyr Ala Asn Tyr Ala Glu Lys Phe
    50                  55                  60

Gln Gly Arg Val Thr Leu Thr Ala Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Val Arg Arg Asn Phe Asp Tyr Trp Gly Gln Gly Thr Leu Val Thr Val
            100                 105                 110

Ser Ser

<210> SEQ ID NO 122
<211> LENGTH: 114
<212> TYPE: PRT
<213> ORGANISM: Artificial Sequence
<220> FEATURE:
<223> OTHER INFORMATION: Humanized HCVR

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile Gly Trp Val Arg Gln Ala Pro Gly Gln Gly Leu Glu Trp Ile
            35                  40                  45

Gly Asp Ile Phe Pro Gly Gly Gly Tyr Thr Asn Tyr Ala Glu Lys Phe
    50                  55                  60

Lys Gly Arg Val Thr Leu Thr Ala Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Val Arg Arg Asn Phe Asp Tyr Trp Gly Gln Gly Thr Leu Val Thr Val
            100                 105                 110

Ser Ser
```

```
<210> SEQ ID NO 123
<211> LENGTH: 114
<212> TYPE: PRT
<213> ORGANISM: Artificial Sequence
<220> FEATURE:
<223> OTHER INFORMATION: Humanized HCVR

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile Gly Trp Val Arg Gln Ala Pro Gly Gln Gly Leu Glu Trp Ile
            35                  40                  45

Gly Asp Ile Phe Pro Gly Gly Gly Tyr Thr Asn Tyr Asn Glu Lys Phe
        50                  55                  60

Gln Gly Arg Val Thr Leu Thr Ala Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Val Arg Arg Asn Phe Asp Tyr Trp Gly Gln Gly Thr Leu Val Thr Val
                100                 105                 110

Ser Ser

<210> SEQ ID NO 124
<211> LENGTH: 114
<212> TYPE: PRT
<213> ORGANISM: Artificial Sequence
<220> FEATURE:
<223> OTHER INFORMATION: Humanized HCVR

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile Gly Trp Val Arg Gln Ala Pro Gly Gln Gly Leu Glu Trp Ile
            35                  40                  45

Gly Asp Ile Phe Pro Gly Gly Gly Tyr Thr Asn Ser Ala Glu Lys Phe
        50                  55                  60

Gln Gly Arg Val Thr Leu Thr Ala Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Val Arg Arg Asn Phe Asp Tyr Trp Gly Gln Gly Thr Leu Val Thr Val
                100                 105                 110

Ser Ser

<210> SEQ ID NO 125
<211> LENGTH: 107
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 31
<223> OTHER INFORMATION: Xaa is selected from Asn (N), Ser (S) and Gly
      (G)
```

```
<400> SEQUENCE: 125

Gln Ile Val Leu Thr Gln Ser Pro Thr Ile Met Ser Ala Ser Pro Gly
1               5                   10                  15

Glu Lys Val Thr Ile Thr Cys Ser Ala Ser Ser Val Ser Xaa Tyr
            20                  25                  30

Met His Trp Phe Gln Gln Lys Thr Gly Thr Ser Pro Arg Leu Trp Ile
        35                  40                  45

Tyr Asn Thr Ala Asn Leu Pro Ser Gly Val Pro Ala Arg Phe Ser Gly
    50                  55                  60

Ser Gly Ser Gly Thr Ser Phe Ser Leu Thr Ile Ser Arg Met Glu Ala
65              70                  75                  80

Glu Asp Ala Ala Thr Tyr Tyr Cys Gln Gln Arg Ser Ser Tyr Pro Leu
                85                  90                  95

Thr Phe Gly Ala Gly Thr Lys Leu Glu Leu Lys
            100                 105

<210> SEQ ID NO 126
<211> LENGTH: 106
<212> TYPE: PRT
<213> ORGANISM: Artificial Sequence
<220> FEATURE:
<223> OTHER INFORMATION: Humanized LCVR

<400> SEQUENCE: 126

Gln Ile Val Leu Thr Gln Ser Pro Thr Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Thr Gly Thr Ser Pro Arg Leu Trp Ile Tyr
        35                  40                  45

Asn Thr Ala Asn Leu Pro Ser Gly Val Pro Ala Arg Phe Ser Gly Ser
    50                  55                  60

Gly Ser Gly Thr Ser Tyr Ser Leu Thr Ile Ser Arg Met Glu Ala Glu
65              70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 127
<211> LENGTH: 7
<212> TYPE: PRT
<213> ORGANISM: Artificial Sequence
<220> FEATURE:
<221> NAME/KEY: SITE
<222> LOCATION: 1
<223> OTHER INFORMATION: Xaa is any amino acid but Ala (A) or Asn (N)
<220> FEATURE:
<223> OTHER INFORMATION: VL-CDR2

<400> SEQUENCE: 127

Xaa Thr Ser Asn Leu Pro Ser
1               5

<210> SEQ ID NO 128
<211> LENGTH: 107
<212> TYPE: PRT
<213> ORGANISM: Artificial Sequence
<220> FEATURE:
<223> OTHER INFORMATION: Humanized LCVR
<220> FEATURE:
```

```
<221> NAME/KEY: SITE
<222> LOCATION: 31
<223> OTHER INFORMATION: Xaa is selected from Asn (N), Ser (S) and Gly
      (G)
<220> FEATURE:
<221> NAME/KEY: SITE
<222> LOCATION: 50
<223> OTHER INFORMATION: Xaa is any amino acid but Ala (A) or Asn (N)

<400> SEQUENCE: 128
```

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Xaa Tyr
            20                  25                  30

Met His Trp Tyr Gln Gln Lys Pro Gly Lys Ala Pro Lys Leu Trp Ile
        35                  40                  45

Tyr Xaa Thr Ser Asn Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Arg Ser Ser Tyr Pro Leu
                85                  90                  95

Thr Phe Gly Gly Gly Thr Lys Val Glu Ile Lys
            100                 105

```
<210> SEQ ID NO 129
<211> LENGTH: 106
<212> TYPE: PRT
<213> ORGANISM: Artificial Sequence
<220> FEATURE:
<223> OTHER INFORMATION: Humanized LCVR
<220> FEATURE:
<221> NAME/KEY: SITE
<222> LOCATION: 49
<223> OTHER INFORMATION: Xaa is any amino acid but Ala (A) or Asn (N)

<400> SEQUENCE: 129
```

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Trp Ile Tyr
        35                  40                  45

Xaa Thr Ser Asn Leu Pro Ser Gly Val Pro Ser Arg Phe Ser Gly Ser
    50                  55                  60

Gly Ser Gly Thr Glu Tyr Thr Leu Thr Ile Ser Ser Leu Gln Pro Glu
65                  70                  75                  80

Asp Phe Ala Thr Tyr Tyr Cys Gln Gln Arg Ser Ser Tyr Pro Leu Thr
                85                  90                  95

Phe Gly Gly Gly Thr Lys Val Glu Ile Lys
            100                 105